United States Patent
Dogué et al.

(10) Patent No.: US 11,571,311 B2
(45) Date of Patent: *Feb. 7, 2023

(54) TOTAL ANKLE REPLACEMENT TRIAL AND PREPARATION SYSTEMS

(71) Applicant: Paragon 28, Inc., Englewood, CO (US)

(72) Inventors: Joseph Dogué, Aurora, CO (US); Daniel J. Lee, Denver, CO (US); Mark Ray Dalton, Austin, TX (US)

(73) Assignee: PARAGON 28, INC., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/345,137

(22) Filed: Jun. 11, 2021

(65) Prior Publication Data

US 2021/0298913 A1 Sep. 30, 2021

Related U.S. Application Data

(63) Continuation of application No. PCT/US2019/066404, filed on Dec. 13, 2019.
(Continued)

(51) Int. Cl.
*A61F 2/42* (2006.01)
*A61F 2/30* (2006.01)
(Continued)

(52) U.S. Cl.
CPC ............ *A61F 2/4202* (2013.01); *A61B 17/15* (2013.01); *A61B 17/1682* (2013.01);
(Continued)

(58) Field of Classification Search
None
See application file for complete search history.

(56) References Cited

U.S. PATENT DOCUMENTS

| 3,710,473 A | 1/1973 | McElwain |
| 3,750,652 A | 8/1973 | Sherwin |

(Continued)

FOREIGN PATENT DOCUMENTS

| WO | 2017164862 | 9/2017 | |
| WO | WO-2019063807 A1 * | 4/2019 | ......... A61B 17/1775 |
| WO | 2019091537 | 5/2019 | |

OTHER PUBLICATIONS

Schweitzer et al., Total Ankle Arthroplasty with a Modern Fixed-Bearing System: The Salto Talaris Prosthesis, JBJS Essential Surgical Techniques, retrieved from the internet at https://www.ncbi.nlm.nih.gov/pmc/articles/PMC6407948/pdf/jbjsest-3-e18.pdf, 9 pages, 2013.

(Continued)

*Primary Examiner* — Ann Schillinger
(74) *Attorney, Agent, or Firm* — Heslin Rothenberg Farley & Mesiti PC; Kristian E. Ziegler, Esq.

(57) ABSTRACT

Instruments, guides, systems and related methods for total ankle prostheses are disclosed. The instruments, guides, systems and related methods facilitate preparation of a tibia and/or talus of a patient for implantation of a total ankle prosthesis therein. The instruments, guides, systems and related methods also facilitate selection of a particular size of a tibial component, a talus component and/or a tibial insert of the total ankle prosthesis that suits the patient. The instruments, guides, systems and related methods include a tibial trial component, a talar trial component and tibial insert trial component that replicate one or more aspects of the tibial component, the talus component and the tibial insert, respectively, of the total ankle prosthesis. The talar trial component includes an articulation surface that articulates with the tibial insert trial component, and slots that (Continued)

facilitate chamfered resection of the patient's talus for the implantation of the talus component thereon.

33 Claims, 131 Drawing Sheets

Related U.S. Application Data

(60) Provisional application No. 62/898,854, filed on Sep. 11, 2019, provisional application No. 62/779,092, filed on Dec. 13, 2018.

(51) Int. Cl.
| | |
|---|---|
| A61B 17/70 | (2006.01) |
| A61B 17/16 | (2006.01) |
| A61B 17/17 | (2006.01) |
| A61B 17/15 | (2006.01) |
| A61F 2/46 | (2006.01) |
| A61B 90/00 | (2016.01) |
| A61B 17/00 | (2006.01) |
| A61B 17/56 | (2006.01) |

(52) U.S. Cl.
CPC ........ *A61B 17/1775* (2016.11); *A61F 2/4606* (2013.01); *A61F 2/4684* (2013.01); *A61B 2017/00707* (2013.01); *A61B 2017/565* (2013.01); *A61B 2090/0811* (2016.02); *A61F 2002/30492* (2013.01); *A61F 2002/30594* (2013.01); *A61F 2002/4205* (2013.01); *A61F 2002/4207* (2013.01)

(56) References Cited

U.S. PATENT DOCUMENTS

| | | | |
|---|---|---|---|
| 4,899,761 A | 2/1990 | Brown | |
| 5,429,121 A | 7/1995 | Gadelius | |
| 6,241,729 B1 | 6/2001 | Estes | |
| 6,261,296 B1 | 7/2001 | Aebi | |
| 6,551,316 B1 | 4/2003 | Rinner | |
| 6,673,116 B2 | 1/2004 | Reiley | |
| 6,739,068 B1 | 5/2004 | Rinner | |
| 6,875,236 B2 | 4/2005 | Reiley | |
| 7,025,790 B2 | 4/2006 | Parks | |
| 7,153,281 B2 | 12/2006 | Holmes | |
| 8,002,841 B2* | 8/2011 | Hasselman | A61B 17/15 623/21.18 |
| 8,439,951 B2 | 5/2013 | Trautwein | |
| 8,979,866 B2 | 3/2015 | Patel | |
| 9,351,773 B2 | 5/2016 | DiDomenico | |
| 9,402,640 B2 | 8/2016 | Reynolds et al. | |
| 9,480,571 B2 | 11/2016 | McGinley et al. | |
| 9,907,561 B2 | 3/2018 | Luna et al. | |
| 9,918,724 B2 | 3/2018 | Luna et al. | |
| 9,974,588 B2 | 5/2018 | Stemniski et al. | |
| 10,058,335 B2 | 8/2018 | Lee et al. | |
| 10,182,832 B1* | 1/2019 | Saltzman | A61B 17/1775 |
| 11,399,949 B2* | 8/2022 | Dogué | A61B 17/15 |
| 2001/0029377 A1 | 10/2001 | Aebi | |
| 2003/0225416 A1 | 12/2003 | Bonvallet | |
| 2005/0004676 A1* | 1/2005 | Schon | A61B 17/15 606/87 |
| 2006/0142870 A1* | 6/2006 | Robinson | A61B 17/142 606/87 |
| 2006/0229730 A1* | 10/2006 | Railey | A61B 17/1775 623/23.44 |
| 2007/0073405 A1 | 3/2007 | Verhulst | |
| 2010/0217338 A1 | 8/2010 | Carroll | |
| 2011/0218542 A1* | 9/2011 | Lian | A61B 17/1775 606/88 |
| 2012/0130376 A1 | 5/2012 | Loring | |
| 2012/0130434 A1* | 5/2012 | Stemniski | A61B 17/15 606/86 R |
| 2012/0232558 A1 | 9/2012 | Berberich | |
| 2012/0239045 A1* | 9/2012 | Li | A61B 17/15 606/88 |
| 2012/0271314 A1* | 10/2012 | Stemniski | A61B 17/1682 606/87 |
| 2013/0046313 A1* | 2/2013 | Lian | A61F 2/46 606/99 |
| 2013/0085499 A1 | 4/2013 | Lian | |
| 2014/0018931 A1* | 1/2014 | Gillard | A61F 2/4202 623/21.18 |
| 2014/0128979 A1 | 5/2014 | Womble et al. | |
| 2014/0163563 A1 | 6/2014 | Reynolds et al. | |
| 2014/0336658 A1* | 11/2014 | Luna | A61F 2/4684 606/87 |
| 2015/0157339 A1* | 6/2015 | McGinley | A61B 17/15 606/87 |
| 2015/0182273 A1 | 7/2015 | Stemniski et al. | |
| 2015/0265265 A1 | 9/2015 | Hynes et al. | |
| 2015/0305753 A1 | 10/2015 | McGinley et al. | |
| 2017/0340450 A1* | 11/2017 | Toro Arbelaez | A61F 2/4202 |
| 2018/0125663 A1* | 5/2018 | Huxel | A61F 2/46 |
| 2018/0146970 A1 | 5/2018 | Luna et al. | |
| 2018/0177511 A1 | 6/2018 | Luna et al. | |
| 2018/0177513 A1 | 6/2018 | Stemniski et al. | |
| 2018/0243023 A1 | 8/2018 | Stemniski et al. | |
| 2018/0289367 A1* | 10/2018 | Mauldin | A61B 17/15 |
| 2018/0317940 A1 | 11/2018 | Stemniski et al. | |
| 2020/0046412 A1* | 2/2020 | Nachtrab | A61B 17/17 |
| 2020/0085452 A1* | 3/2020 | Siegler | A61B 17/1703 |
| 2020/0113712 A1* | 4/2020 | Luna | A61B 17/1631 |

OTHER PUBLICATIONS

International Search Report and Written Opinion of the International Searching Authority for PCT/US2019/066404, dated Feb. 24, 2020, 12 pages.

Non-Final Office Action issued in U.S. Appl. No. 17/345,135, dated Dec. 9, 2021, 16 pages.

Non-Final Office Action issued in U.S. Appl. No. 17/345,402, dated Feb. 1, 2022, 17 pages.

* cited by examiner

TOTAL ANKLE REPLACEMENT TRIAL AND PREPARATION SYSTEMS

CROSS REFERENCE TO RELATED APPLICATIONS

This application is a continuation of International Application No. PCT/US2019/066404, filed Dec. 13, 2019, and entitled Instruments, Guides and Related Methods for Total Ankle Replacement, which claims priority benefit of U.S. Provisional Patent Application No. 62/779,092, filed Dec. 13, 2018, and entitled Instruments, Guides and Related Methods for Total Ankle Replacement, and U.S. Provisional Patent Application No. 62/898,854, filed Sep. 11, 2019, and entitled "Distractors Having Attachable Paddles, Impaction Devices, And Methods For Use In Total Ankle Replacement," which are hereby incorporated herein by reference in their entireties.

TECHNICAL FIELD

The present disclosure relates generally to general, podiatric, and orthopaedic surgery related to joint deformities. More specifically, but not exclusively, the present disclosure relates to instruments, guides, systems and related methods for maintaining, correcting and/or repairing a joint deformity and/or injury.

BACKGROUND

Total ankle replacement (TAR), or ankle arthroplasty, is a surgical procedure to replace deformed and/or damaged articular surfaces of the human ankle joint with a prosthetic joint. TAR is becoming the treatment of choice for patients with a deformed and/or injured/damaged ankle joint, replacing the conventional use of arthrodesis (i.e. fusion of the ankle bones). One of the main advantages of TAR compared with ankle arthrodesis is preservation of functional range of motion (ROM), which is sacrificed in ankle fusion. Improved ROM allows patients to better perform activities of daily living and possibly regain athletic activities Many types of total ankle prostheses have been developed, such as the cylindric-type ankle replacement prosthesis, the spherical-type ankle replacement prosthesis, and the sliding cylindric-type ankle replacement prosthesis. These and other typical total ankle replacement (TAR) prosthesis comprise a tibial prosthesis component, a talus prosthesis component, and a tibial bearing or insert component positioned between the tibial and talus prosthesis components. In these types of TAR prostheses, the tibial component is implanted on/in a tibia, the talus component is implanted on/in a talus, and the tibial insert is fixed to the tibial component and articulates with the talus component to form a replacement ankle joint.

The proper size and position/orientation/alignment of the tibial component of a TAR prosthesis with respect to the distal end of a tibia and the corresponding ankle joint, the proper size and position/orientation of the talus component of the TAR prosthesis with respect to the proximal end of a talus and the corresponding ankle joint, and the proper size and position/orientation/alignment of the tibial insert of the TAR prosthesis with respect to the tibial component, the talus component and the corresponding ankle joint, are all important to achieving a stable replacement ankle joint and a replacement ankle joint that provides for full articulation/motion (e.g., achieving a range of motion of typical "healthy" ankle joints). For example, proper sizing and position/orientation of the tibial prosthesis, the talus prosthesis and the tibial insert of a TAR prosthesis with respect to an ankle joint of a particular patient can prevent overstuffing or understuffing of the replacement ankle joint (and thereby provide full articulation/motion) and can ensure proper coverage of the tibial prosthesis on the tibial and the talus prosthesis on the talus. As another example, the position/orientation/alignment of the tibial prosthesis, the talus prosthesis and the tibial insert with respect to the mechanical axis of an ankle joint of a particular patient (e.g., the mechanical axis of the tibia) can ensure the mechanical forces of the replacement ankle joint are properly distributed and full and properly-oriented range of motion is achieved.

Total ankle replacement instrumentation, guides, systems and methods that facilitate the selection of a properly sized tibial prosthesis, talus prosthesis, and tibial insert of a total ankle replacement implant system for an ankle joint of a particular patient are thereby desirable. Further, total ankle replacement instrumentation, guides, systems and methods that facilitate implantation of the tibial prosthesis in/on a tibia, and implantation of the talus prosthesis in/on a talus, of a total ankle replacement implant system in proper positions and orientations (and thereby the proper position and orientation of the corresponding tibial insert) for an ankle joint of a particular patient are thereby also desirable.

SUMMARY

The present disclosure is directed toward instruments, guides, systems and related methods for total ankle replacement prostheses. The instruments, guides, systems and related methods may facilitate preparation of a tibia and/or talus of a patient for implantation of a total ankle prosthesis therein. The instruments, guides, systems and related methods may also facilitate selection of a particular size of a tibial component, a talus component and/or a tibial insert of the total ankle prosthesis that suits the patient. The instruments, guides, systems and related methods include a tibial trial component, a talar/talus trial component and tibial insert trial component that replicate one or more aspects of the tibial component, the talus component and the tibial insert, respectively, of the total ankle prosthesis.

In one aspect of the present application, a total ankle replacement (TAR) trial and bone preparation guide system comprising a tibial trial and bone preparation first component and a talar trial and bone preparation second component is disclosed. The tibial trial and bone preparation first component comprises a base portion and an arm portion. The base portion comprises a first side with a first tibial engagement surface configured to engage a resected distal tibia and at least one bone aperture formation guide through hole extending from the first tibial engagement surface to a second tibial insert engagement side, and the arm portion extends proximally from an anterior portion of the base portion and is configured to engage an anterior side of the resected distal tibia. The talar trial and bone preparation second component comprises a first talar engagement surface, a posterior trial articulation surface, an anterior window, a posterior cut slot and a plurality of pin apertures. The first talar engagement surface is positioned on a distal side of the second component and is configured to engage a portion of a resected talus. The posterior trial articulation surface is positioned on a proximal side of the second component and is anteriorly-posteriorly arcuately convex. The anterior window extends through the second component between the proximal side and the distal side thereof. The posterior cut slot extends through the second component between the proximal side and the distal side thereof that is angled posteriorly as in extends from the proximal side to the distal side. The plurality of pin apertures extend through the second component between the proximal side and the distal side.

In some embodiments, the resected distal tibia and the resected talus for implantation therein and therebetween, a TAR prosthesis comprising a tibial component comprising a second tibial engagement surface and at least one bone engagement projection, a tibial insert configured to removably couple with the tibial component and comprising a second tibial articulation surface, and a talar component comprising a second talar engagement surface and a talar articulation surface that articulates with the second tibial articulation surface.

In some embodiments, the system further comprises a tibial trial insert comprising a distal side with a first talar trial engagement surface that is configured to engage the posterior trial articulation surface of the second component, and a proximal side configured to removably couple with the second tibial insert engagement side of the first component. In some embodiments, the second tibial insert engagement side of the first component comprises a coupling slot, and wherein the tibial trial insert comprises a coupling projection configured to removably mate within the coupling slot. In some embodiments, the coupling slot is a dove-tail shaped slot, and wherein the coupling projection is a dove-tail shaped projection configured to mate with the dove-tail shaped slot. In some embodiments, the coupling slot and the coupling projection extend and are elongated anteriorly-posteriorly. In some embodiments, at least one through hole of the at least one bone aperture formation guide through hole is positioned within the coupling slot.

In some embodiments, the configuration of the first talar trial engagement surface corresponds to at least a portion of the second tibial articulation surface. In some embodiments, the first talar trial engagement surface is arcuately concave anteriorly-posteriorly. In some embodiments, the first talar trial engagement surface comprises an anterior rail portion that extends medially-laterally and defines an engagement surface that is flat or convex anteriorly-posteriorly, and a posterior rail portion that extends medially-laterally and defines an engagement surface that is flat or convex anteriorly-posteriorly. In some embodiments, the first talar trial engagement surface further comprises a strut portion that extends anteriorly-posteriorly, and wherein the posterior trial articulation surface of the second component comprises a strut slot that extends anteriorly-posteriorly and is configured to accept the strut portion therein.

In some embodiments, at least a portion of the first tibial engagement surface corresponds in size and shape to at least a portion of the second tibial engagement surface.

In some embodiments, the first tibial engagement surface is convex medially-laterally.

In some embodiments, the first side of the base portion of the first component includes at least one reference slot extending medially-laterally through at least a portion of the first tibial engagement surface. In some embodiments, the at least one reference slot comprises at least one of: a center reference slot positioned in the medial-lateral center of the base portion and/or corresponding to the medial-lateral center of the tibial component; a bone aperture formation reference slot extending through at least a portion of the at least one bone aperture formation guide through hole; an anterior reference slot positioned in an anterior end portion of the base portion corresponding to an anterior end of the tibial component; and an posterior reference slot positioned in a posterior end portion of the base portion corresponding to a posterior end of the tibial component.

In some embodiments, the arm portion of the first component comprises a plurality of pin through holes extending therethrough anteriorly-posteriorly. In some embodiments, the arm portion of the first component comprises a medial wing and a lateral wing, the medial and lateral wings each comprising at least one pin through hole of the plurality of pin through holes, and wherein the at least one pin through hole of the medial and lateral wings converge medially-laterally as they extend posteriorly. In some embodiments, the plurality of pin through holes comprise at least one pair of aligned pin through holes that are medially-laterally spaced.

In some embodiments, the arm portion of the first component comprises a positioning mechanism that is configured to engage the anterior side of the resected distal tibia and adjust the anterior-posterior position of the base portion of the first component relative to the resected distal tibia. In some embodiments, the positioning mechanism comprises at least one adjustment screw threadably coupled with the arm portion.

In some embodiments, the first talar engagement surface is planar and is configured to engage a planar portion of the resected talus. In some embodiments, the first talar engagement surface comprises medial and lateral side edges that are exposed at medial and lateral sides of the second component. In some embodiments, the distal side of the second component further comprises a medially-laterally extending center reference slot extending through the first talar engagement surface corresponding to the medial-lateral center of the talar component, the medially-laterally extending center reference slot being exposed at medial and lateral sides of the second component.

In some embodiments, the posterior cut slot is exposed at medial and lateral sides of the second component at the distal side of the second component. In some embodiments, the posterior cut slot defines a posterior end of the medially-laterally extending center reference slot.

In some embodiments, the distal side of the second component further comprises a medially-laterally extending anterior reference slot, the medially-laterally extending anterior reference slot being exposed at medial and lateral sides of the second component and corresponding to the position and orientation of an anterior-posterior pathway of the posterior trial articulation surface at the distal side of the second component.

In some embodiments, the system further comprises at least one anterior cut guide configured to engage the proximal side of the second component and extend at least partially over the anterior window, the at least one anterior cut guide comprising a bone cutting guide through hole configured to mate with at least one cutting implement to form an anterior chamfer on the resected talus. In some embodiments, the distal side of the second component further comprises a medially-laterally extending anterior cut reference slot, the medially-laterally extending anterior cut reference slot being exposed at medial and lateral sides of the second component and corresponding to the position and orientation of the anterior chamfer on the resected talus.

In some embodiments, the posterior trial articulation surface corresponds in size and shape to at least a portion of the talar articulation surface of the talar component. In some embodiments, the posterior cut slot is positioned anteriorly-posteriorly between at least a portion of the posterior trial articulation surface and the anterior window. In some embodiments, the posterior cut slot is configured to accept a cutting blade therethrough to form a posterior chamfer on the resected talus.

In some embodiments, the second component further comprises a plurality of pin through holes extending therethrough between the proximal and distal sides thereof. In some embodiments, the plurality of pin through holes of the second component comprise at least one pair of through holes that are medially-laterally spaced and converge medially-laterally as they extend from the proximal side to the and distal side of the second component. In some embodiments, the plurality of pin through holes of the second component comprise at least one pair of aligned pin through holes that are medially-laterally spaced.

In some embodiments, the second component further comprises a handle that forms an anterior end of the second component. In some embodiments, the second component further comprises a socket that forms an anterior end of the second component. In some embodiments, the system further comprises a distractor, and wherein the socket is configured to couple with a first arm of the distractor. In some embodiments, the distractor further comprises a second arm with a paddle coupled thereto, and wherein the paddle is configured to engage with the second tibial insert engagement side of the base portion of the first component.

In some embodiments, the system further comprises a chamfer checker instrument, the chamfer checker instrument comprising at least one third talar engagement surface configured to engage the resected talus, a fourth talar engagement surface extending from the at least one third talar engagement surface configured to engage an anterior chamfer of the resected talus formed via the anterior window of the second component, and a fifth talar engagement surface extending from the at least one third talar engagement surface configured to engage a posterior chamfer of the resected talus formed via the cut slot of the second component. In some embodiments, the at least one third talar engagement surface comprises a medially-laterally extending center reference slot corresponding to the medial-lateral center of the talar component, the center reference slot of the at least one third talar engagement surface being exposed at medial and lateral sides of the chamfer checker. In some embodiments, the chamfer checker further comprises first and second medially-laterally extending through hole positioned proximally of the at least one third talar engagement surface, the first medially-laterally extending through hole being tangent to a reference line extending along the fourth talar engagement surface and the second medially-laterally extending through hole being tangent to a reference line extending along the fifth talar engagement surface.

In some embodiments, the system further comprises a talar chamfer trial comprising: a fifth talar engagement surface on a distal side of the talar chamfer trial configured to engage the resected talus; a second posterior trial articulation surface on a proximal side of the talar chamfer trial that comprises an anteriorly-posteriorly and medially-laterally arcuately convex portion; at least one bone aperture formation guide through hole; and a plurality of pin through holes extending between the proximal and distal sides thereof. In some embodiments, at least a portion of the second posterior trial articulation surface corresponds in size and shape to at least a portion of the second tibial engagement surface. In some embodiments, the fifth talar engagement surface comprises a first planar surface for engaging a planar surface of the resected talus, a second planar surface extending anteriorly from the first planar surface on a distal angle configured to engage an anterior chamfer surface of the resected talus formed via the anterior window of the second component, and a third planar surface extending posteriorly from the first planar surface on a distal angle configured to engage a posterior chamfer of the resected talus formed via the cut slot of the second component. In some embodiments, the at least one bone aperture formation guide through hole of the talar chamfer trial comprises an elongated slot at an anterior end portion of the talar chamfer trial that extends through the second planar surface. In some embodiments, the system further comprises a bone aperture formation guide configured to couple to the anterior end portion of the talar chamfer trial, the bone aperture formation guide comprising a second elongated slot that extends over the elongated slot when coupled to the anterior end portion, the second elongated slot configured to accept a bone cutting instrument therethrough to form an elongated aperture in the anterior chamfer surface of the resected talus formed via the anterior window of the second component. In some embodiments, the at least one bone aperture formation guide through hole comprises a pair of medially-laterally spaced drill guide through holes that extend through the second posterior trial articulation surface to the distal side of the talar chamfer trial.

In another aspect of the present application, a method comprising trialing a total ankle replacement (TAR) prosthesis, preparing a resected tibia of the ankle joint, and preparing the resected talus of the ankle joint. The trialing the TAR prosthesis in the ankle joint comprises trialing a TAR prosthesis that includes a tibial component, a tibial insert with a tibial articulation surface, and a talar component with a talar articulation surface via a total ankle replacement (TAR) guide system. The TAR guide system comprises a tibial trial and bone preparation first component and a talar trial and bone preparation second component is disclosed. The tibial trial and bone preparation first component comprises a base portion and an arm portion. The base portion comprises a first side with a first tibial engagement surface configured to engage a resected distal tibia and at least one bone aperture formation guide through hole extending from the first tibial engagement surface to a second tibial insert engagement side, and the arm portion extends proximally from an anterior portion of the base portion and is configured to engage an anterior side of the resected distal tibia. The talar trial and bone preparation second component comprises a first talar engagement surface, a posterior trial articulation surface, an anterior window, a posterior cut slot and a plurality of pin apertures. The first talar engagement surface is positioned on a distal side of the second component and is configured to engage a portion of a resected talus. The posterior trial articulation surface is positioned on a proximal side of the second component and is anteriorly-posteriorly arcuately convex. The anterior window extends through the second component between the proximal side and the distal side thereof. The posterior cut slot extends through the second component between the proximal side and the distal side thereof that is angled posteriorly as in extends from the proximal side to the distal side. The plurality of pin apertures extend through the second component between the proximal side and the distal side. The preparing the resected tibia of the ankle joint comprises preparing the resected tibia of the ankle joint for the implantation of at least one projection of an engagement side of the tibial component therein, comprising coupling the arm portion of the first component to the anterior side of the resected distal tibia with the first tibial engagement surface of the first component engaged with the resected distal tibia, and passing at least one projection of a bone aperture formation instrument though the at least one bone aperture formation guide through hole of the base portion of the first component and into the resected distal tibia to form at least one aperture in the resected distal tibia that is configured to accept the at least one projection of the tibial component therein. The preparing the resected talus of the ankle joint comprises preparing the resected talus of the ankle joint for coupling with an engagement side of the talar component, comprising: coupling the second component to the resected distal talus such that the first talar engagement surface of the second component engage a surface portion of the resected talus; passing a bone cutting instrument through the anterior window of the second component to form an anterior chamfer surface on the resected talus; and passing a bone cutting blade through the posterior cut slot the second component to form a posterior chamfer surface on the resected talus.

In some embodiments, the system further comprises a talar chamfer trial comprising: a second talar engagement surface on a distal side of the talar chamfer trial configured to engage the surface portion, the anterior chamfer and the posterior chamfer of the resected talus; a second posterior trial articulation surface on a proximal side of the talar chamfer trial that comprises an anteriorly-posteriorly and medially-laterally arcuately convex portion; at least one bone aperture formation guide through hole; and a plurality of pin through holes extending between the proximal and distal sides thereof. In some embodiments, the method further comprises preparing the resected talus of the ankle joint for the implantation of at least one projection of the engagement side of the talar component therein, comprising: coupling the second talar engagement surface in engagement with the surface portion, the anterior chamfer and the posterior chamfer of the resected talus by passing a plurality of pin through the plurality of pin through holes and into the resected talus; and passing at least one projection of a bone aperture formation instrument though the at least one bone aperture formation guide through hole of the talar chamfer trial and into the resected talus to form at least one aperture in the resected talus that is configured to accept the at least one projection of the talar component therein.

In another aspect of the present application, a total ankle replacement (TAR) guide system for a TAR prosthesis including a tibial component, a tibial insert with a tibial articulation surface, and a talar component with a talar articulation surface and a talar engagement side opposing the articulation surface is disclosed. The TAR guide system comprises a tibial trial component, a tibial trial insert, and a talar trial component. The tibial trial component comprises a base portion and an arm portion extending proximally from an anterior portion of the base portion. The tibial trial insert comprises an anterior rail portion that extends in a medial-lateral direction and defines an engagement surface that is flat or convex in the anterior-posterior direction, a posterior rail portion that extends in a medial-lateral direction and defines an engagement surface that is flat or convex in the anterior-posterior direction, and a strut portion that extends in an anterior-posterior direction. The anterior and posterior rail portions approximate anterior and posterior portions of the tibial articulation surface of the tibial insert. The talar trial component comprises a trial articulation surface that approximates the talar articulation surface of the talar component, a posterior cut slot extending through the articulation surface in the medial-lateral direction, a strut slot extending through the articulation surface in the anterior-posterior direction, an anterior window positioned anterior to the posterior cut slot. The tibial trial insert and the tibial trial are coupled together. The anterior and posterior rail portions are engaged with the trial articulation surface, and the strut portion is positioned within the strut slot. In some embodiments, the talar trial component further comprises a pair of apertures extending therethrough that converge or diverge.

In another aspect of the present application a method is disclosed. The method comprises trialing a total ankle replacement (TAR) prosthesis in an ankle joint that includes a tibial component, a tibial insert with a tibial articulation surface, and a talar component with a talar articulation surface via a total ankle replacement (TAR) guide system. The TAR guide system comprises a tibial trial component, a tibial trial insert, and a talar trial component. The tibial trial component comprises a base portion and an arm portion extending proximally from an anterior portion of the base portion. The tibial trial insert comprises an anterior rail portion that extends in a medial-lateral direction and defines an engagement surface that is flat or convex in the anterior-posterior direction, a posterior rail portion that extends in a medial-lateral direction and defines an engagement surface that is flat or convex in the anterior-posterior direction, and a strut portion that extends in an anterior-posterior direction. The anterior and posterior rail portions approximate anterior and posterior portions of the tibial articulation surface of the tibial insert. The talar trial component comprises a trial articulation surface that approximates the talar articulation surface of the talar component, a posterior cut slot extending through the articulation surface in the medial-lateral direction, a strut slot extending through the articulation surface in the anterior-posterior direction, an anterior window positioned anterior to the posterior cut slot. The tibial trial insert and the tibial trial are coupled together. The anterior and posterior rail portions are engaged with the trial articulation surface, and the strut portion is positioned within the strut slot. The method further comprises preparing a talus bone of the ankle joint for the implantation of the talar component therein by resecting a posterior portion of the talus bone via a cut slot of the talar trial component, and by resecting an anterior portion of the talus bone via an anterior window of the talar trial component.

In some embodiments, the talar trial component further comprises a pair of apertures extending therethrough that converge or diverge.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

FIG. 118 illustrates a distal view of the tibial trial insert of FIG. 116, in accordance with an aspect of the present disclosure;

FIG. 119 illustrates a medial side view of the tibial trial insert of FIG. 116, in accordance with an aspect of the present disclosure;

FIG. 120 illustrates an anterior view of the second talar trial guide of FIG. 112 coupled to a resected and chamfered talus, in accordance with an aspect of the present disclosure;

FIG. 121 illustrates an elevational anterior perspective view of the second talar trial guide of FIG. 112 and a bone removal guide and bone cutting instrument engaged therewith, in accordance with an aspect of the present disclosure;

FIG. 122 illustrates an elevational posterior perspective view of the second talar trial guide, the bone removal guide and the bone cutting instrument of FIG. 121, in accordance with an aspect of the present disclosure;

FIG. 123 illustrates an anterior perspective view of the second talar trial guide, the bone removal guide and the bone cutting instrument of FIG. 121, in accordance with an aspect of the present disclosure;

FIG. 124 illustrates a proximal view of the second talar trial guide, the bone removal guide and the bone cutting instrument of FIG. 121 forming an aperture in a resected talus, in accordance with an aspect of the present disclosure;

Figure 121:
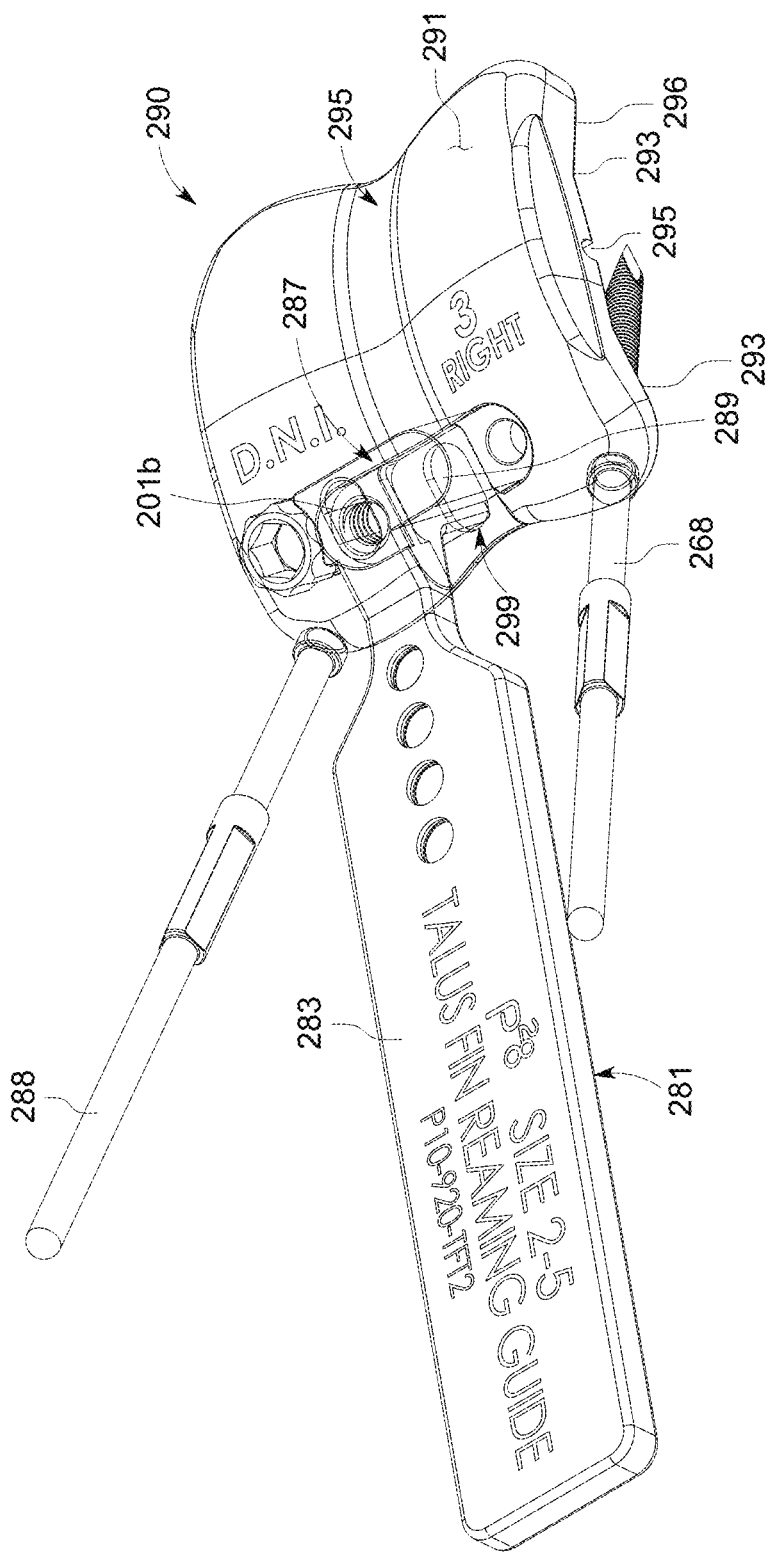
Figure 125:
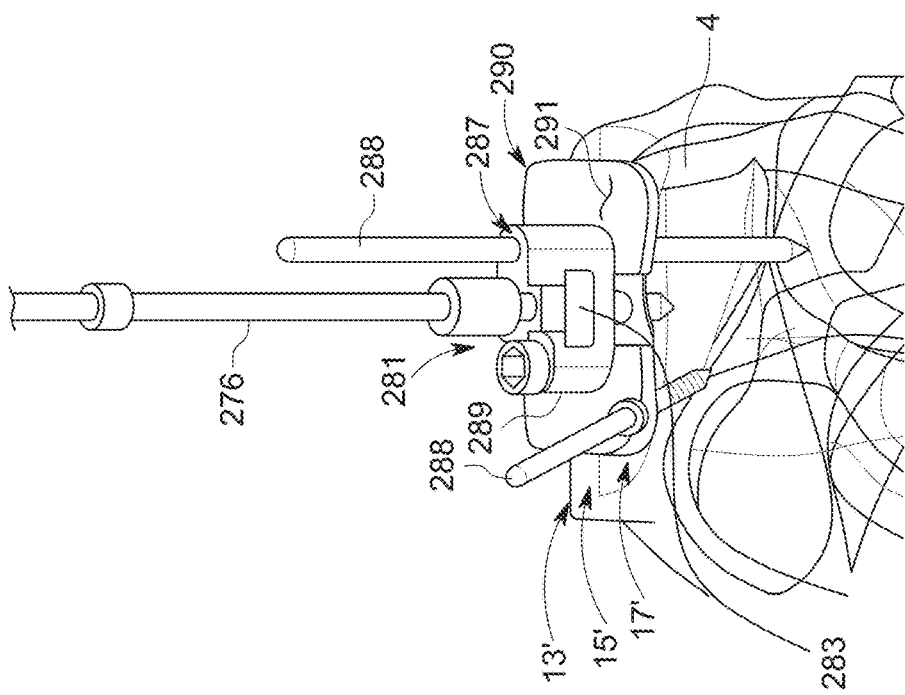
Figure 126:
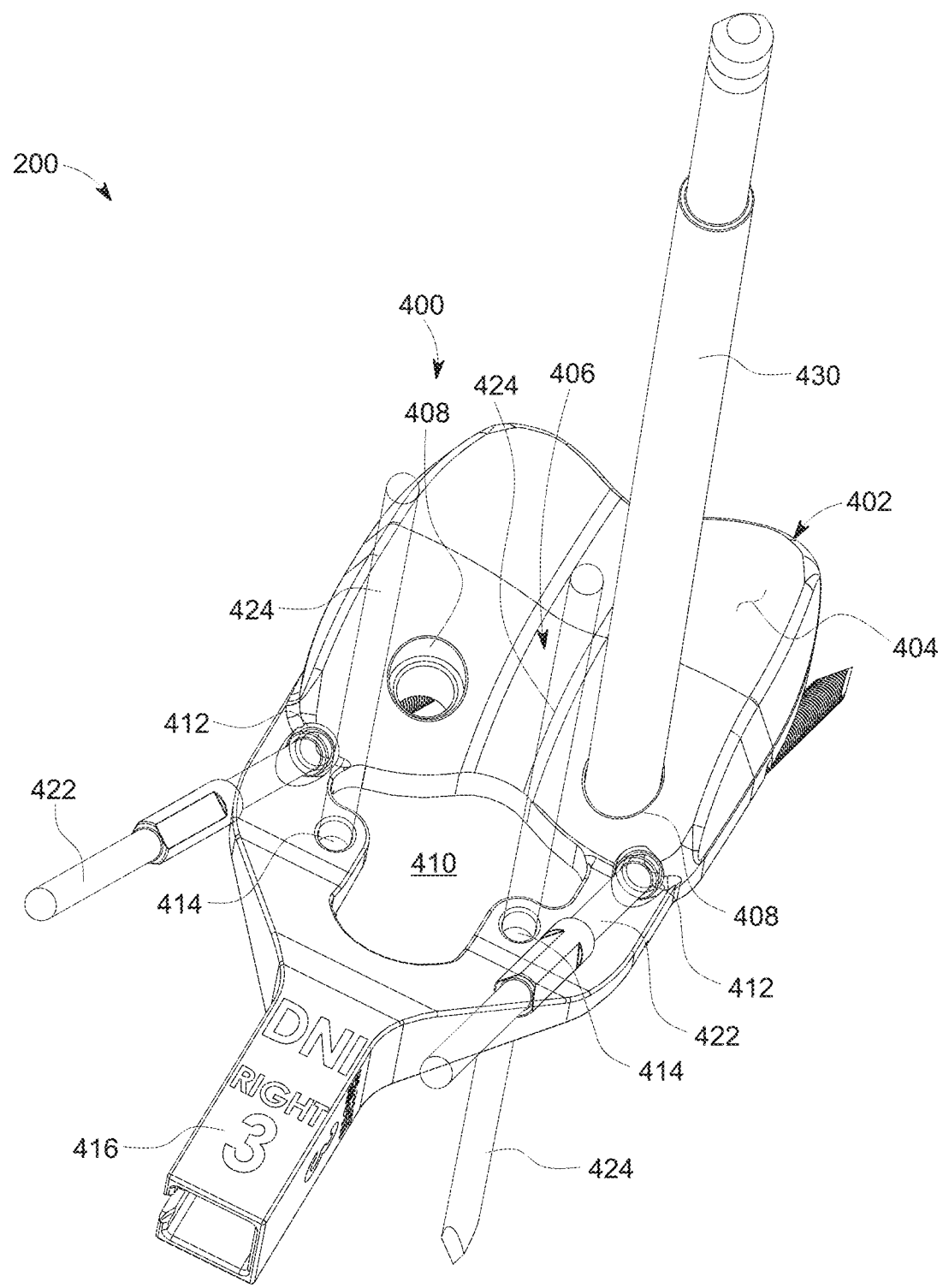
Figure 127:
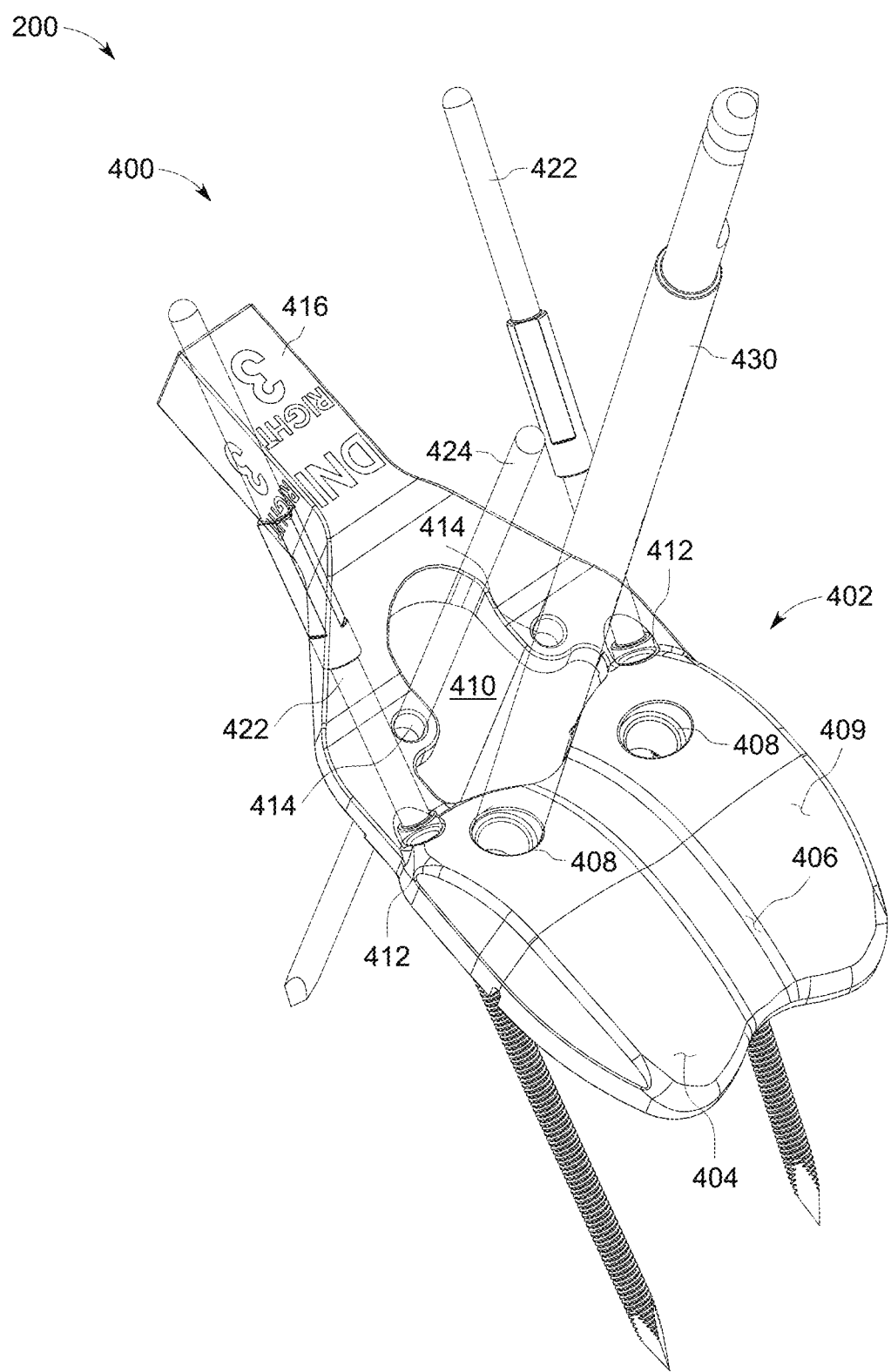
Figure 128:
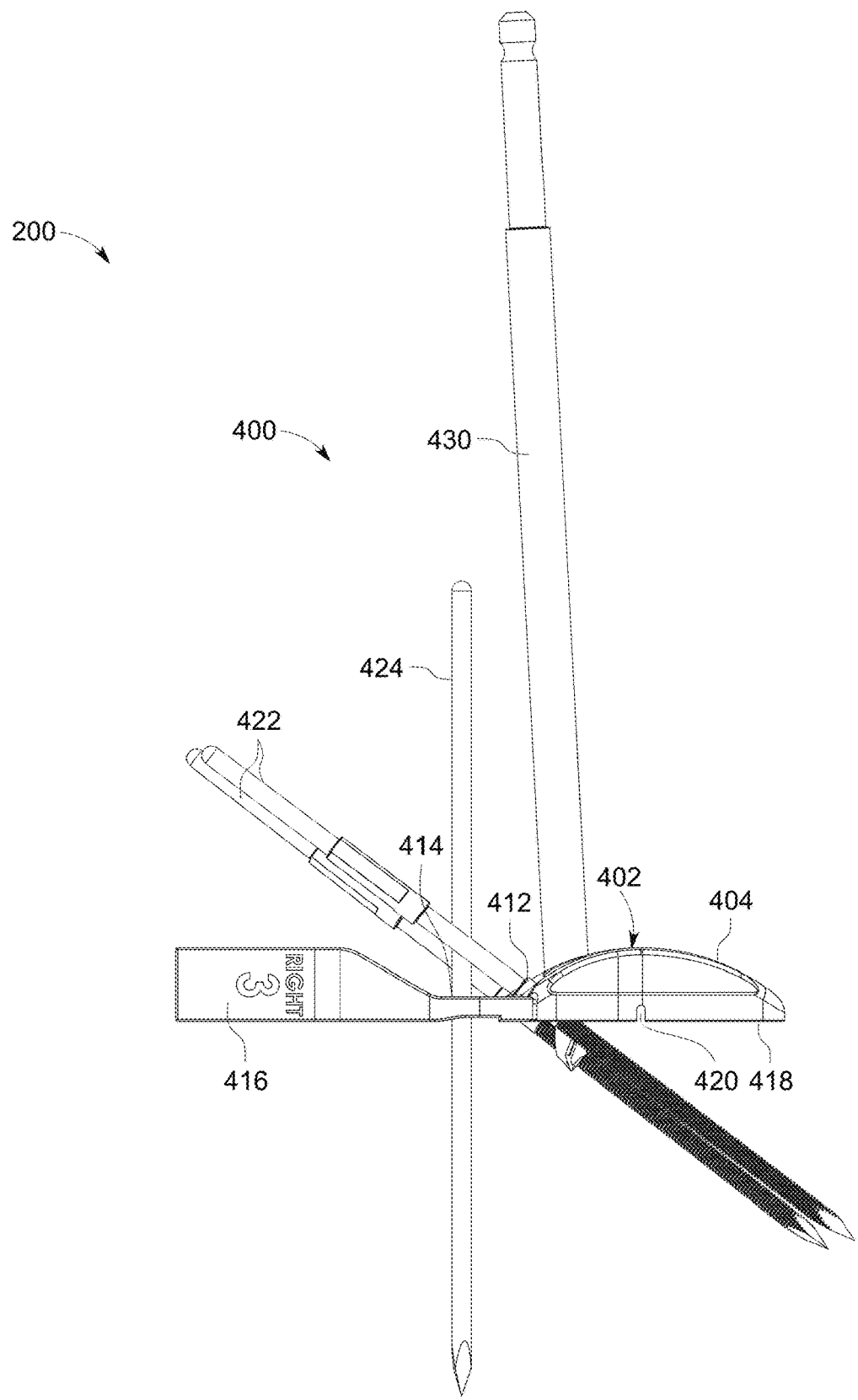
Figure 129:
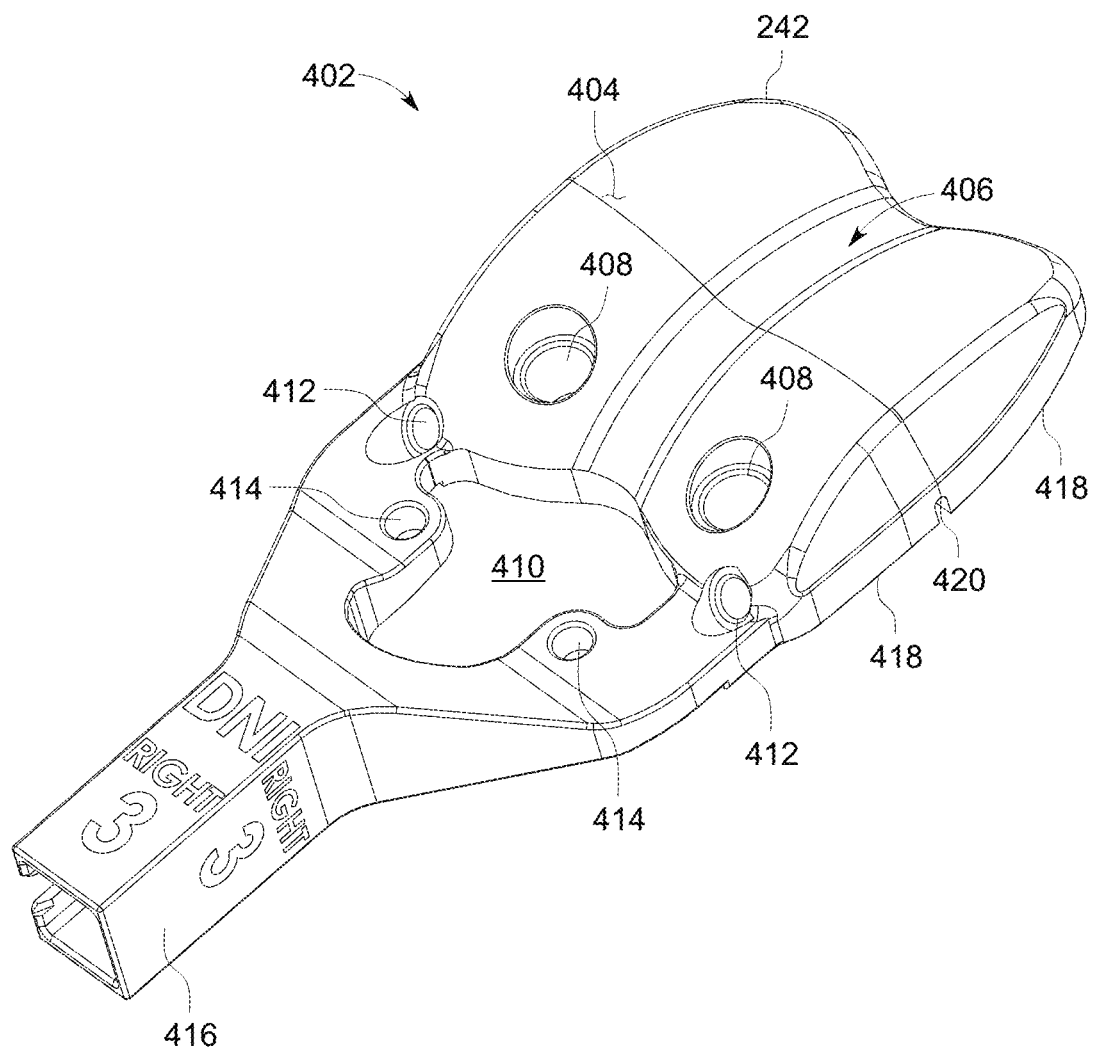
Figure 130:
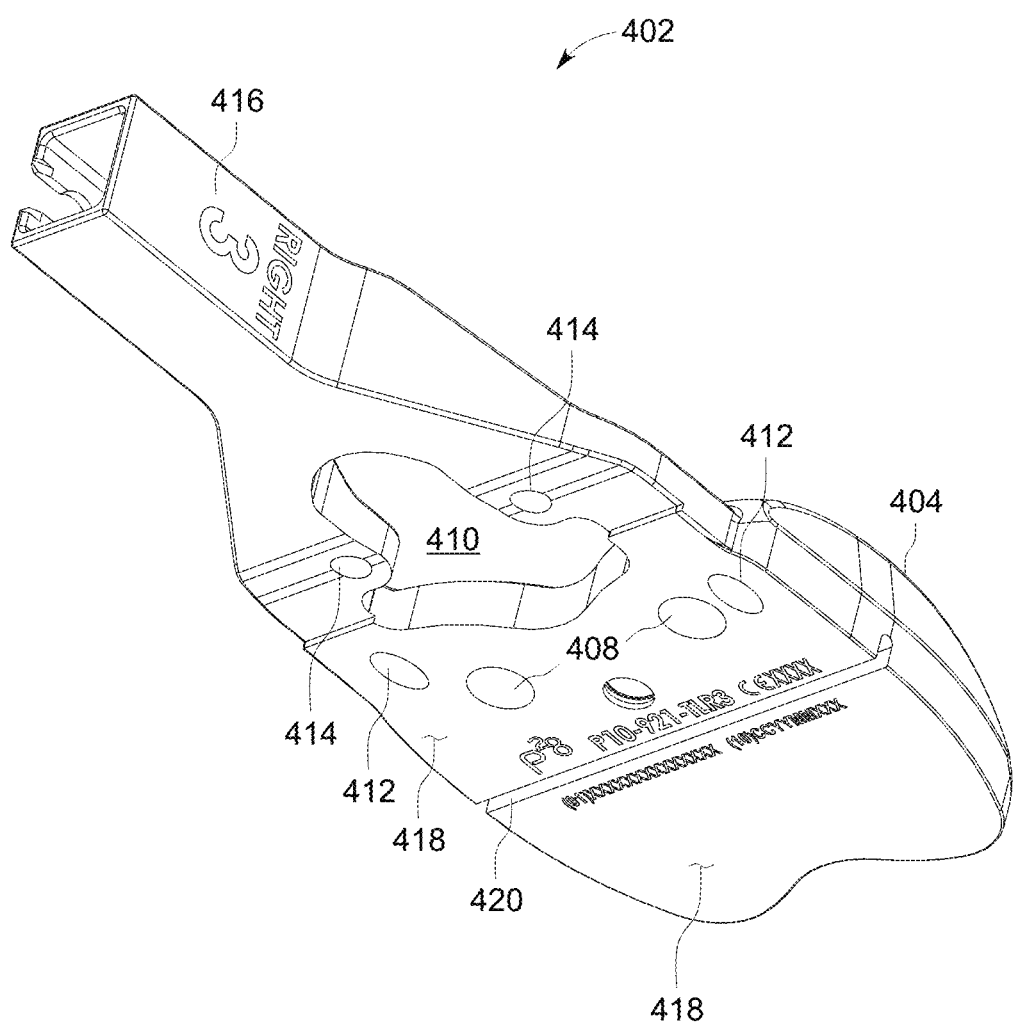
Figure 131:
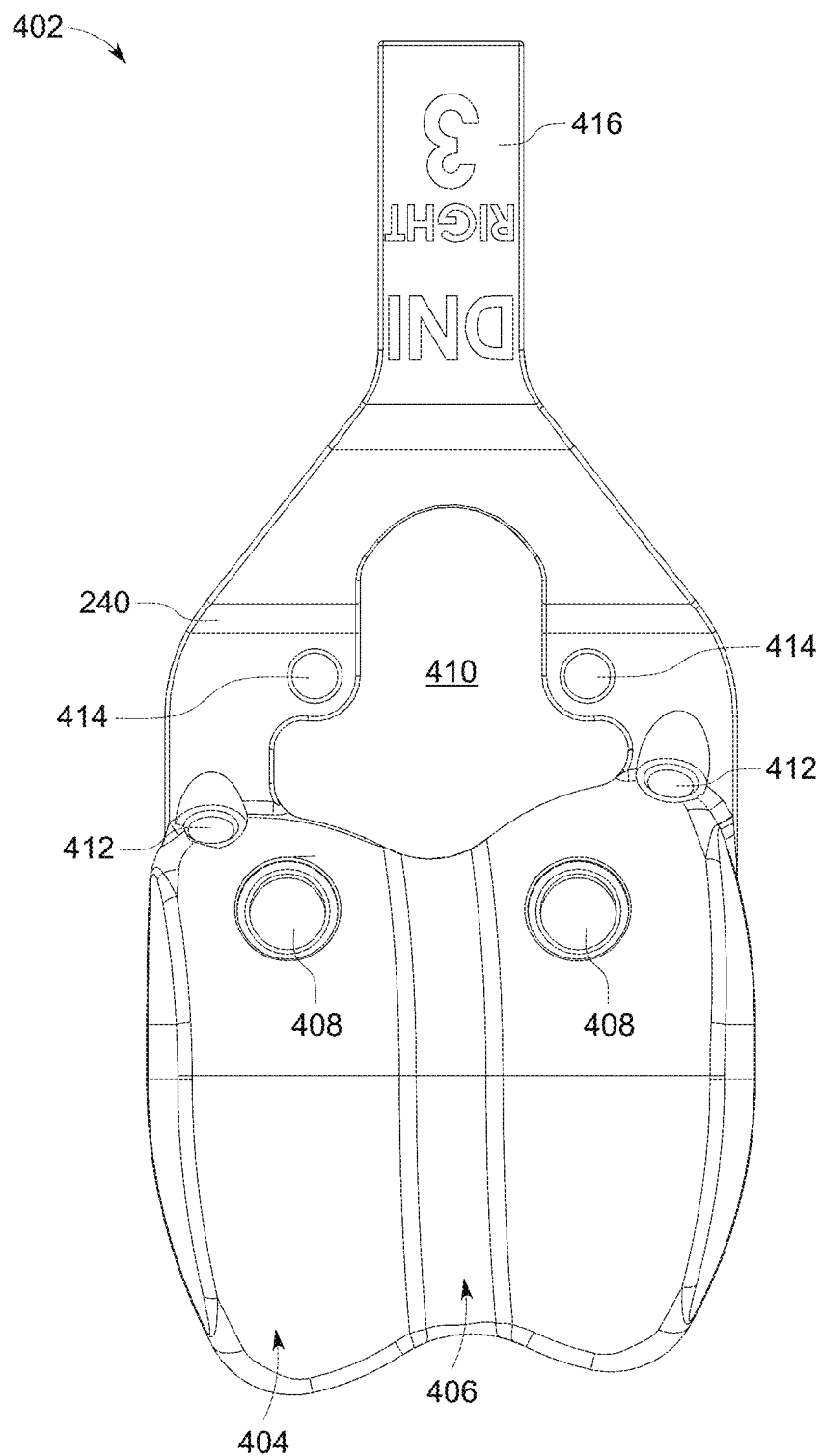
Figure 132:
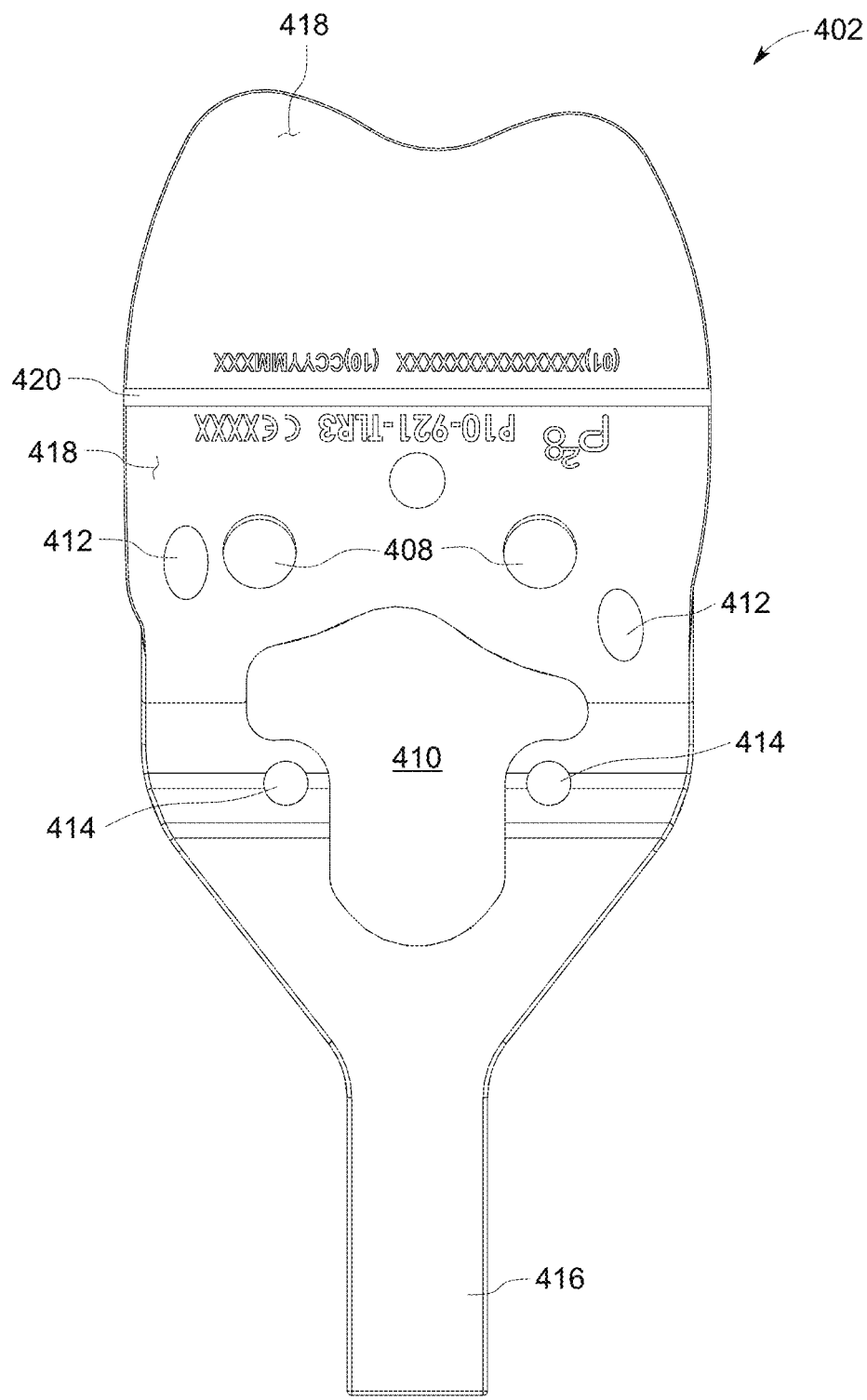
Figure 133:
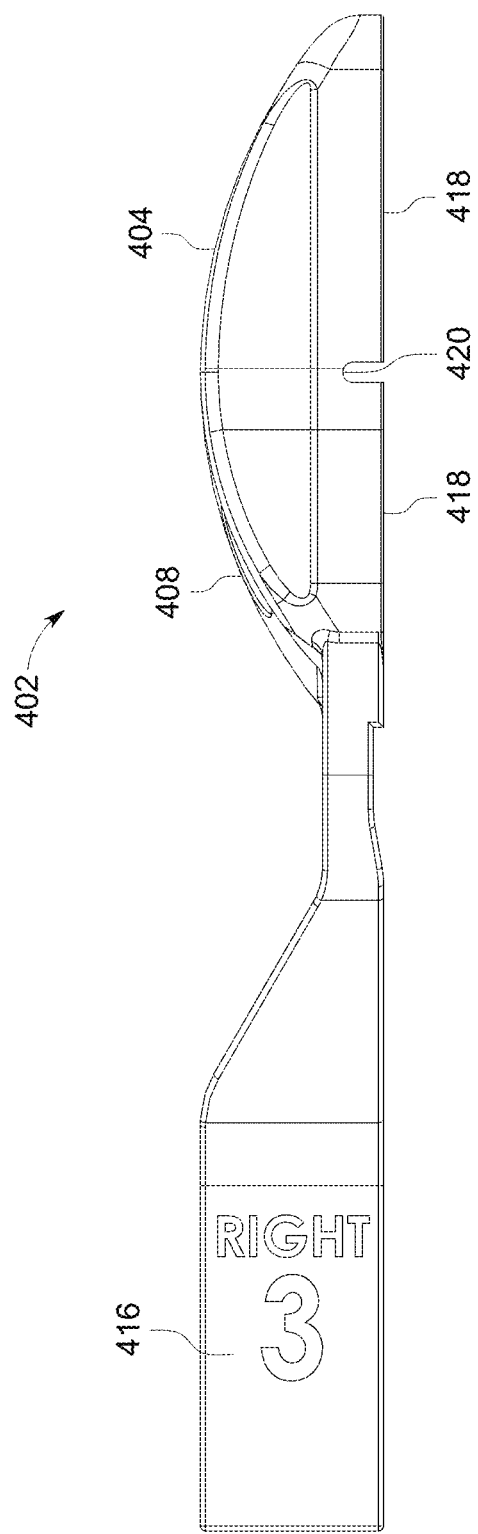

FIG. 125 illustrates a anterior view of the second talar trial guide, the bone removal guide and the bone cutting instrument of FIG. 121 forming an aperture in a resected talus, in accordance with an aspect of the present disclosure FIG. 126 illustrates an elevational anterior perspective view of a third talar trial guide and a bone aperture formation instrument engaged therewith for a TAR trial and guide system, in accordance with an aspect of the present disclosure;

FIG. 127 illustrates an elevational posterior perspective view of the third talar trial guide and the bone aperture formation instrument of FIG. 126, in accordance with an aspect of the present disclosure;

FIG. 128 illustrates a medial side view of the third talar trial guide and the bone aperture formation instrument of FIG. 126, in accordance with an aspect of the present disclosure;

FIG. 129 illustrates an elevational anterior perspective view of the third talar trial guide of FIG. 126, in accordance with an aspect of the present disclosure;

FIG. 130 illustrates a distal anterior perspective view of the third talar trial guide of FIG. 129, in accordance with an aspect of the present disclosure;

FIG. 131 illustrates a proximal view of the third talar trial guide of FIG. 129, in accordance with an aspect of the present disclosure;

FIG. 132 illustrates a distal view of the third talar trial guide of FIG. 129, in accordance with an aspect of the present disclosure; and FIG. 133 illustrates a medial side view of the third talar trial guide of FIG. 129, in accordance with an aspect of the present disclosure.

DETAILED DESCRIPTION

Generally stated, disclosed herein are instruments, guides, systems and related methods for total ankle replacement prostheses. The instruments, guides, systems and related methods may facilitate preparation of a tibia and/or talus of a patient for implantation of a total ankle replacement prosthesis therein. The instruments, guides, systems and related methods may also facilitate selection of a particular size of a tibial component, a talus component and/or a tibial insert of the total replacement ankle prosthesis that suits the patient. The instruments, guides, systems and related methods include a tibial trial component, a talar/talus trial component and tibial insert trial component that replicate one or more aspects of the tibial component, the talus component and the tibial insert, respectively, of the total ankle prosthesis. The talar trial component may include an articulation surface that articulates with convex articulation surface of the tibial insert trial component. The talar trial component may also include slots that facilitate resection of the patient's talus for the implantation of the talus component therein.

In this detailed description and the following claims, the words proximal, distal, anterior or plantar, posterior or dorsal, medial, lateral, superior and inferior are defined by their standard usage for indicating a particular part or portion of a bone, joint (or any other anatomical structure) or implant according to the relative disposition of the natural bone, joint (or any other anatomical structure) or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot and/or ankle, the term "dorsal" refers to the top of the foot and the term "plantar" refers the bottom of the foot.

Similarly, positions or directions may be used herein with reference to anatomical structures or surfaces. For example, as the current instruments, guides, systems and related methods (and components thereof) are described herein with reference to use with the bones of the ankle, the bones of the foot, ankle and lower leg may be used to describe the surfaces, positions, directions or orientations of the instruments, guides, systems and related methods (and components thereof). Further, the instruments, guides, systems and related methods, and the aspects, components, features and the like thereof, disclosed herein may be described with respect to one side of the body (e.g., the left for right ankle) for brevity purposes. However, as the human body is relatively symmetrical or mirrored about a line of symmetry (midline), it is hereby expressly contemplated that the instruments, guides, systems and related methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the instruments, guides, systems and related methods, and the aspects, components, features and the like thereof, described herein with respect to the right ankle of a patient may be mirrored so that they likewise function with the left ankle of the patient. Further, the instruments, guides, systems and related methods, and the aspects, components, features and the like thereof, disclosed herein are described with respect to the ankle for brevity purposes, but it should be understood that the instruments, guides, systems and related methods (and components thereof) may be used with other joints of a human body (or other mammalian body) having similar structures.

Figure 1A:
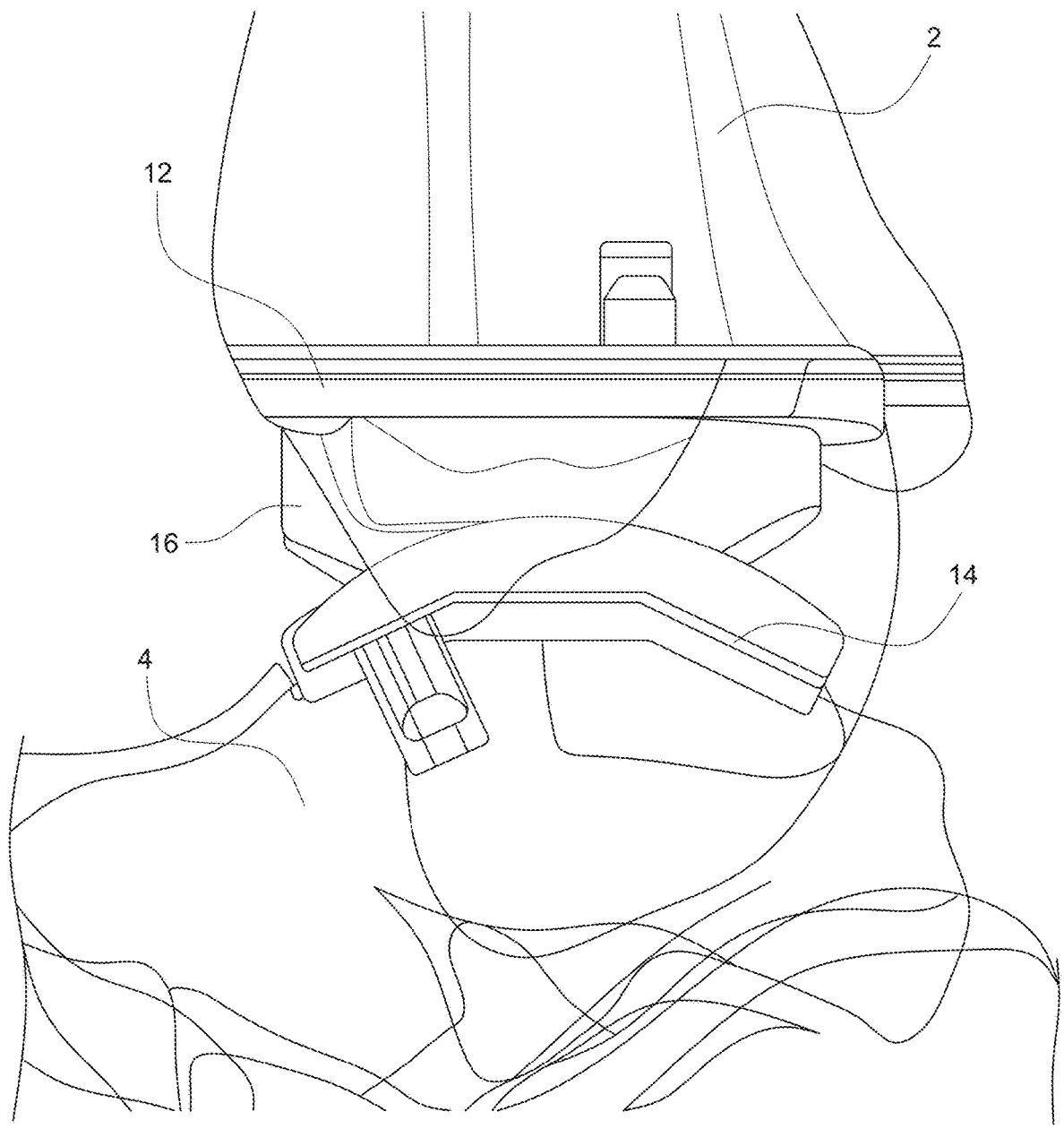
FIG. 1A illustrates a side view of an exemplary embodiment of a total ankle replacement (TAR) prosthesis formed of tibial component implanted on the tibia, a talar component implanted on the talus, and a tibial insert coupled to the tibial component and articulating on the talar component, in accordance with an aspect of the present disclosure.
Figure 1B:
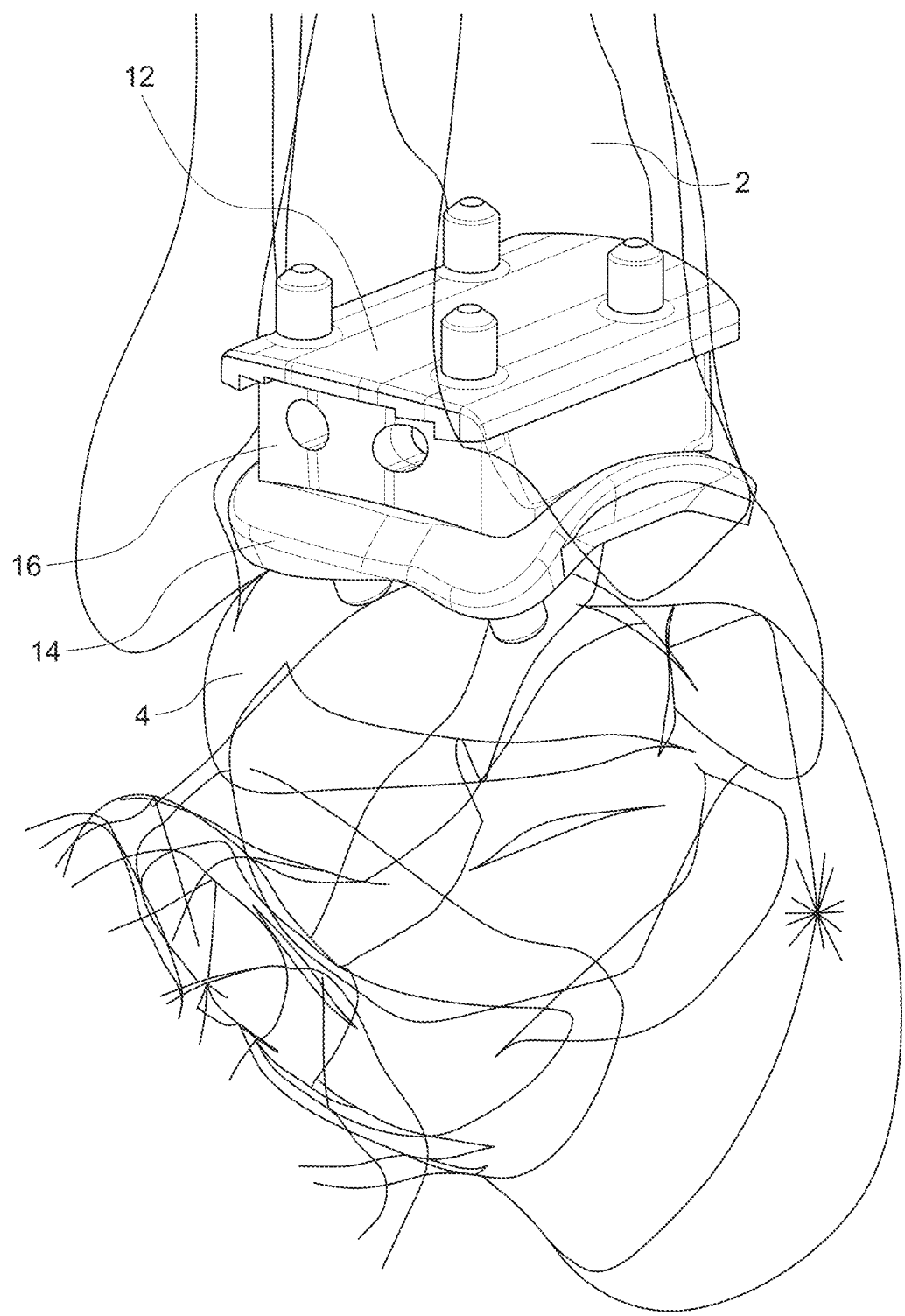
FIG. 1B illustrates a perspective view of the exemplary TAR prosthesis of FIG. 1A, in accordance with an aspect of the present disclosure.
Figure 2:
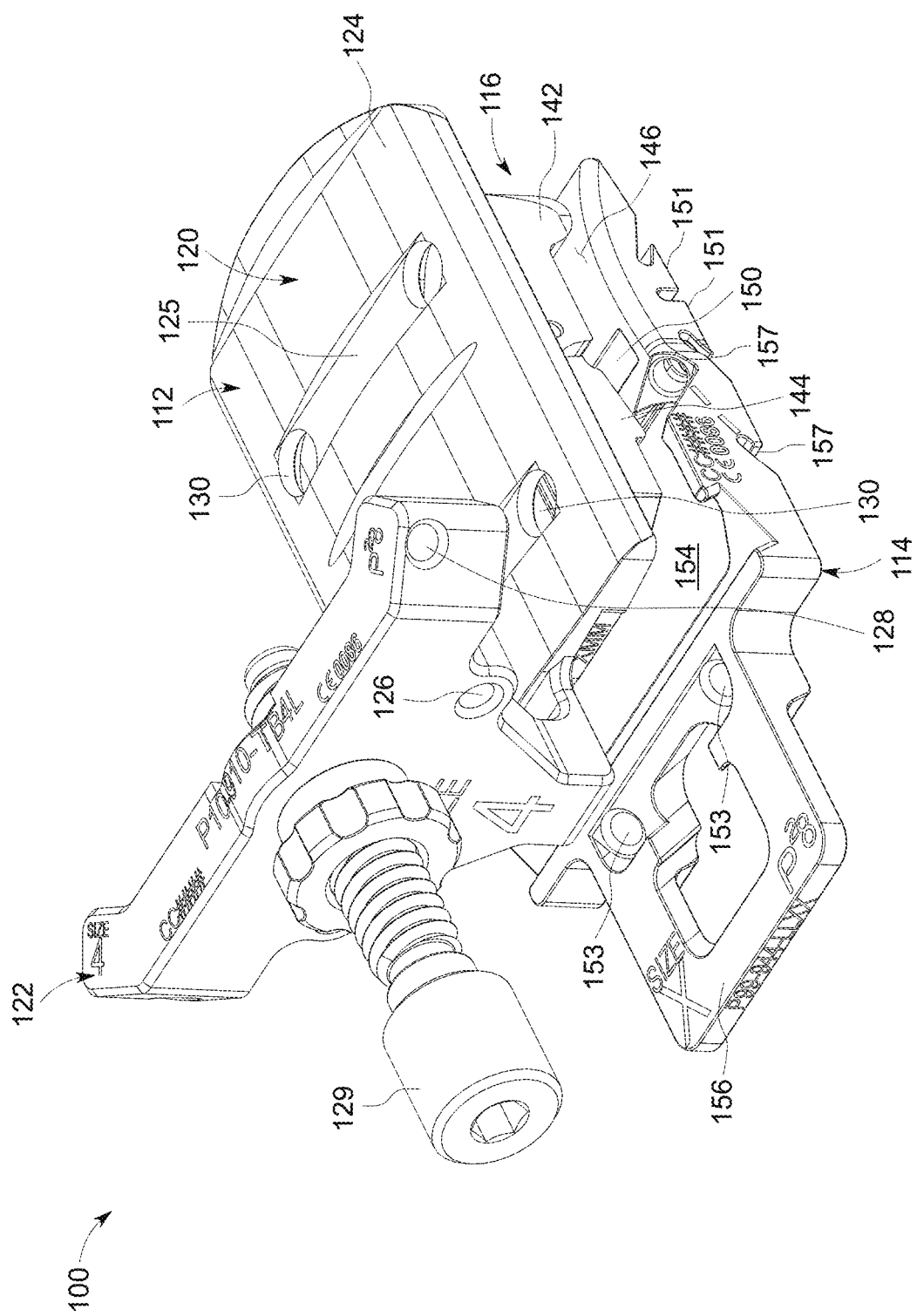
FIG. 2 illustrates an elevational perspective view of a total ankle replacement (TAR) trial and guide system including a tibial trial guide, a tibial trial insert and a talar trial guide for facilitating selection of a TAR prosthesis and preparation of a tibia and talus therefore, in accordance with an aspect of the present disclosure.
Figure 3:
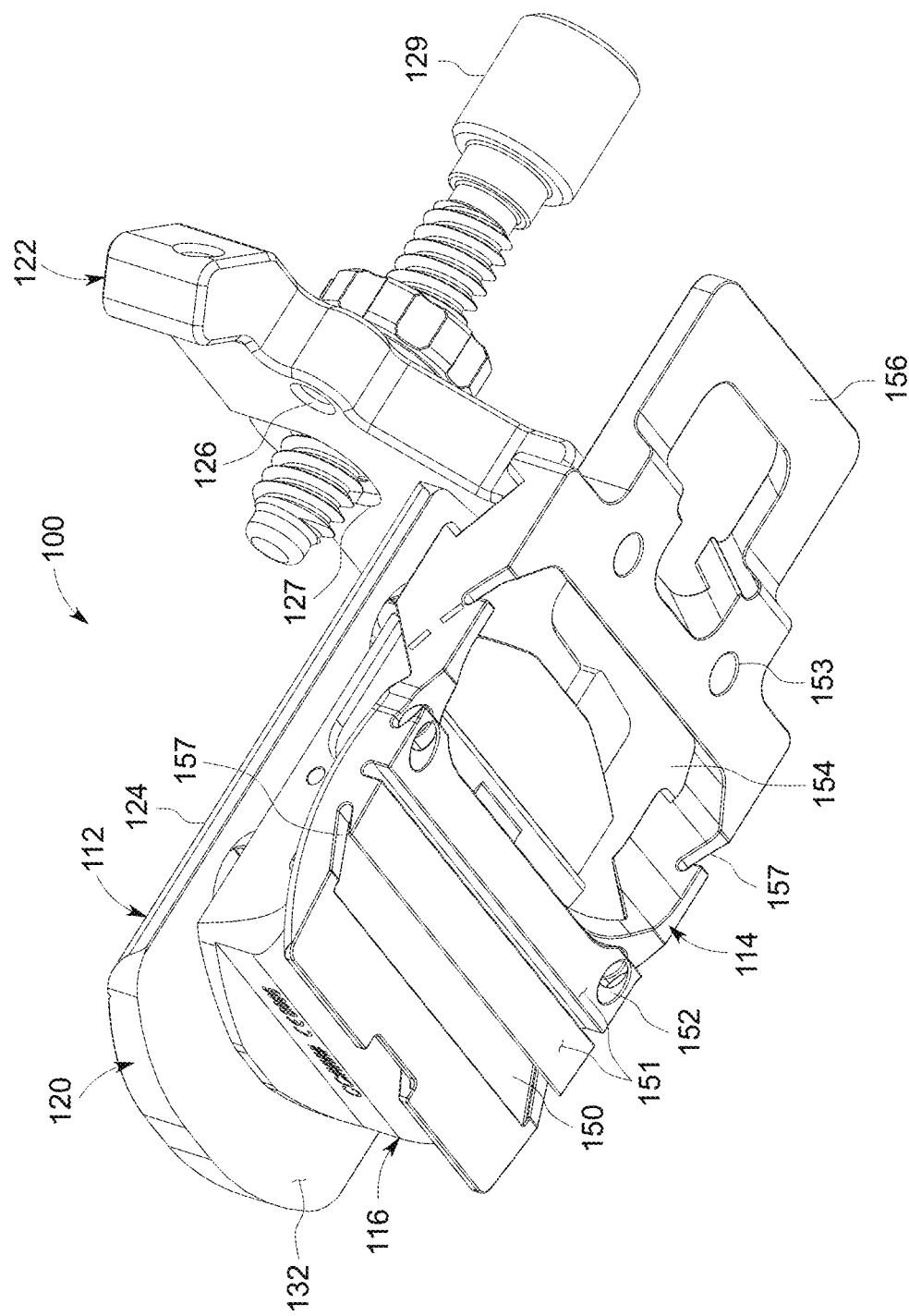
FIG. 3 illustrates a bottom perspective view of the TAR trial and guide system of FIG. 2, in accordance with an aspect of the present disclosure.
Figure 4:
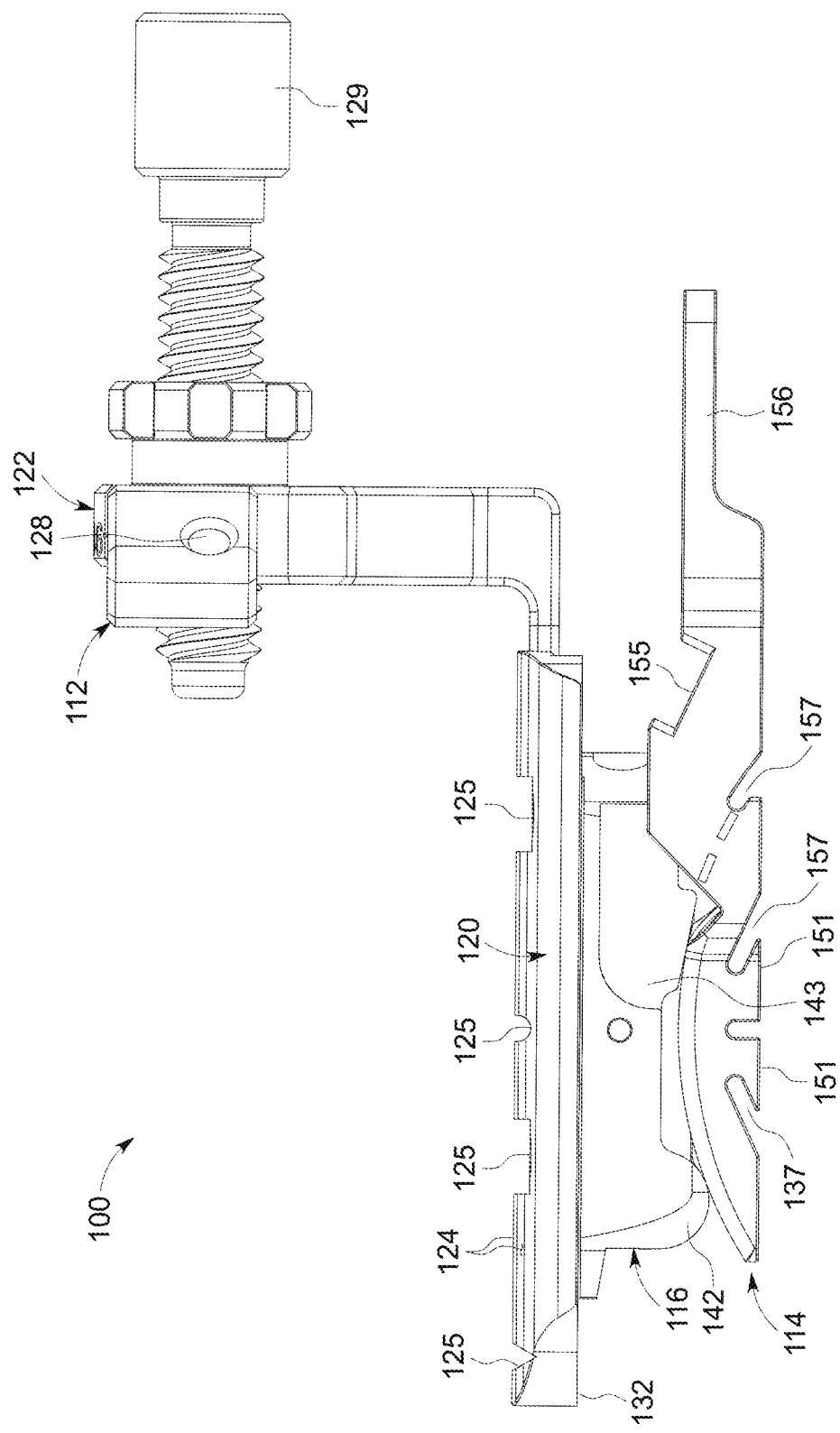
FIG. 4 illustrates a medial/lateral side view of the TAR trial and guide system of FIG. 2, in accordance with an aspect of the present disclosure.
Figure 5:
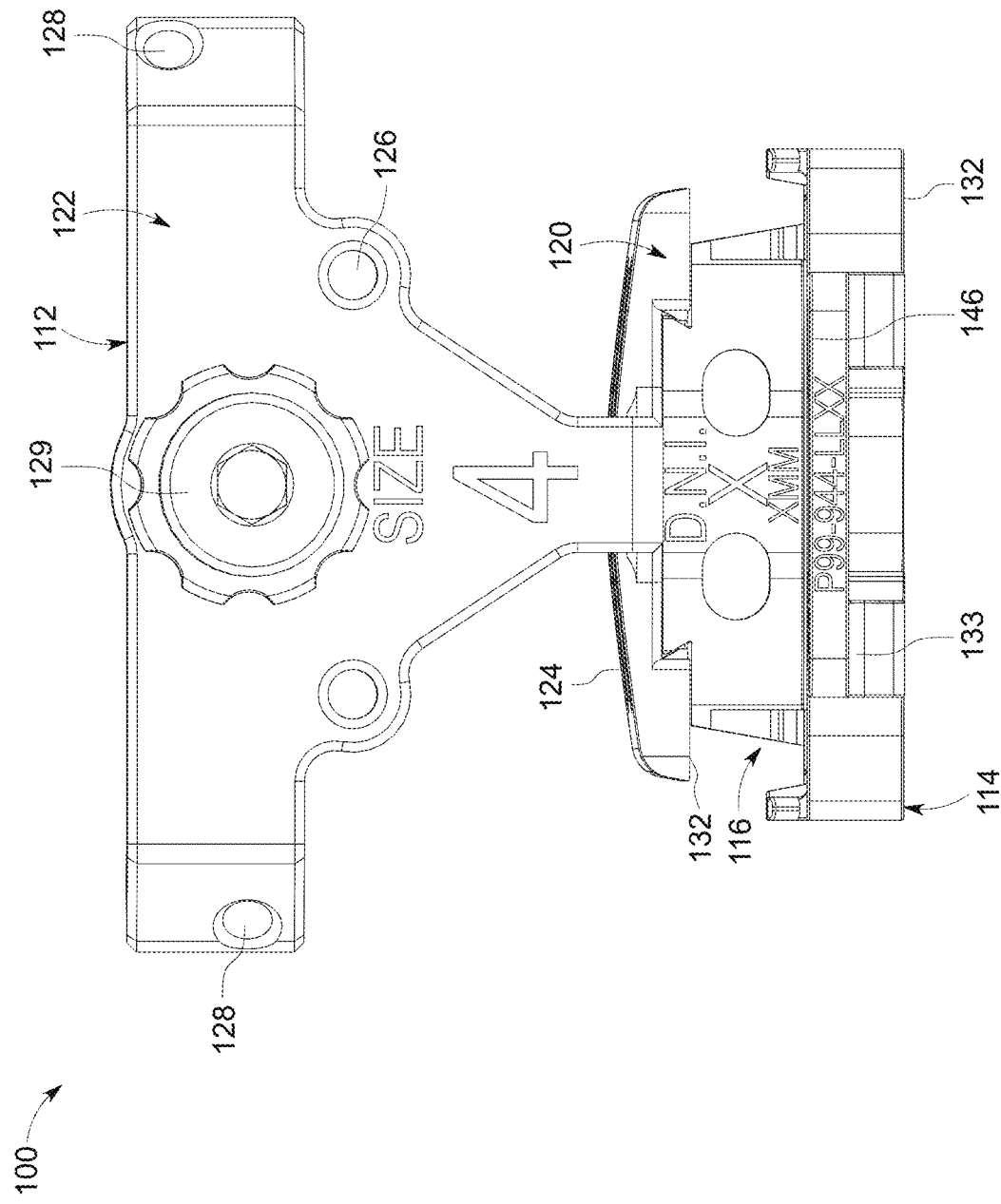
FIG. 5 illustrates an anterior view of the TAR trial and guide system of FIG. 2, in accordance with an aspect of the present disclosure.
Figure 6:
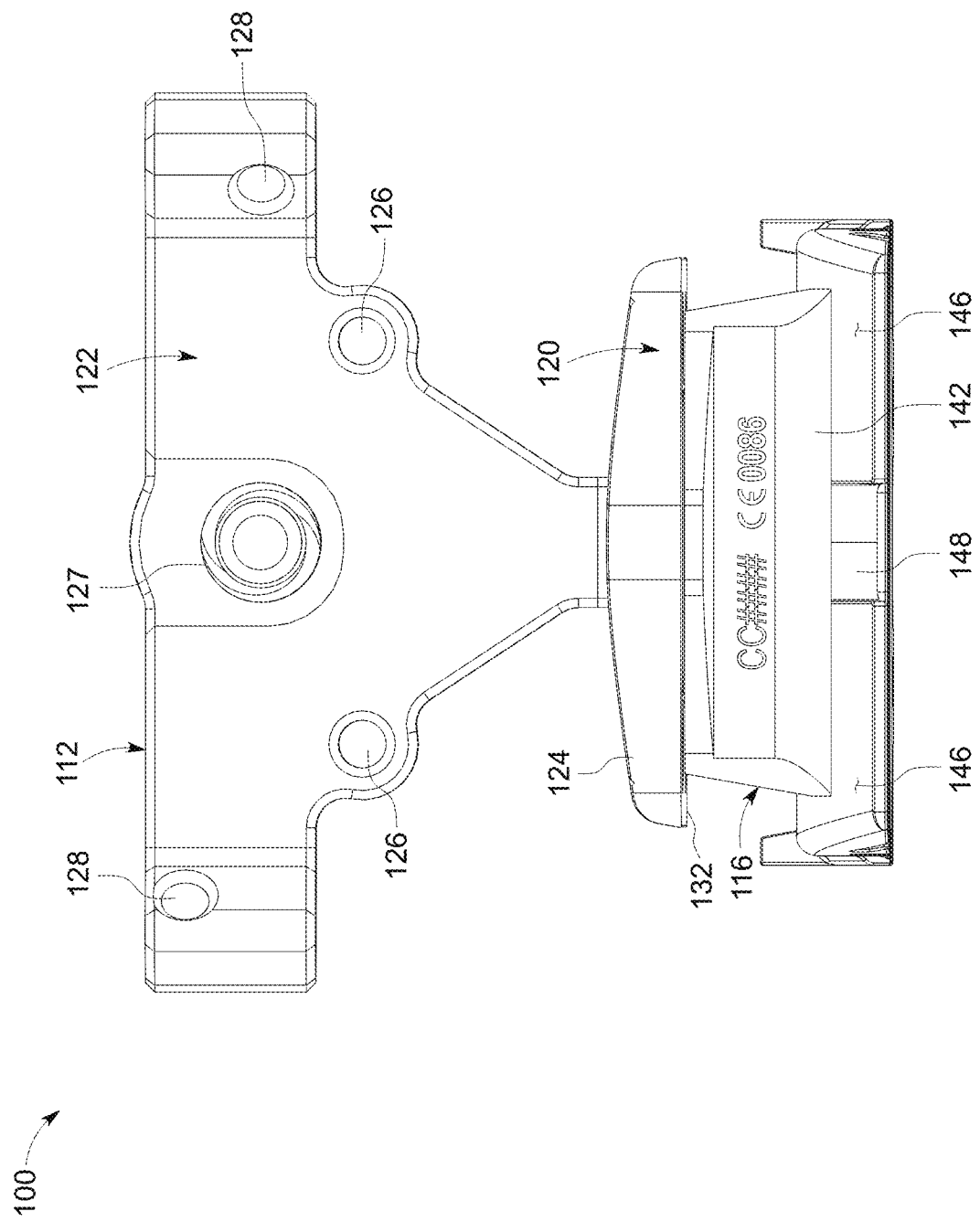
FIG. 6 illustrates a posterior view of the TAR trial and guide system of FIG. 2, in accordance with an aspect of the present disclosure.
Figure 7:
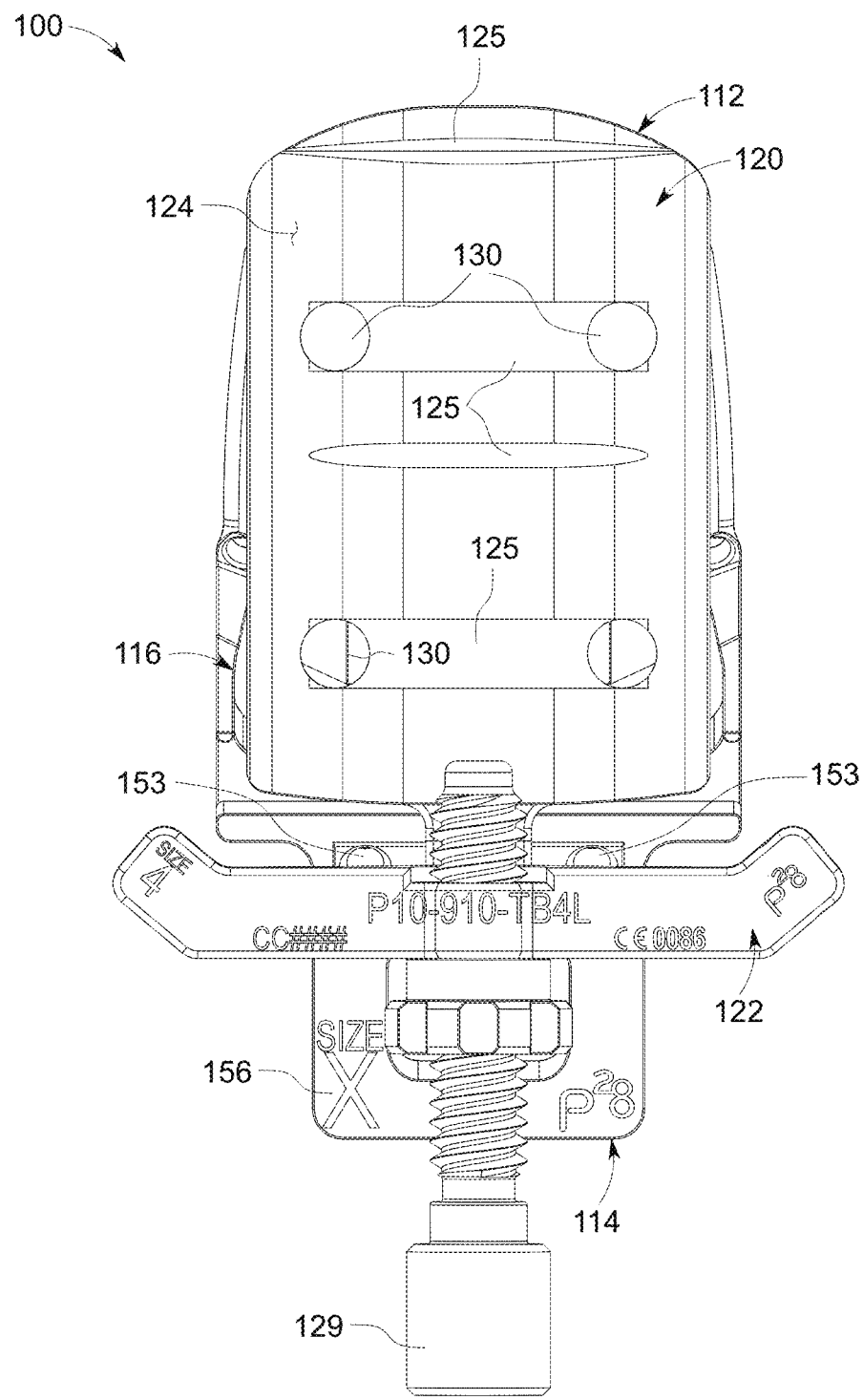
FIG. 7 illustrates a proximal view of the TAR trial and guide system of FIG. 2, in accordance with an aspect of the present disclosure.
Figure 8:
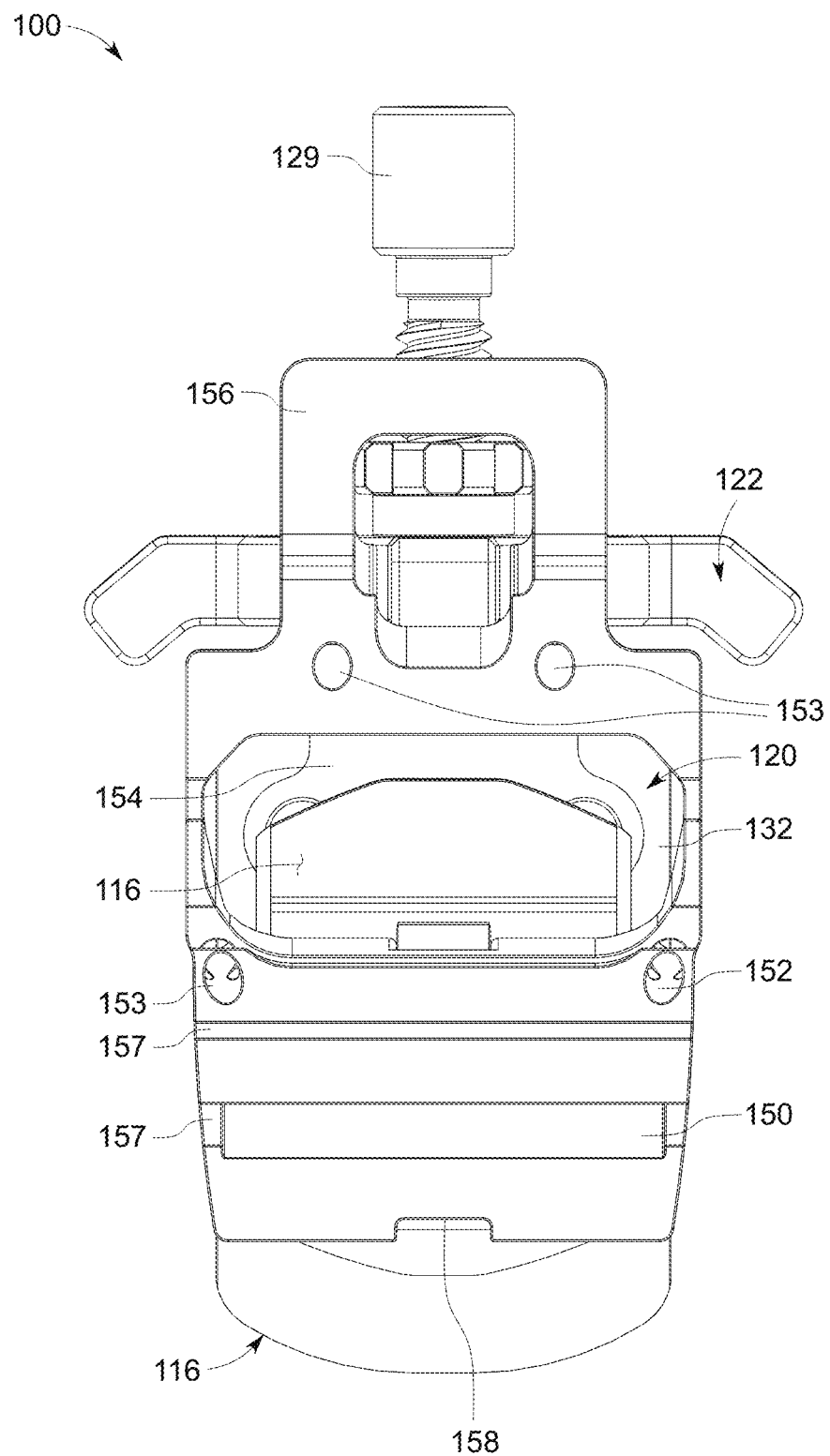
FIG. 8 illustrates a distal view of the TAR trial and guide system of FIG. 2, in accordance with an aspect of the present disclosure.
Figure 9:
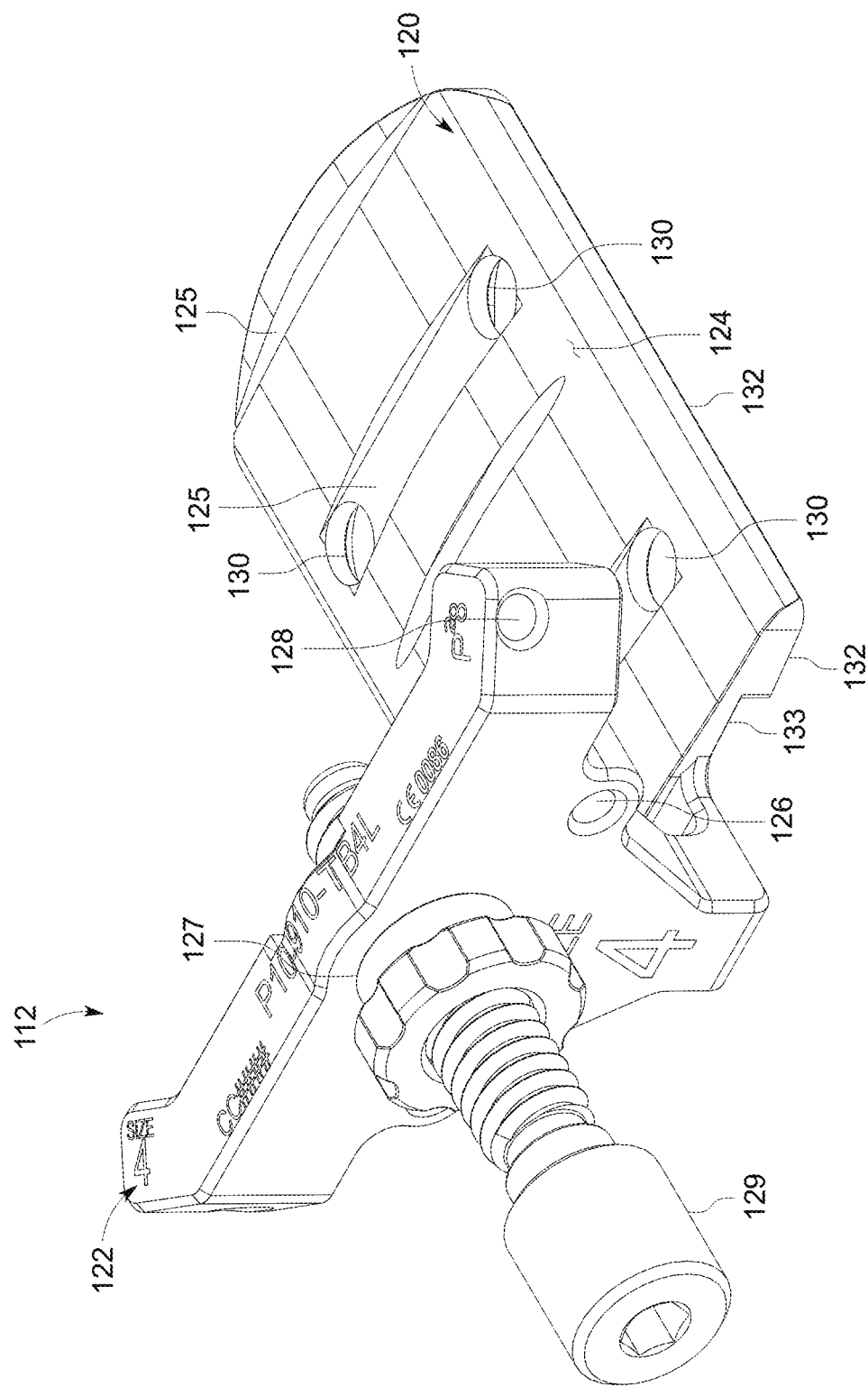
FIG. 9 illustrates an elevational perspective view of the tibial trial guide of the TAR trial and guide system of FIG. 2, in accordance with an aspect of the present disclosure.
Figure 10:
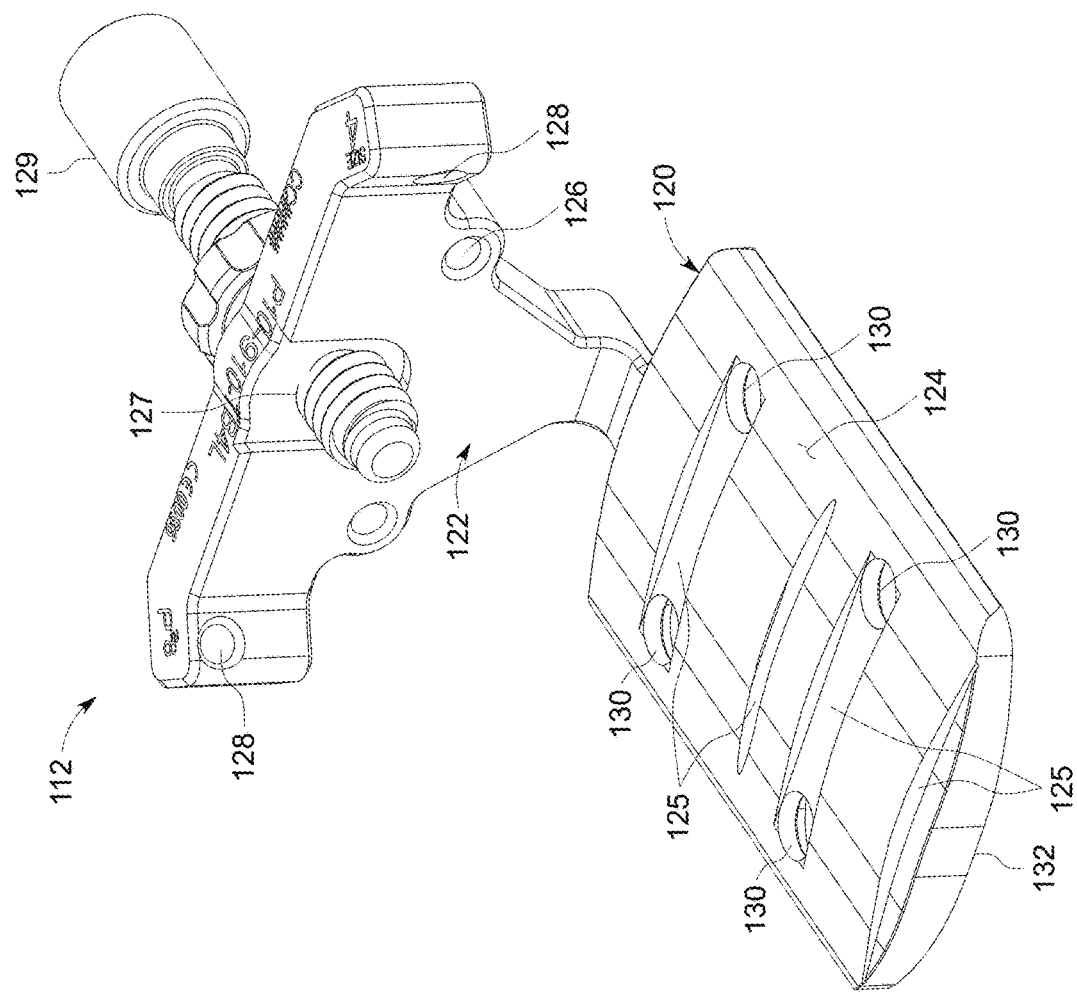
FIG. 10 illustrates another elevational perspective view of the tibial trial guide of FIG. 9, in accordance with an aspect of the present disclosure.

Referring to the drawings, wherein like reference numerals are used to indicate like or analogous components throughout the several views, and with particular reference to FIG. 1, there is illustrated an example of a total ankle replacement (TAR) prosthesis 10. The TAR prosthesis 10 includes a tibial prosthesis component or implant 12, a talar (or talus) prosthesis component or implant 14, and a tibial bearing or insert component 16 positioned between the tibial and talar components 12, 14. The tibial component 12 of the TAR prosthesis 10 engages the distal end of a tibia 2 of a patient and may be implanted partially therein, as shown in FIG. 1. In some examples, the distal end of the tibia 2 may be resected, and the tibial component 12 may engage at least the resected portion of the distal end of the tibia 2 and/or at least one post or other projection of the tibial component 12 may be implanted into the resected portion of the tibia 2. The talar/talus component 14 of the TAR prosthesis 10 engages the proximal portion of a talus 4 of the patient and may be implanted partially therein, as shown in FIG. 1. In some examples, the proximal portion or end of the talus 4 may be resected, and the talar component 14 may engage at least the resected portion of the proximal portion of the talus 4 and/or at least one post or other projection of the talar component 14 may be implanted into the resected portion of the talus 4.

As shown in FIG. 1, the tibial insert 16 of the TAR prosthesis 10 couples to the tibial component 12 and engages the talar component 14. The tibial insert 16 may fixedly or removably couple with the tibial component 12 such that the tibial insert 16 is positioned at least partially between the tibial component 12 and the talar component 14. Specifically, as discussed further below, the tibial insert 16 and the talar component 14 each include at least one articular surface that engage and articulate with each other. The articular surface of the tibial insert 16 may be concave and is defined by at least one first radius, and the articular surface of the talar component 14 may be convex and is defined by at least one second radius. The articular surfaces of the tibial insert 16 and the talar component 14 may correspond or match (e.g., the at least one first and second radii thereof may be the same or substantially similar). The tibial insert 16 and the talar component 14 may articulate with each other via sliding/gliding motion over the articular surfaces thereof.

Turning to FIGS. 2-36, a total ankle replacement (TAR) guide, instrumentation and/or system 100 (and related methods) that facilitates use of a TAR prosthesis, such as TAR prosthesis 10 of FIG. 1, to replace an ankle joint of a patient is shown. The TAR guide 100 can facilitate the selection of a properly sized tibial component 12, talar component 14 and/or tibial insert 16 of the TAR prosthesis 10 based on the size/configuration of the ankle joint of the particular patient. For example, as described further below, the TAR guide 100 may be positioned between the tibia and talus (potentially at least partially resected) of the patient, and the ankle joint formed thereby potentially articulated, to ensure the particular tibial component 12, talar component 14 and/or tibial insert 16 achieve a stable replacement ankle joint (e.g., the TAR prosthesis 10 sufficiently distributes the forces acting through the joint) that provides for full articulation/motion of the joint (e.g., the TAR prosthesis 10 does not overstuff or understuff the ankle joint). Further, the TAR guide 100 can facilitate implantation of the tibial component 12 in/on the distal end tibia of the patient, and/or implantation of the proximal aspect of the talar component 14 in/on the talus of the patient, in proper positions and orientations (and thereby the proper position and orientation of the corresponding tibial insert 16) for the ankle joint of the particular patient. For example, as described further below, the TAR guide 100 may be positioned between the tibia and talus (potentially at least partially resected) of the patient, and the ankle joint formed thereby potentially articulated, and the TAR guide 100 utilized to resect or otherwise remove one or more portions of the tibia and/or talus for engagement and implantation of the tibial component 12 in/on the tibia, and/or the talar component 14 in/on the talus.

As shown in FIGS. 2-18, the TAR guide 100 includes a tibial trial component 112, a talar/talus trial component 114 and a tibial trial insert 116. The tibial trial component 112 of the TAR guide 100 may correspond, in at least one aspect, to the tibial component 12 of the TAR prosthesis 10. The talar trial component 114 of the TAR guide 100 may correspond, in at least one aspect, to the talar component 14 of the TAR prosthesis 100. The tibia trial insert 116 of the TAR guide 100 may correspond, in at least one aspect, to the tibia insert 16 of the TAR prosthesis 100. For example, the proximal-distal thickness, the medial-lateral width and/or the anterior-posterior size/dimension, shape and/or orientation of at least one aspect of the tibial trial component 112, the talar trial component 114 and the tibial trial insert 116 may correspond (e.g., match or closely approximate) to that of the tibial component 12, the talar component 14 and the tibial trial insert 16, respectively. As noted above, differently sized tibial components 12, talar components 14 and tibial trial inserts 16 may be utilized based on a particular patient. As such, the tibial trial component 112, the talar trial component 114 and the tibial trial insert 116 may be configured or provided in differing sizes that correspond to the differently sized tibial components 12, talar components 14 and tibial trial inserts 16, respectively. For example, a plurality of tibial trial components 112, talar trial components 114 and tibial trial inserts 116 may be configured or provided with differing anterior-posterior lengths, medial-lateral widths and/or proximal-distal thicknesses thereof. Based on the trialing of one or more tibial trial component 112, one or more talar trial component 114 and/or one or more tibial trial insert 116, a particular size of the tibial trial component 112, talar trial component 114 and/or tibial trial insert 116 (and thereby corresponding tibial component 12, talar component 14 and tibial trial insert 16) may be selected based on the particular patient/ankle that best suits the patient/ankle (and utilized to prepare the tibia and/or talus to implantation of the tibial trial component 112 and talar trial component 114, respectively, therein/thereon). The tibial trial component 112, the talar trial component 114 and the tibial trial insert 116 may comprise a radio radiopaque material such that at least a portion of the components are visible under fluoroscopy or other imaging in situ.

The tibial trial component 112 of the TAR prosthesis 100 is configured to be coupled to a distal tibia (e.g., a resected portion thereof) and be utilized as a sizing and orientation trial instrument, and/or a punch/drill/cut guide to the distal tibia, for one or more corresponding tibial components 12. As shown in FIGS. 2-18, the tibial trial component 112 may comprise a base portion 120 and an arm or wing portion 122. The proximal-distal thickness, the medial-lateral width and/or the anterior-posterior size/dimension, shape and/or orientation of the base portion 120 of the tibial trial component 112 may correspond (e.g., match or closely approximate) to that of the tibial component 12 of the TAR prosthesis 10. The base portion 120 includes a proximal bone engagement surface or side 124 configured to engage/abut the distal tibia (potentially resected) of a patient. In some embodiments, the proximal bone engagement surface 124 of the base portion 120 is convex (e.g., arcuately convex) along the medial-lateral direction, as shown in FIG. 18. In some other embodiments (not shown), the proximal bone engagement surface 124 of the base portion 120 is flat/planar along the medial-lateral direction, as shown in FIG. 18.

The base portion 120 includes at least one through hole or aperture 130 that extends through the base portion 120 along the proximal-distal direction from the proximal bone engagement surface 124 to a distal insert engagement surface or side 132 that opposes the proximal bone engagement surface 124, as shown in FIGS. 2, 7 and 9-13.

In some embodiments, the base portion 120 includes a plurality of through holes 130. The at least one through hole 130 is configured as a guide hole for a bone removal and/or aperture formation instrument (e.g., a sharp tipped trocar, drill, punch, etc.) to remove portions of the distal tibia to accommodate at least one peg of a corresponding tibial component 12 therein. The at least one through hole 130 may thereby correspond to the position/location (and potentially size and/or orientation) of at least one implantable post of a corresponding tibial component 12. For example, in some embodiments, the system 100 may include a distractor that forces at least one projection/pin through the at least one through hole 130 and into the resected distal tibia 2 to form an aperture in the bone that is configured to accept or mate with at least one peg of a corresponding tibial component 12, such as that disclosed in U.S. Provisional Patent Application No. 62/898,854 filed Sep. 11, 2018 and entitled Distractors Having Attachable Paddles, Impaction Devices, and Methods for Use in Total Ankle Replacement and/or International PCT Patent Application filed on Dec. 13, 2019, and entitled Distractors Having Attachable Paddles, Impaction Devices, and Methods for Use in Total Ankle Replacement, which are hereby incorporated herein by reference in their entireties. As another example, in some embodiments, include an impactor tool (in addition to, or instead of, the distractor) that forces at least one projection/pin through the at least one through hole 130 and into the resected distal tibia 2 to form an aperture in the bone that is configured to accept or mate with at least one peg of a corresponding tibial component 12, such as that disclosed in U.S. Provisional Patent Application No. 62/898,854 filed Sep. 11, 2018, and entitled Distractors Having Attachable Paddles, Impaction Devices, and Methods for Use in Total Ankle Replacement and/or International PCT Patent Application filed on Dec. 13, 2019, and entitled Distractors Having Attachable Paddles, Impaction Devices, and Methods for Use in Total Ankle Replacement.

It is noted that differing tibial trial components 112 may correspond to differing corresponding tibial components 12 (e.g., differing sized components), and thereby may include differing numbers, locations and/or configurations of the at least one through hole 130 to correspond to the at least one implantable peg of a respective corresponding tibial trial component 112. As shown in FIGS. 2, 7 and 9-13, the illustrative embodiment includes four through holes 130 comprising an anterior and medial through hole 130, an anterior and lateral through hole 130, a posterior and medial through hole 130, and a posterior and lateral through hole 130.

Figure 14:
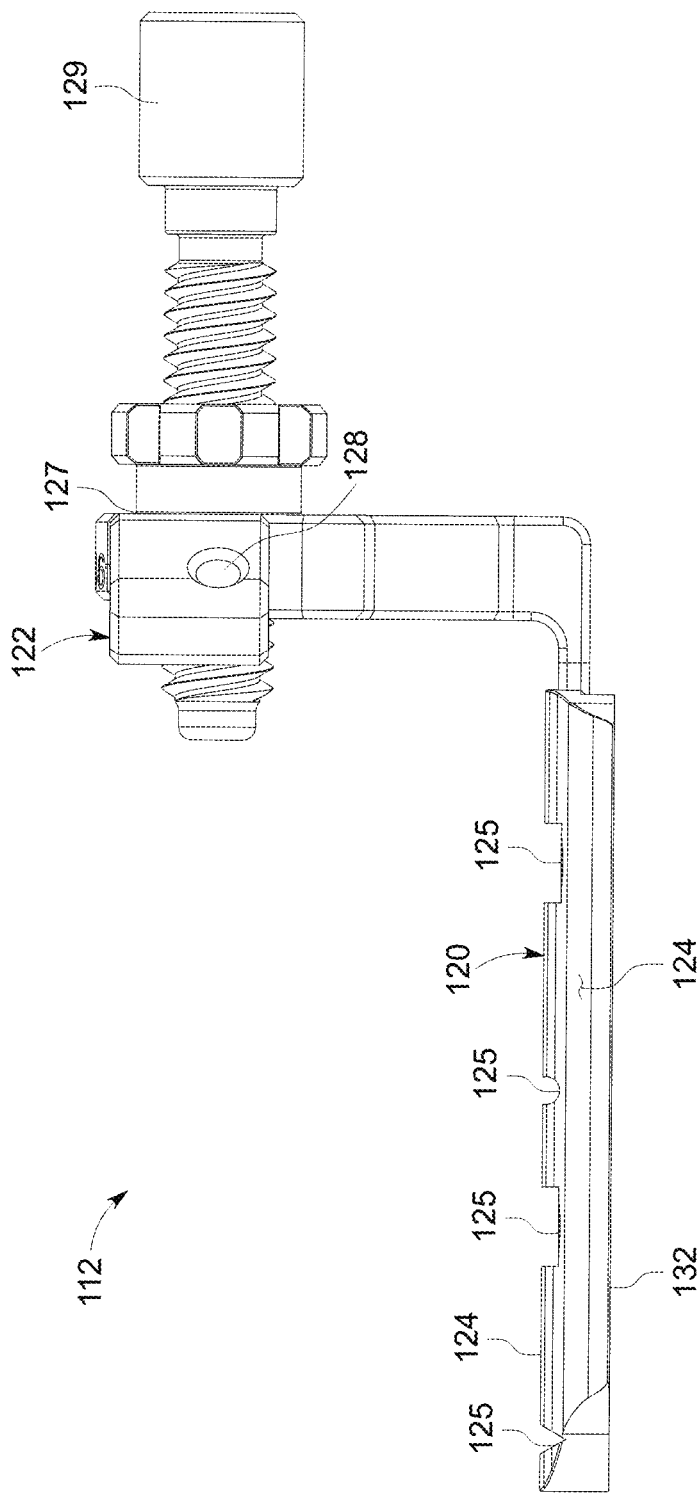
FIG. 14 illustrates a medial side view of the tibial trial guide of FIG. 9, in accordance with an aspect of the present disclosure.
Figure 15:
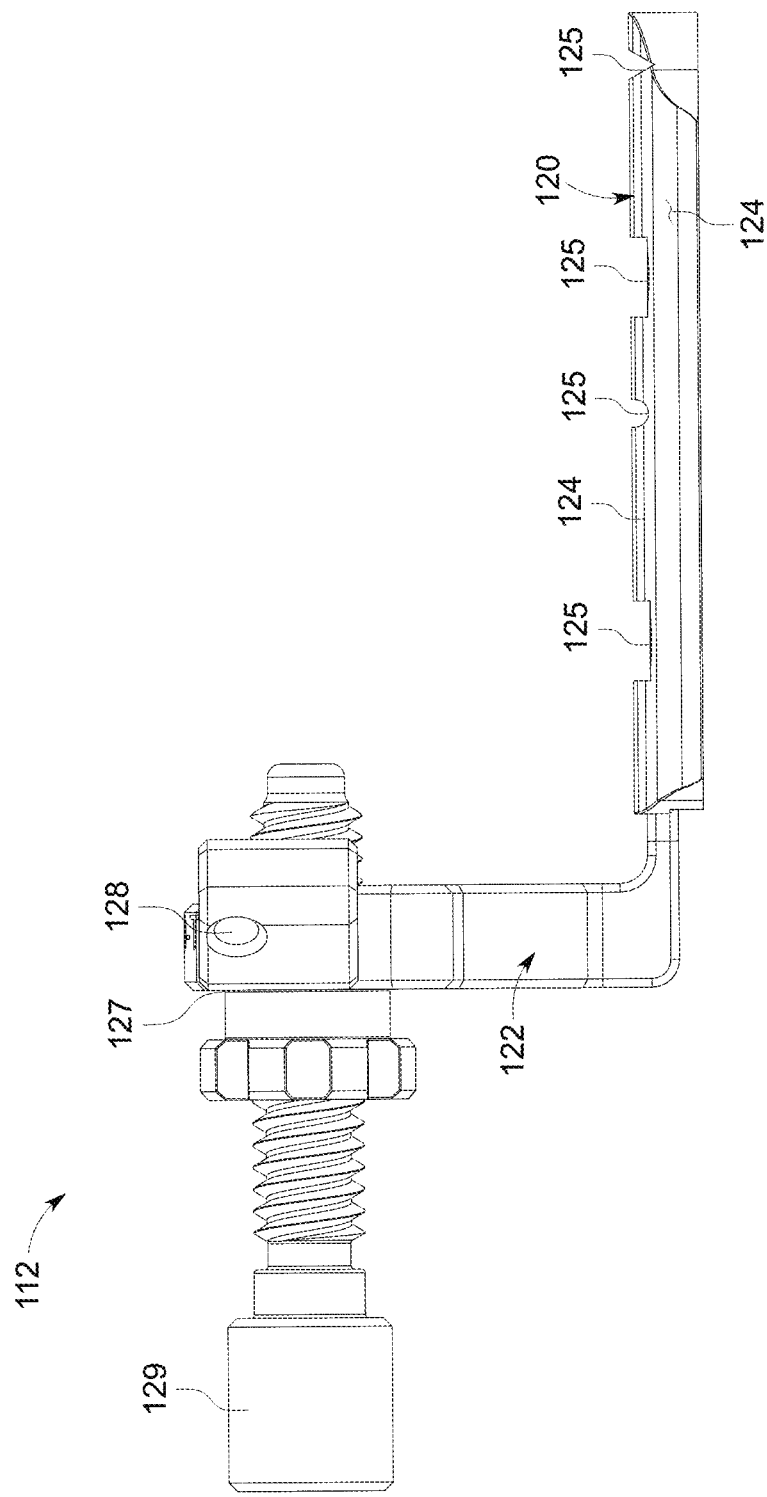
FIG. 15 illustrates a lateral side view of the tibial trial guide of FIG. 9, in accordance with an aspect of the present disclosure.
Figure 16:
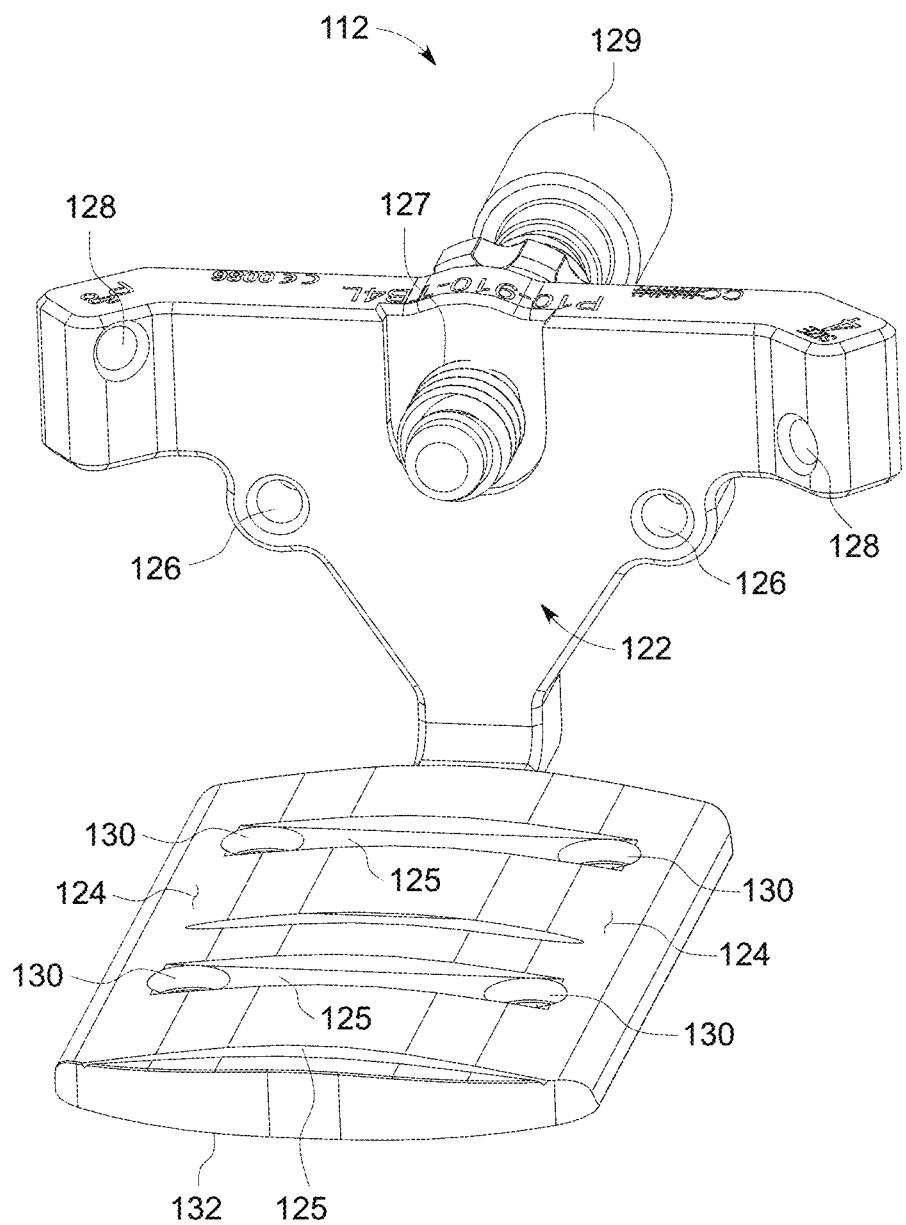
FIG. 16 illustrates a posterior perspective view of the tibial trial guide of FIG. 9, in accordance with an aspect of the present disclosure.

The proximal bone engagement surface 124 may include at least one slot or indentation 125 extending therein, such as at least one slot that is elongated along the medial lateral direction, as shown in FIGS. 7, 10, 12, 14 and 15. The at least one slot 125 may extend at least through the proximal apex or highest surface portion of the bone engagement surface 124 such that the at least one slot 125 (i.e., the edges thereof) is visible when viewed along the medial-lateral direction (e.g., visible under fluoroscopy or other imaging in situ), as shown in FIGS. 14 and 15. In this way, the at least one slot 125 may be utilized to identify portions or aspects of the base portion 120 that may not be visible, or may be difficult to decipher when viewed at least along the medial-lateral direction (e.g., under fluoroscopy or other imaging in situ). In some embodiments, the base portion 120 may include a plurality of slots 125 in the proximal bone engagement surface 124. For example, the illustrative embodiment includes an anterior slot 125 and a posterior slot 125 that passes through or corresponds to the anterior through holes 125 and the posterior through holes 125, respectively. As another example, the illustrative embodiment also includes a central slot 125 that passes through or corresponds to the center of the base portion 120 (and thereby the corresponding tibial component 12) along the anterior-posterior direction, which may be utilized to align the base portion 120 to the long and/or mechanical axis of the tibia along the anterior-posterior direction. Still further, the illustrative embodiment also includes at least one posterior end slot 125 that passes through a posterior end portion of the base portion 120 that corresponds to at least one posterior end of at least one first "standard" corresponding tibial component 12 and/or tibial insert 16. The posterior end of the base portion 120 may correspond to the posterior end of at least one second "long" corresponding tibial component 12 and/or tibial insert 16. The at least one posterior end slot 125 and the posterior end of the base portion 120 may thereby be utilized to correctly position the base portion 120 and/or the tibial component 12 relative to the tibia 2 (e.g., align a center thereof with an axis of the tibia 2 along the anterior-posterior direction) and determine an appropriately size (e.g., "standard" or "long") of the tibial component 12 and/or tibial insert 16 to be used with the particular tibia 2 (e.g., a tibial component 12 that extends over the maximum area of the tibia 2 to distribute the forces acting through the joint).

Figure 45:
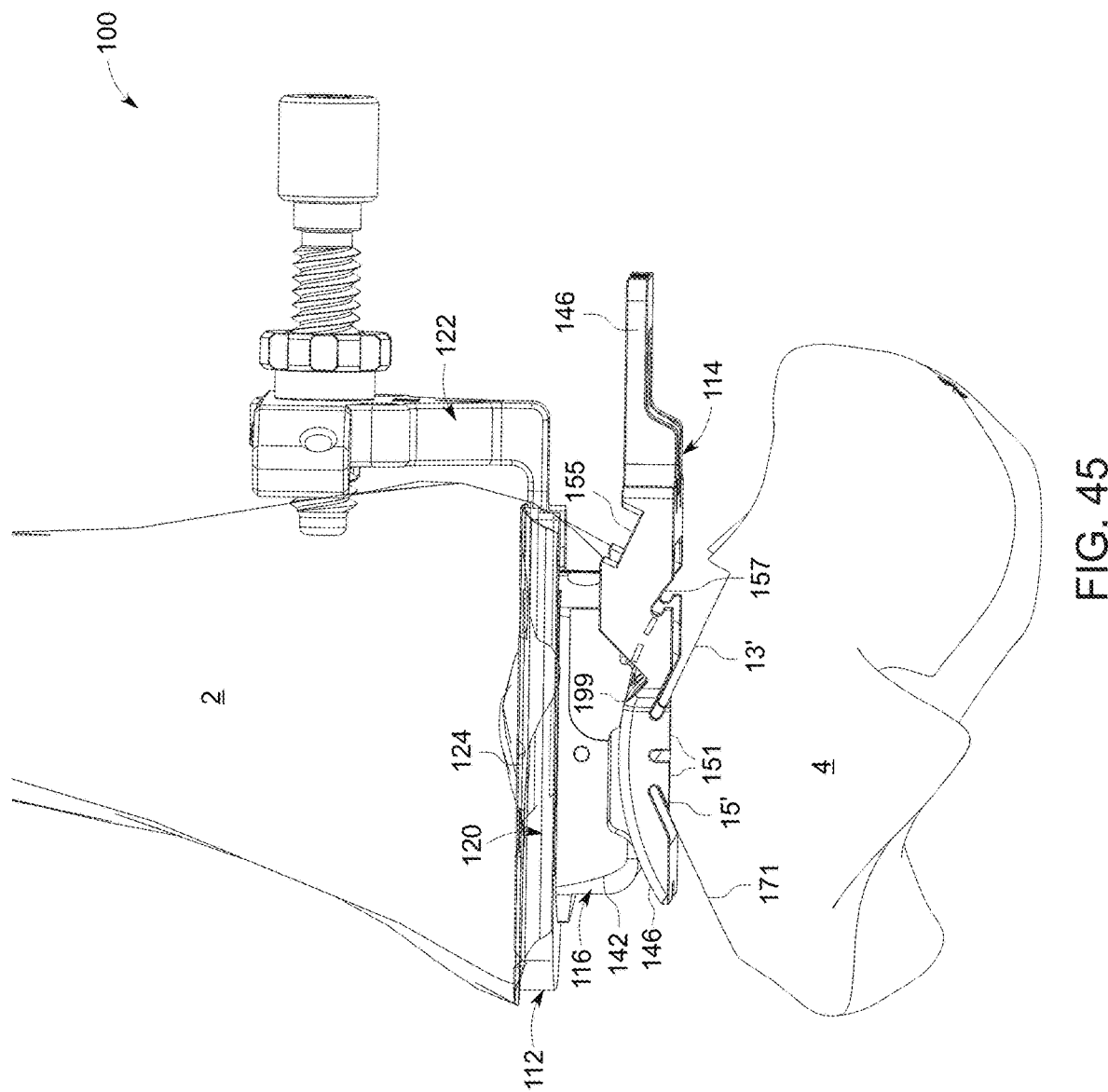
FIG. 45 illustrates a lateral side view of the TAR prosthesis of FIGS. 1A and 2B forming an ankle joint between a tibia and talus, in accordance with an aspect of the present disclosure.

As shown in FIGS. 2-18, the arm portion 122 of the tibial component 112 extends proximally from the anterior end of the base portion 120. The proximal end of the arm portion 122 may be wider in the medial-lateral direction than the distal end thereof. The arm portion 122 includes an adjustment screw 129 threadably extending through an adjustment aperture 127 along the anterior-posterior direction, as shown in FIGS. 2-18. The position of the adjustment screw 129 relative to the arm portion 122 along the anterior-posterior may adjusted by rotation of the adjustment screw 129. The anterior-posterior position/location of the adjustment screw 129 relative to the arm portion 122 may be adjusted with the posterior tip of the adjustment screw 129 contacting the anterior face of the tibia 2 proximal to the resected portion thereof (e.g., the anterior crown of the tibia 2), as shown in FIG. 45. In this way, the anterior-posterior position/location of the base portion 120 on the distal tibia 2 can be adjusted via anterior-posterior adjustment (e.g., via rotation) of the adjustment screw 129. In some embodiments, the adjustment screw 129 may include a nut or other mechanism that selectively locks the anterior-posterior position of the adjustment screw 129 in at least one direction along the anterior-posterior direction. The adjustment screw 129 and adjustment aperture 127 may be aligned with, or positioned proximate to, the medial-lateral midline of the base portion 120.

As shown in FIGS. 5, 6, 10, 11, 17 and 18, the arm portion 122 of the tibial component 112 may include a plurality of pin apertures 126, 128 extending therethrough along the anterior-posterior direction. The pin apertures 126, 128 may be configured to accept a pin, k-wire or other bone fixation member therethrough and into the tibia 2. For example, the illustrative embodiment of the arm portion 122 includes at least a pair of first pin apertures 126 that are aligned with each other and the anterior-posterior direction (i.e., extend normal to the coronal plane (and parallel to the sagittal plane)), as shown in FIGS. 5, 6, 10, 11, 17 and 18. As also shown in FIGS. 5, 6, 10, 11, 17 and 18, the illustrative embodiment of the arm portion 122 includes at least a pair of second pin apertures 128 that converge (or diverge) as the extend posteriorly (i.e., are angled with respect to the sagittal plane). The pair of first pin apertures 126, and/or the pair of second pin apertures 128, may each include a pin aperture positioned on a medial side of the medial-lateral midline of the base portion 120, and a pin aperture positioned on a lateral side of the medial-lateral midline of the base portion 120. The first and second pin apertures 126, 128 may be configured to house pins or other fixation members extending therethrough and into the tibia 2.

Figure 46:
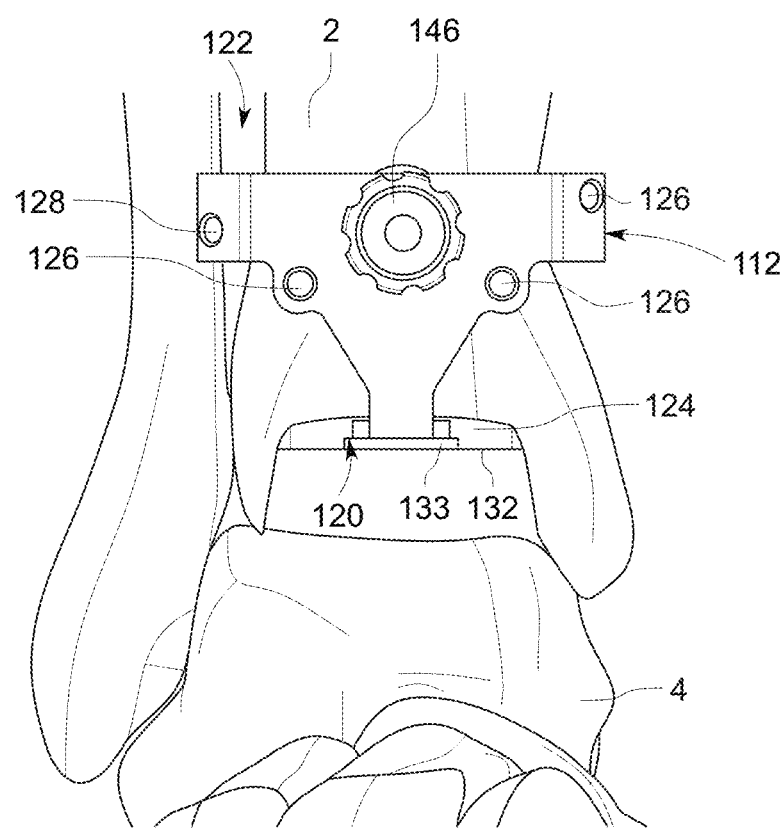
FIG. 46 illustrates an anterior view of the tibial trial guide of FIG. 9 positioned on a resected distal tibia, in accordance with an aspect of the present disclosure.
Figure 47:
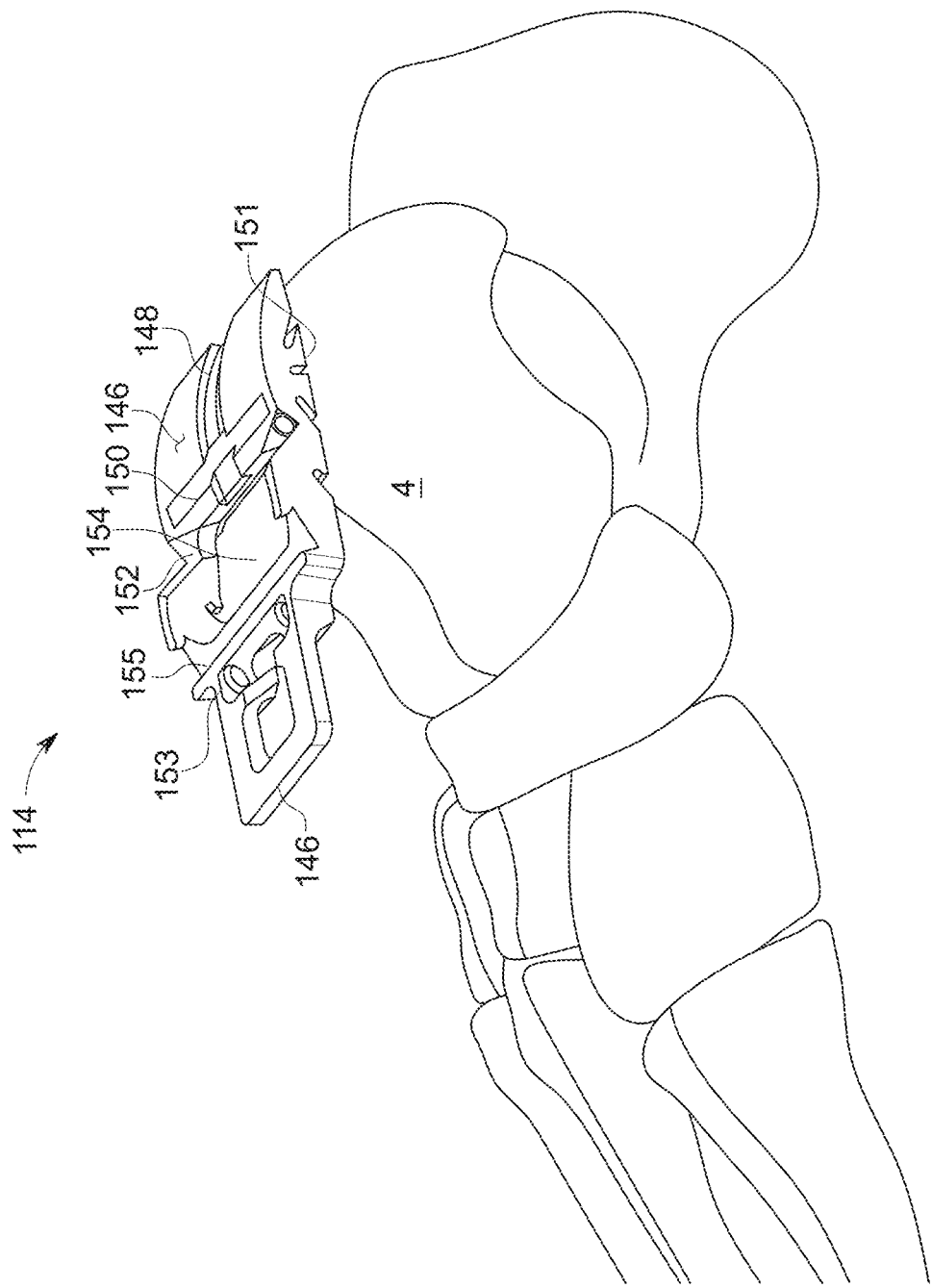
FIG. 47 illustrates an anterior elevational perspective view of the talar trial guide of FIG. 29 positioned on a talus, in accordance with an aspect of the present disclosure.
Figure 48:
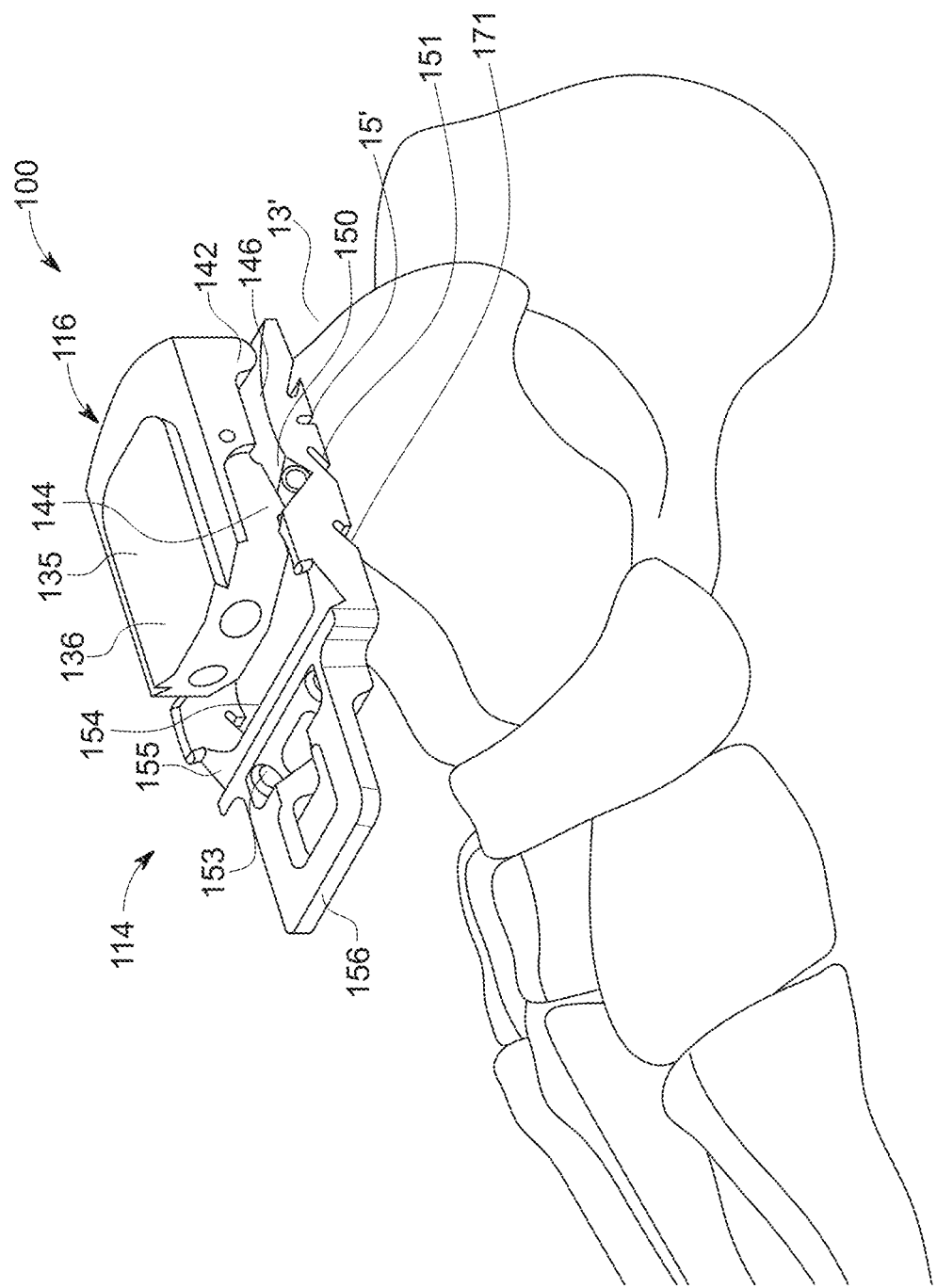
FIG. 48 illustrates an anterior elevational perspective view of the talar trial guide of FIG. 29 and the tibial trial insert of FIG. 19 positioned on a talus, in accordance with an aspect of the present disclosure.

The first pin apertures 126 may facilitate insertion of first pins or other fixation members therethrough and into the tibia 2 with the proximal bone engagement surface 124 of the base portion 120 engaged with the distal end (e.g., resected) of the tibia 2 between the tibia 2 and the talus 4 (see FIG. 46). The adjustment screw 129 can then be adjusted to translate the tibial component 112 over the first pins along the anterior-posterior to adjust the anterior-posterior position of the base portion 120 on the distal tibia 2 (e.g., to align the center thereof, potentially indicated by a slot 125) with the axis of the tibia 2. The first pins extending through the first pin apertures 126 may thereby fix the tibial component 112 along the medial-lateral and proximal-distal directions while allowing adjustment of the tibial component 112 (particularly the base portion 120 thereof) along the anterior-posterior direction along the first pins via the adjustment screw 129. It is noted that the adjustment screw 129 (which may be fixed via a nut or other mechanism) may also prevent the tibial component 112 from translating posteriorly toward the tibia 2. Once the base portion 120 is positioned in a desirable location (e.g., the center thereof aligned with the anatomical and/or mechanical axis of the tibia 2), the second pins or other fixation members may be inserted through the second pin apertures 128 and the tibia 2 to lock the anterior-posterior position of the tibial component 112 (and particularly the base portion 120 thereof).

Figure 11:
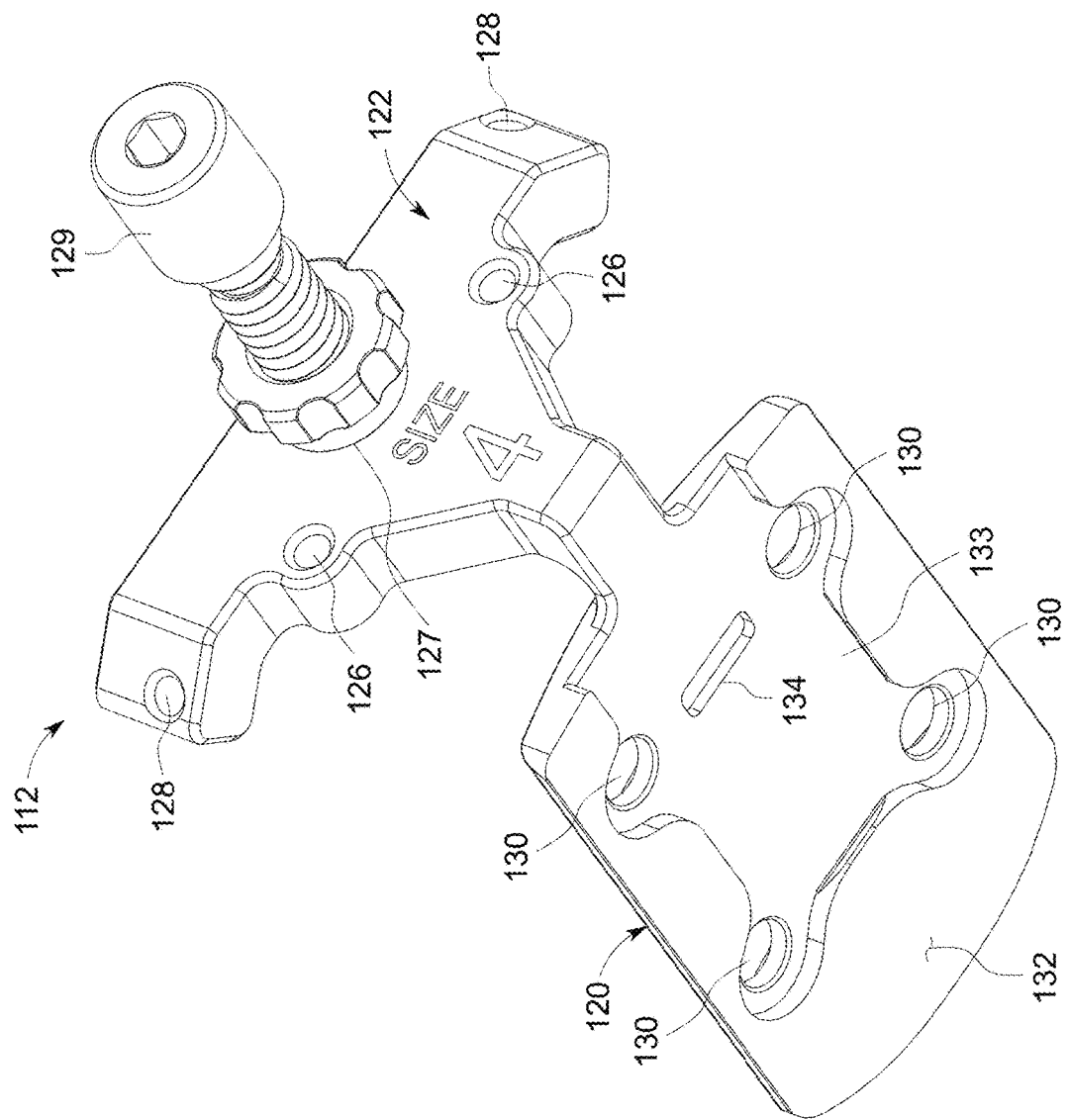
FIG. 11 illustrates a bottom perspective view of the tibial trial guide of FIG. 9, in accordance with an aspect of the present disclosure.
Figure 12:
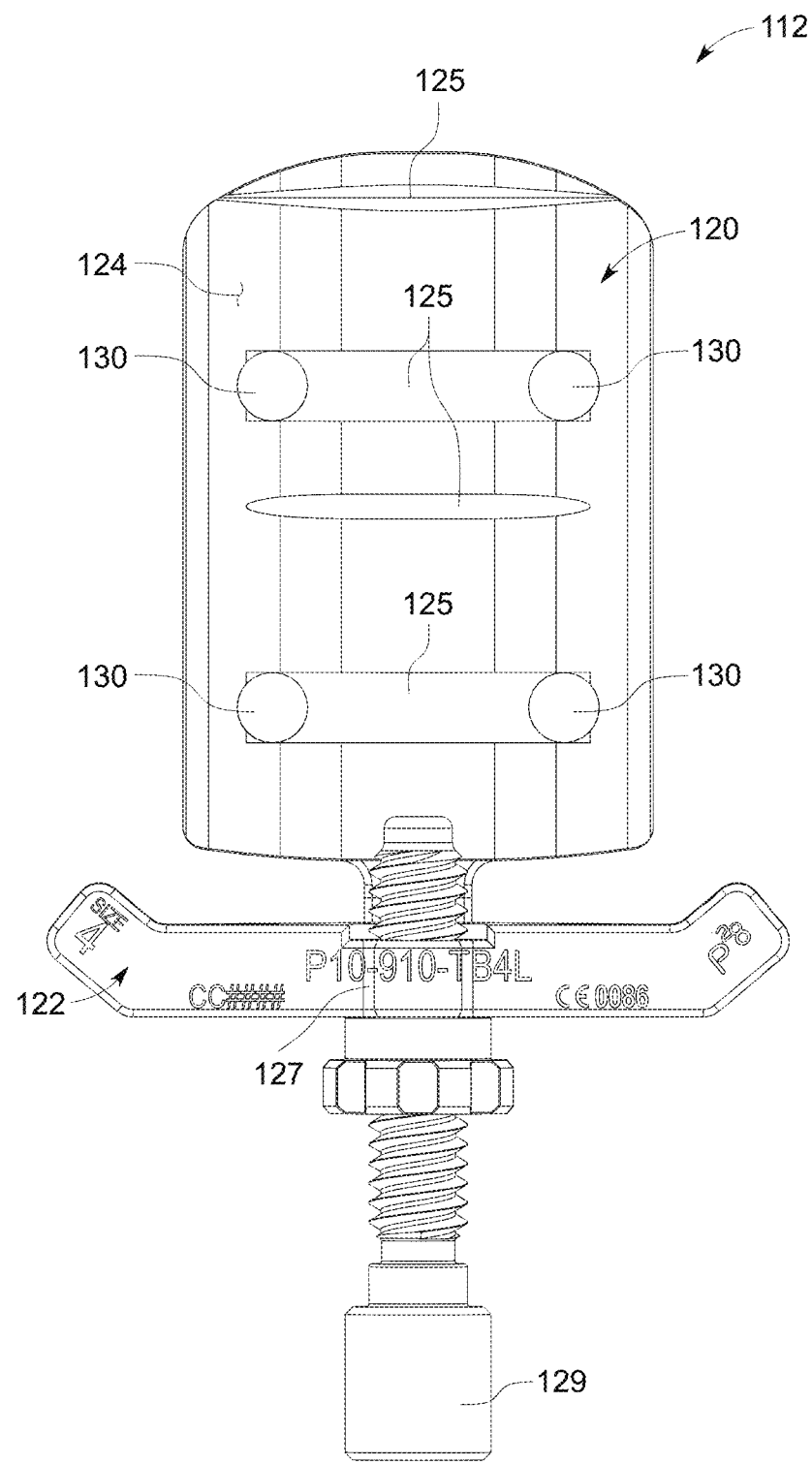
FIG. 12 illustrates a bottom perspective view of the tibial trial guide of FIG. 9, in accordance with an aspect of the present disclosure.
Figure 13:
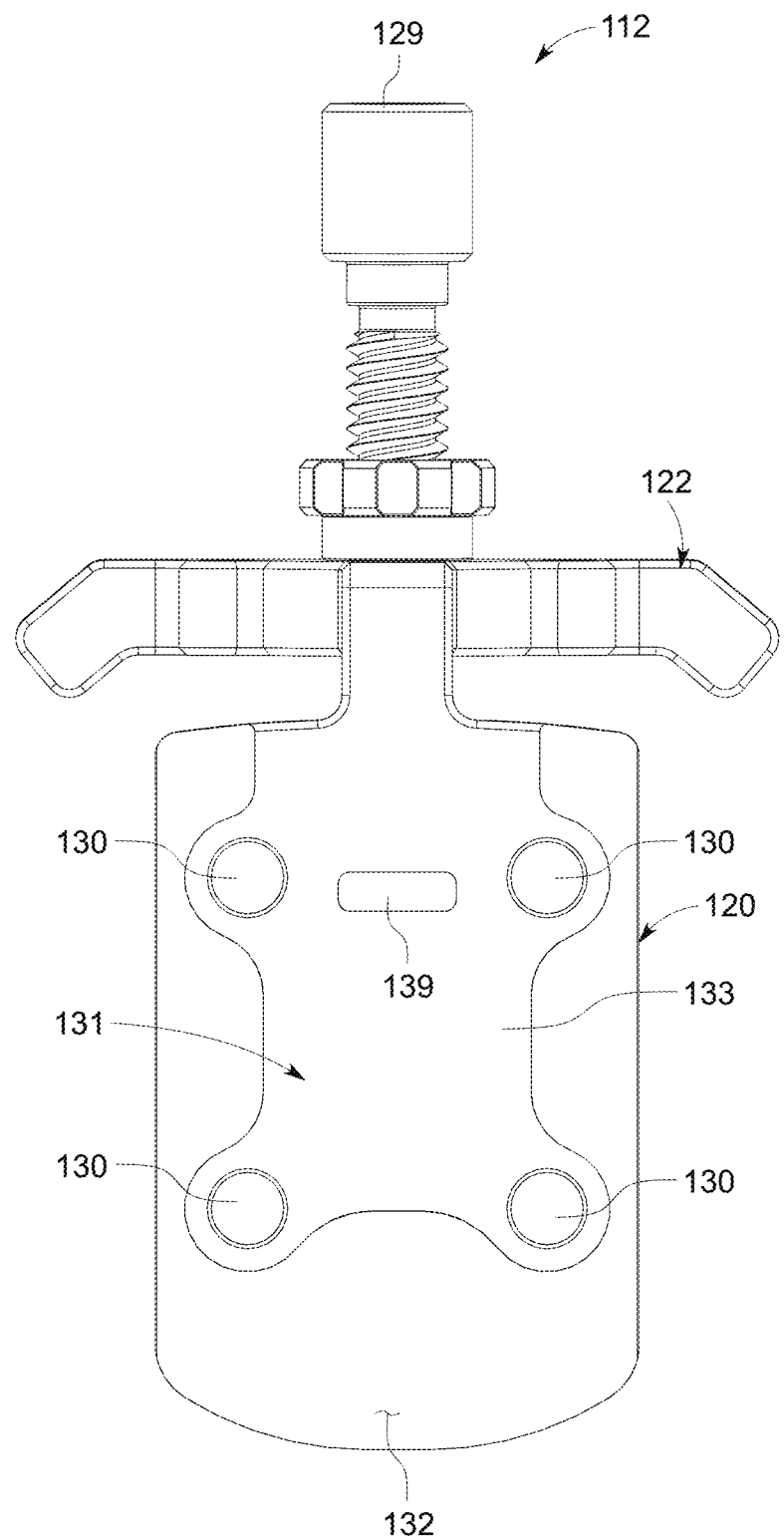
FIG. 13 illustrates a bottom view of the tibial trial guide of FIG. 9, in accordance with an aspect of the present disclosure.
Figure 17:
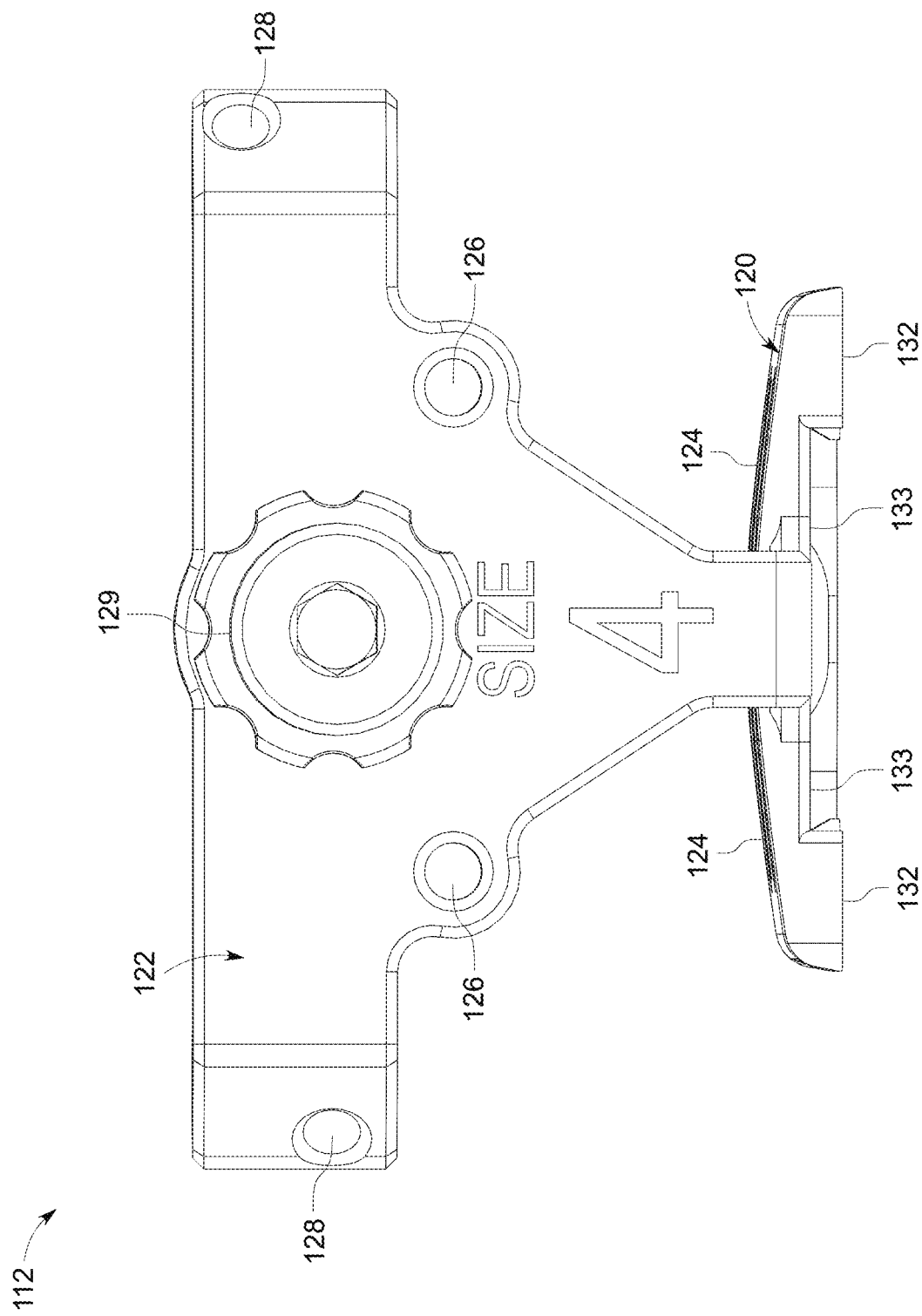
FIG. 17 illustrates an anterior view of the tibial trial guide of FIG. 9, in accordance with an aspect of the present disclosure.
Figure 18:
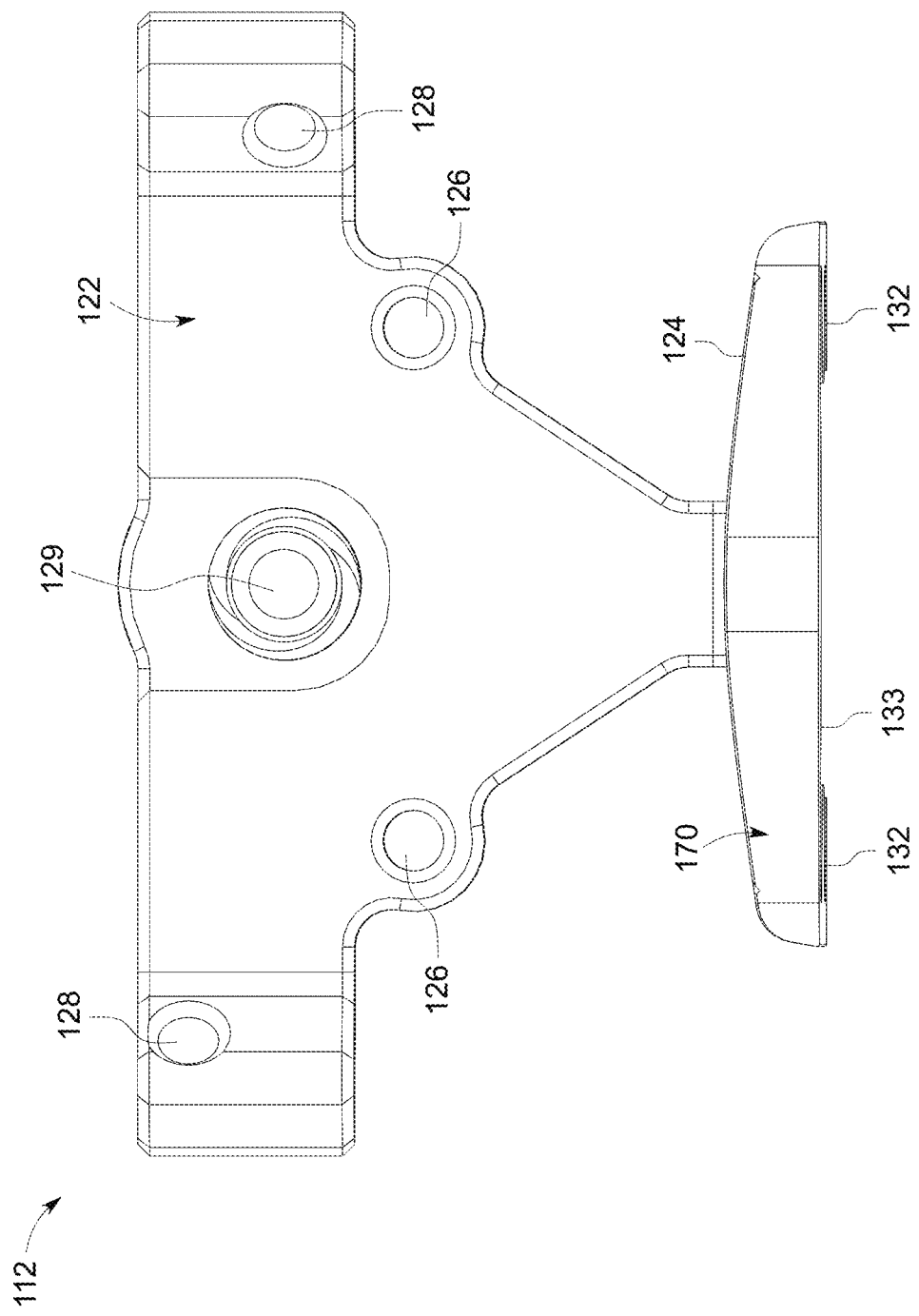
FIG. 18 illustrates a posterior view of the tibial trial guide of FIG. 9, in accordance with an aspect of the present disclosure.
Figure 19:
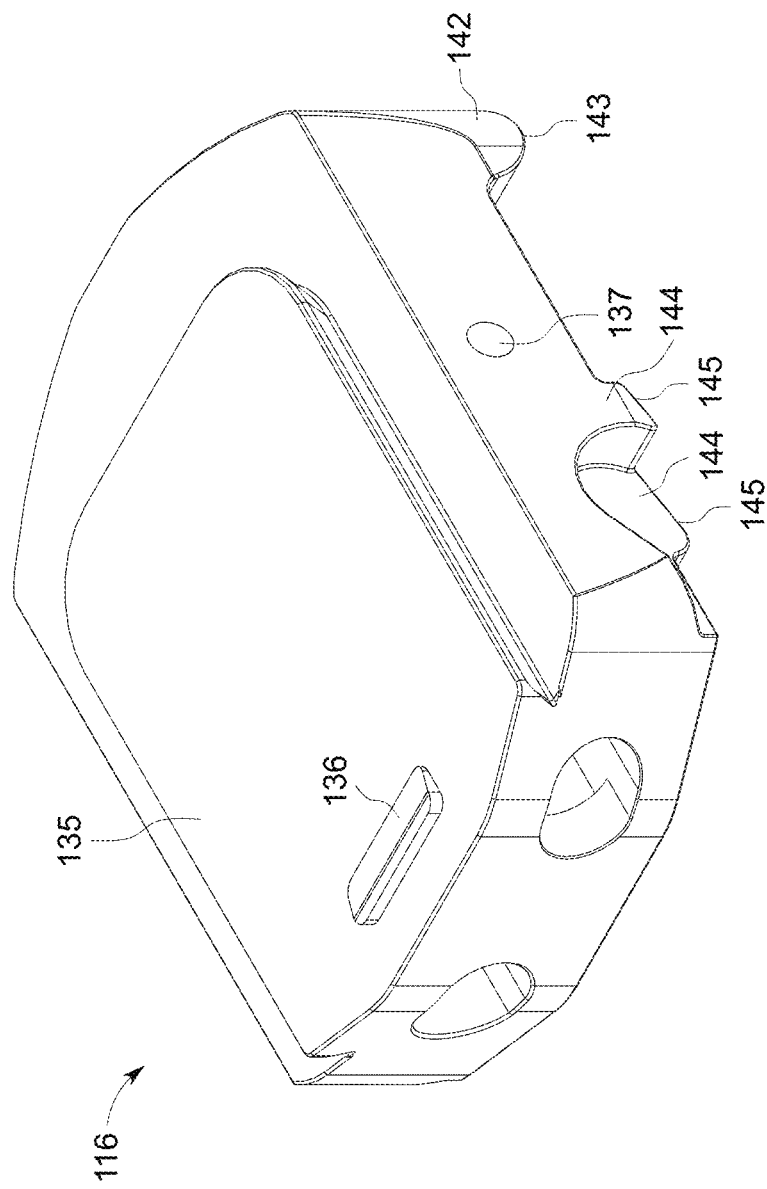
FIG. 19 illustrates an elevational anterior perspective view of the tibial trial insert of the TAR trial and guide system of FIG. 2, in accordance with an aspect of the present disclosure.
Figure 20:
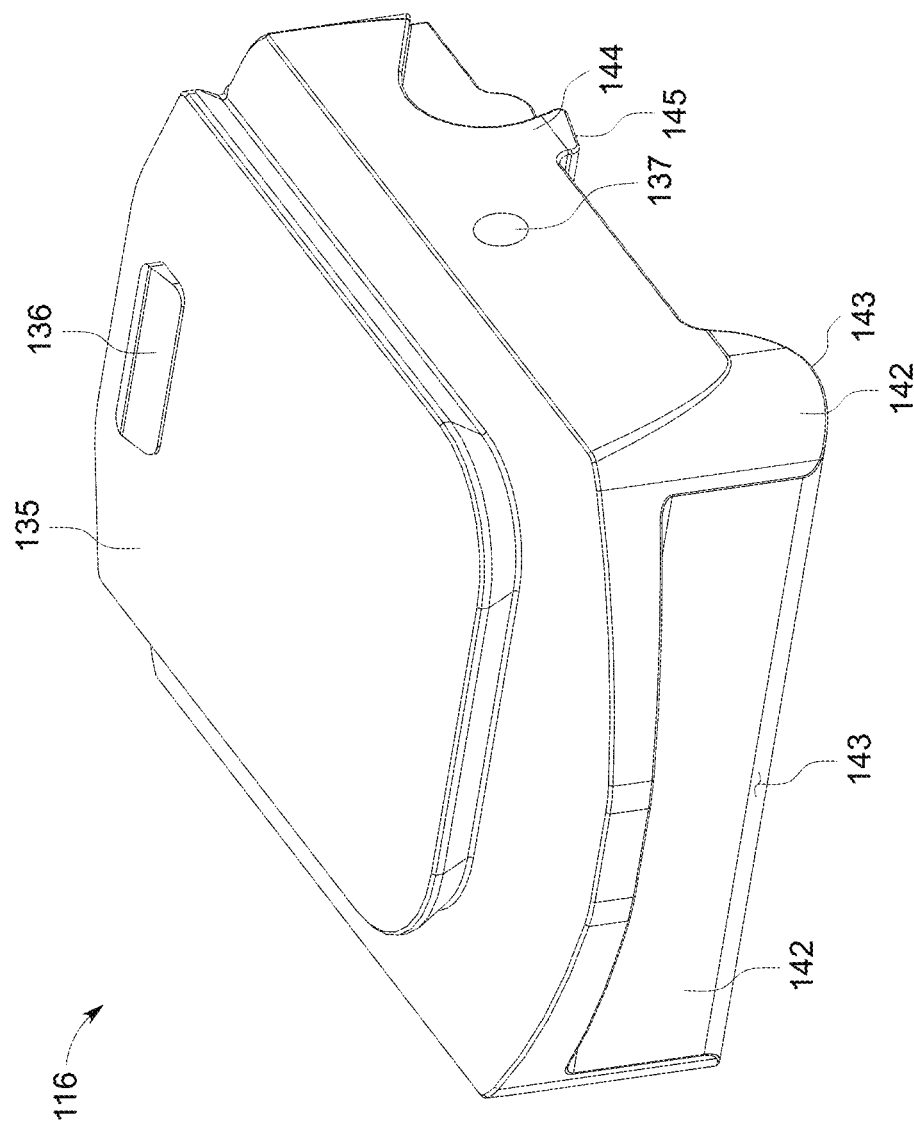
FIG. 20 illustrates an elevational posterior perspective view of the tibial trial insert of FIG. 19, in accordance with an aspect of the present disclosure.
Figure 21:
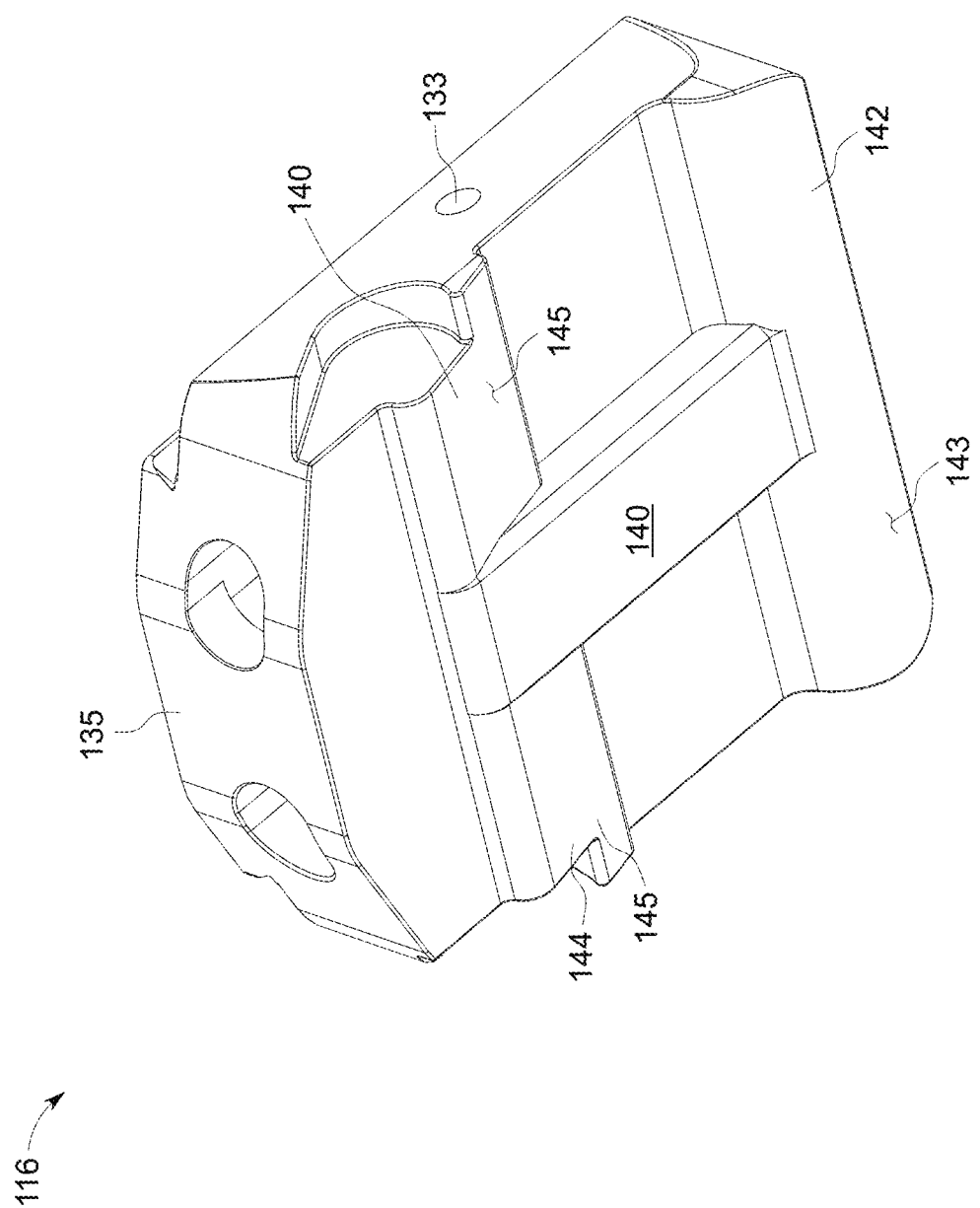
FIG. 21 illustrates a bottom anterior perspective view of the tibial trial insert of FIG. 19, in accordance with an aspect of the present disclosure.
Figure 22:
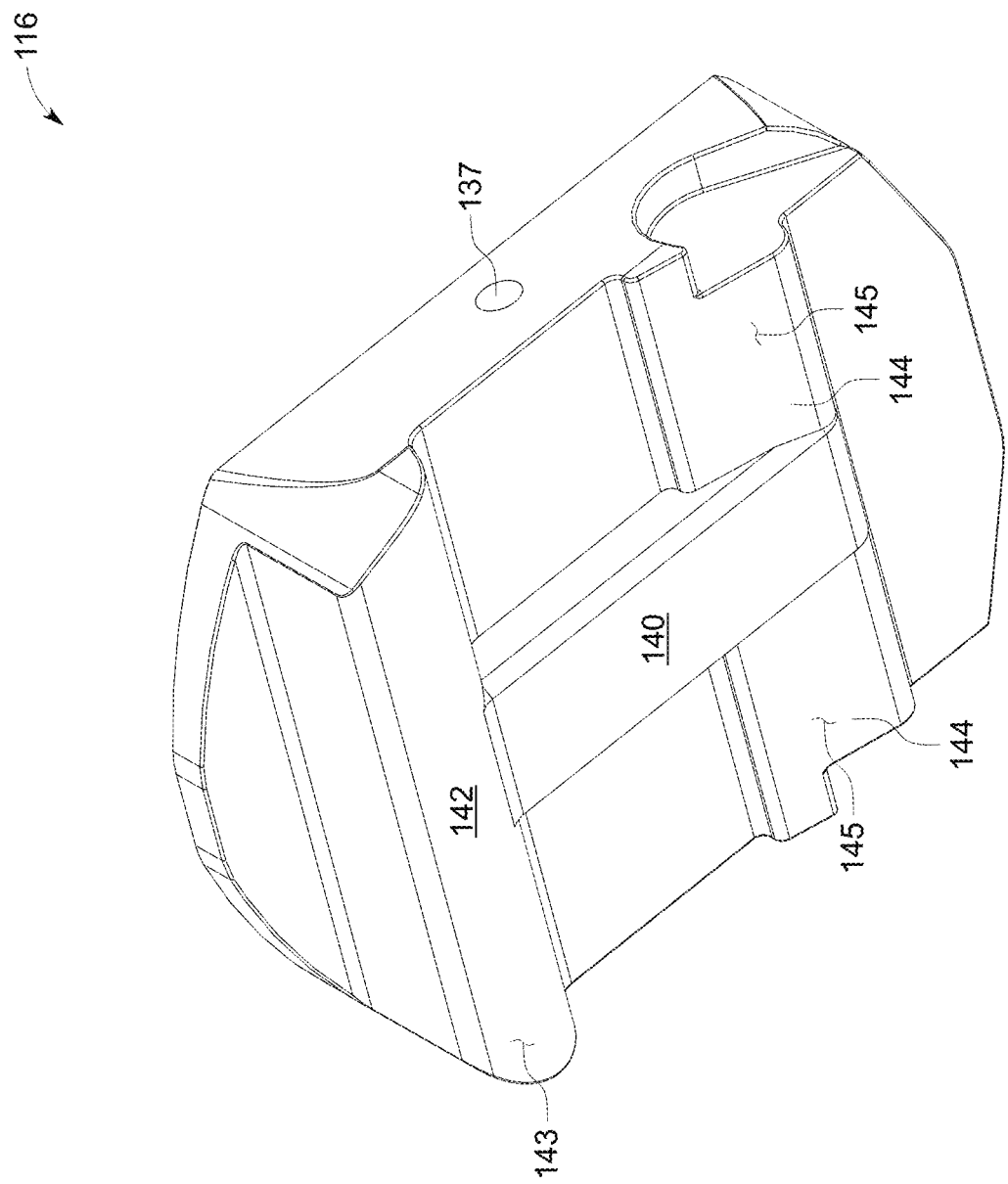
FIG. 22 illustrates a bottom posterior perspective view of the tibial trial insert of FIG. 19, in accordance with an aspect of the present disclosure.
Figure 23:
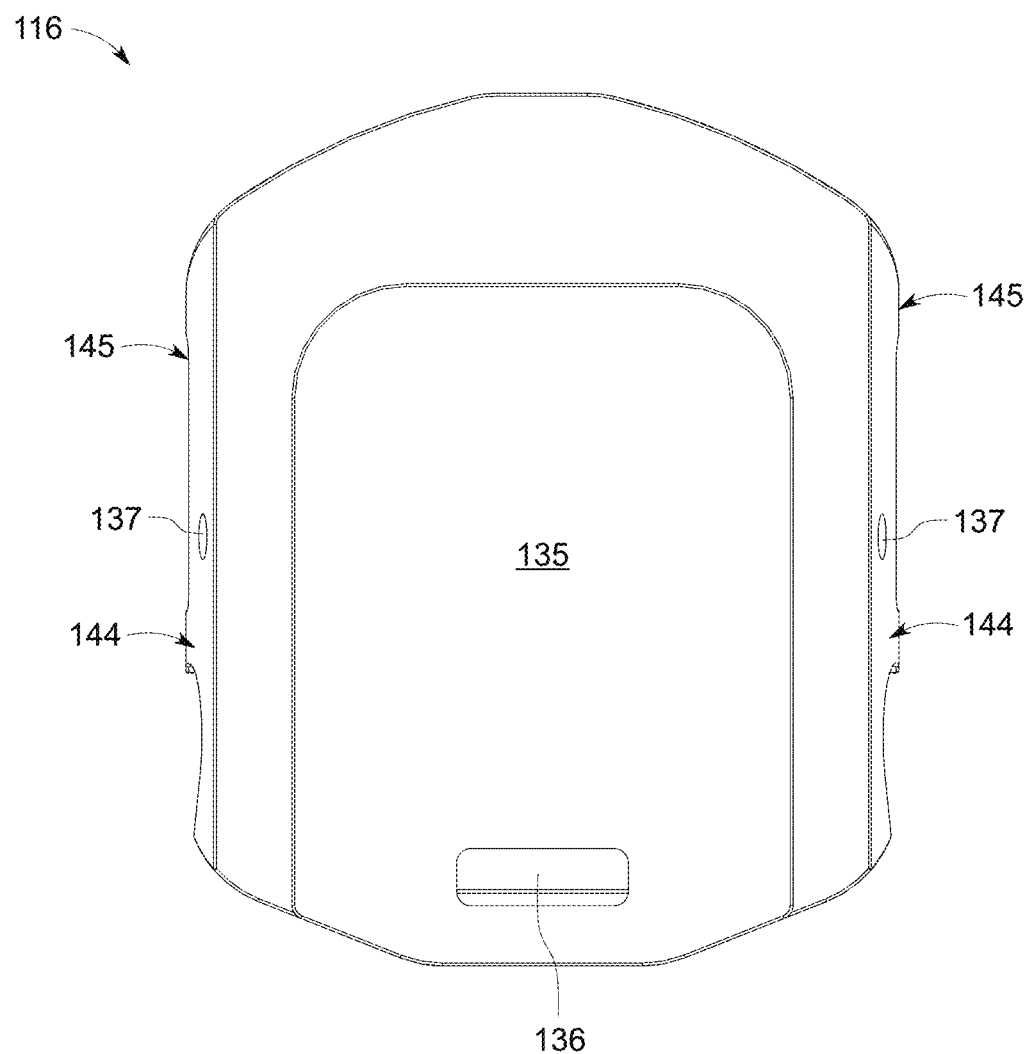
FIG. 23 illustrates a proximal view of the tibial trial insert of FIG. 19, in accordance with an aspect of the present disclosure.
Figure 24:
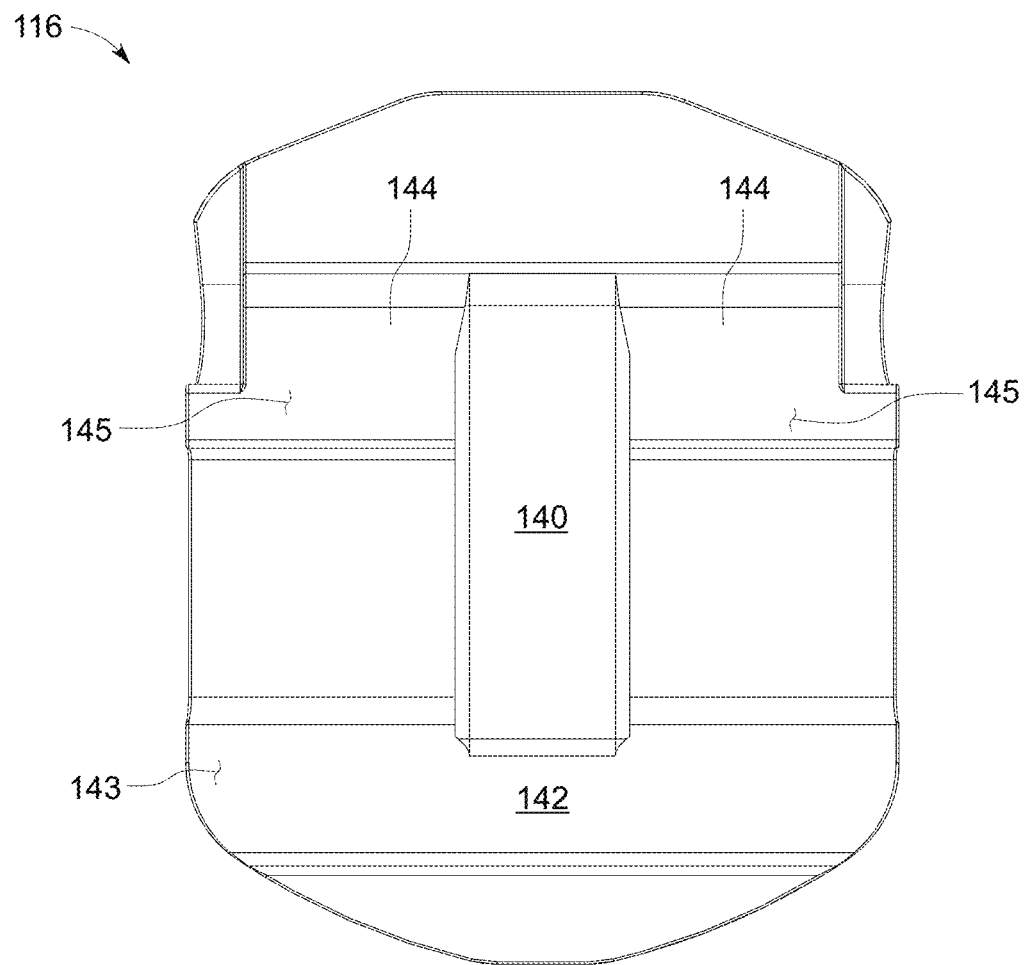
FIG. 24 illustrates a distal view of the tibial trial insert of FIG. 19, in accordance with an aspect of the present disclosure.

The distal insert side 132 of the base portion 120 includes a distal recessed portion 133, as shown in FIGS. 11, 13 and 17. The recessed portion 133 of the distal insert side 132 engages and couples with the tibial trial insert 116, as shown in FIGS. 3-6. As shown in FIGS. 11 and 17, sides of the recessed portion 133 may include an undercut or otherwise be angled toward (or away) the periphery of the base portion 120 as they extend proximally to a planar proximal end surface to form a sliding dovetail socket or female portion. The recessed portion 133 (and thereby the socket/female portion formed thereby) may be open on one side thereof. For example, in the illustrative embodiment the recessed portion 133 (and thereby the socket/female portion formed thereby) is open at the anterior end of the base portion 120 distal to the arm portion 122. The proximal end surface of the recessed portion 133 may include a slot or indentation 134, as shown in FIGS. 11 and 14.

The tibial trial insert 116 includes a proximal projection or male portion 135 on a proximal side thereof, as shown in FIGS. 19, 20, 22, 23 and 25-28. The projection 135 of the tibial trial insert 116 is configured to mate with the recessed portion 133 of the distal insert side 132 of the base portion 120, as shown in FIGS. 3-6. For example, the sides of the projection 135 may include an undercut or otherwise be angled away (or toward) the periphery of the tibial trial insert 116 as they extend proximally to a planar proximal end surface to form a sliding dovetail male portion. The projection 135 of the tibial trial insert 116 may include a boss 136, as shown in FIGS. 19, 20, 22, 23 and 25-28. The boss 136 is configured to mate within the slot or indentation 134.

The proximal projection 135 of the tibial trial insert 116 (e.g., a sliding dovetail male portion) may engage the recessed portion 133 of the base portion 120 (e.g., a sliding dovetail socket/female portion), as shown in FIGS. 3-6. The proximal projection 135 may slidingly engage the recessed portion 133 along the anterior-posterior direction, and access the recessed portion 133 via the anterior opening thereof. The configuration of the proximal projection 135 and the recessed portion 133 may couple or fix the tibial trial insert 116 and the base portion 120 of the tibial trial component 112 along the medial-lateral and proximal-distal directions. Alternatively, the base portion 120 may include the projection 135, and the tibial trial insert 116 may include the recessed portion 133, to couple the base portion 120 and the trial insert 116 together.

The tibial trial insert 116 and the base portion 120 may be fixed or coupled along the anterior-posterior direction via the slot 134 within the recessed portion 133 of the base portion 120 and the boss 136 of the projection 135 of the tibial trial insert 116. The tibial trial insert 116 may slide posteriorly within the recessed portion 133 (e.g., in situ) until the boss 136 is seated within the slot 134 to selectively fix the tibial trial insert 116 and the base portion 120 of the tibial trial component 112 along the medial-lateral, proximal-distal and anterior-posterior directions. It is also noted that the posterior end of the projection 135 of the tibial trial insert 116 may engage the posterior end of the recessed portion 133 of the base portion 120.

The relative position of the tibial trial insert 116 on the base portion 120 along the anterior-posterior direction may be thereby established by the anterior-posterior location of the boss 136 and/or the posterior end of the projection 135. As shown in FIGS. 4, 19-23, 25 and 26, at least one of the medial and lateral sides of the tibial trial insert 116 may include a marker or identifier portion 137 that provides a visual (and potentially tactile) identification of the center of the tibial trial insert 116 along the anterior-posterior direction. In some embodiments, the marker 137 may extend through the width of the tibial trial insert 116 between the medial and lateral sides of the tibial trial insert 116. In some other embodiments, one marker 137 may be positioned on the medial side, and another marker 137 may be positioned on the lateral side, of the tibial trial insert 116. The marker 137 may comprise a radio radiopaque material such the marker visible under fluoroscopy or other imaging in situ. Other portions of the tibial trial insert 116 may comprise a material that is less visible under fluoroscopy or other imaging than that of the material forming the marker 137. For example, the portions of the tibial trial insert 116 may be formed of polypheylsulfone (e.g., Radel (PPSU)), and the marker 137 may be formed of a metal material.

The marker 137 may be utilized to ensure the center of the tibial trial insert 116 (and thereby the tibial insert 16 corresponding thereto) is aligned with the anatomical and/or or mechanical axis of the tibia 2. The marker 137 of the tibial trial insert 116 may also be utilized to align the tibial trial insert 116 (and thereby the tibial insert 16 corresponding thereto) appropriately with the mechanical axis of the talus 4. For example, differing tibial trial inserts 116 may include bosses 136 and/or posterior ends of the projection 135 positioned in different anterior-posterior locations (as compared to other portions of the tibial trial inserts 116). For example, a "long" tibial trial insert 116 (corresponding to a "long" tibial trial insert 16) may be longer in the anterior-posterior direction than a "short/standard" tibial trial insert 116 (corresponding to a "short/standard" tibial insert 16). The boss 136 and/or posterior end of the projection 135 of the "long" tibial trial insert 116 may positioned further posteriorly (and the anterior-posterior center and marker 137 thereby positioned further anteriorly) than that of the "short/standard" tibial trial insert 116. A "long" or "short/standard" tibial trial insert 116 may thereby be selected to ensure the tibial trial insert 116 is aligned with the anatomical and/or or mechanical axis of the tibia 2 in the anterior-posterior direction (and the talus 4 is appropriately aligned with the axis of the talus 4 for a particular patient, as the tibial trial insert 116 may effectively position, at least in part, the talar trial component 114, and thereby the corresponding talar component 14 and talus 4) (i.e., a particular tibia 2 and talus 4).

Figure 55:
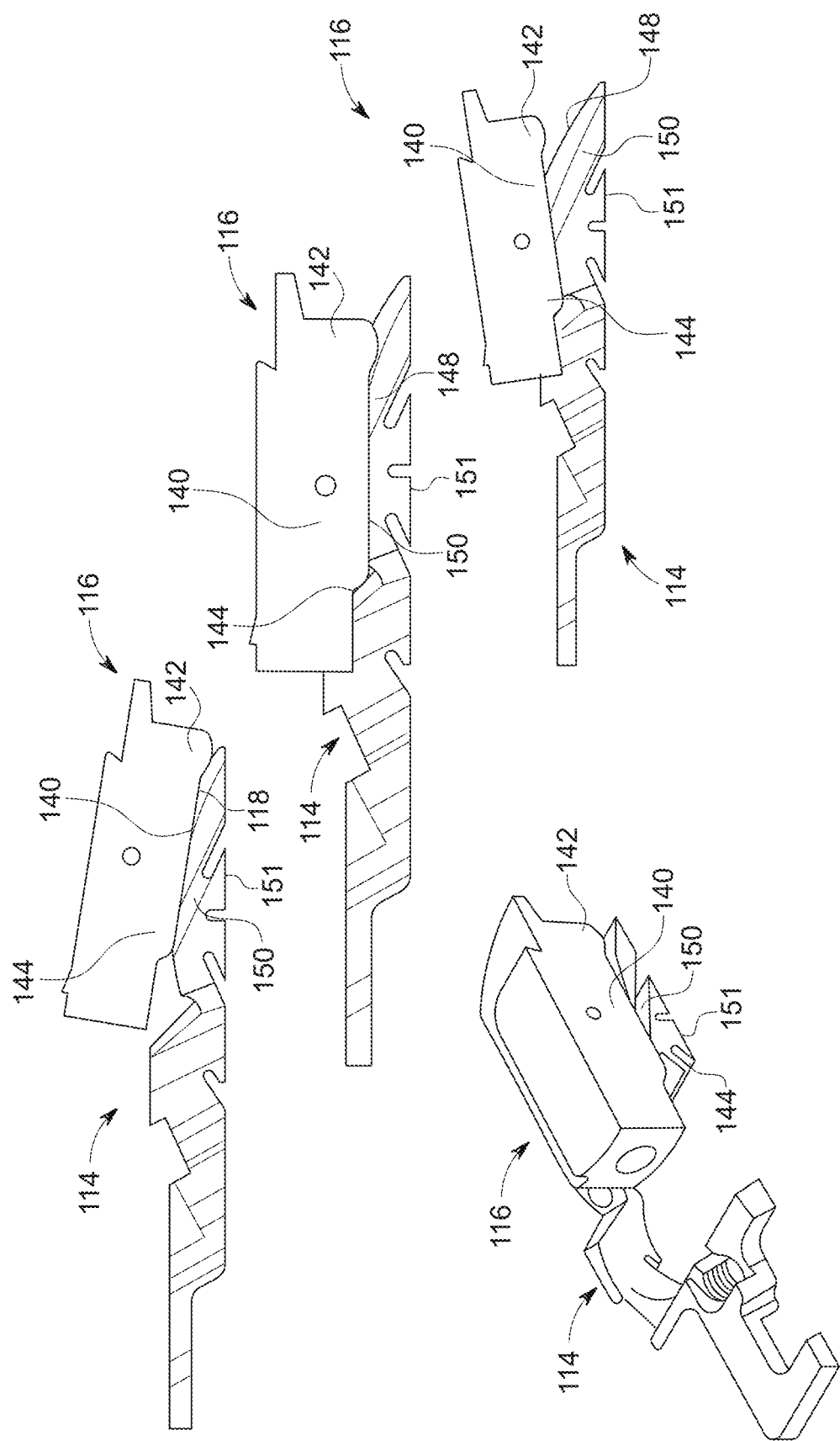
FIG. 55 illustrates a series of cross-sectional views of the talar trial guide of FIG. 29 engaged with the tibial trial insert of FIG. 19 along a range of motion therebetween, in accordance with an aspect of the present disclosure.
Figure 56:
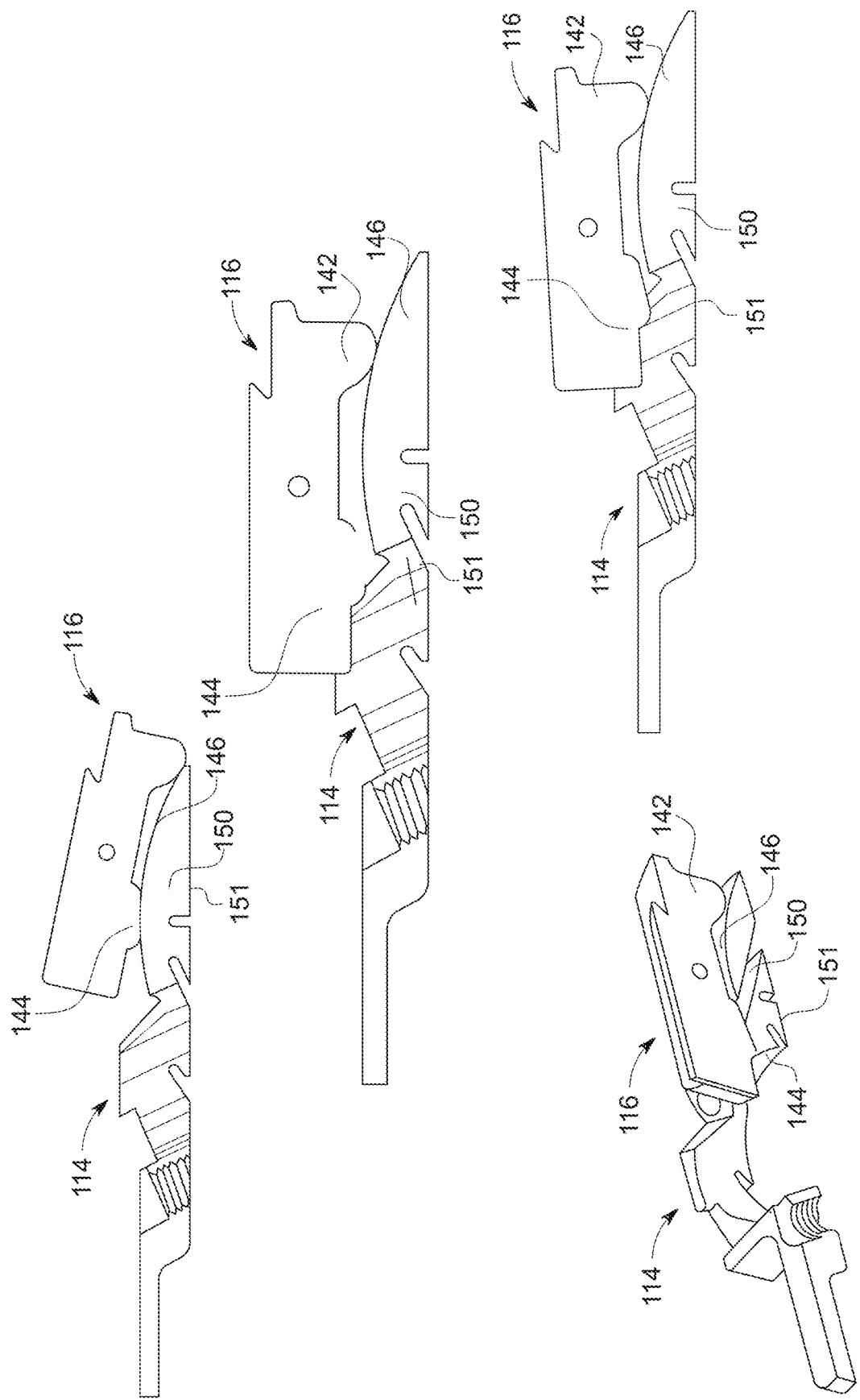
FIG. 56 illustrates a series of additional cross-sectional views of the talar trial guide of FIG. 29 engaged with the tibial trial insert of FIG. 19 along a range of motion therebetween, in accordance with an aspect of the present disclosure.

As shown in FIGS. 4, 19-22, 24-26 and 53-56, the distal side of the tibial trial insert 116 opposing the projection 135 includes at least one posterior rail portion 142 and at least one anterior rail portion 144 that are each extended along the medial-lateral direction and spaced from each other along the anterior-posterior direction. The at least one posterior rail portion 142 and the at least one anterior rail portion 144 provide sliding/gliding articulation over an articulation surface 146 of the talar trial component 114, and thereby about a point or axis of rotation of the talar trial component 114 (and thereby a point or axis of a corresponding talar component 14) and/or the talar 4, as shown in FIGS. 2, 4, 53 and 56. In some embodiments, the at least one posterior rail portion 142 and the at least one anterior rail portion 144 provide sliding/gliding articulation over the articulation surface 146 of the talar trial component 114 about an axis of rotation of the talar trial component 114 and/or the talar 4 that extends along the medial-lateral direction (e.g., provides sagittal rotation of the talar trial component 114 over the talar trial component 114), as shown in FIG. 56.

Figure 25:
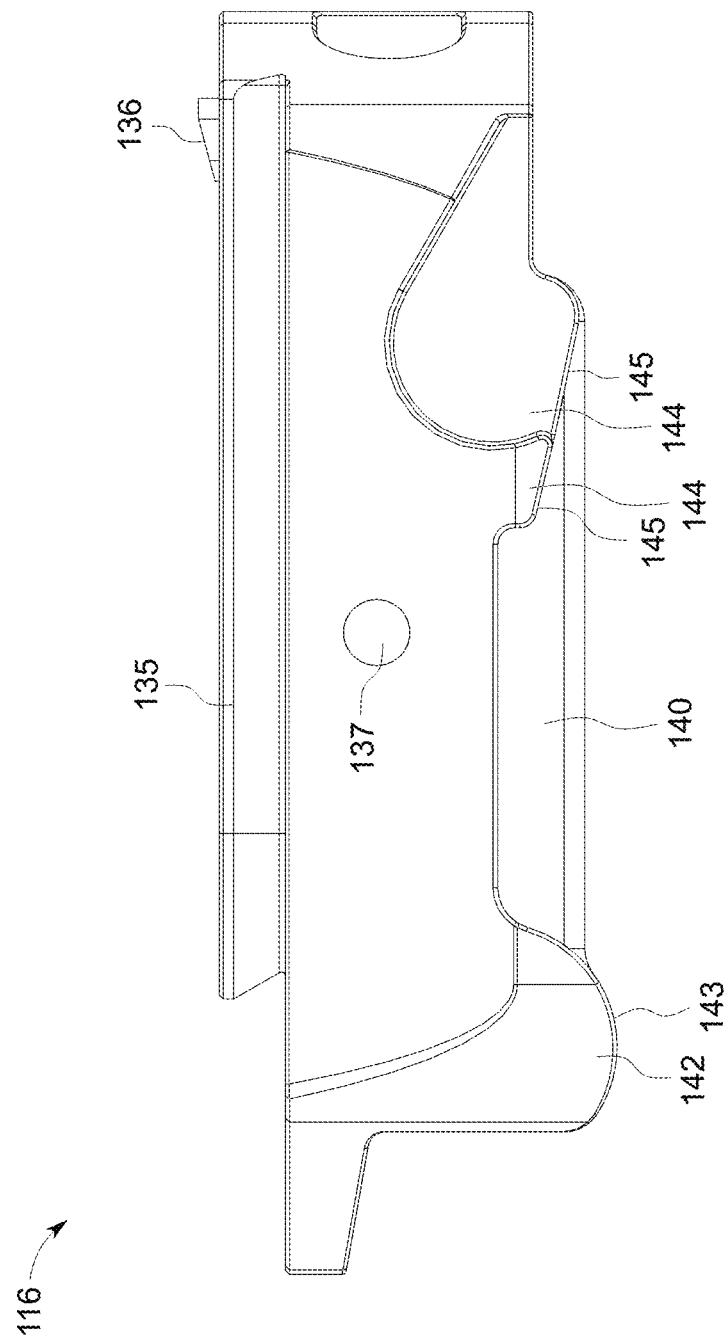
FIG. 25 illustrates a medial side view of the tibial trial insert of FIG. 19, in accordance with an aspect of the present disclosure.
Figure 26:
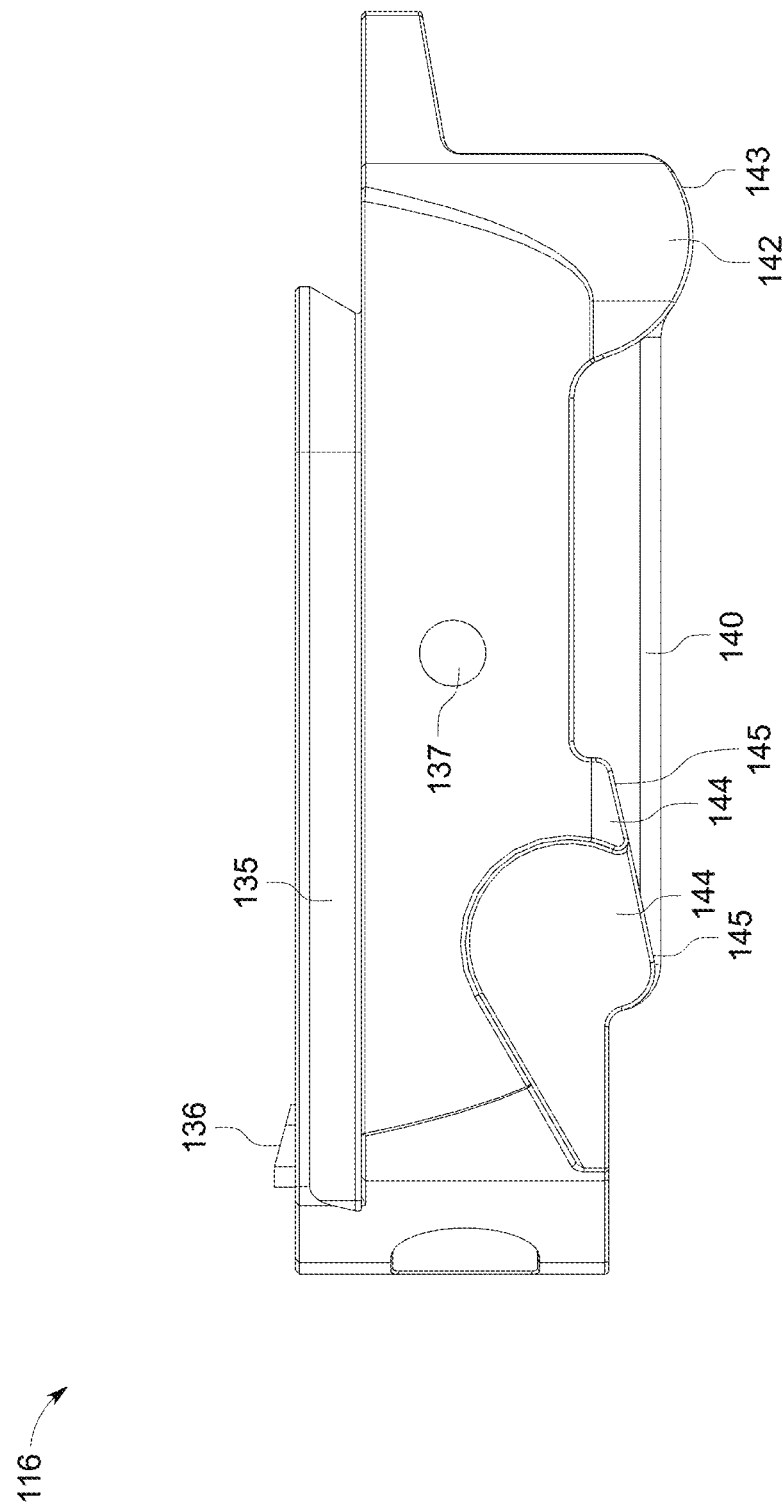
FIG. 26 illustrates a lateral side view of the tibial trial insert of FIG. 19, in accordance with an aspect of the present disclosure.
Figure 27:
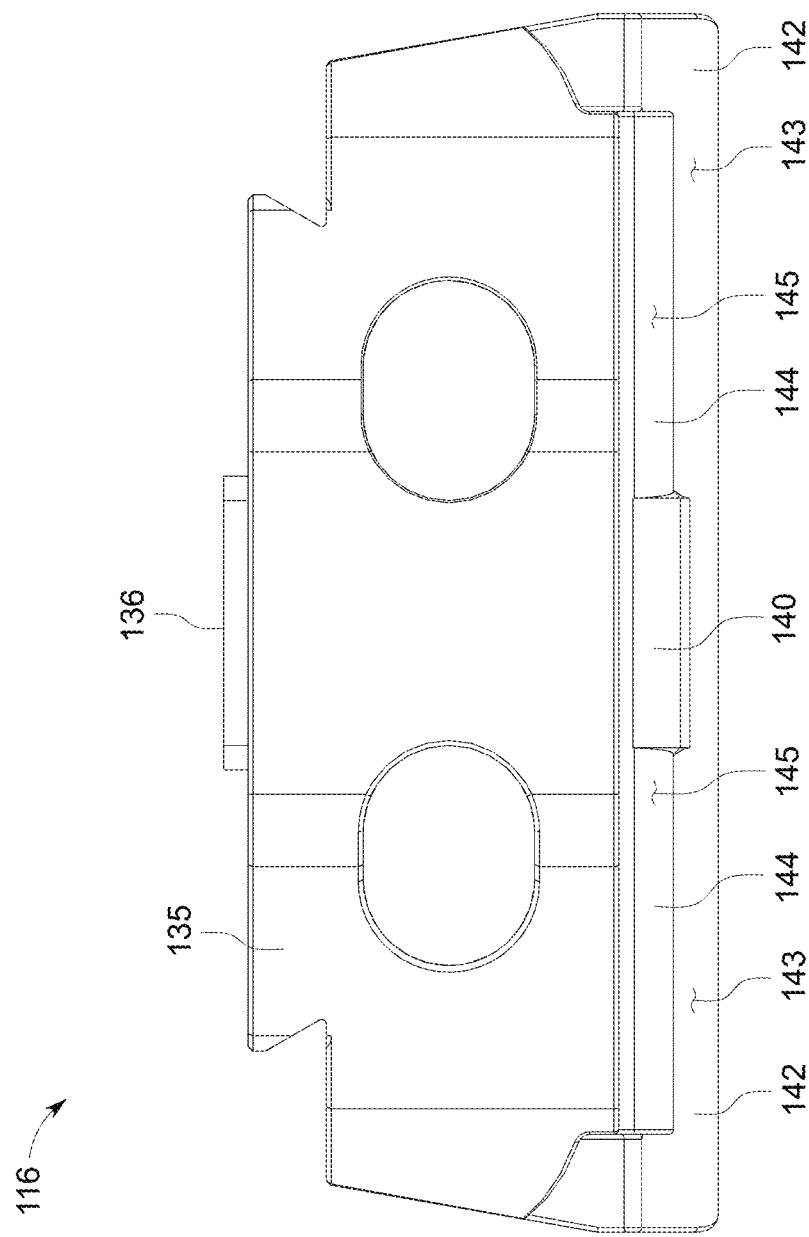
FIG. 27 illustrates an anterior view of the tibial trial insert of FIG. 19, in accordance with an aspect of the present disclosure.
Figure 28:
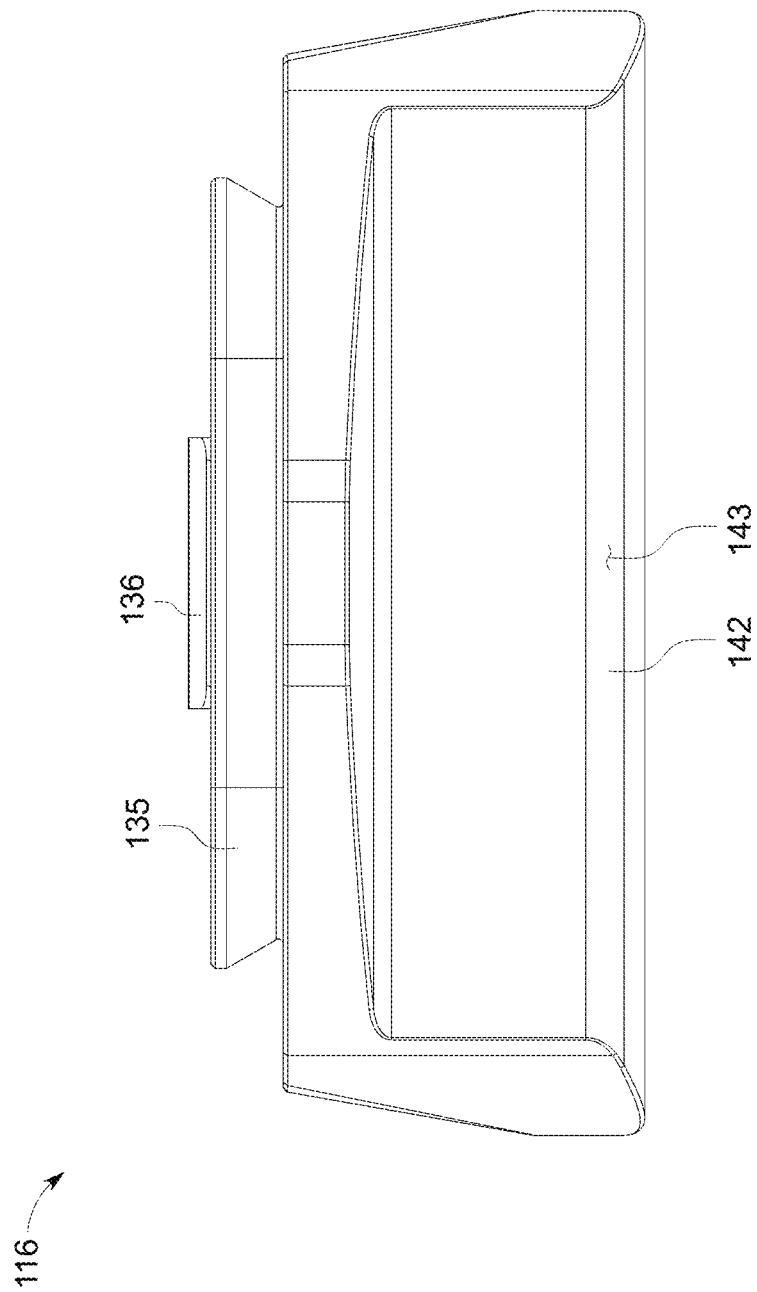
FIG. 28 illustrates a posterior side view of the tibial trial insert of FIG. 19, in accordance with an aspect of the present disclosure.
Figure 29:
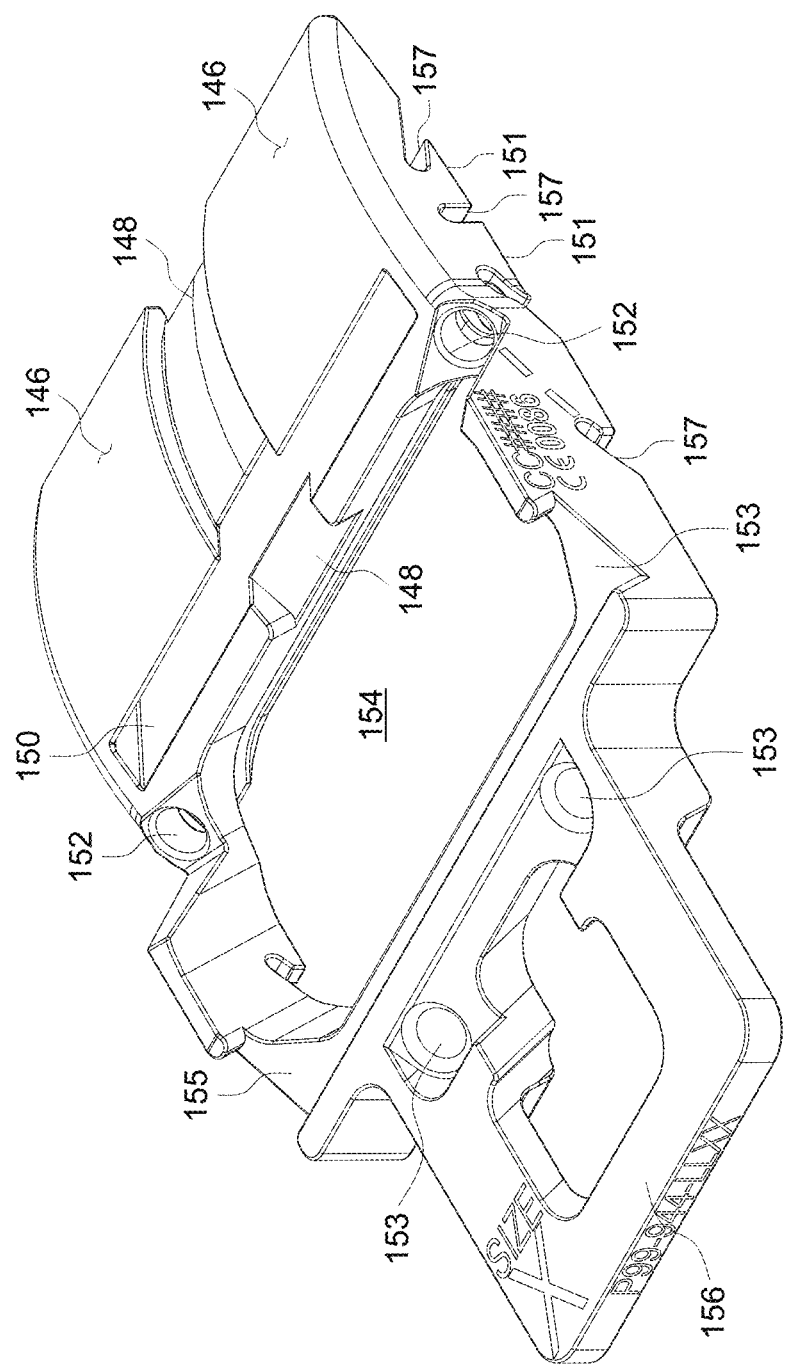
FIG. 29 illustrates an elevational anterior perspective view of the talar trial guide of the TAR trial and guide system of FIG. 2, in accordance with an aspect of the present disclosure.
Figure 30:
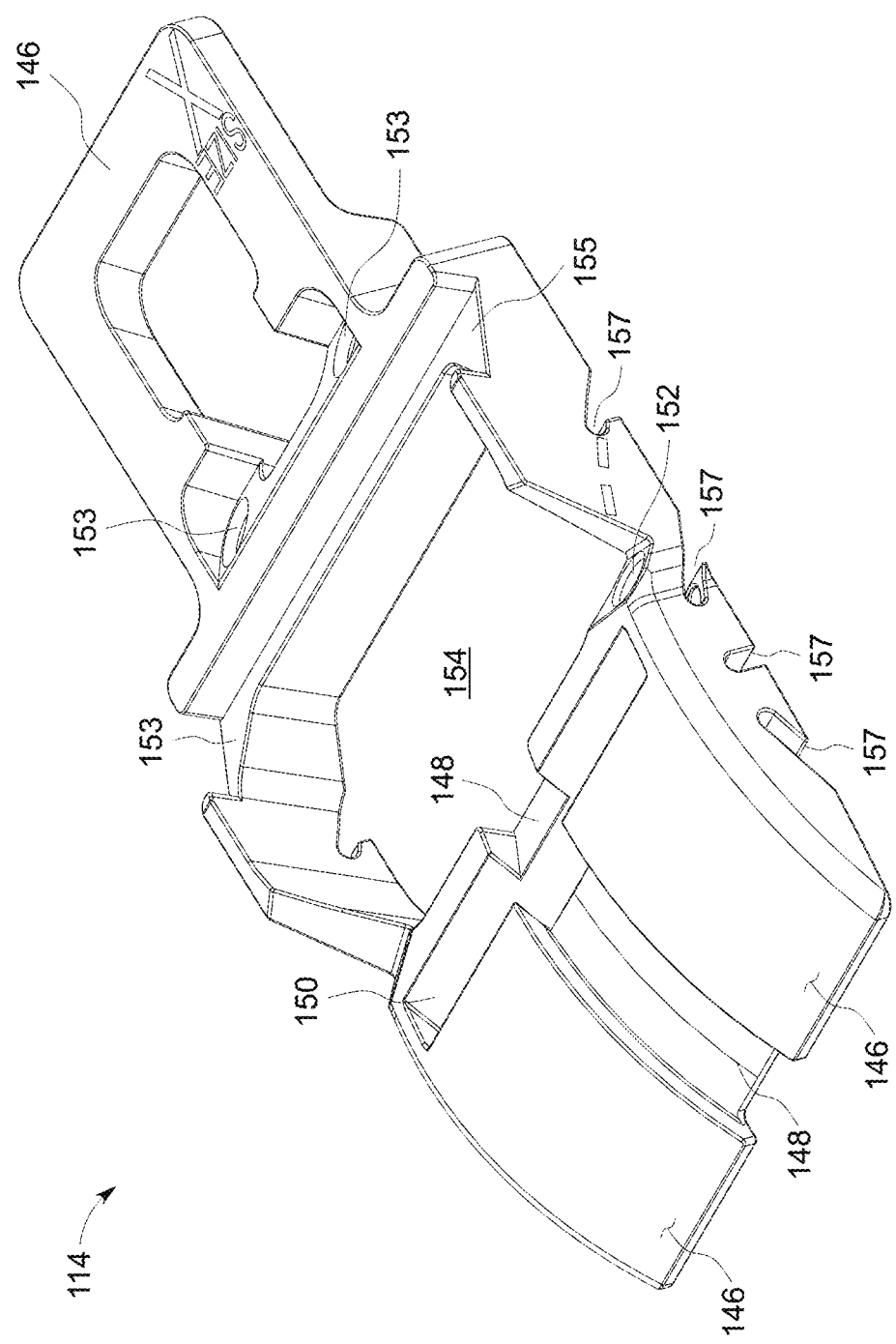
FIG. 30 illustrates an elevational posterior perspective view of the talar trial guide of FIG. 29, in accordance with an aspect of the present disclosure.
Figure 31:
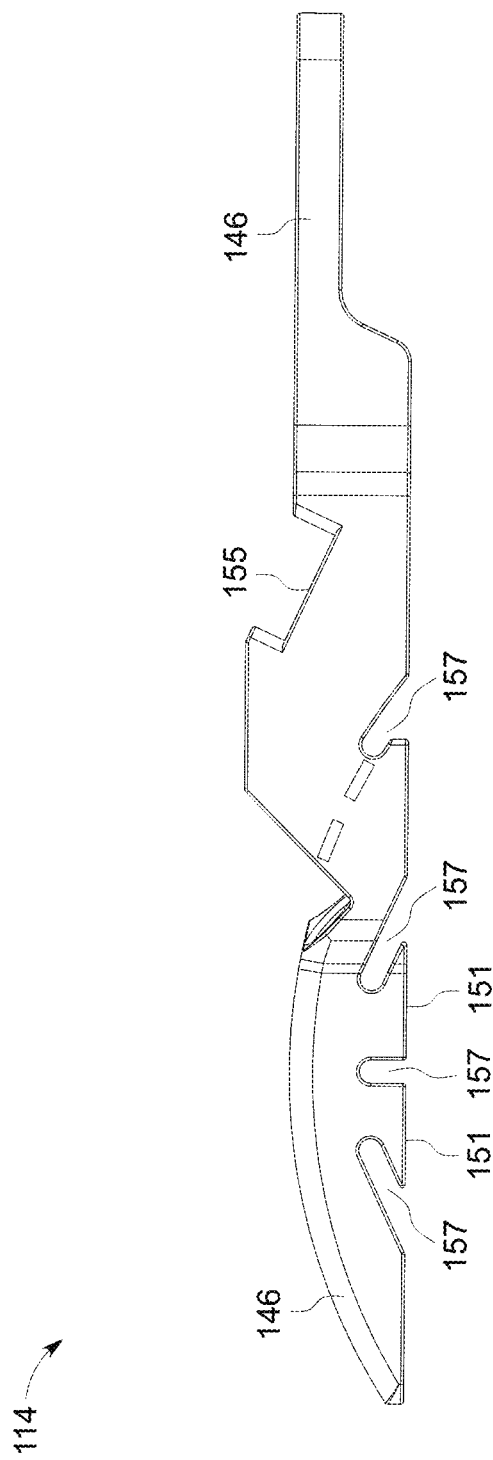
FIG. 31 illustrates a lateral side view of the talar trial guide of FIG. 29, in accordance with an aspect of the present disclosure.
Figure 32:
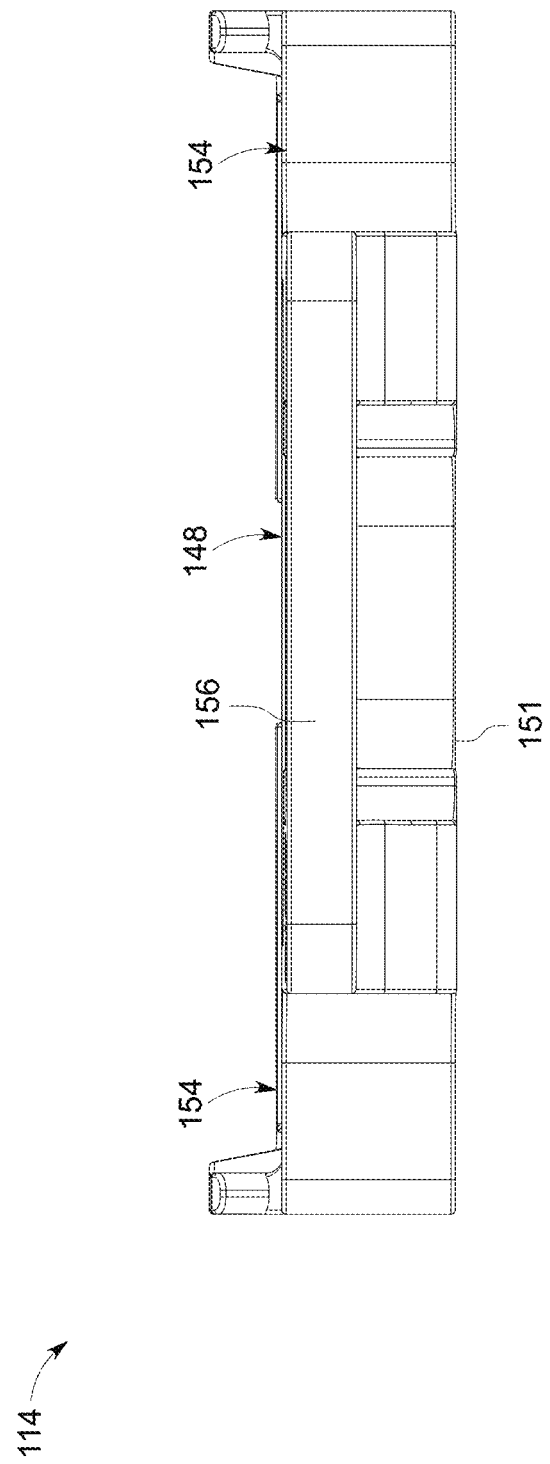
FIG. 32 illustrates an anterior view of the talar trial guide of FIG. 29, in accordance with an aspect of the present disclosure.
Figure 33:
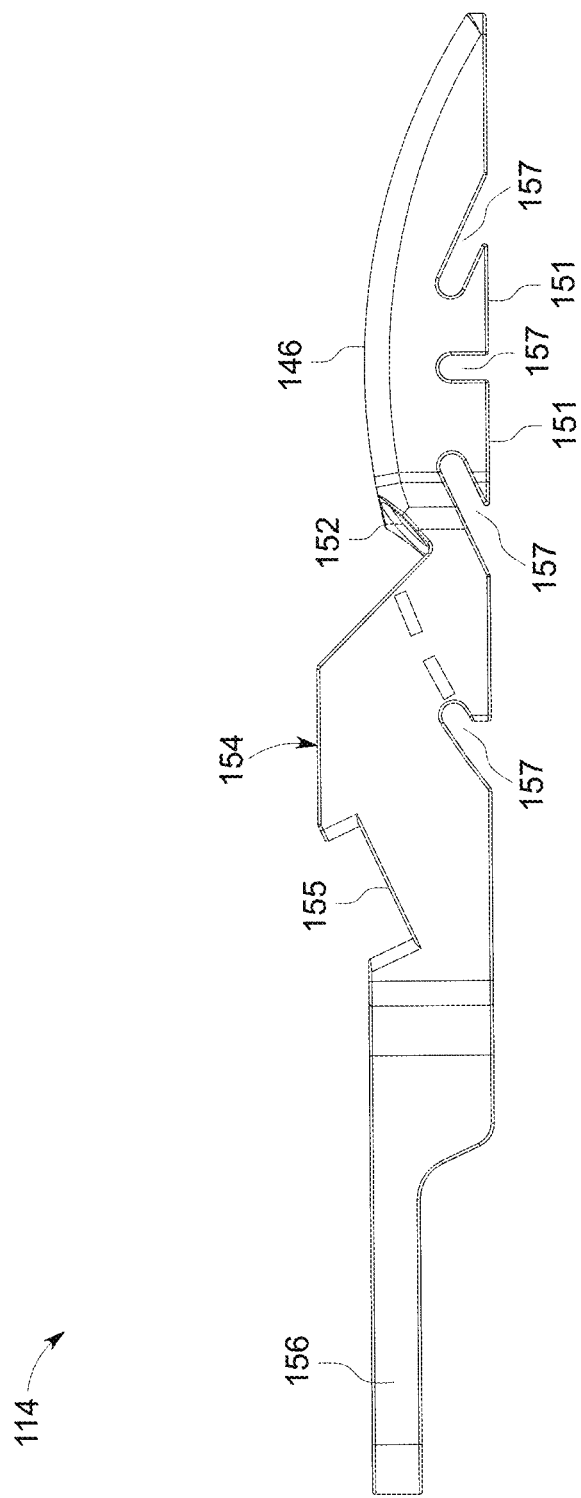
FIG. 33 illustrates a medial side view of the talar trial guide of FIG. 29, in accordance with an aspect of the present disclosure.
Figure 34:
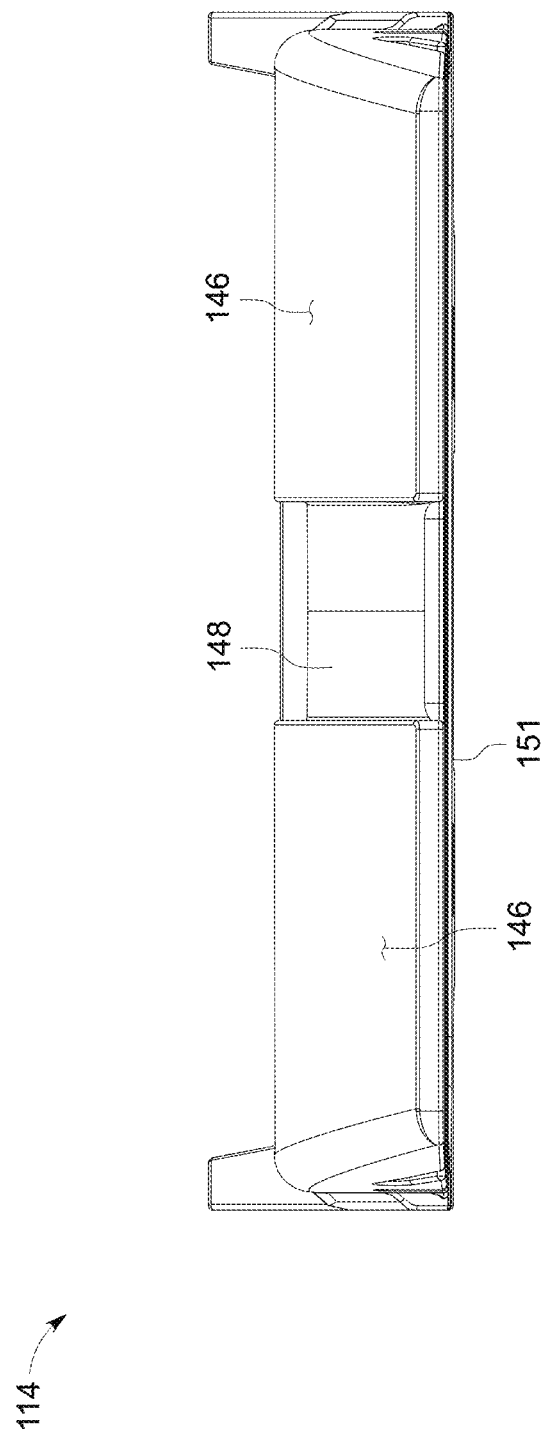
FIG. 34 illustrates a posterior view of the talar trial guide of FIG. 29, in accordance with an aspect of the present disclosure.

As shown in FIGS. 21, 22, 24 and 54, the tibial trial insert 116 may comprise a pair of anterior rail portions 144 that are positioned on respective medial and lateral sides of a strut portion 140 that is extended in the anterior-portion direction to the at least one posterior rail portion 142. In some other embodiments, the tibial trial insert 116 may comprise a single anterior rail portion 144 that is not segmented by the strut portion 140. The strut portion 140 may extend further distally than the distal apex of the engagement surface 145 of the anterior rail portions 144, as shown in FIGS. 25 and 26. As also shown in FIGS. 25 and 26, the engagement surface 145 of the anterior rail portions 144, which engage and articulate on the articulation surface 146 of the talar trial component 114 as shown in FIG. 56, may be flat or convex (i.e., not concave). In some embodiments, the engagement surface 143 of the posterior rail portion 142, which engage and articulate on the articulation surface 146 of the talar trial component 114 as shown in FIG. 56, may be flat or convex (i.e., not concave). In some embodiments, both the engagement surface 143 of the posterior rail portion 142 and the engagement surface 145 of the anterior rail portions 144 are arcuately convex with the engagement surface 143 of the posterior rail portion 142 being defined by a larger radius than a radius defining the engagement surface 145 of the anterior rail portions 144, as shown in FIG. 56. In some examples, the engagement surface 143 of the posterior rail portion 142 is defined by at least a first radius within the range of 3 mm to 10 mm, or more preferably within the range of 3 mm to 5 mm. In some examples, the engagement surfaces 145 of the anterior rail portions 144 are arcuately convex and defined by at least one second radius within the range of 50 mm to 150 mm, or more preferably within the range of 100 mm to 110 mm. It is noted that the posterior portion of the articulation surface 146 of the talar trial component 114 may be interrupted by a cut slot 150, as shown in FIGS. 29, 30, 35, 36, 47, 49-52, 55 and 56 and described further below. If the engagement surface 143 of the posterior rail portion 142 is arcuately convex, the engagement surface 143 may be defined by a radius that is at least twice the length of the anterior-posterior length of the cut slot 150, such as at least 2.5, 3, 3.5, 4, 4.5 or 5 times the width, so that the anterior rail portion 145 can articulate over the cut slot 150 without binding or extending within the cut slot 150 such that the articulation is prevented or unsatisfactorily disrupted, as shown in FIG. 56. If the engagement surface 143 of the posterior rail portion 142 is flat (i.e., planar), the anterior-posterior width of the engagement surface 143 of the posterior rail portion 142 may be wider that the anterior-posterior length of the cut slot 150, such as at least 1.5 times the length, so that the posterior rail portion 142 can articulate over the cut slot 150 without binding or extending within the cut slot 150 such that the articulation is prevented or unsatisfactorily disrupted.

Figure 53:
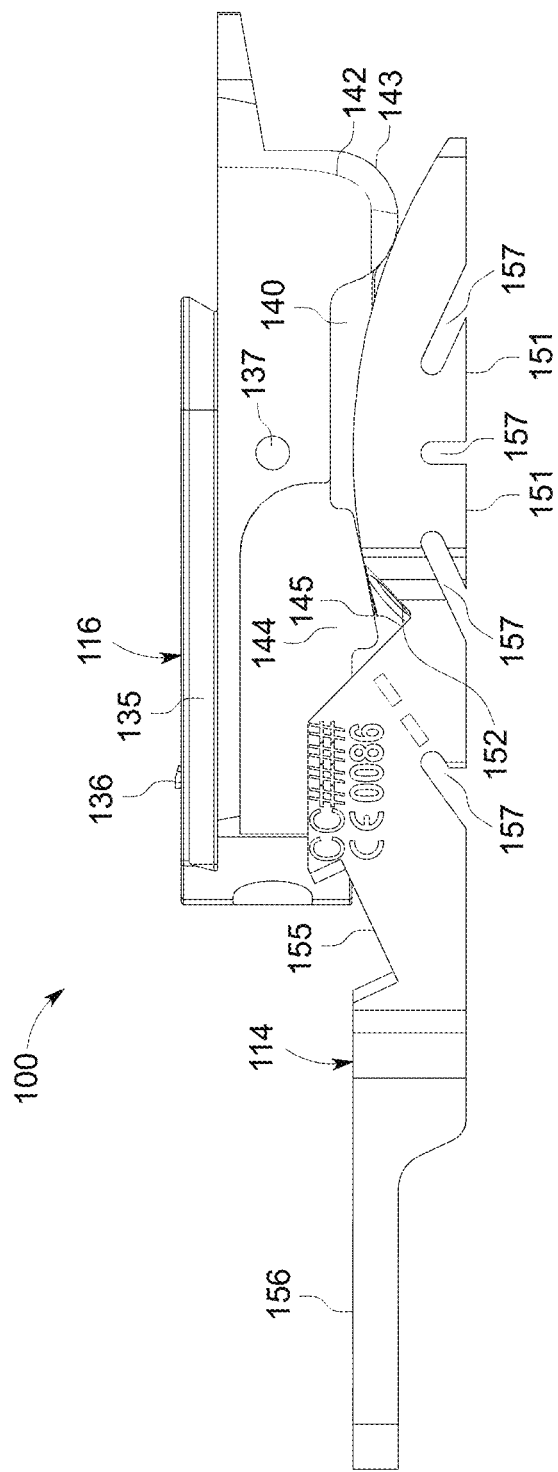
FIG. 53 illustrates a medial side view of the talar trial guide of FIG. 29 engaged with the tibial trial insert of FIG. 19, in accordance with an aspect of the present disclosure.
Figure 54:
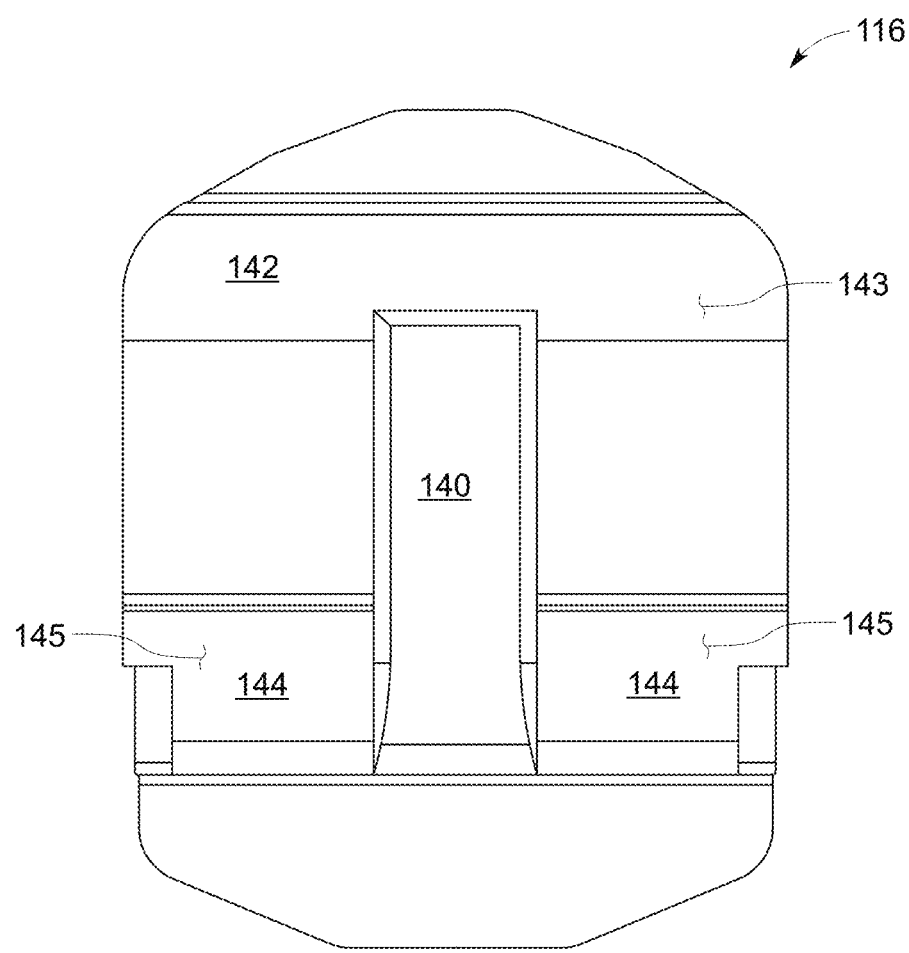
FIG. 54 illustrates a distal view of the tibial trial insert of FIG. 19, in accordance with an aspect of the present disclosure.

As shown in FIG. 53, the anterior rail portion 144 and the posterior rail portions 142 may be spaced along the anterior-posterior direction such that a portion of the height H1 of the articulation surface 146 of the talar trial component 114 extends above (e.g., proximally) the points of contact between the engagement surfaces 143, 145 and the articulation surface 146 that allows the tibial trial insert 116 to be inserted between the tibial trial component 112 and the talar trial component 114 in situ and prevents the tibial trial insert 116 from "squeezing" or otherwise being compressed out from the tibial trial component 112 and the talar trial component 114 in situ. In such embodiments, the posterior rail portion 142 and the anterior rail portions 144 may be spaced along the anterior-posterior direction such that 2 mm of height H1 of the articulation surface 146 of the talar trial component 114 extends above (e.g., proximally) the points of contact between the engagement surfaces 143, 145 and the articulation surface 146, as shown in FIG. 53. It is noted that differently sized talar trial components 114 (corresponding to differently sized trial components 14) may include articulation surfaces 146 defined by differing radii, and therefore differently sized tibial trial inserts 116 (corresponding to differently sized trial components 14) may include differently configured posterior and anterior rail portions 142, 144 (e.g., differently spaced along the anterior-posterior direction) such that the proper height H1 of the articulation surface 146 (i.e., 2 mm) extends above (e.g., proximally) the points of contact between the engagement surfaces 143, 145 posterior and anterior rail portions 142, 144 and the articulation surface 146.

Figure 49:
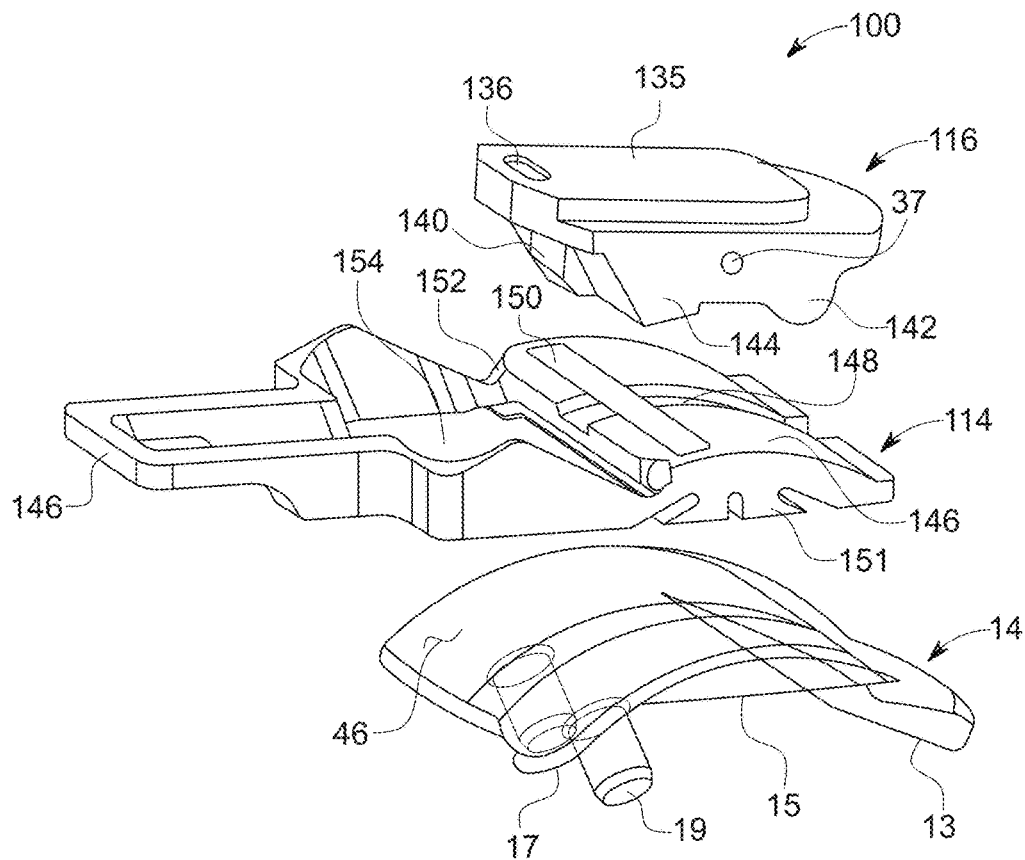
FIG. 49 illustrates a medial perspective exploded view of the talar trial guide of FIG. 29, the tibial trial insert of FIG. 19 and the talus component of FIG. 37, in accordance with an aspect of the present disclosure.
Figure 50:
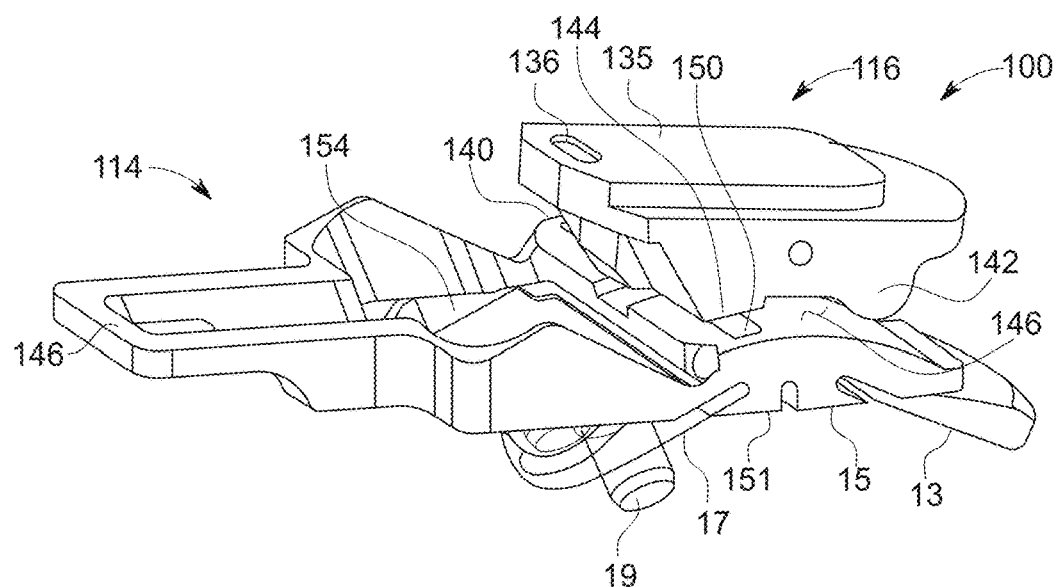
FIG. 50 illustrates a medial perspective view of the talar trial guide of FIG. 29 engaged with the tibial trial insert of FIG. 19, and the talus component of FIG. 37 overlaid on the tibial trial insert of FIG. 19, in accordance with an aspect of the present disclosure.
Figure 51:
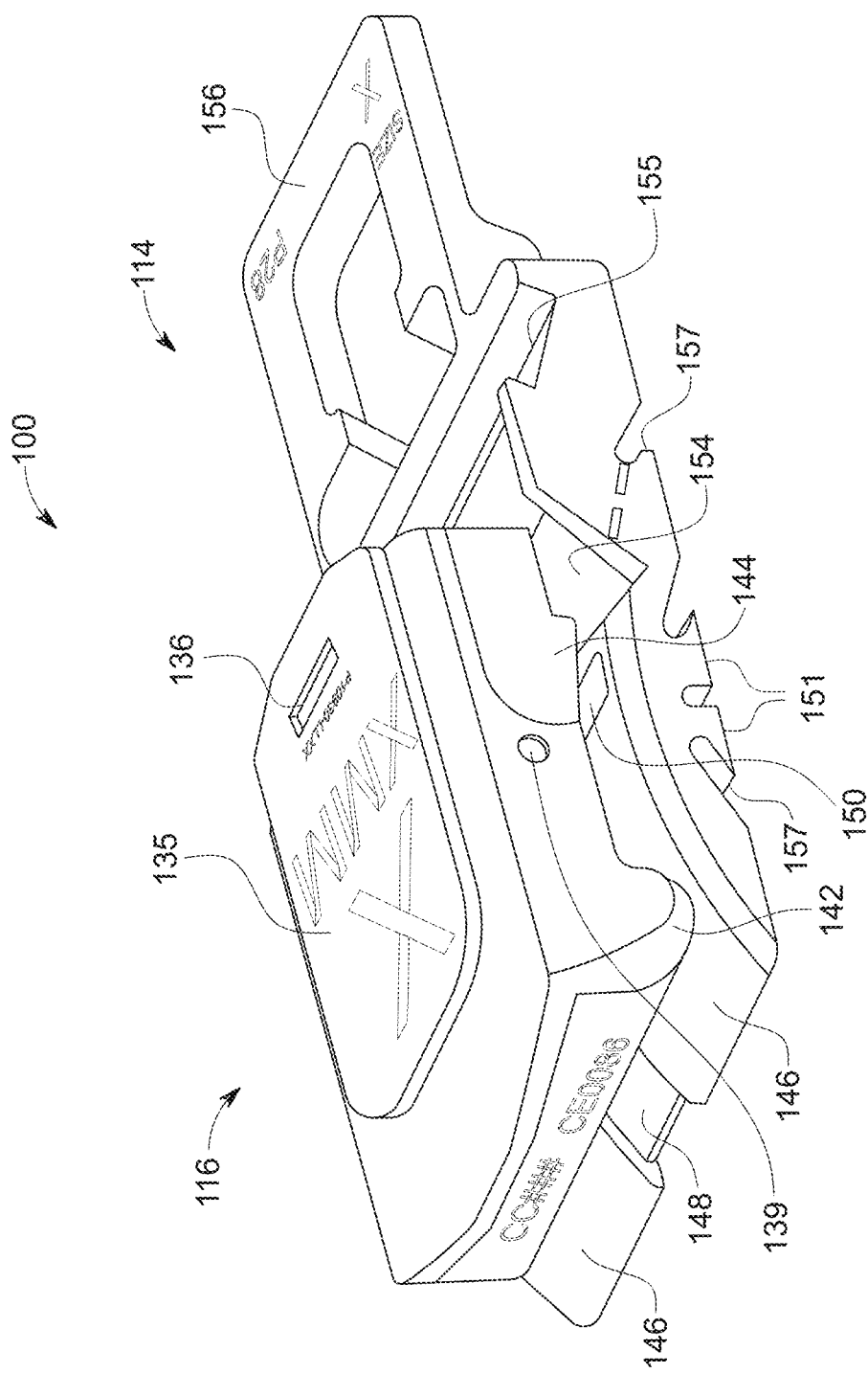
FIG. 51 illustrates a posterior elevational perspective view of the talar trial guide of FIG. 29 engaged with the tibial trial insert of FIG. 19, in accordance with an aspect of the present disclosure.
Figure 52:
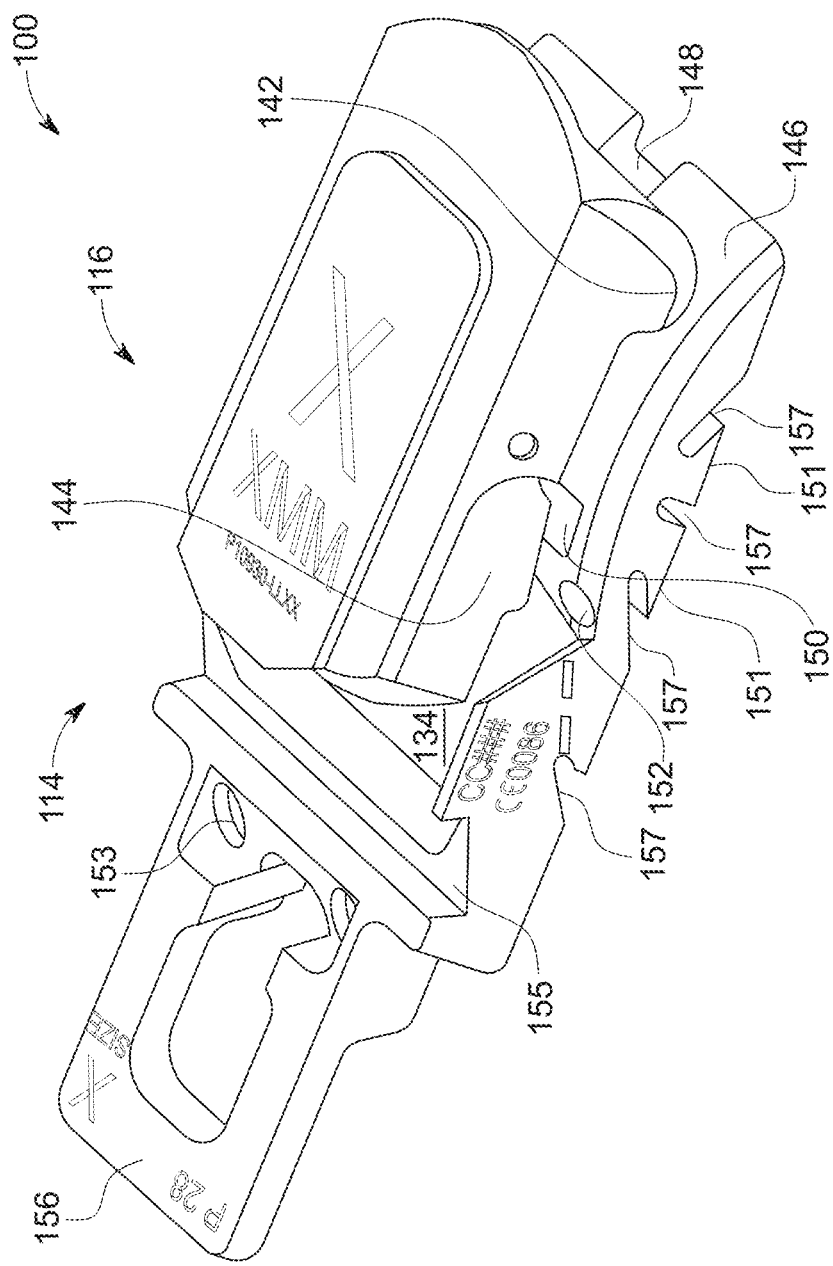
FIG. 52 illustrates an anterior elevational perspective view of the talar trial guide of FIG. 29 engaged with the tibial trial insert of FIG. 19, in accordance with an aspect of the present disclosure.

As also shown in FIGS. 4, 19-22, 24-26, 54 and 55, the strut portion 140 is extended along the anterior-portion direction. As shown in FIGS. 49, 50 and 55, the strut portion 140 seats within a strut slot 148 in the articulation surface 146 of the talar trial component 114 that corresponds to the medial-lateral width, and is at least as deep as the strut 140 on the proximal-distal direction, of the talar trial component 114 to lock relative motion/rotation of the tibial trial insert 116 and the talar trial component 114 about the inversion-eversion (I-E) direction (i.e., lock inversion-eversion rotation) over the articulation range of motion. The strut portion 140 and strut slot 148 may thereby also fix the tibial trial insert 116 and the talar trial component 114 along the medial-lateral direction. As shown in FIGS. 21, 22, 24, 54 and 55, the strut portion 140 may extend from/past the anterior rail portions 144 to an anterior portion of the posterior rail portion 142 along the anterior-posterior direction.

As shown in FIGS. 29-36, the posterior end portion of the proximal side of the talar trial component 114 may include the articulation surface 146, the strut slot 148 and the cut slot 150. As noted above, the articular surface 146 of the tibial trial insert 116 may be convex (in the anterior-posterior direction), and the posterior and anterior rails 142, 144 of the tibial trial insert 116 may engage and articulate thereover via a sliding/gliding motion. The articular surface 146 may be arcuately convex along the anterior-posterior direction, and defined by at least one radius extending from a point or axis of rotation of the corresponding talar component 14 and/or the talus 4. In some embodiments, the articular surface 146 may be flat/linear in the medial-lateral direction. The at least one radius of the articular surface 146 may thereby corresponds, approximate or generalize the articular surface 46 of the corresponding talar component 14. For example, the articular surface 146 at least one radius within the range of 13 mm to 37 mm, or 18 mm to 22 mm, or 23 mm to 27 mm. In some embodiments, as shown in FIGS. 29-36, the articular surface 146 of the tibial trial insert 116 is defined by a single radius, such as a single radius within the range of 13 mm to 37 mm, or 18 mm to 22 mm, or 23 mm to 27 mm. It is noted that differently sized talar trial components 114 (corresponding to differently sized trial components 14) may include articulation surfaces 146 defined by differing radii. For example, differently sized talar trial components 114 may include differing anterior-posterior lengths, medial-lateral widths and/or proximal-distal thicknesses. Such differently sized talar trial components 114 may also include articulation surfaces 146 defined by differing radii, such as radii that differ by ½-2 mm, or by 1 mm, for example (e.g., each within the range of 13 mm to 37 mm, or 18 mm to 22 mm, or 23 mm to 27 mm). In some embodiments, some differently sized talar trial components 114 may include articulation surfaces 146 defined by the same radius.

As shown in FIGS. 29, 30, 35 and 36, the cut slot 150 may extend through the talar trial component 114 from the proximal side to the distal side thereof. The cut slot 150 may be angled posteriorly as is extends through the talar trial component 114 from the proximal side to the distal side thereof. As explained further below, when a talar engagement surface portion 151 of the posterior end portion of the distal side of the talar trial component 114 engages a resected surface of a portion of a talus 4, the cut slot 150 may be angled posteriorly as is extends through the talar trial component 114 from the proximal side to the distal side thereof such that the cut slot 150 can be utilized as a cut guide for the removal of a posterior portion of the talus 4 that extends (and therefore is angled) distally and posteriorly from the resected proximal surface of the talus 4, as shown in FIGS. 44, 45 and 70-73 (when the talar trial component 114 is pinned to the talus 4). The cut slot 150 may extend through an anterior portion of the articulation surface 146 such that the articulation surface 146 includes a posterior portion on the posterior side of the cut slot 150 and an anterior portion on the anterior side of the cut slot 150.

Figure 35:
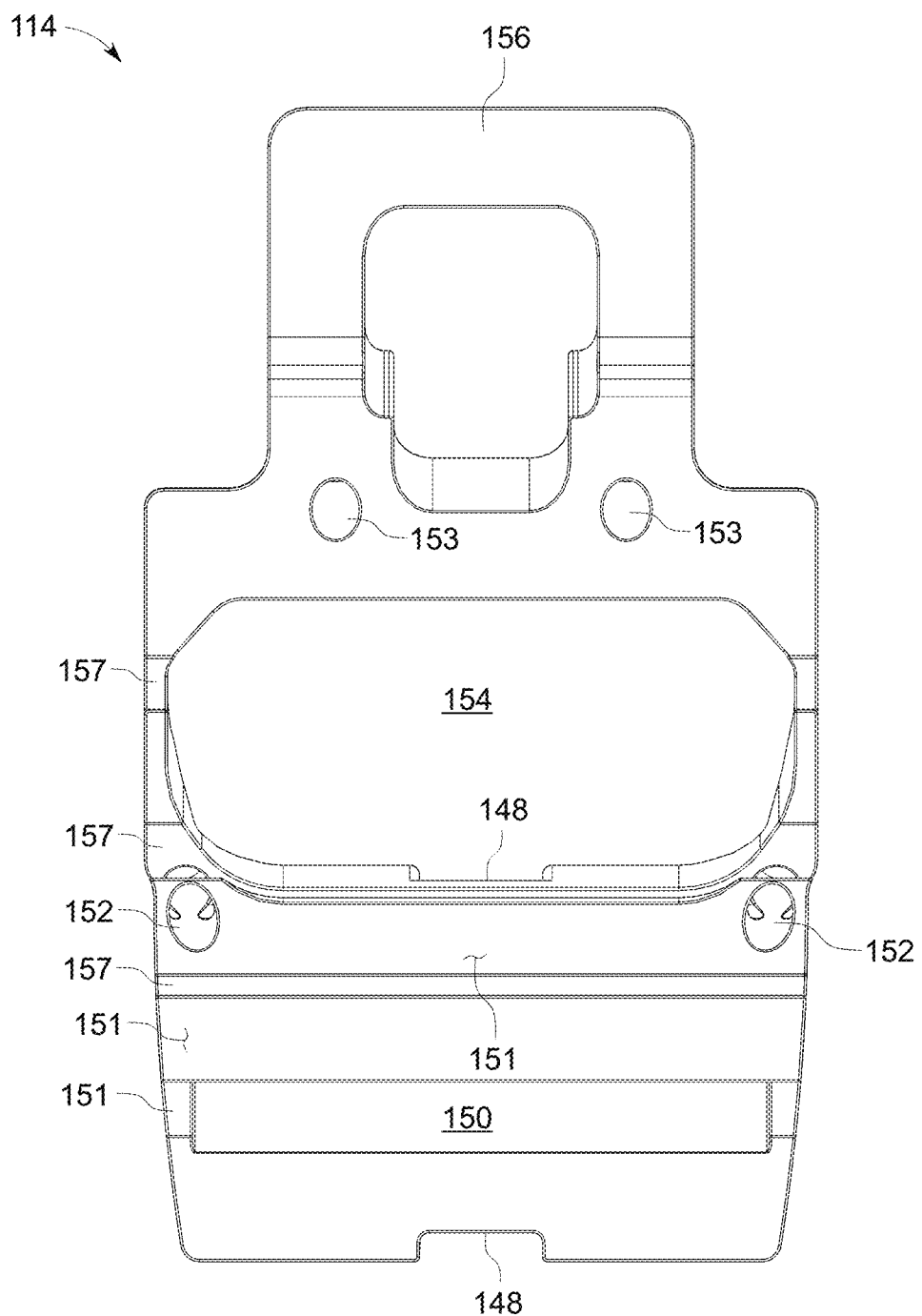
FIG. 35 illustrates a distal view of the talar trial guide of FIG. 29, in accordance with an aspect of the present disclosure.
Figure 36:
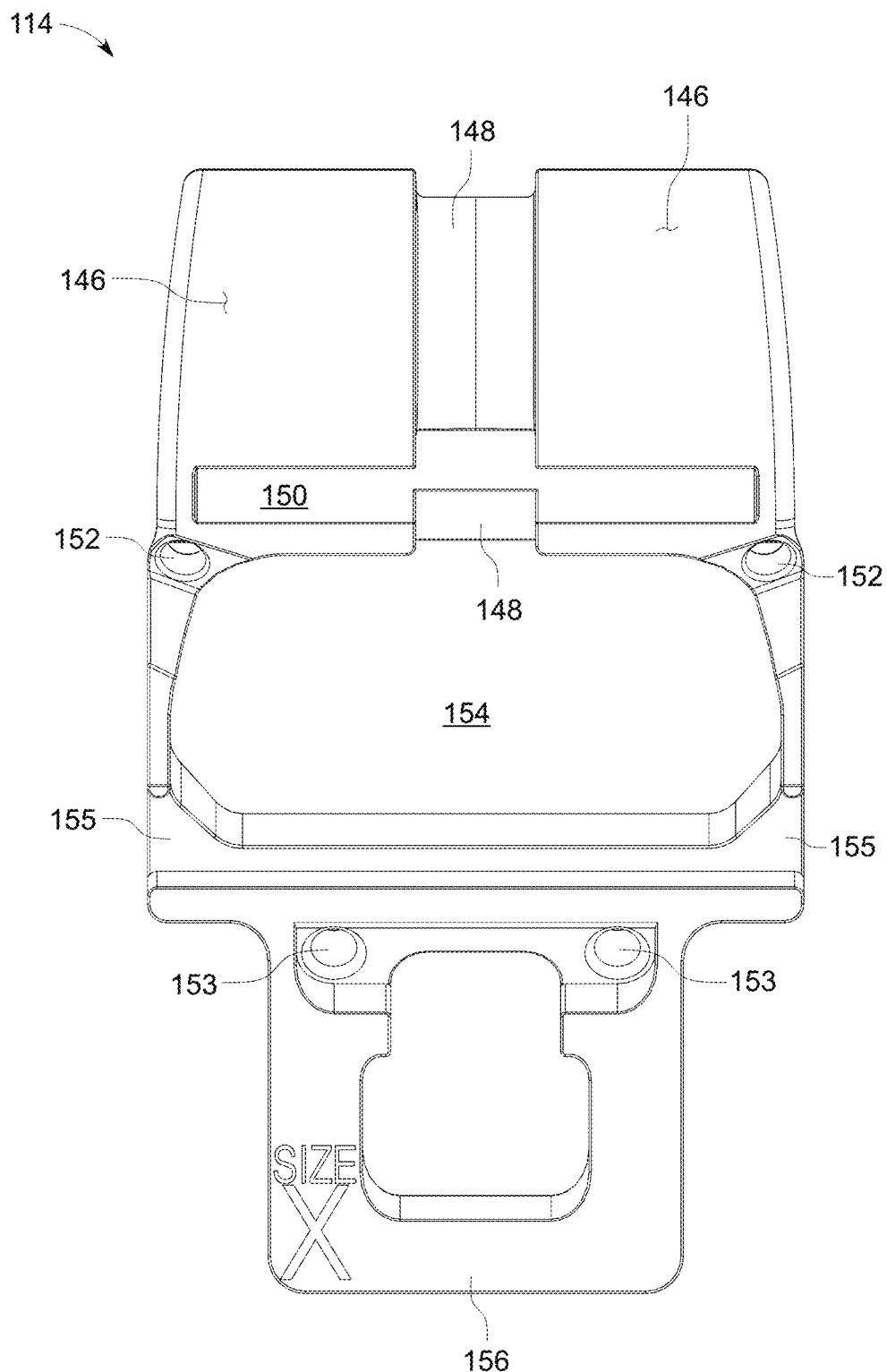
FIG. 36 illustrates a proximal view of the talar trial guide of FIG. 29, in accordance with an aspect of the present disclosure.
Figure 37:
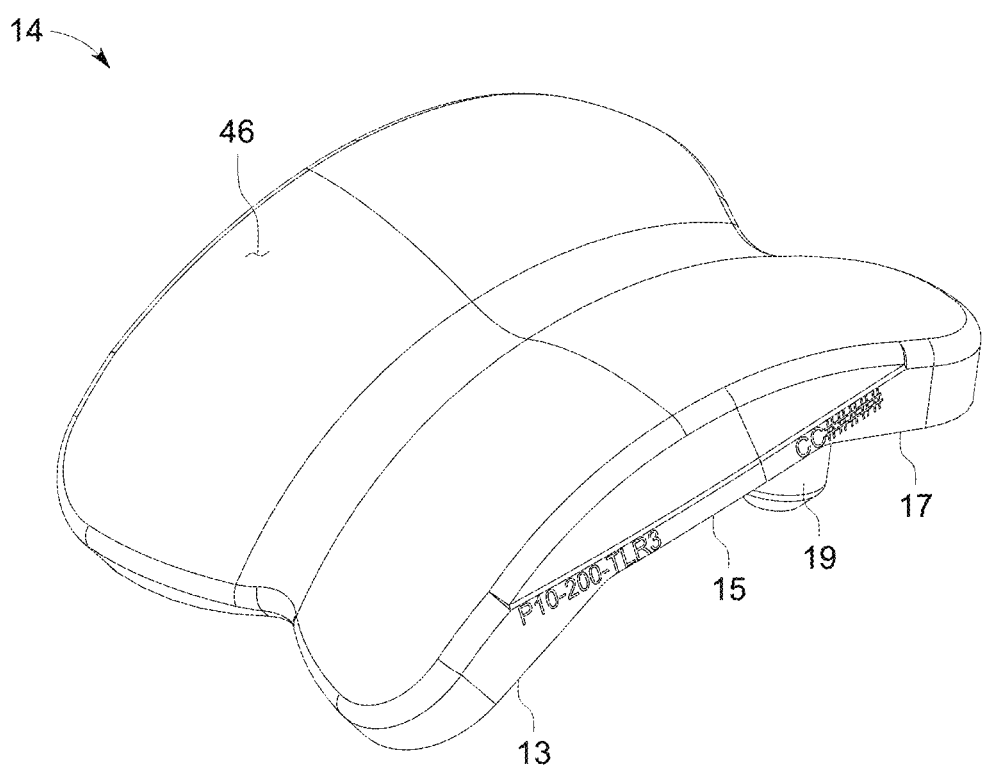
FIG. 37 illustrates a posterior elevational perspective view of the talus component of the TAR prosthesis of FIGS. 1A and 2B, in accordance with an aspect of the present disclosure.

As also shown in FIGS. 29, 30, 35 and 36, the strut slot 148 of the talar trial component 114 may extend along the anterior-posterior direction, and potentially through the entirety of the anterior-posterior length of the articulation surface 146. The strut slot 148 may thereby house the strut 140 of the tibial trial insert 116 therein over the entire range of motion (e.g., along the anterior-posterior direction) between the talar trial component 114 and the tibial trial insert 116 to lock relative I-E rotation over the entire range of motion. The strut slot 148 may also extend across the cut slot 150 such that the strut slot 148 includes a posterior portion on the posterior side of the cut slot 150 and an anterior portion on the anterior side of the cut slot 150. The anterior portion of the strut slot 148 may be utilized by one or more cut guide to resect/chamfer anterior and/or posterior aspects of the talus 4, as described further below. The talar trial component 114 may include at least three pin apertures 152, 153 extending therethrough along the proximal-distal direction, as shown in FIGS. 29, 30, 35 and 36. The pin apertures 152, 153 may be configured to accept a pin, k-wire or other bone fixation member therethrough and into a talus 4. For example, the illustrative embodiment the talar trial component 114 includes at least a pair of first pin apertures 152 that converge (or diverge) as the extend distally (i.e., are angled with respect to the sagittal plane), as shown in FIGS. 35 and 36. As also shown in FIGS. 35 and 36, the illustrative embodiment of the talar trial component 114 includes at least one second pin aperture 153 that is positioned anteriorly from the first pin apertures 152. In some embodiments, the talar trial component 114 may include at least a pair of second pin apertures 153 that are positioned anteriorly from the first pin apertures 152. In such embodiments, second pin apertures 153 may be aligned with each other (i.e., extend parallel on all planes). The pair of first pin apertures 152, and/or the pair of second pin apertures 153 (if provided), may each include a pin aperture positioned on a medial side of the medial-lateral midline of the talar trial component 114, and a pin aperture positioned on the lateral side of the medial-lateral midline of the talar trial component 114. The first and second pin apertures 152, 153 may be angled posteriorly as they extend through the talar trial component 114 from the proximal side thereto to the distal side thereof.

The first pin apertures 152 may facilitate insertion of first pins or other fixation members therethrough and into the talus 4 with the distal bone engagement surface 151 of the talar trial component 114 engaged with the proximal end (e.g., resected) of the talus 2 and positioned between the tibia 2 and the talus 4 (see FIGS. 60-69) with the talar trial component 114 positioned in a desirable location (e.g., the center thereof aligned with the anatomical and/or mechanical axis of the tibia 2 and/or talus 4), to fix or lock the talar trial component 114 to the resected talus 4 (e.g., along the medial-lateral, proximal-distal and anterior-posterior directions). The at least one second aperture 153 may also facilitate insertion of at least one second pin or other fixation member therethrough and into the talus 4 for a third point of fixation of the talar trial component 114 to the talus 4. Such at least one second pin extending through the at least one second aperture 153 may also be utilized as a reference pin for further processing/resecting/cutting the talus 4, such as after removal of the talar trial component 114 from the talus 4 (e.g., a chamfer cutting jig or other cut guide may utilize the at least one second pin for processing/resecting/cutting the talus 4). In some embodiments, the first pin apertures 152 and the at least one second pin aperture 153 may be non-threaded or threaded (e.g., for threaded engagement with a bushing or the like). It is noted that the talar trial component 114 and the talus 4 may need to be placed into plantar flexion to access the first pin apertures 152 and/or the second pin apertures 153 in situ (i.e., to translate pins therethrough) (as the tibial component 112, the tibial insert trial 116 and/or anatomical structure(s) of the patient may block access to the first pin apertures 152 and/or the second pin apertures 153 when the talar trial component 114 and the patient's foot is not in plantar flexion.

As shown in FIGS. 29, 30, 35 and 36, the talar trial component 114 may include an anterior window or aperture 154 extending therethrough from the proximal side to the distal side thereof. In some embodiments, at least a portion of the anterior window 154 may be positioned between the first pin apertures 152, and the second pin apertures 153, if provided, along the medial-lateral direction. In some embodiments, at least a portion of the anterior window 154 may be positioned between the first pin apertures 152 and the at least one second pin aperture 153. As explained further below, when the talar engagement surface portion 151 of the posterior end portion of the distal side of the talar trial component 114 engages a resected surface of a portion of the talus 4, the anterior window 154 may be positioned over the anterior side of the talus 4 such that the anterior window 154 can be utilized with a cut guide for the removal of an anterior portion of the talus 4 that extends (and therefore is angled) distally and anteriorly from the resected surface of the talus 4, as shown in FIGS. 44, 45, 47, 48 and 70-73 (when the talar trial component 114 is pinned to the talus 4).

As also shown in FIGS. 29, 30, 35 and 36, the talar trial component 114 may include at least one anterior cut guide support surface 155 (which may be recessed from the proximal surface of the talar trial component 114). The anterior cut guide support surface 155 may be angled anteriorly as it extends partially through the talar trial component 114 from the proximal side toward the distal side thereof. The anterior cut guide support surface 155 is positioned anteriorly of at least a portion of the anterior window 154, as shown in FIGS. 29, 30, 35 and 36. The anterior cut guide support surface 155 may be configured to accept and support an anterior cut guide over the anterior window 154. The anterior cut guide support surface 155 may be configured to prevent movement of a cut guide positioned thereon (as explained further below) relative to the talar trial component 114 along the anterior-posterior direction and the distal direction (and potentially along the medial-lateral direction). The anterior end portion of the talar trial component 114 may include a manually engageable handle portion 156 that may be utilized to manipulate the talar trial component 114 and the talus 4 (i.e., the patients foot), such as plantar and dorsal flexion.

Figure 38:
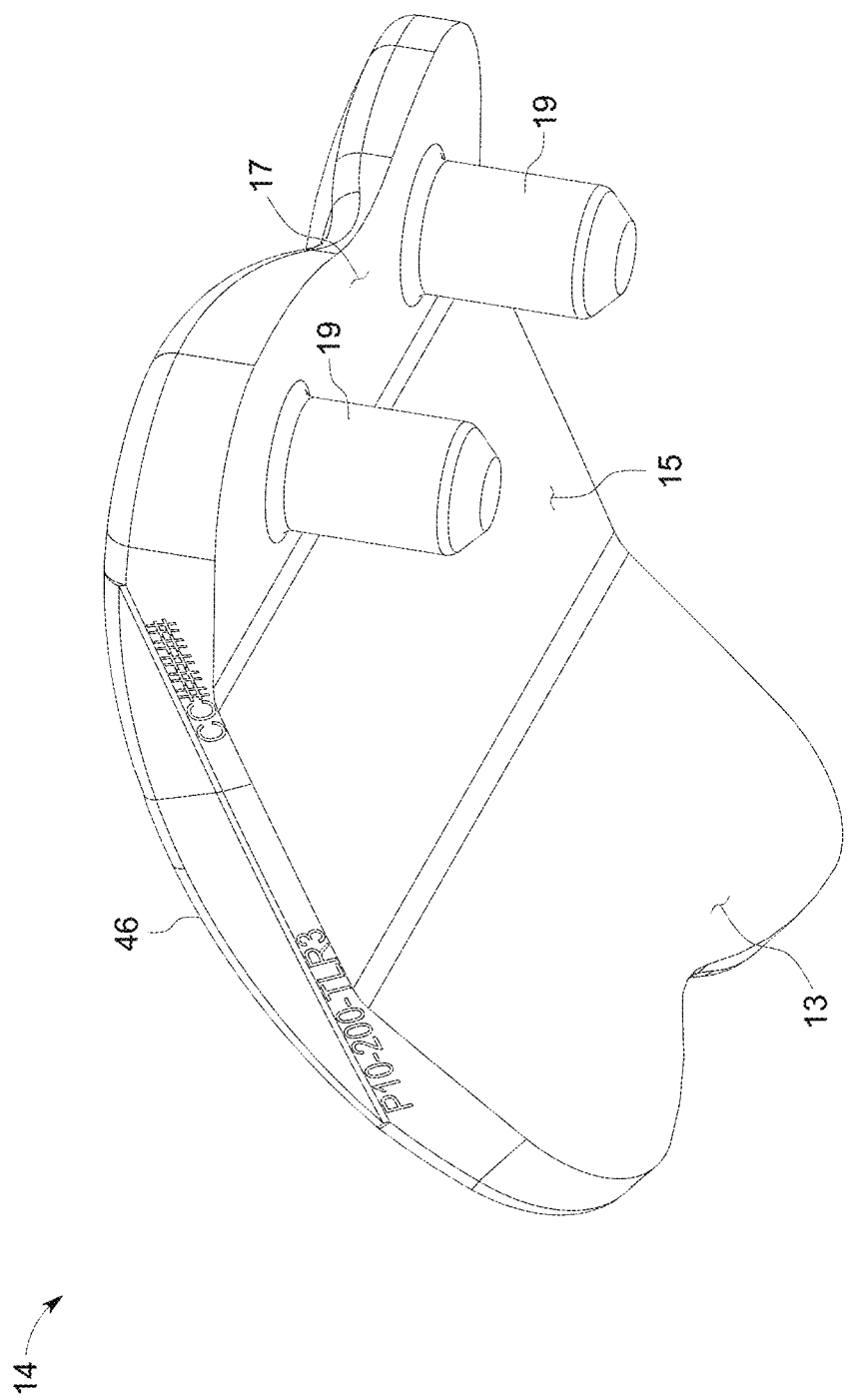
FIG. 38 illustrates an anterior bottom perspective view of the talus component of FIG. 37, in accordance with an aspect of the present disclosure.
Figure 39:
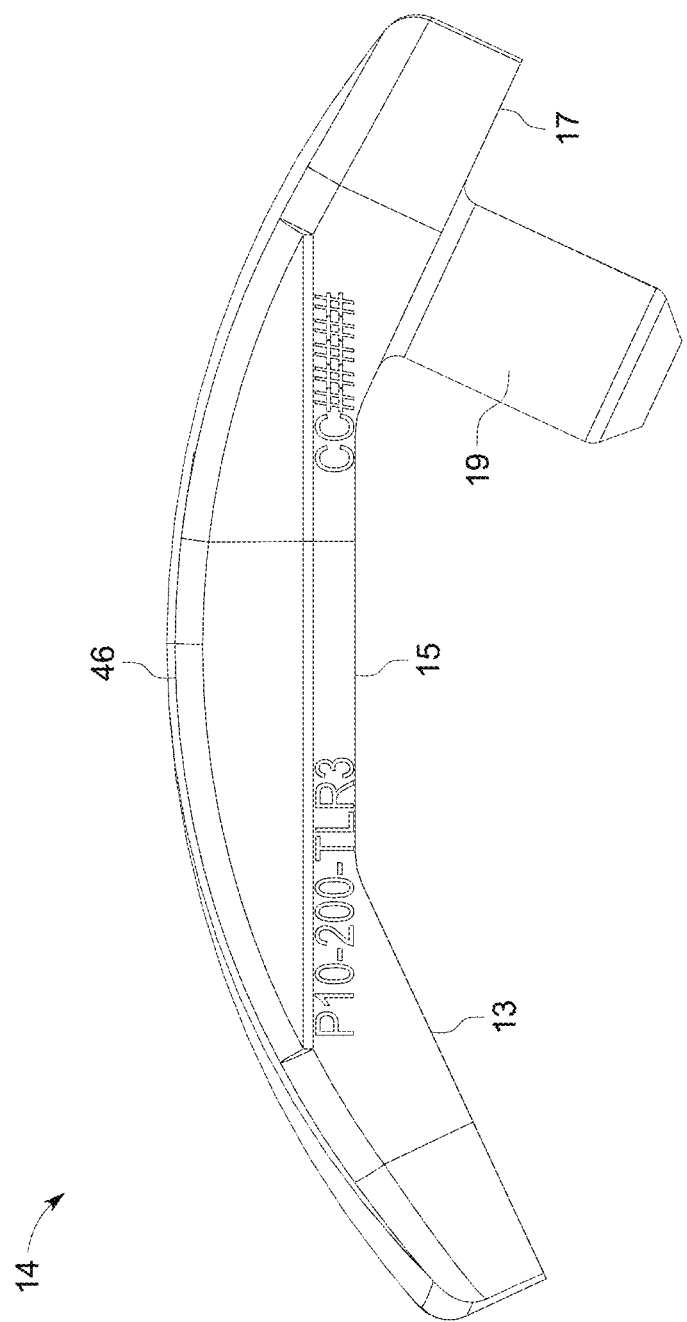
FIG. 39 illustrates a lateral side view of the talus component of FIG. 37, in accordance with an aspect of the present disclosure.
Figure 40:
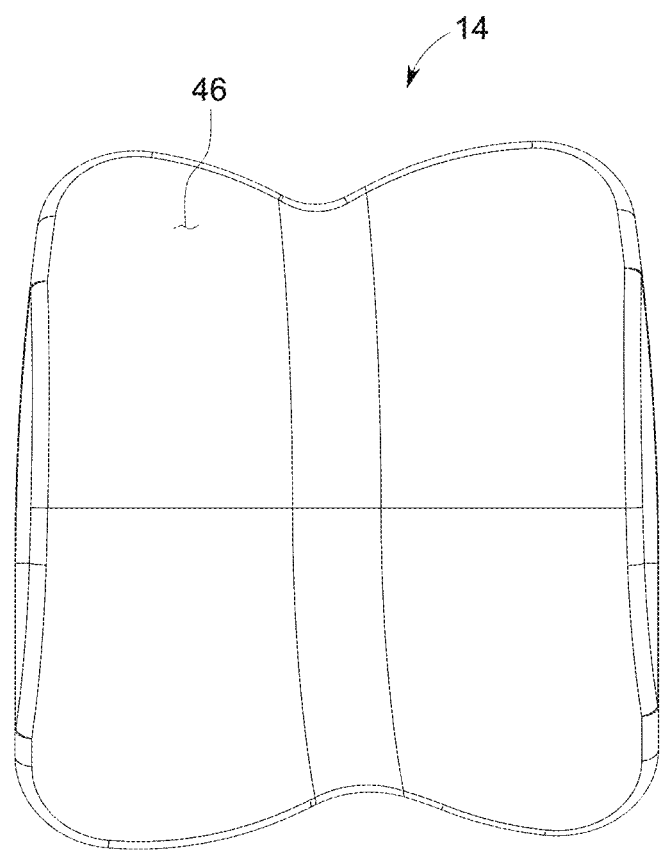
FIG. 40 illustrates a proximal view of the talus component of FIG. 37, in accordance with an aspect of the present disclosure.
Figure 41:
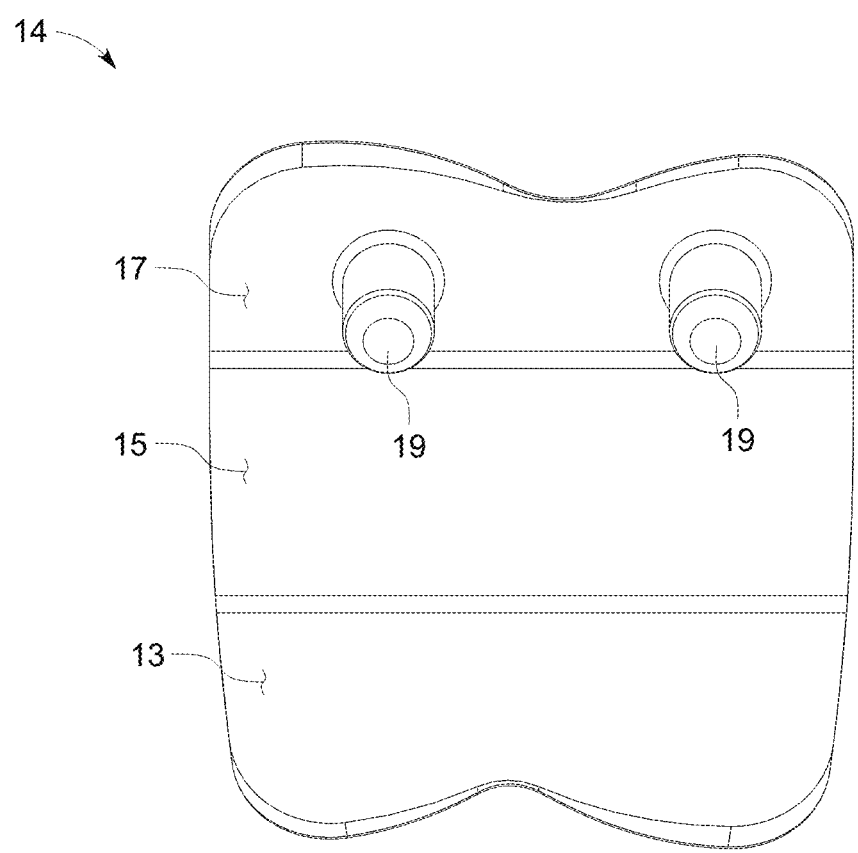
FIG. 41 illustrates a distal view of the talus component of FIG. 37, in accordance with an aspect of the present disclosure.
Figure 42:
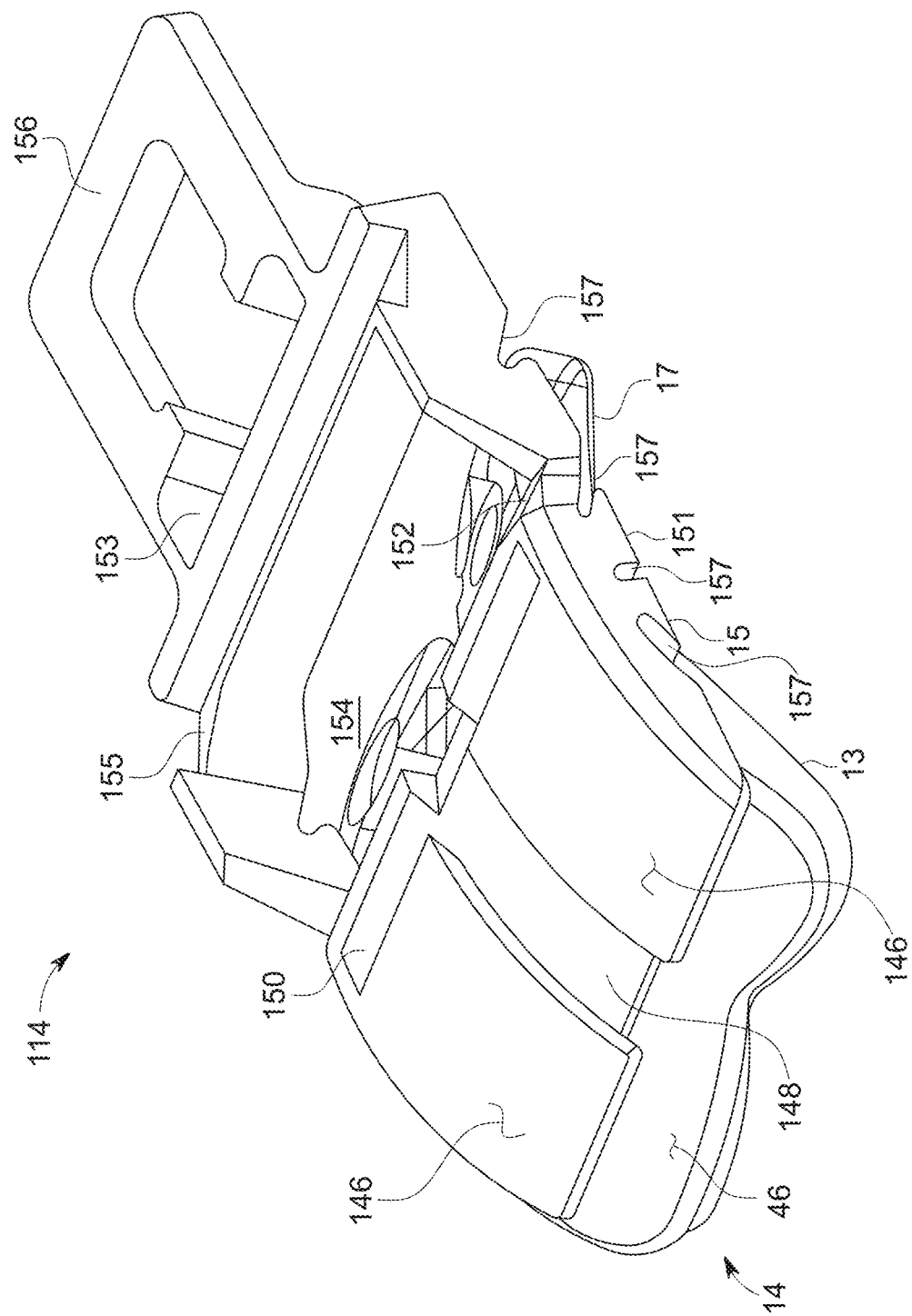
FIG. 42 illustrates a posterior elevational perspective view of the talus component of FIG. 37 overlaid with the talar trial guide of FIG. 29, in accordance with an aspect of the present disclosure.
Figure 43:
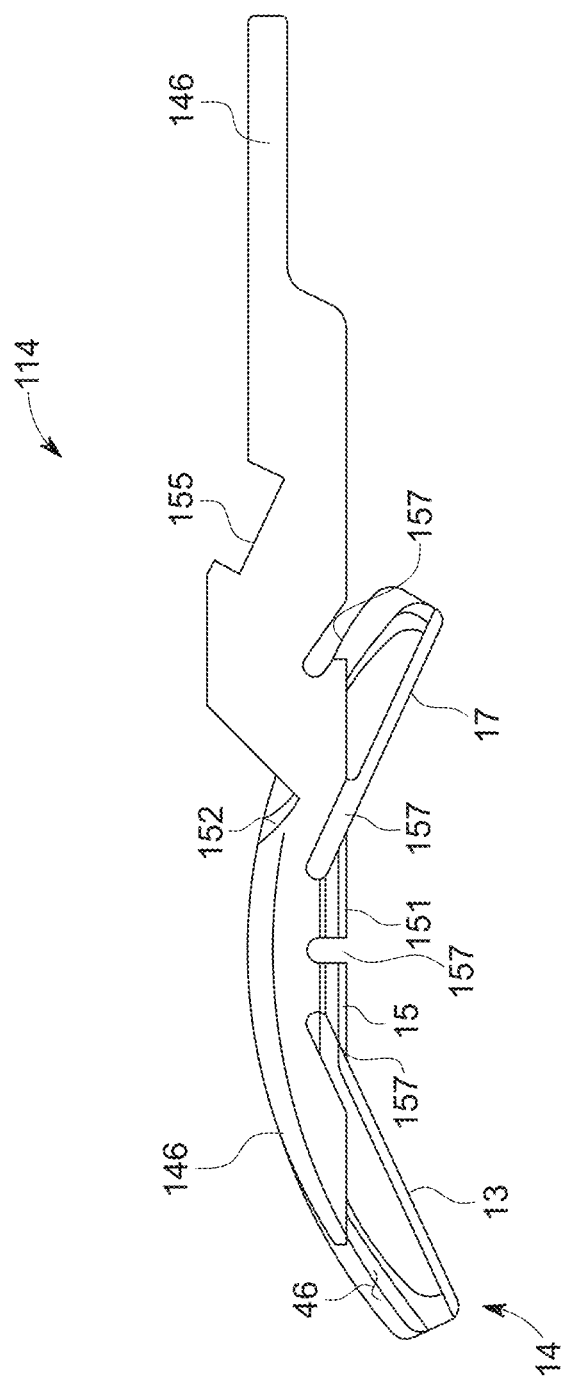
FIG. 43 illustrates a lateral side view of the talus component of FIG. 37 overlaid with the talar trial guide of FIG. 29, in accordance with an aspect of the present disclosure.

As shown in FIGS. 29, 30, 32, 33, 35, 36, 43, 45, 51, 52, 53, 71 and 73, the distal side of the talar trial component 114 may include at least one reference slot or indentation 157 extending therein from at least one of the medial and lateral sides thereof, such as at least one reference slot 157 that is elongated along the medial lateral direction. The at least one reference slot 157 may be visible at least when the talar trial component 114 is viewed along the medial-lateral direction (e.g., visible under fluoroscopy or other imaging in situ), as shown in FIGS. 31, 43, 45, 71 and 73. In this way, the at least one slot 157 may be utilized to identify portions or aspects of the talar trial component 114 (and/or a corresponding talar component 14) that may not be visible, or may be difficult to decipher, when the talar trial component 114 is viewed at least along the medial-lateral direction (e.g., under fluoroscopy or other imaging in situ). In some embodiments, the talar trial component 114 may include a plurality of reference slots 157 in the distal side. For example, the talar trial component 114 may include a posterior reference slot 157 that corresponds to the location of one or more posterior support pegs 19 of a corresponding talar component 14, which may be utilized to align the talar trial component 114 so that the one or more pegs 19 are properly located in the talus 4. In some embodiments, as shown in FIGS. 38, 39 and 41, the talar trial component 114 may include an anterior reference slot 157 that corresponds to the position of an anterior portion of the articulation surface 46 of the corresponding talar component 14, which may be utilized as a reference for alignment of the talar trial component 114 so that the anterior resection of the talus 4 and the corresponding talar component 14 is properly located (see FIGS. 38, 39 and 41). As another example, the illustrative embodiment also includes a posterior angled reference slot 157 that is aligned and corresponds with the posterior cut slot 150, which may be utilized as a reference for alignment of the talar trial component 114 so that the posterior resection of the talus 4 and corresponding portion 16 of a corresponding talar component 14 is properly located (see FIGS. 38, 39 and 41). Still further, the illustrative embodiment also includes at least one articulation reference slot 157 that corresponds to the center (e.g., of the radius or articulation axis of) the articulation surface 146 of the talar trial component 114 (and potentially thereby that of a corresponding tibial component 14) along the anterior-posterior direction, which may be utilized to align articulation surface 146 of the talar trial component 114 (and thereby that of the correspond tibial component 14) to the mechanical axis of the tibia 2 and/or talus 4 along the anterior-posterior direction. As yet another example, the illustrative embodiment also includes a posterior angled reference slot 157 that is aligned and corresponds with an anterior resection of the talus 4 via an anterior cut guide 170 and the anterior window 154, which may be utilized as a reference for alignment of the talar trial component 114 so that the anterior resection of the talus 4 and corresponding portion 13 of a corresponding talar component 14 is properly located (see FIGS. 38, 39 and 41).

As shown in FIGS. 37-43, 49 and 50, the articulation surface 146 of the talar trial component 114 may correspond to a talar component 14 that includes an articulation surface 46 that contacts and articulates (via sliding/gliding motion) with that of a corresponding tibial insert 16 (see FIG. 1). The articulation surface 46 of the talar component 14 may be defined by a plurality of radii. The articulation surface 146 of the talar trial component 114 may approximate or substantially correspond to the articulation surface 46 of the talar component 14. For example, the articulation surface 146 of the talar trial component 114 may be defined by a radius extending from an axis of rotation that corresponds to or matches that of at least one portion of the articulation surface 46 of the talar component 14. As another example, the articulation surface 146 of the talar trial component 114 may be defined by a radius extending from an axis of rotation that corresponds to an average or general approximation of the radii of the articulation surface 46 of the talar component 14. The articulation surface 146 of the talar trial component 114 may thereby provide a close approximation of the articulation surface 46 of the corresponding talar component 14 such that the size and range of motion of the corresponding talar component 14 be tested or trialed via the articulation surface 146 of the talar trial component 114 (and the tibial trial insert 114).

As shown in FIGS. 38, 39, 41, the distal side of a talar component 14 may be comprised of a plurality of planar surfaces that engage a talus 4. For example, a talar component 14 may include a planar posterior surface 13, a planar central surface 15 and a planar anterior surface 17, as shown in FIGS. 38, 39, 41. The planar posterior surface 13 may extend posteriorly and distally from the planar central surface 15, and the planar anterior surface 17 may extend anteriorly and distally from the planar central surface 15. The planar anterior surface 17 may include one or more support pegs 19 extending distally therefrom for implantation into the talus 4.

The talar engagement surface portion 151 of the distal side of the talar trial component 114 may correspond to at least a portion of the planar central surface 15 of the talar component 14. In some embodiments, the size and shape of the talar engagement surface portion 151 of the distal side of the talar trial component 114 matches that of the planar central surface 15 of the talar component 14. It is noted that a talus 4 may be resected to form a planar central surface 15' corresponding to the planar central surface 15 of the talar component 14 via a guide system not disclosed herein, as shown in FIGS. 45, 48 and 70-73.

As shown in FIGS. 45, 48 and 70-73, the talar engagement surface portion 151 of the distal side of the talar trial component 114 may be positioned on (i.e., engage or abut) the resected planar central surface 15' of the talus 4 and utilized to further resect the talus 4 to include a chamfered planar posterior surface 13' that corresponds to the planar posterior surface 13 of the talar component 14 (via the posterior cut slit 150) and a chamfered planar anterior surface 17' that corresponds to the planar anterior surface 17 of the talar component 14 (via an anterior cut guide 170 and the anterior window 154), as explained further below.

Figure 44:
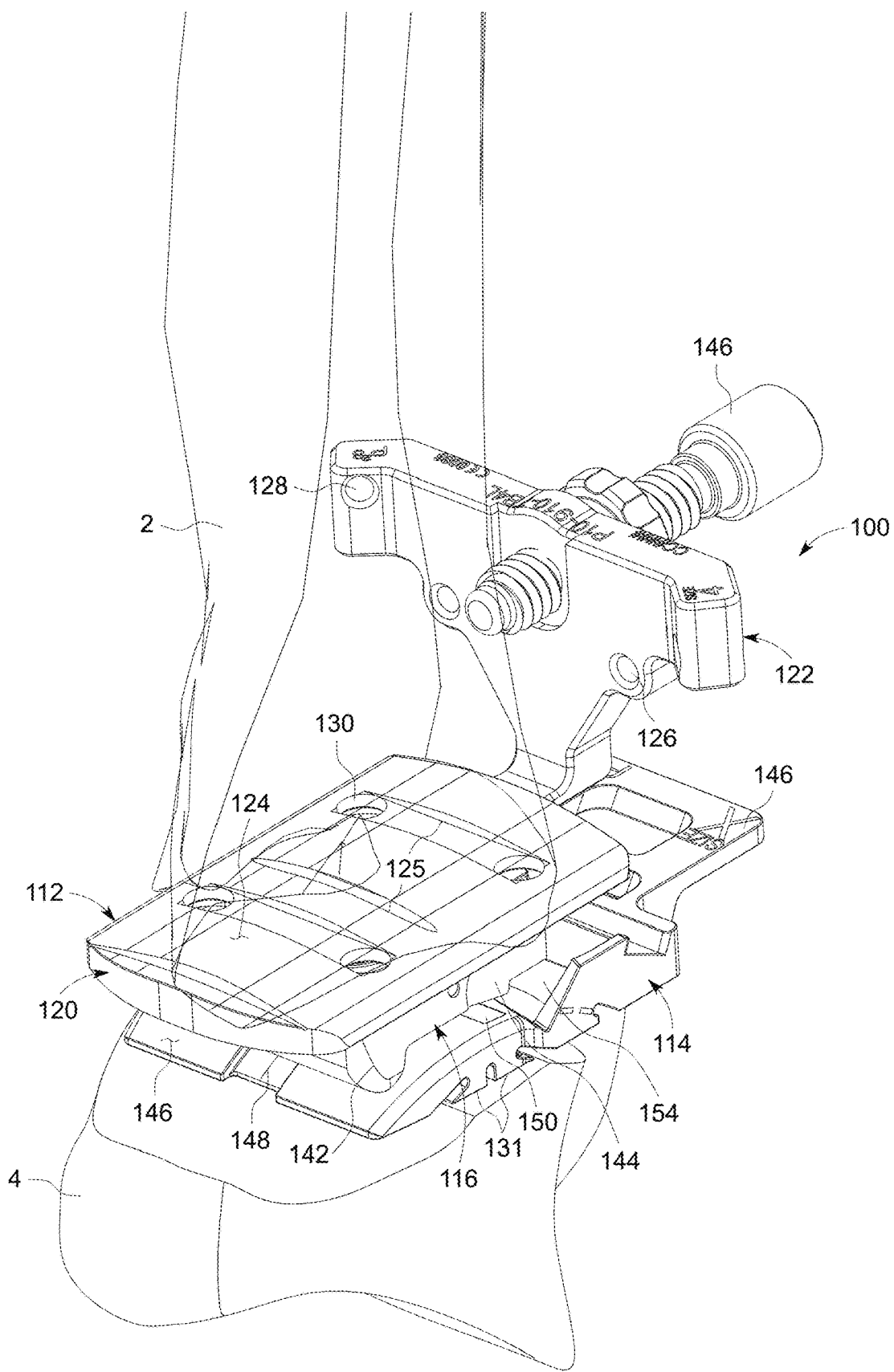
FIG. 44 illustrates an elevational posterior perspective view of the TAR prosthesis of FIGS. 1A and 2B forming an ankle joint between a tibia and talus, in accordance with an aspect of the present disclosure.

As shown in FIGS. 44 and 45 and discussed above, the TAR guide 100 may be utilized with a resected ankle joint of a patient (i.e., between a resected distal tibia 2 and a resected proximal talus 4) to facilitate the selection of a properly sized tibial component 12, talar component 14 and/or tibial insert 16 of a TAR prosthesis 10 based on the size/configuration of the ankle joint of the particular patient, as well as facilitate implantation of the tibial component 12 in/on the tibia 2 and/or implantation of the talar component 14 in/on the talus 4, in proper positions and orientations (and thereby the proper position and orientation of the corresponding tibial insert 16) for the particular ankle joint.

Figure 57:
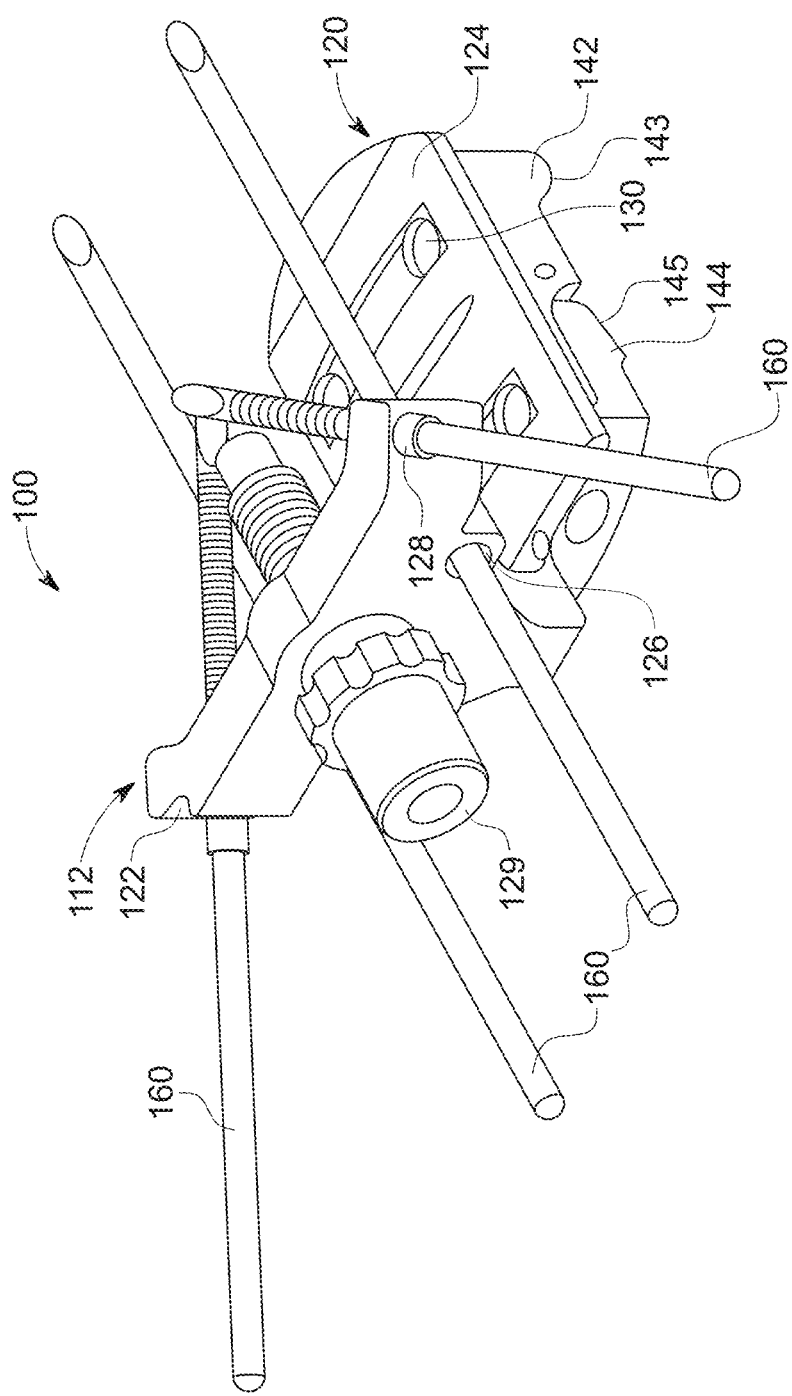
FIG. 57 illustrates an anterior elevation perspective view of the tibial trial guide of FIG. 9 engaged with a plurality of pin members and the tibial trial insert of FIG. 19, in accordance with an aspect of the present disclosure.
Figure 58:
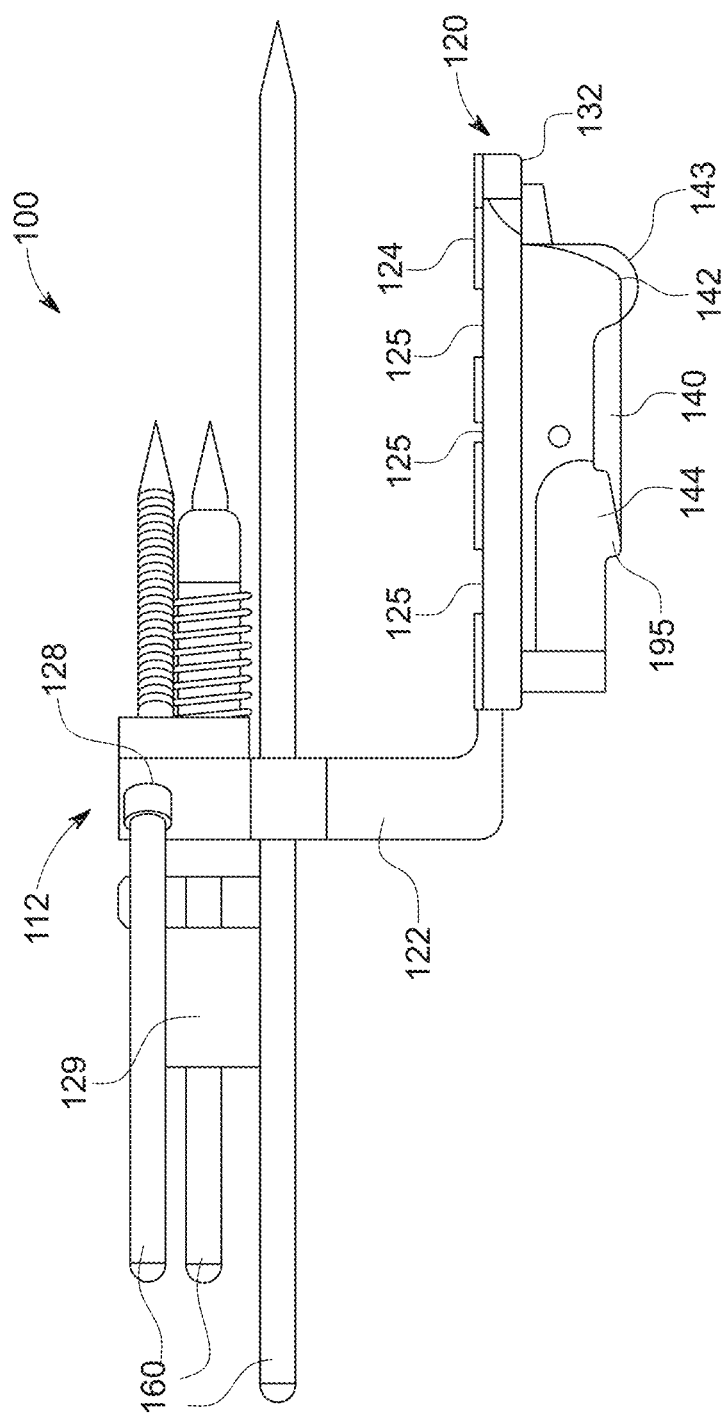
FIG. 58 illustrates a medial side view of the tibial trial guide of FIG. 9 engaged with a plurality of pin members and the tibial trial insert of FIG. 19, in accordance with an aspect of the present disclosure.
Figure 59:
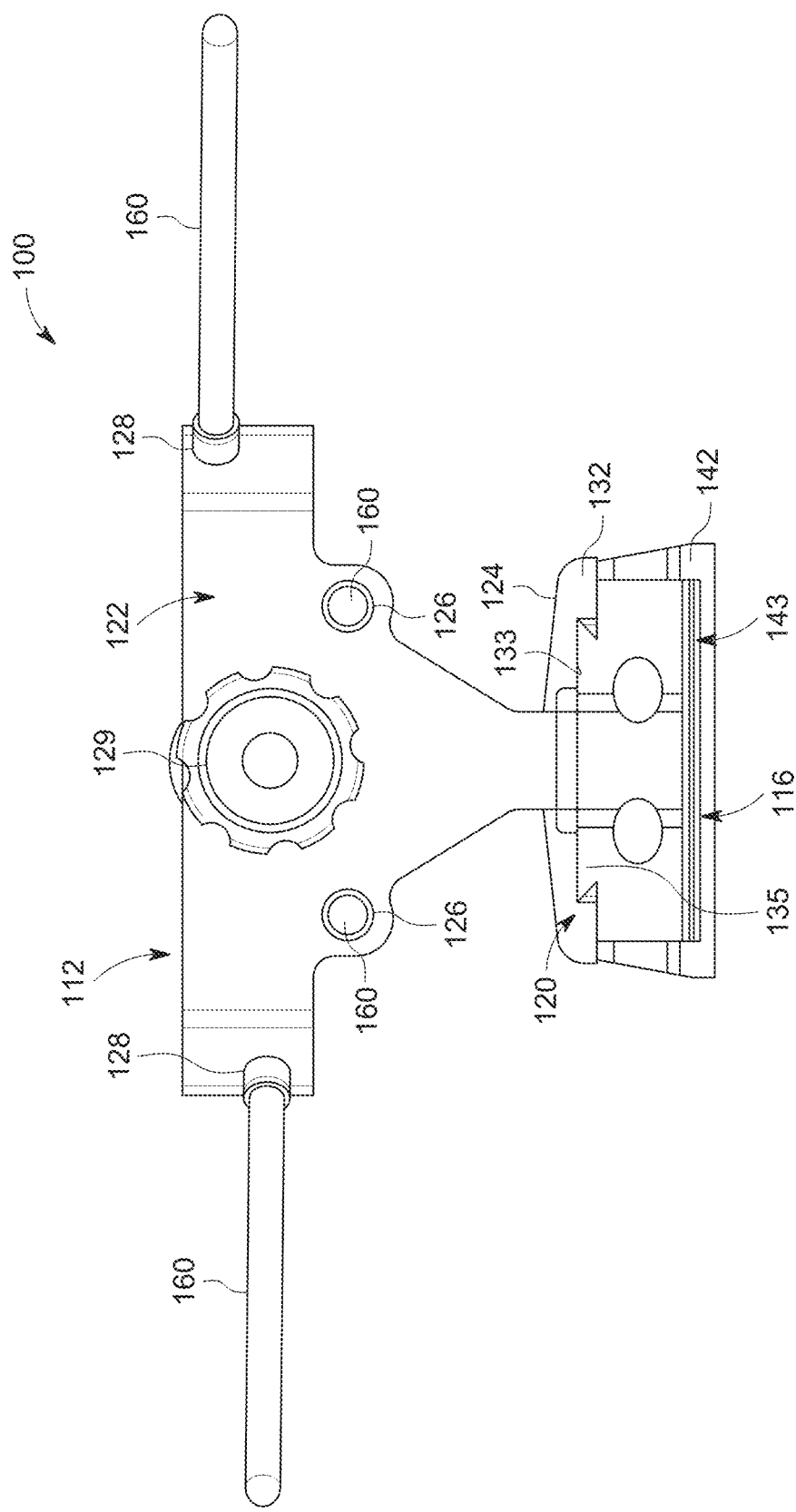
FIG. 59 illustrates an anterior view of the tibial trial guide of FIG. 9 engaged with a plurality of pin members and the tibial trial insert of FIG. 19, in accordance with an aspect of the present disclosure.
Figure 60:
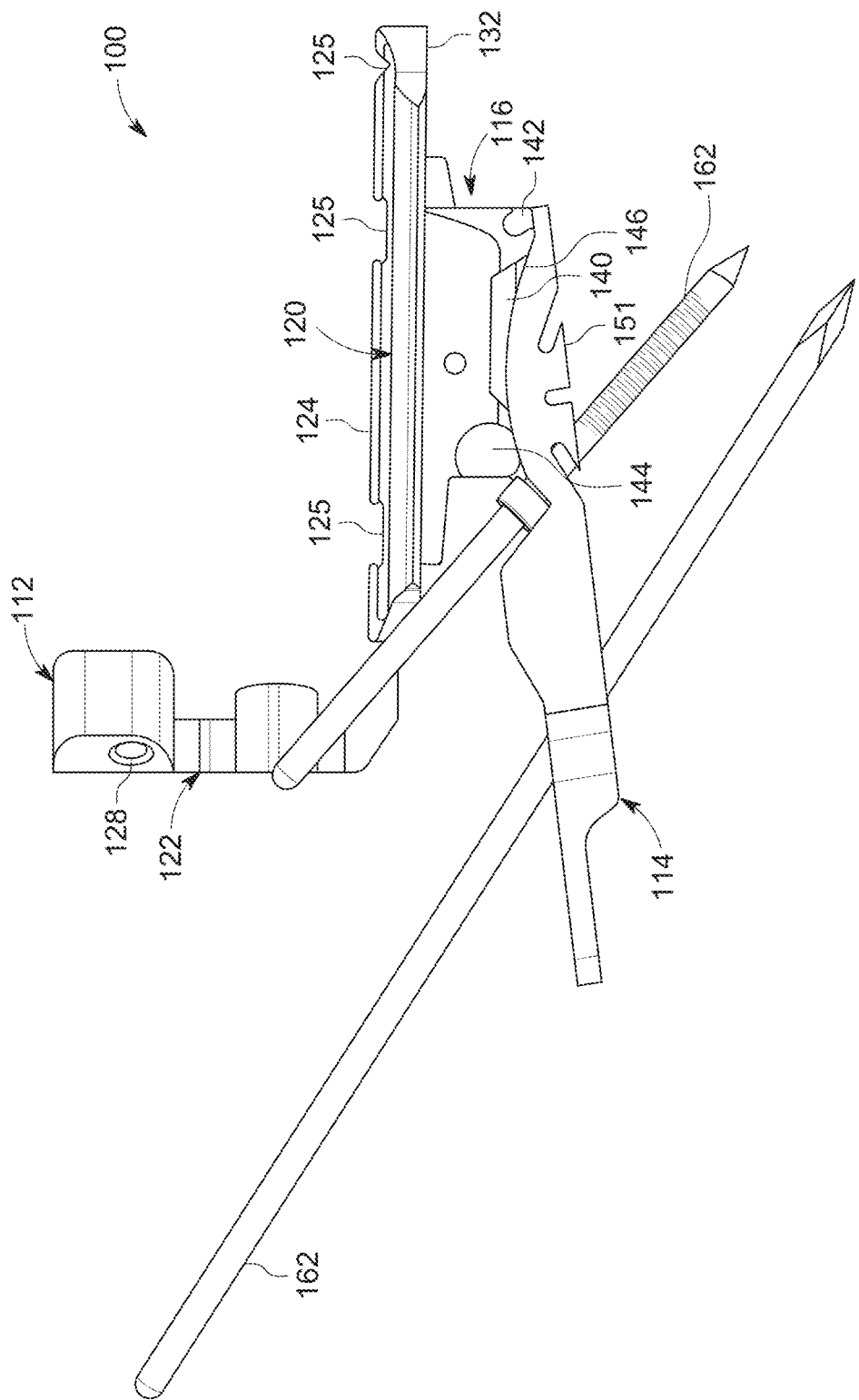
FIG. 60 illustrates an anterior elevation perspective view of the tibial trial guide of FIG. 9 engaged with the tibial trial insert of FIG. 19, and the talar trial guide of FIG. 29 engaged with a plurality of pin members and the tibial trial insert of FIG. 19, in accordance with an aspect of the present disclosure.
Figure 61:
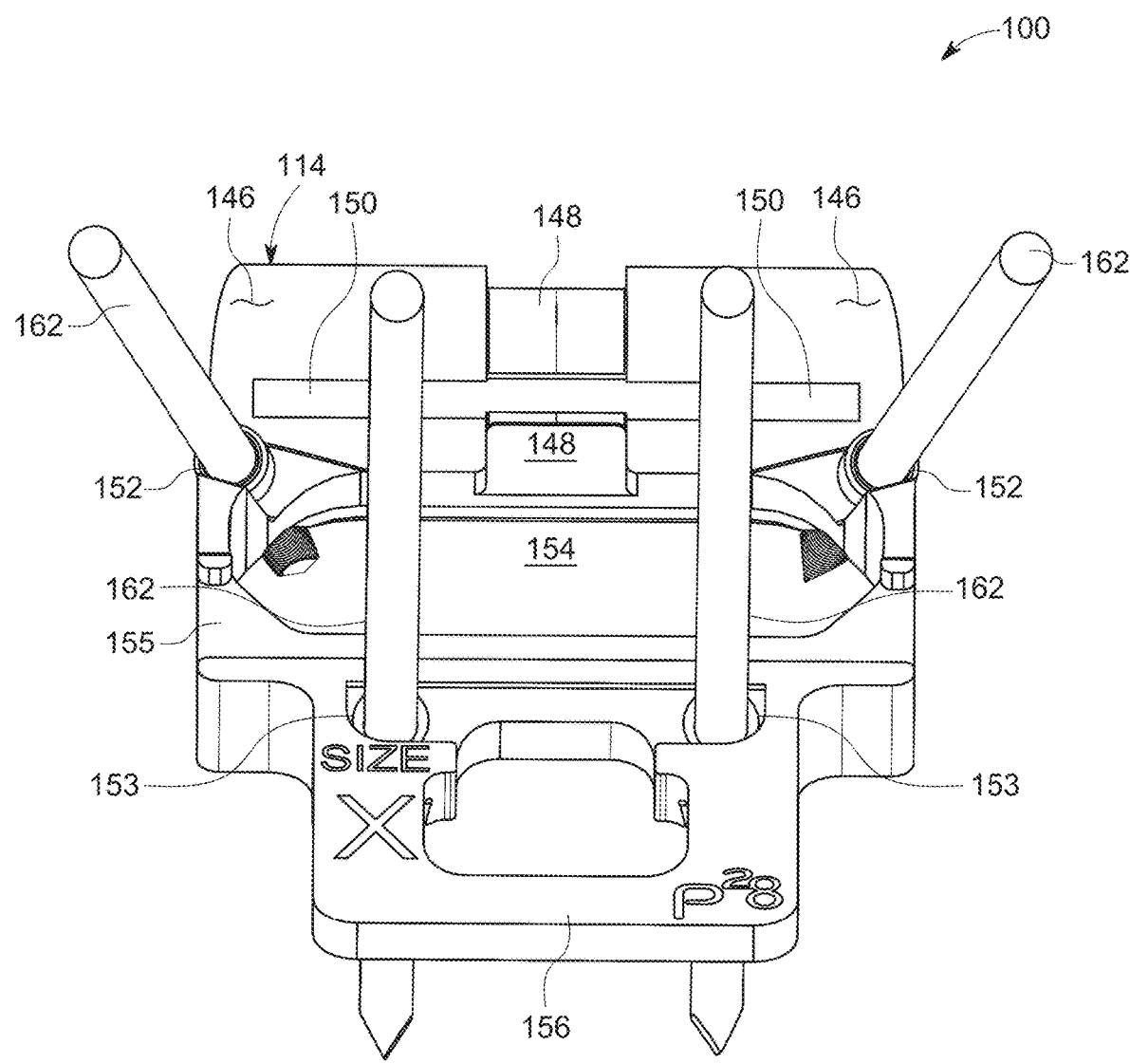
FIG. 61 illustrates an anterior elevation view of the talar trial guide of FIG. 29 engaged with a plurality of pin members, in accordance with an aspect of the present disclosure.
Figure 62:
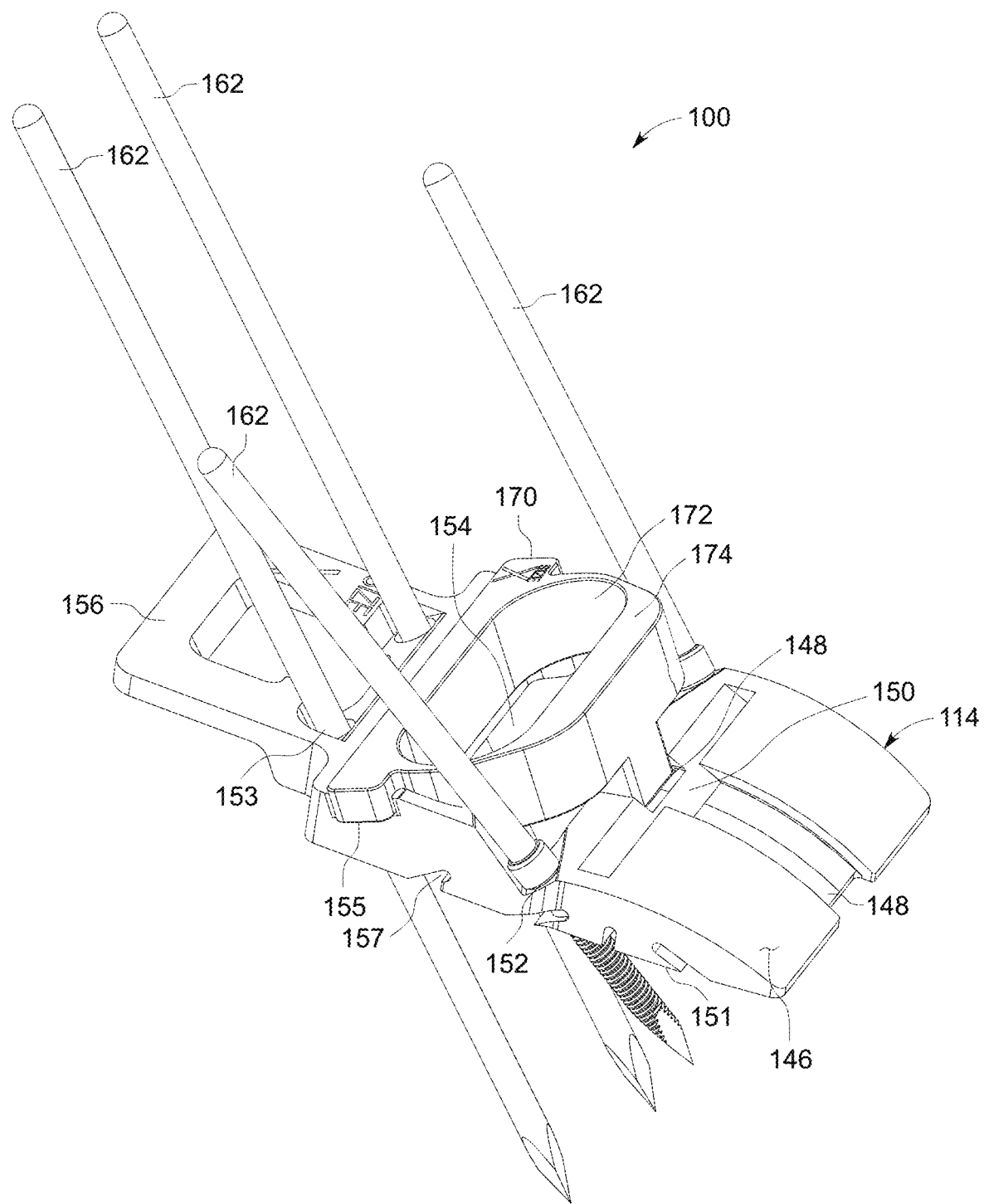
FIG. 62 illustrates a medial elevation perspective view of the talar trial guide of FIG. 29 engaged with a plurality of pin members and a bone removal guide, in accordance with an aspect of the present disclosure.
Figure 63:
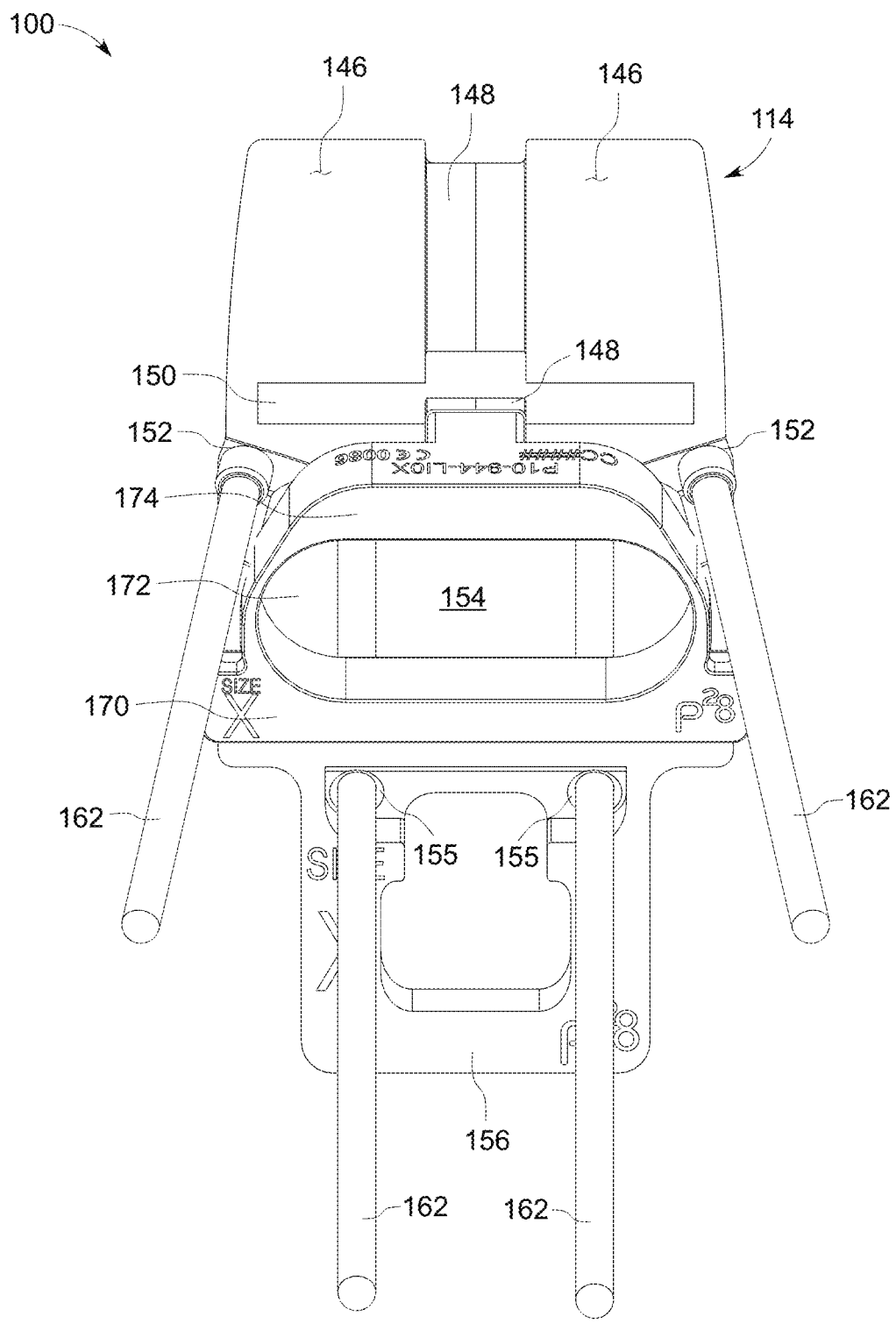
FIG. 63 illustrates a proximal view of the talar trial guide of FIG. 29 engaged with the plurality of pin members and the bone removal guide of FIG. 62, in accordance with an aspect of the present disclosure.
Figure 64:
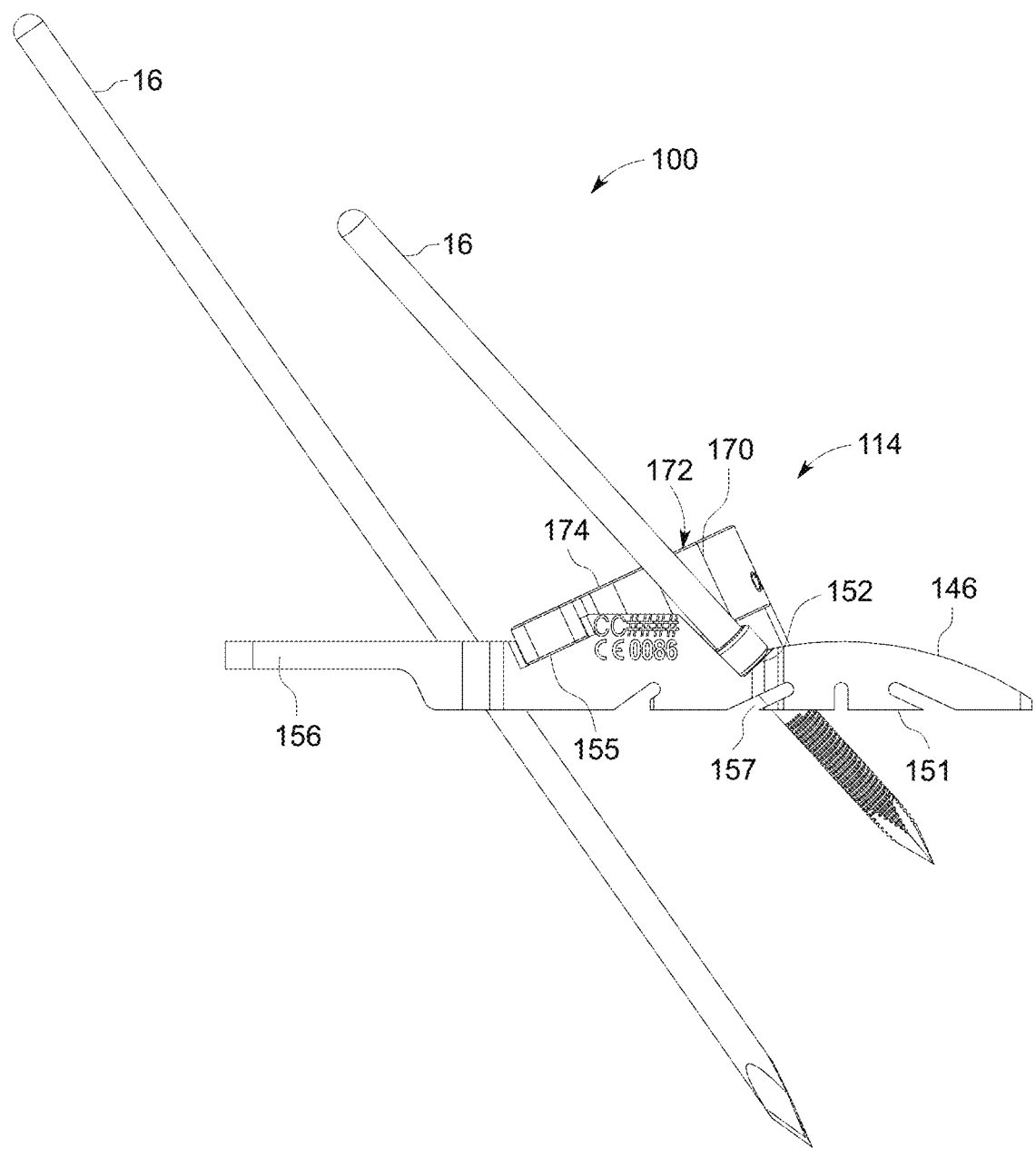
FIG. 64 illustrates a medial view of the talar trial guide of FIG. 29 engaged with the plurality of pin members and the bone removal guide of FIG. 62, in accordance with an aspect of the present disclosure.
Figure 65:
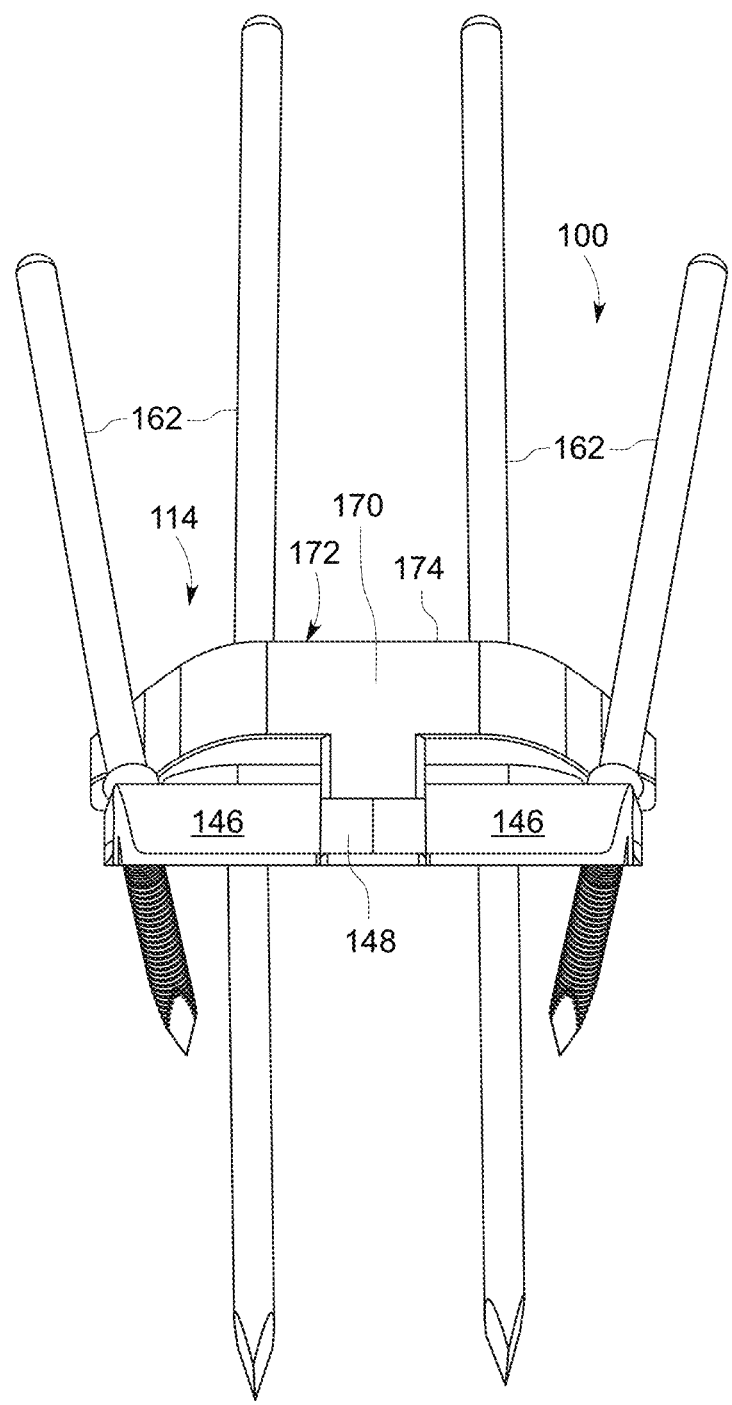
FIG. 65 illustrates a posterior view of the talar trial guide of FIG. 29 engaged with the plurality of pin members and the bone removal guide of FIG. 62, in accordance with an aspect of the present disclosure.
Figure 66:
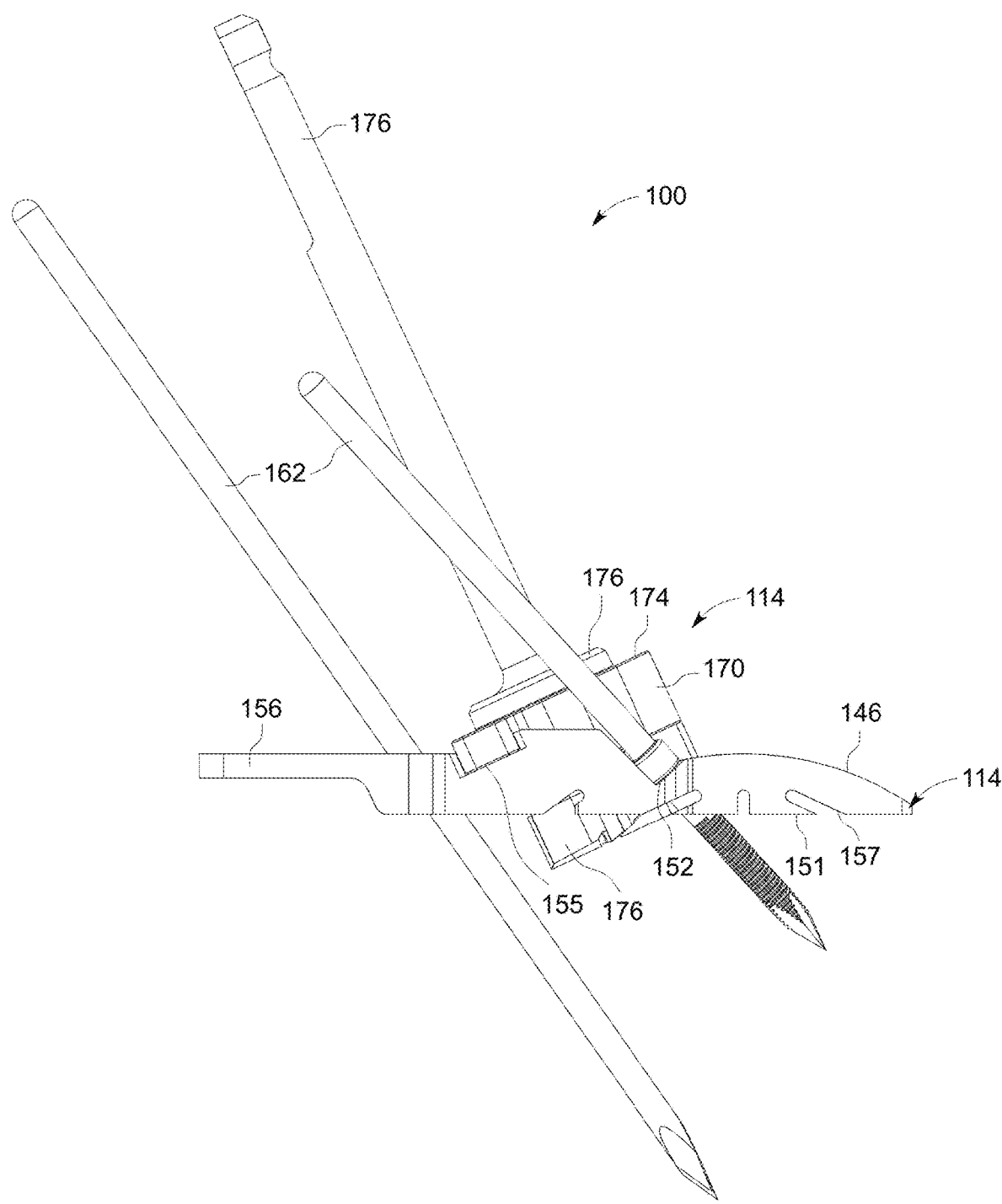
FIG. 66 illustrates a medial view of the talar trial guide of FIG. 29 engaged with the plurality of pin members and the bone removal guide of FIG. 62, and a bone aperture formation instrument engaged with the bone removal guide of FIG. 62, in accordance with an aspect of the present disclosure.

As shown in FIGS. 44-56, the engagement surface 124 of the base portion 120 of the tibial trial component 112 may be positioned on the resected portion of the distal tibia 2 and adjusted into a correct or preferable position (and/or swapped for a differing sized tibial trial component 112), which may be tactically and/or visually (directly or under fluoroscopy or other imaging) determined, as described above. For example, the peripheral edges of the tibial trial component 112 (including the reference slots 125) may be utilized to position the tibial trial component 112 with respect to the tibia 4. Once properly positioned, a plurality of pins 160 may be driven through the pin apertures 126, 128 of the arm portion 122 of the tibial trial component 112 and into the tibia 2 to fix the tibial trial component 112 to the tibia 2, as shown in FIGS. 57-59. In some embodiments, the plurality of through holes 130 may be utilized to with a cutting instrument (e.g., a sharp tipped trocar) to remove portions of the distal tibia 2 for implantation of at least one peg of the corresponding tibial component 12 therein.

With the tibial trial component 112 coupled to the tibia 2, the engagement surface portion 151 of the posterior end portion of the distal side of the talar trial component 114 may be positioned in the resected surface portion 15' of the talus 4, as shown in FIGS. 44, 45, 47, 48 and 70-73. The size of the tibial trial component 112 may be inspected to determine if the tibial trial component 112 (and thereby the corresponding talar component 14) provides proper coverage of the talus 4 and is properly positioned, and the anterior and posterior resected surface portions or chamfers 13', 17' formed via cut slot 150 and the window 154 of the tibial trial component 112 would be properly positioned, as described above. Once a proper size of the talar trial component 114 is chosen and properly positioned on the resected talus 4, the tibial trial insert 116 may be inserted between the tibial trial component 112 and the talar trial component 114, as shown in FIGS. 44, 45, 60 and 61, as described above. For example, the tibial trial insert 116 may be inserted into the recess 133 of the base portion 120 of the tibial trial component 112, as shown in FIGS. 44, 45, 57-61, and the posterior and anterior articulation rails 142, 144 engaged with the articulation surface 146 of the talar trial component 114, as shown in FIGS. 44, 45, 48-53, 55, 56 and 60. The tibial trial insert 116 and the patient's foot may then be dorsiflexed and plantar flexed to test or trial the articulation afforded by the TAR guide system 100 (and thereby the corresponding TAR prosthesis 10), as shown in FIGS. 55 and 56 and described above. Once the proper articulation and soft-tissue balancing provided by the TAR prosthesis 100 is determined or achieved (e.g., via selection of differing sized tibial trial inserts 116 (e.g., thicknesses thereof), and the tibial trial insert 116 is properly positioned, a plurality of pins 162 may be driven through the pin apertures 152, 153 of the talar trial component 114 and into the talus 2 to fix the tibial trial component 112 to the tibia 2, as shown in FIGS. 60-69. As noted above, the patient's foot may need to be plantar flexed to access the pin apertures 152, 153.

With the tibial trial component 112 fixed to the tibia 2 via the plurality of pins 162 driven through the pin apertures 152, 153 and into the talus 2, the tibial trial component 112 and the tibial trial insert 116 may be removed from the ankle joint. The talar trial component 114 may then be utilized to form the anterior and posterior resected surface portions or chamfers 17', 13' via the anterior window 154 and the cut slot 150, respectively. For example, as shown in FIGS. 62-66, an anterior cut guide 170 may be engaged with, or coupled to, the tibial trial insert 116 via the anterior cut guide support surface 155 and/or the strut slot 148 such that it extends over the anterior window 154, and thereby over the anterior portion of the talus 4. For example, the anterior cut guide 170 may include an anterior support portion that seats/engages within/on the anterior cut guide support surface 155, and/or a posterior projection that seats within the strut slot 148. The anterior cut guide 170 may include one or more apertures 172 extending therethrough along the proximal-distal direction that are aligned over the anterior window 154 and the anterior portion of the talus 4, as shown in FIGS. 62-65. In some embodiments, the anterior cut guide 170 includes a plurality of apertures 172, as shown in FIGS. 62-65. In alternative embodiments, the anterior cut guide 170 includes a single aperture 172 (not shown).

The cut guide 170 may include an exposed proximal guide surface 174 that is be planar and angled at an orientation that matches the orientation of the planar anterior surface 17 of the talar component 14, and thereby the desired chamfered planar anterior surface 17' corresponding thereto. As shown in FIGS. 66 and 70-73, a cutting end of a cutting implement 176 may be passed through the at least one aperture 172 of the cut guide 170, and a guide surface of the cutting implement 176 (e.g., provided by a shoulder and/or bushing thereof, for example) engaged with the guide surface 174, to cut/chamfer the anterior portion of the talus 4 and form the chamfered planar anterior surface 17' (see FIGS. 70-73). The cutting implement 176 may be configured to form a planar cut surface of the anterior portion of the talus 4. In some embodiments, the cutting implement 176 may be a one-piece instrument. It is noted that the cutting implement 176 be moved or translated within the at least one aperture 172 of the cut guide 170, and/or more than one cut guide 170 with differing positioned apertures 172 may be utilized, to fully cut the anterior portion of the talus 4 and form the chamfered planar anterior surface 17'. Further, multiple cutting implements 176 with one or more one cut guides 170 may be utilized to fully cut the anterior portion of the talus 4 and form the chamfered planar anterior surface 17'.

Figure 67:
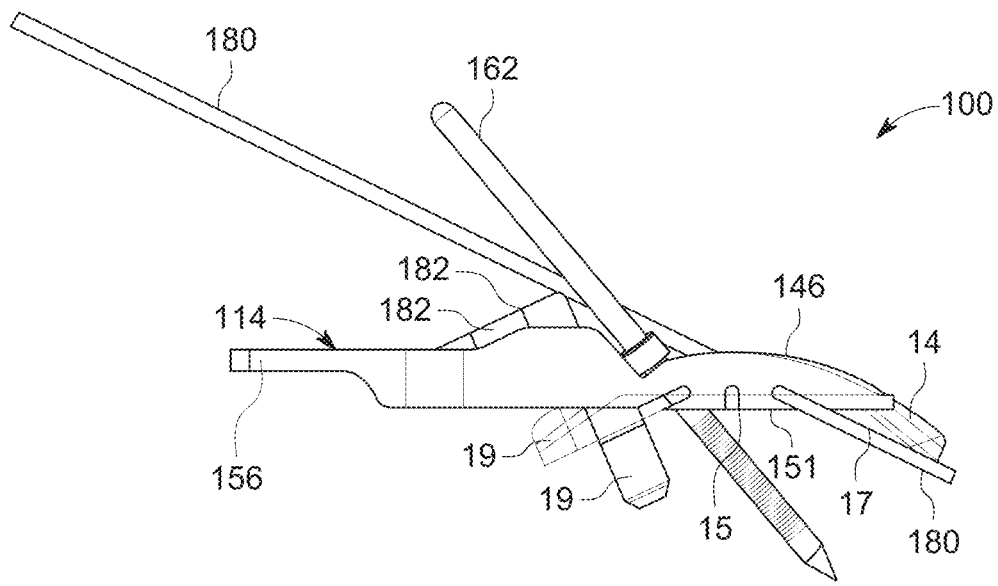
FIG. 67 illustrates a medial view of the talar trial guide of FIG. 29 engaged with a bone cutting blade, a plurality of pin members and a bone cutting blade support member, and the tibial trial insert of FIG. 19 overlaid on the talar trial guide of FIG. 29, in accordance with an aspect of the present disclosure.
Figure 68:
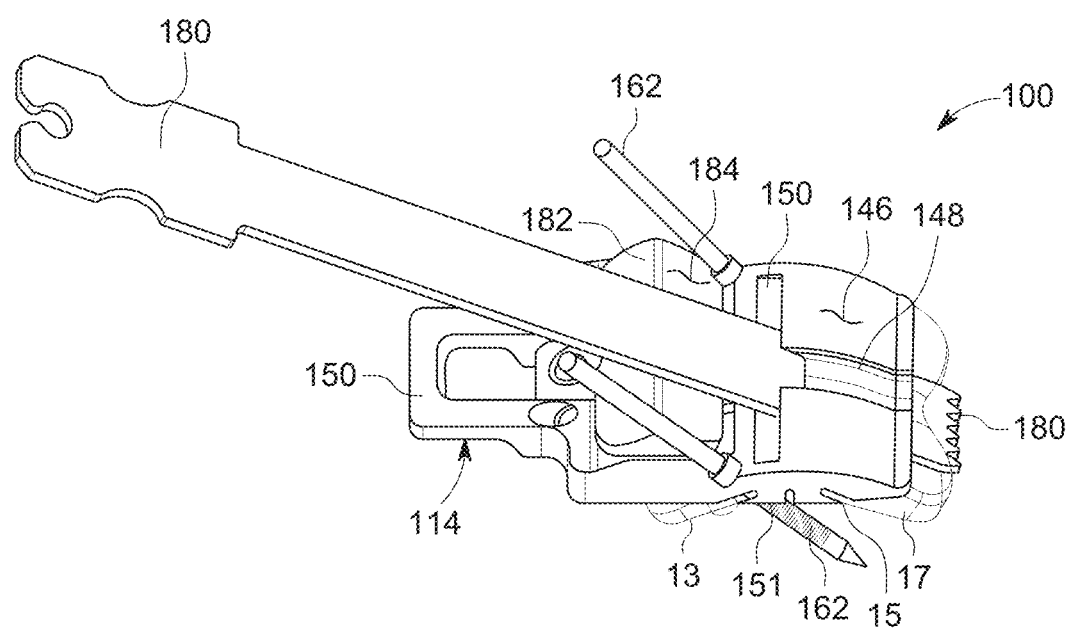
FIG. 68 illustrates a medial elevational perspective view of the talar trial guide of FIG. 29 engaged with a bone cutting blade, a plurality of pin members and a bone cutting blade support member, and the tibial trial insert of FIG. 19 overlaid on the talar trial guide of FIG. 29, in accordance with an aspect of the present disclosure.
Figure 69:
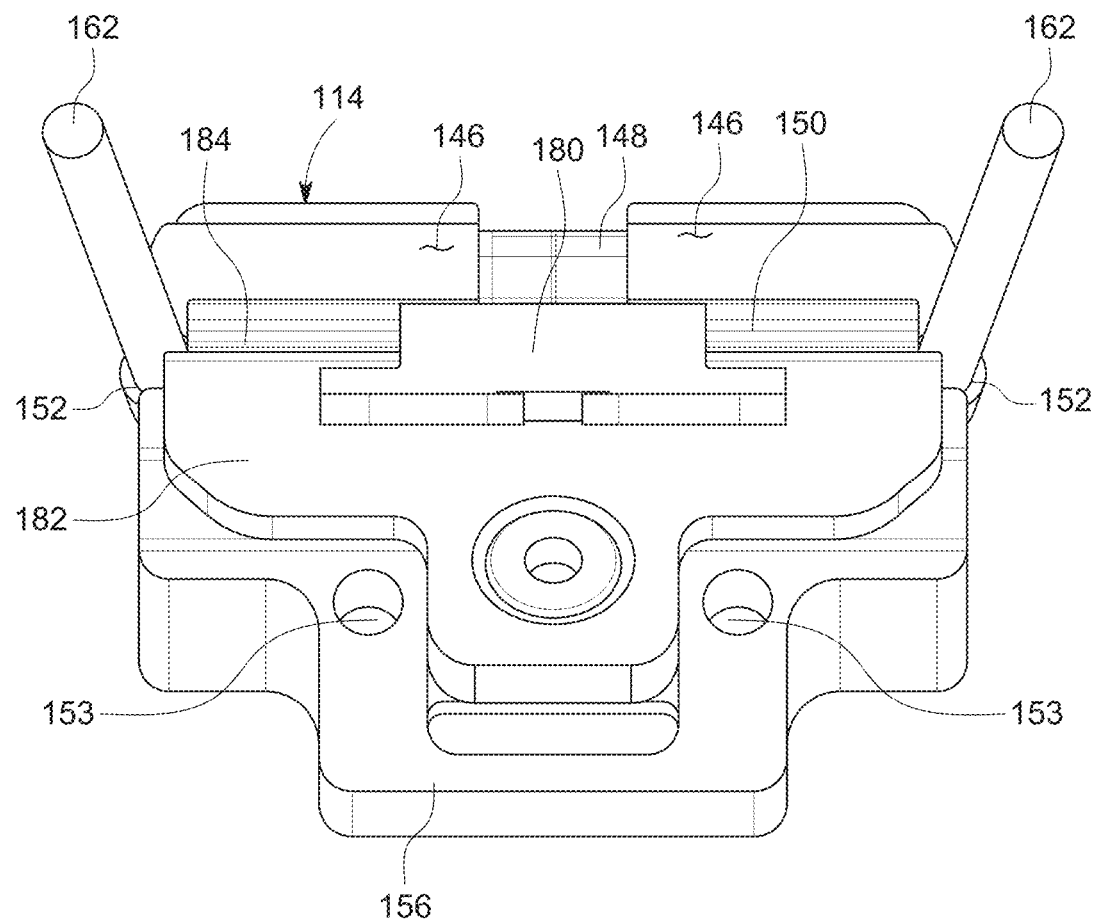
FIG. 69 illustrates an anterior view of the talar trial guide of FIG. 29 engaged with a bone cutting blade, a plurality of pin members and a bone cutting blade support member, and the tibial trial insert of FIG. 19 overlaid on the talar trial guide of FIG. 29, in accordance with an aspect of the present disclosure.
Figure 70:
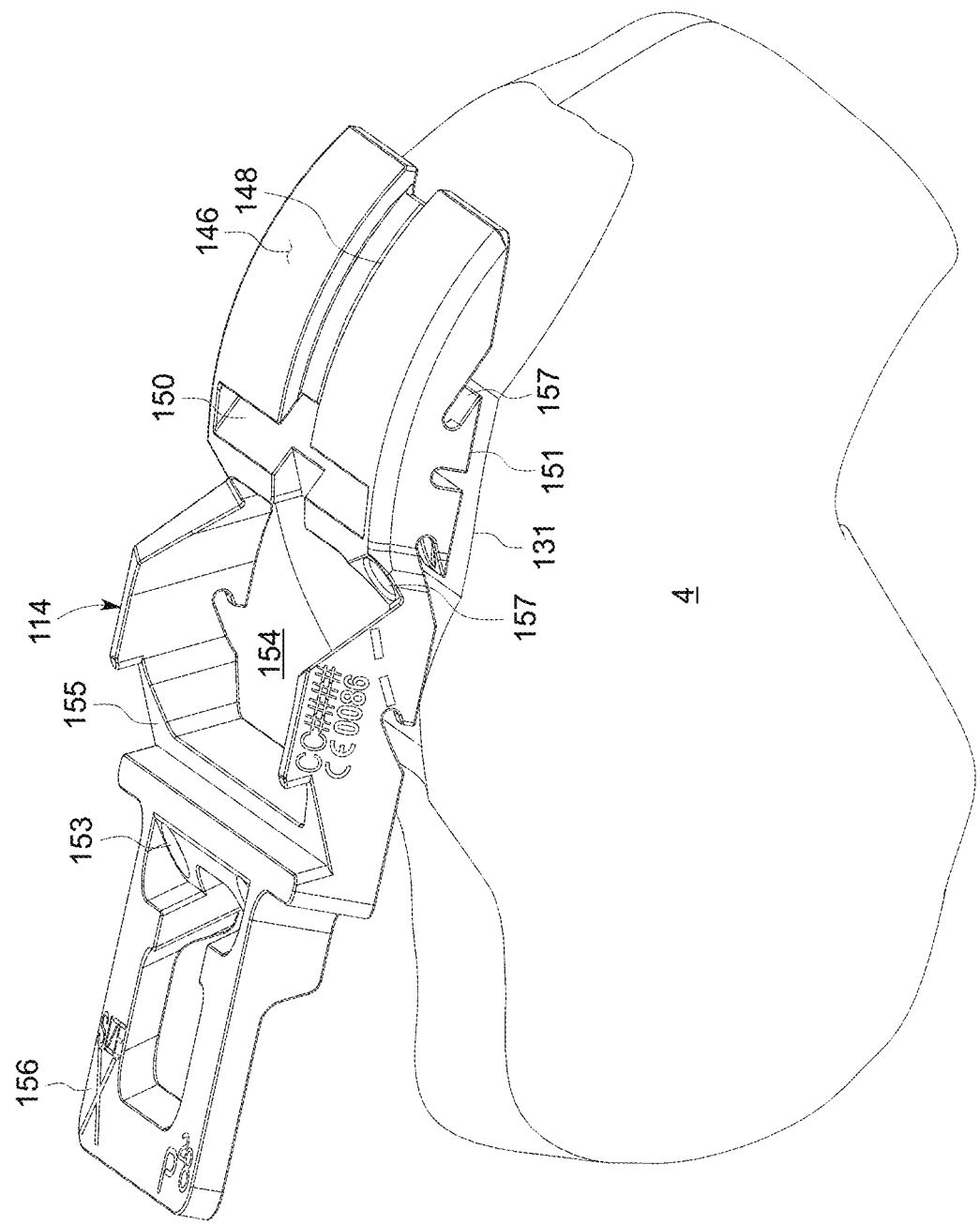
FIG. 70 illustrates a medial elevation perspective view of the talar trial guide of FIG. 29 positioned on a resected talus, in accordance with an aspect of the present disclosure.
Figure 71:
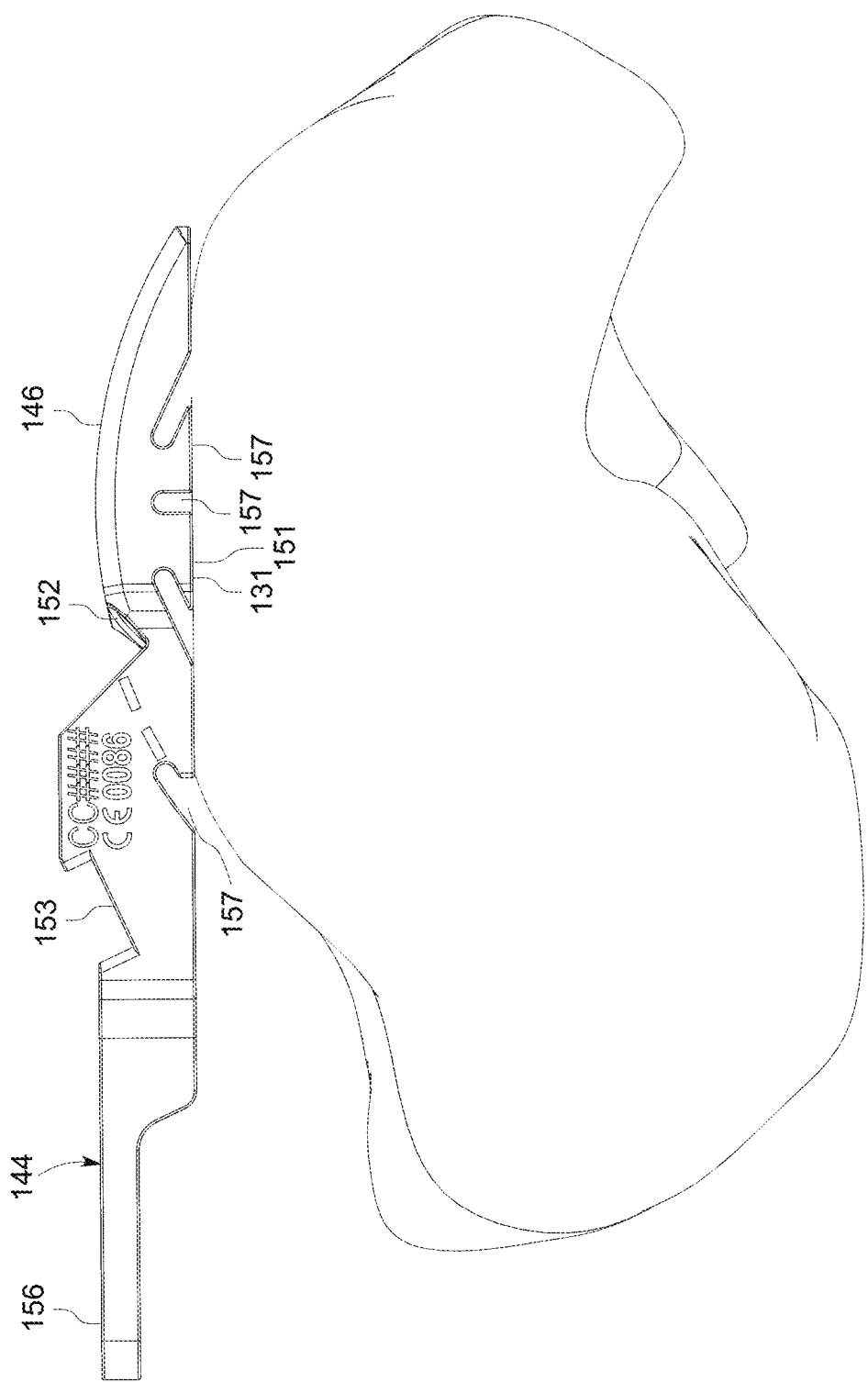
FIG. 71 illustrates a medial side view of the talar trial guide and the resected talus of FIG. 71, in accordance with an aspect of the present disclosure.
Figure 72:
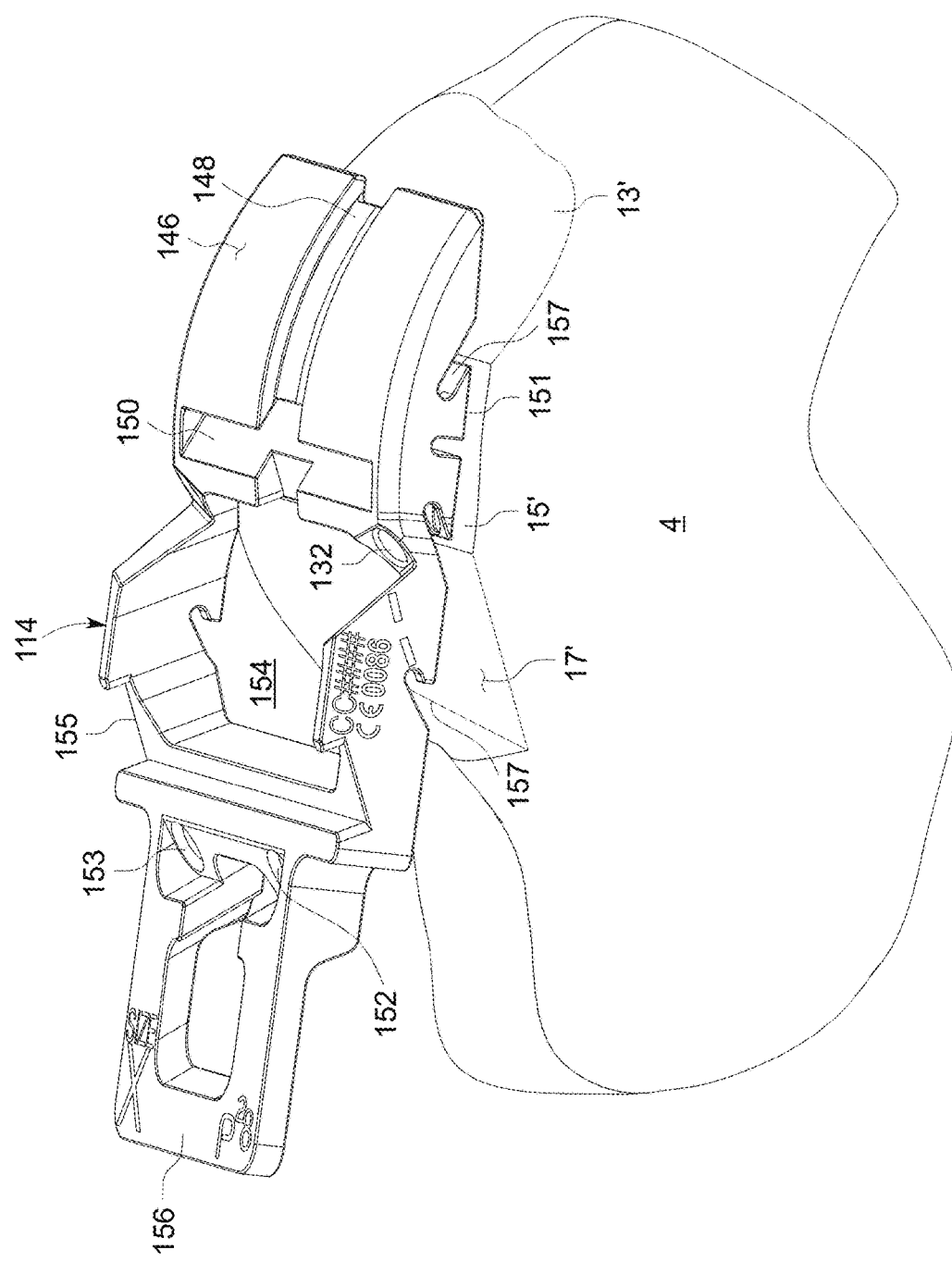
FIG. 72 illustrates a medial elevation perspective view of the talar trial guide of FIG. 29 positioned on a resected and chamfered talus, in accordance with an aspect of the present disclosure.
Figure 73:
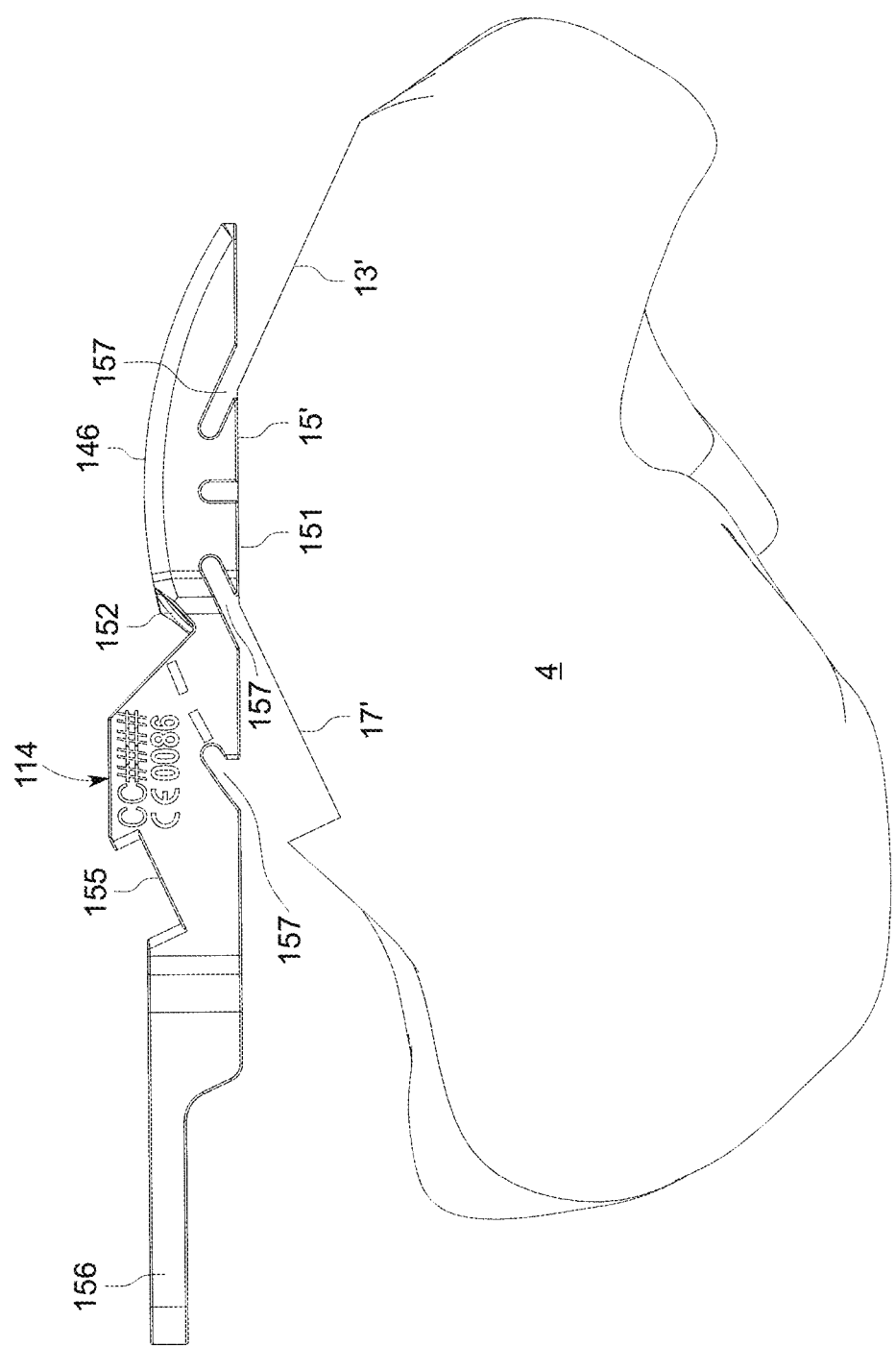
FIG. 73 illustrates a medial side view of the talar trial guide and the resected and chamfered talus of FIG. 72, in accordance with an aspect of the present disclosure.

With the tibial trial component 112 and the tibial trial insert 116 removed from the ankle joint and the tibial trial component 112 fixed to the tibia 2 via the plurality of pins 162 driven through the pin apertures 152, 153 and into the talus 2, the tibial trial insert 116 may also be utilized to form the posterior resected surface portion or chamfer 13' via the posterior cut slot 150 and at least one cutting implement 180. For example, as shown in FIGS. 67-69, a posterior cutting guide 182 may be coupled to the tibial trial insert 116 via the cut anterior cut guide support surface 155 and/or the strut slot 148 (and/or an anterior aperture) such that it extends adjacent (e.g., anteriorly) or over the cut slot 150. In some embodiments, the posterior cutting guide 182 may be engaged with, or coupled to, the tibial trial insert 116 via the anterior cut guide support surface 155 and/or the strut slot 148 such that it extends to the posterior cut slot 150. For example, the posterior cutting guide 182 may include an anterior support portion that seats/engages within/on the anterior cut guide support surface 155, and/or a posterior projection that seats within the strut slot 148. In some embodiments, the posterior cutting guide 182 may extend over and cover/block off the anterior window 154.

The posterior cut guide 182 may include an exposed guide surface 184 that is planar and aligned with the cut slot 150 (e.g., angled at an orientation that matches angle of the cut slot 150), and thereby aligned with the planar posterior surface 13 of the talar component 14 and the desired chamfered planar posterior surface 13' corresponding thereto. In one alternative embodiment, the posterior cut guide 182 may include an angled slot, as opposed to the planar exposed guide surface 184, that is configured to accept the at least one cutting implement 180 therethrough that is angled at an orientation that matches the orientation of the planar posterior surface 13 of the talar component 14. As shown in FIGS. 67-69, the cutting implement 180 (e.g., a saw blade) may be passed through the posterior cut slot 150 of the talar trial component 114, and engaged or rested on the guide surface 184 of the posterior cut guide 182, and operated to cut/chamfer the posterior portion of the talus 4 to form the chamfered planar posterior surface 13' (see FIGS. 70-73).

As shown in FIGS. 70-73, the talar trial component 114 of the TAR guide 100 may thereby be utilized to both trial a corresponding talar component 14 of a TAR prosthesis and to form anterior and posterior resected surface portions or chamfers 17', 13' (via the anterior window 154 and the anterior cut guide 170, and via the cut slot 150 and posterior cut guide 182, respectively) on the proximal talus 4 for implantation of the talar component 14 thereon/therein.

Figure 74:
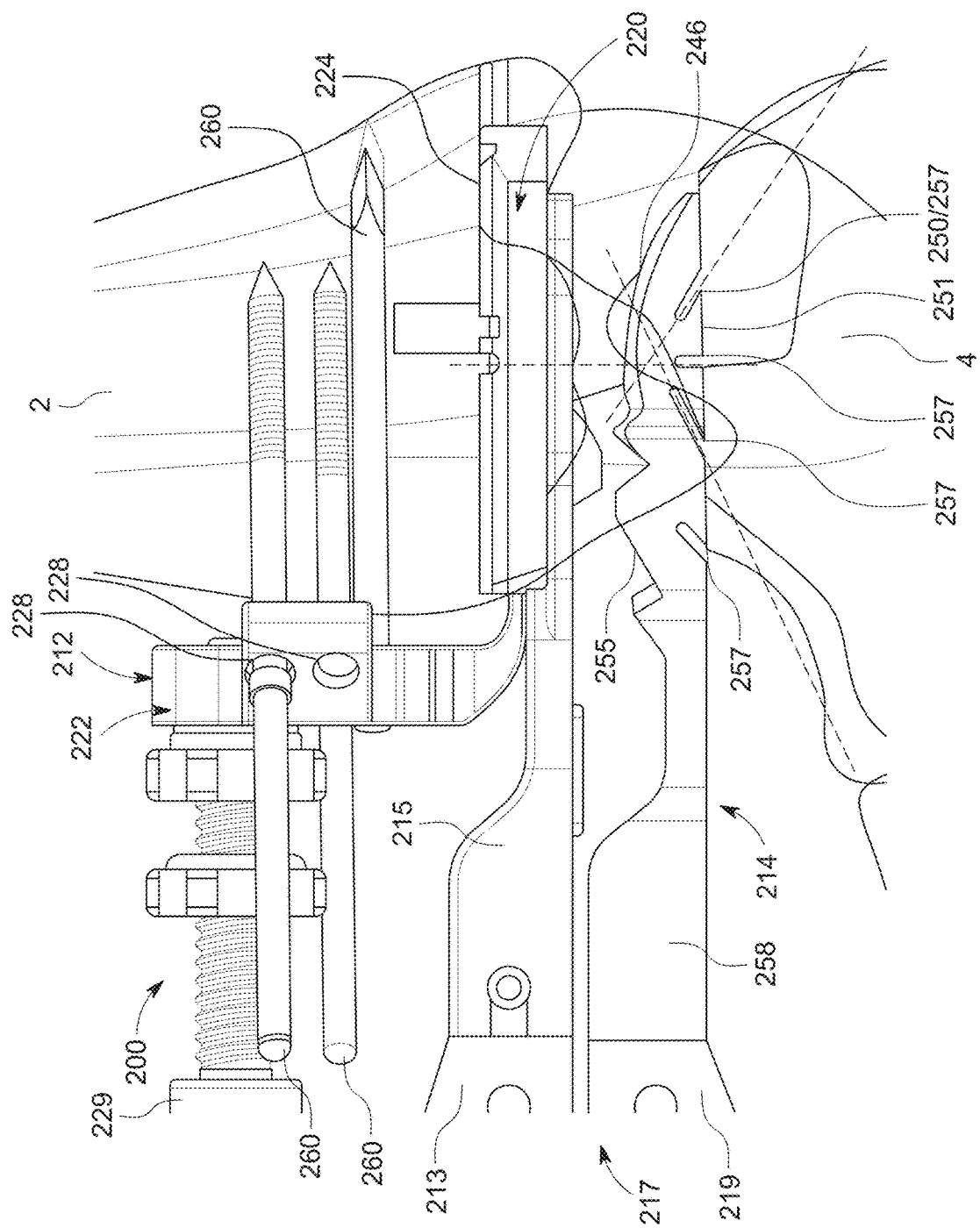
FIG. 74 illustrates a medial side view of another TAR trial and guide system including a tibial trial guide, a first talar trial guide and a distractor for facilitating selection of a TAR prosthesis and preparation of a tibia and talus therefore, in accordance with an aspect of the present disclosure.
Figure 75:
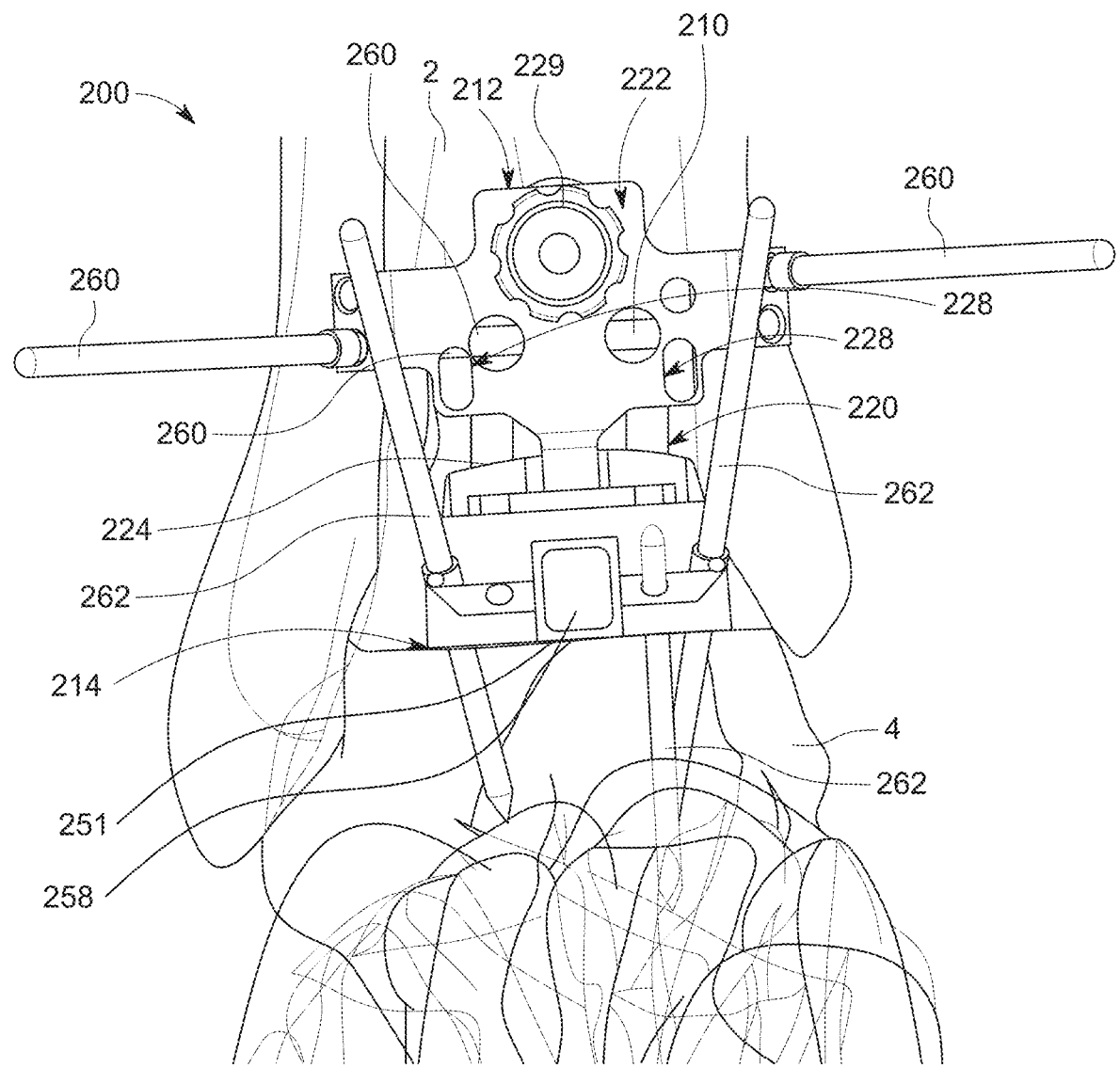
FIG. 75 illustrates an anterior view of the TAR trial and guide system of FIG. 74, in accordance with an aspect of the present disclosure.

FIGS. 74-133 illustrate components of another TAR trial and bone preparation guide system 200, in accordance with the present disclosure, that is configured to trial, and prepare a resected distal tibia and a resected talus for implantation therein and therebetween, a TAR prosthesis comprising a tibial component comprising a tibial engagement surface with at least one bone engagement projection/peg, a tibial insert configured to removably couple with the tibial component and comprising a tibial articulation surface, and a talar component comprising a talar engagement surface with at least one bone engagement projection/peg/fin and a talar articulation surface that articulates with the tibial articulation surface of the tibial insert. At least some component of the TAR trial and bone preparation guide system 200 of FIGS. 74-133 are similar to that of the TAR trial and bone preparation guide system 100 of FIGS. 2-73, and therefore like reference numerals preceded with "2" are used to indicate like components, portions, aspects, features and functions, and the description above directed thereto (including any alternative embodiments thereof) equally applies to the TAR trial and bone preparation guide system 200 and is not repeated hereinbelow only for brevity sake.

Figure 76:
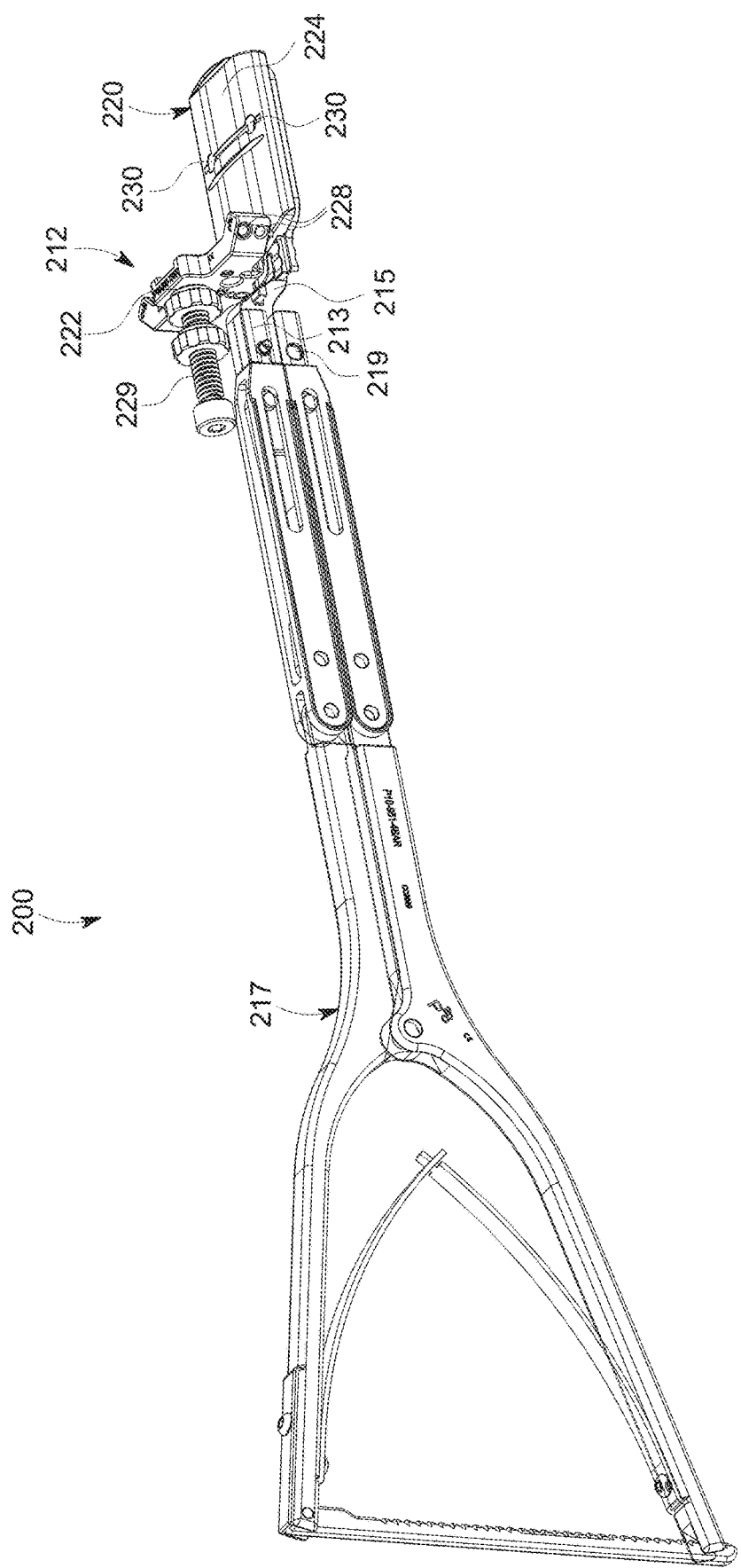
FIG. 76 illustrates an elevational anterior perspective view of the tibial trial guide and the distractor of the TAR trial and guide system of FIG. 74, in accordance with an aspect of the present disclosure.
Figure 77:
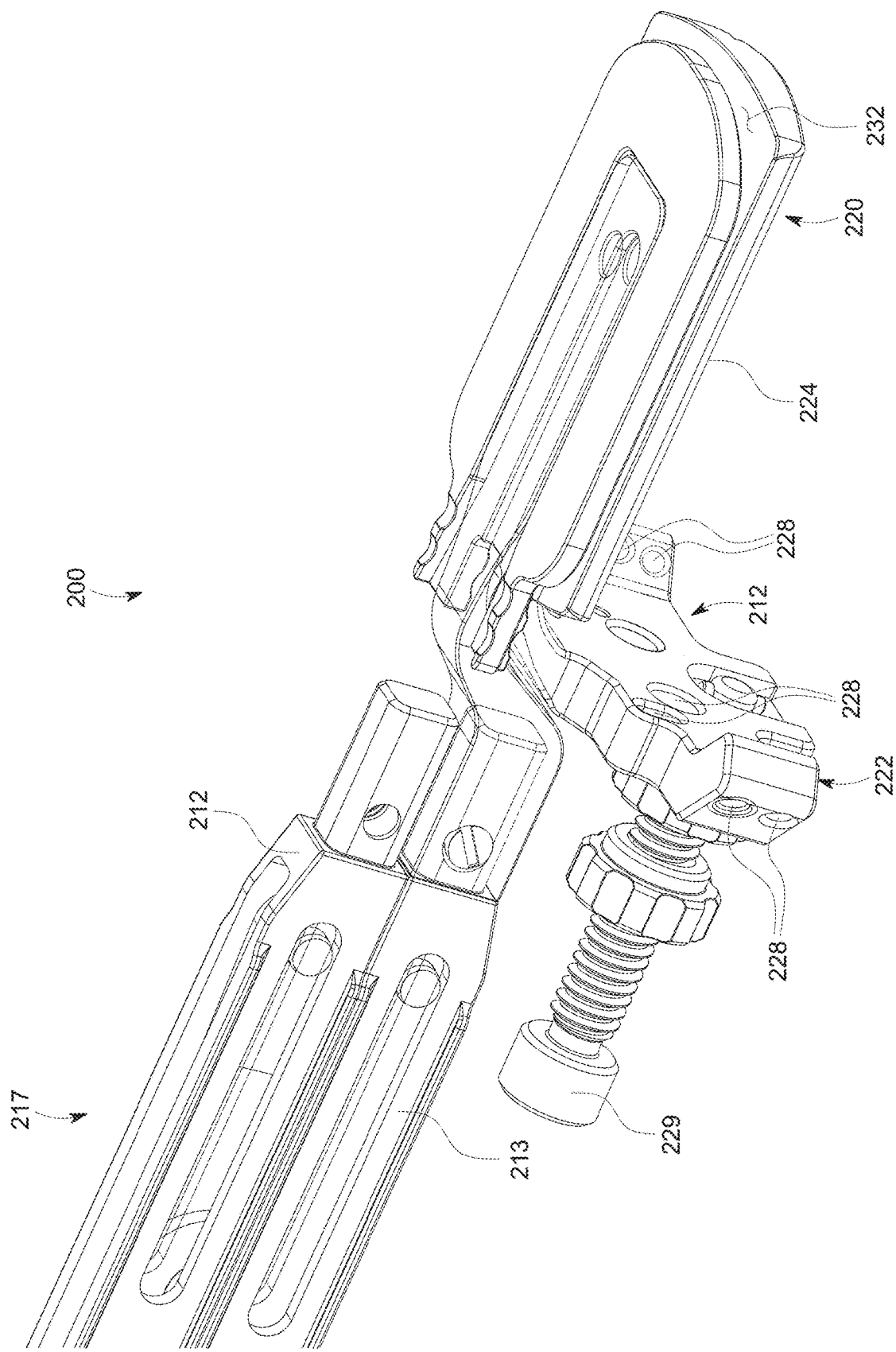
FIG. 77 illustrates a distal medial perspective view of the tibial trial guide and the distractor of FIG. 76, in accordance with an aspect of the present disclosure.
Figure 78:
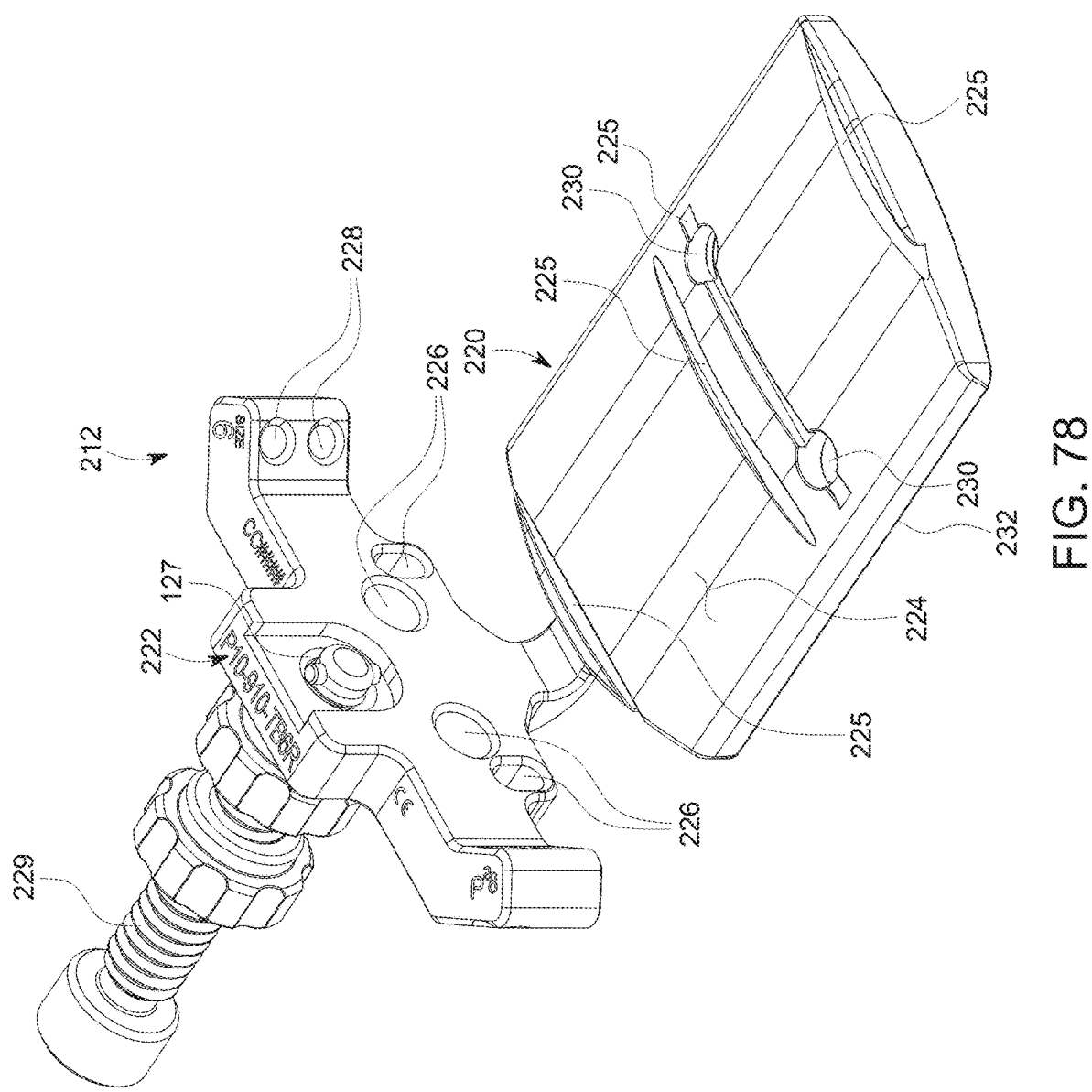
FIG. 78 illustrates an elevational posterior perspective view of the tibial trial guide of the TAR trial and guide system of FIG. 74, in accordance with an aspect of the present disclosure.
Figure 85:
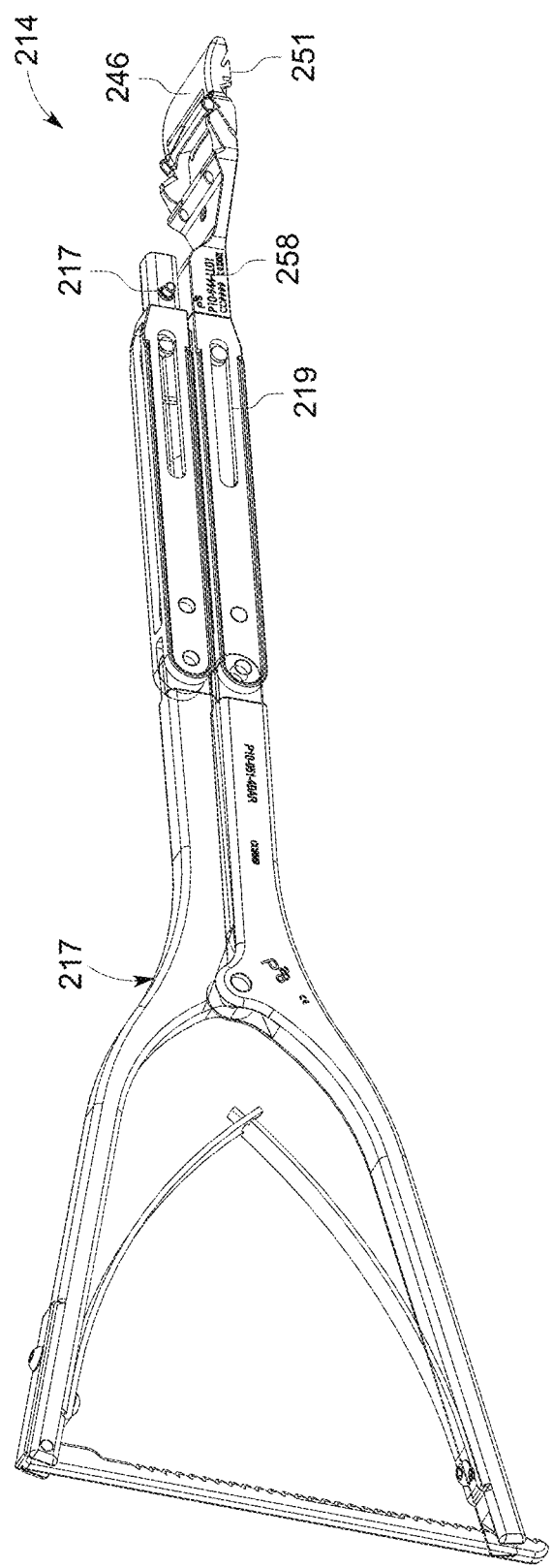
FIG. 85 illustrates a distal elevational perspective view of the first talar trial guide and the distractor of FIG. 76, in accordance with an aspect of the present disclosure.
Figure 86:
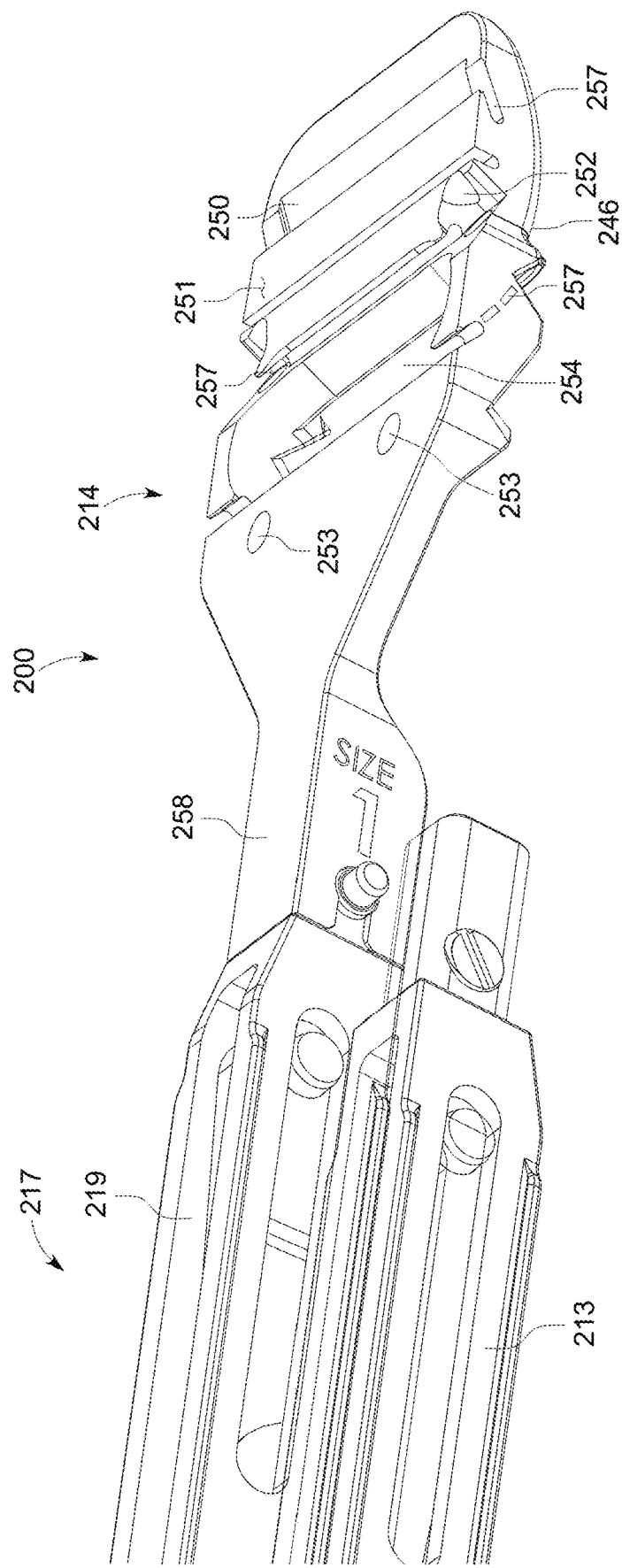
FIG. 86 illustrates a distal medial perspective view of the tibial trial guide and the distractor of FIG. 85, in accordance with an aspect of the present disclosure.
Figure 87:
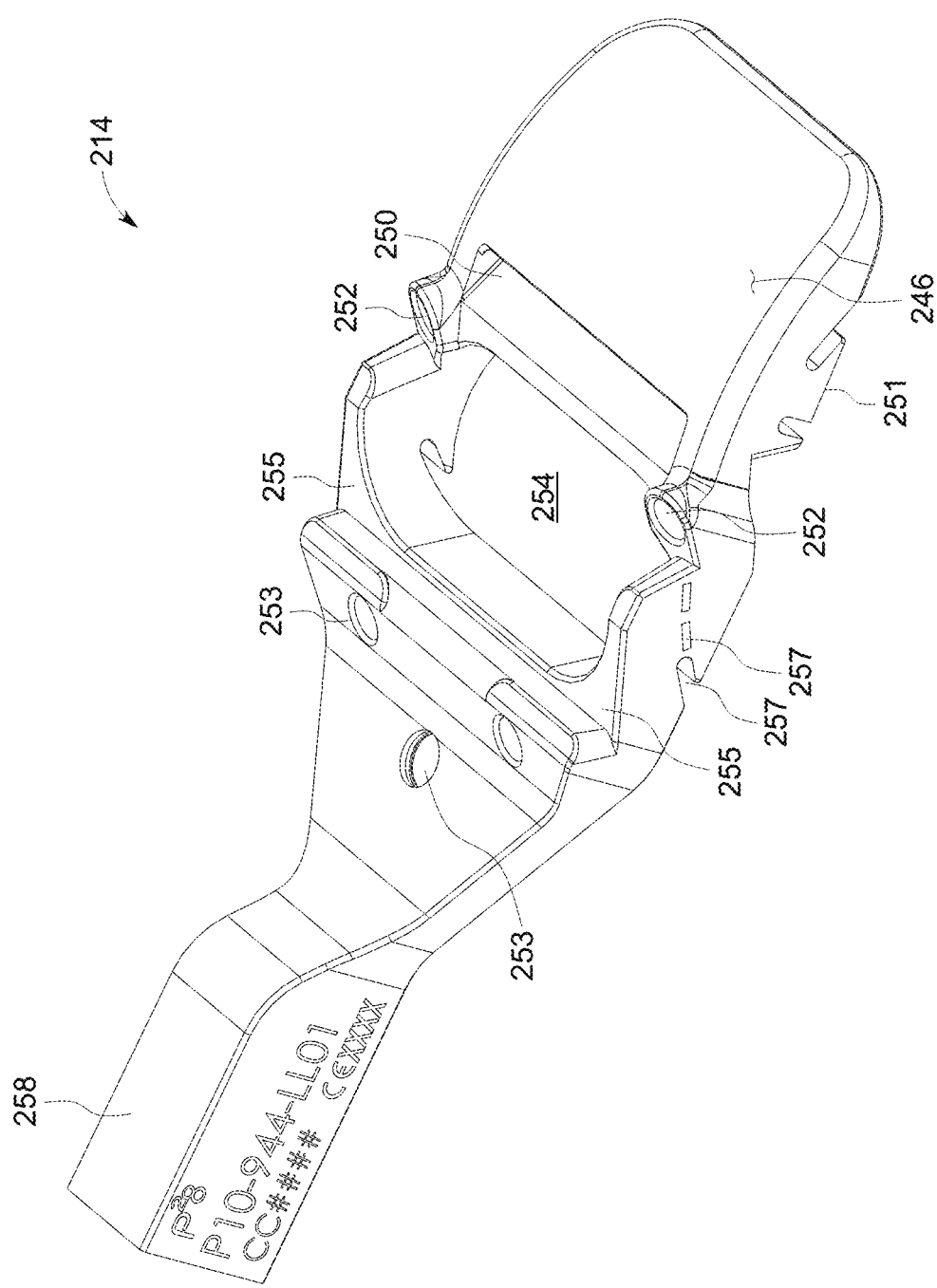
FIG. 87 illustrates an elevational posterior perspective view of the first talar trial guide of the TAR trial and guide system of FIG. 74, in accordance with an aspect of the present disclosure.

As shown in FIGS. 74, 76, 77, 85, 86 and 94, the system 200 may include a distractor 217. The distractor 217 may include a first arm 215 and a second arm 219 that are configured to engage the base portion 220 of the tibial trial guide 212 and the anterior end 258 of the first talar trial guide 214, respectively. For example, the first arm 215 may include a tool (e.g., at least one paddle) that presses (directly or indirectly) against the distal side of the base portion 220 of the tibial trial guide 212 and/or forces a projection through bone aperture formation hole(s) 230 thereof (and into the resected distal tibia 2), as shown in FIGS. 74, 76 and 77. As another example, the second arm 219 may couple with a socket anterior end portion 258 of the of the first talar trial guide 214, as shown in FIGS. 74, 85 and 86. The distractor 217 may be configured to be manually manipulated to effectuate movement of the first arm 215 and the second arm 258 together and apart anteriorly-posteriorly. The distractor 217 may thereby be utilized to form one or more aperture in the resected distal tibia 2, distract the ankle joint, and/or facilitate engagement/coupling of the tibial trial guide 212 with the resected distal tibia 2 and/or the first talar trial guide 214 with the resected talus 4, for example. In some embodiments, the distractor 217 may be a distractor disclosed in U.S. Provisional Patent Application No. 62/898,854 filed Sep. 11, 2018 and entitled Distractors Having Attachable Paddles, Impaction Devices, and Methods for Use in Total Ankle Replacement and/or International PCT Patent Application filed on Dec. 13, 2019, and entitled Distractors Having Attachable Paddles, Impaction Devices, and Methods for Use in Total Ankle Replacement.

As shown in FIGS. 78-84, the tibial trial guide 212 of the system 200 may differ from the tibial trial guide 112 with respect to the configuration of the second pin apertures 228. As shown in FIGS. 78-84, the medial and lateral wings of the arm portion 222 may each include a pair of second pin apertures 228 that are proximally-distally spaced. It is noted that in some embodiments, a proximal second pin aperture 228 and a distal second pin aperture 228 of the medial and lateral (or lateral and medial) wing portions may be utilized via pin members 260 (e.g., shoulder pins) to couple the tibial trial guide 212 to the resected distal tibia 2.

As also shown in FIGS. 78-84, the tibial trial guide 212 may differ from the tibial trial guide 112 with respect to the configuration of the first pin apertures 226. As shown in FIGS. 78-84, the arm portion 222 may include a pair of medially-laterally spaced proximally-distally elongated or oblong first pin apertures 228 and a pair of medially-laterally spaced circular first pin apertures 228. The pair of medially-laterally spaced proximally-distally elongated or oblong first pin apertures 228 may converge medially-laterally as they extend posteriorly. The pair of medially-laterally spaced proximally-distally elongated or oblong first pin apertures 228 may be configured to accept pin members 260 (e.g., threaded shoulder pins) therethrough and into the resected distal tibia 2 to couple the tibial trial guide 212 to the resected distal tibia 2. The pair of medially-laterally spaced circular first pin apertures 228 may be aligned and configured to accept pin members 260 (e.g., smooth Steinmann pins) therethrough and into the resected distal tibia 2 to couple the tibial trial guide 212 to the resected distal tibia 2. It is noted that in some embodiments only the medial first pin aperture 228 of the pair of medially-laterally spaced circular first pin apertures 228 may be utilized with a pin member 260.

As further shown in FIGS. 78-84, the tibial trial guide 212 may differ from the tibial trial guide 112 with respect to the configuration of the anterior-posterior adjustment screw mechanism 229. As shown in FIGS. 78-84, the adjustment screw mechanism 229 may include a double nut configuration to lock the anterior-posterior position of the adjustment screw mechanism 229 within the arm portion 222. As also shown in FIGS. 78-84, the adjustment screw mechanism 229 may include an anti-removal member or feature that prevents the adjustment screw 229 from disengaging from the arm portion 222.

Figure 79:
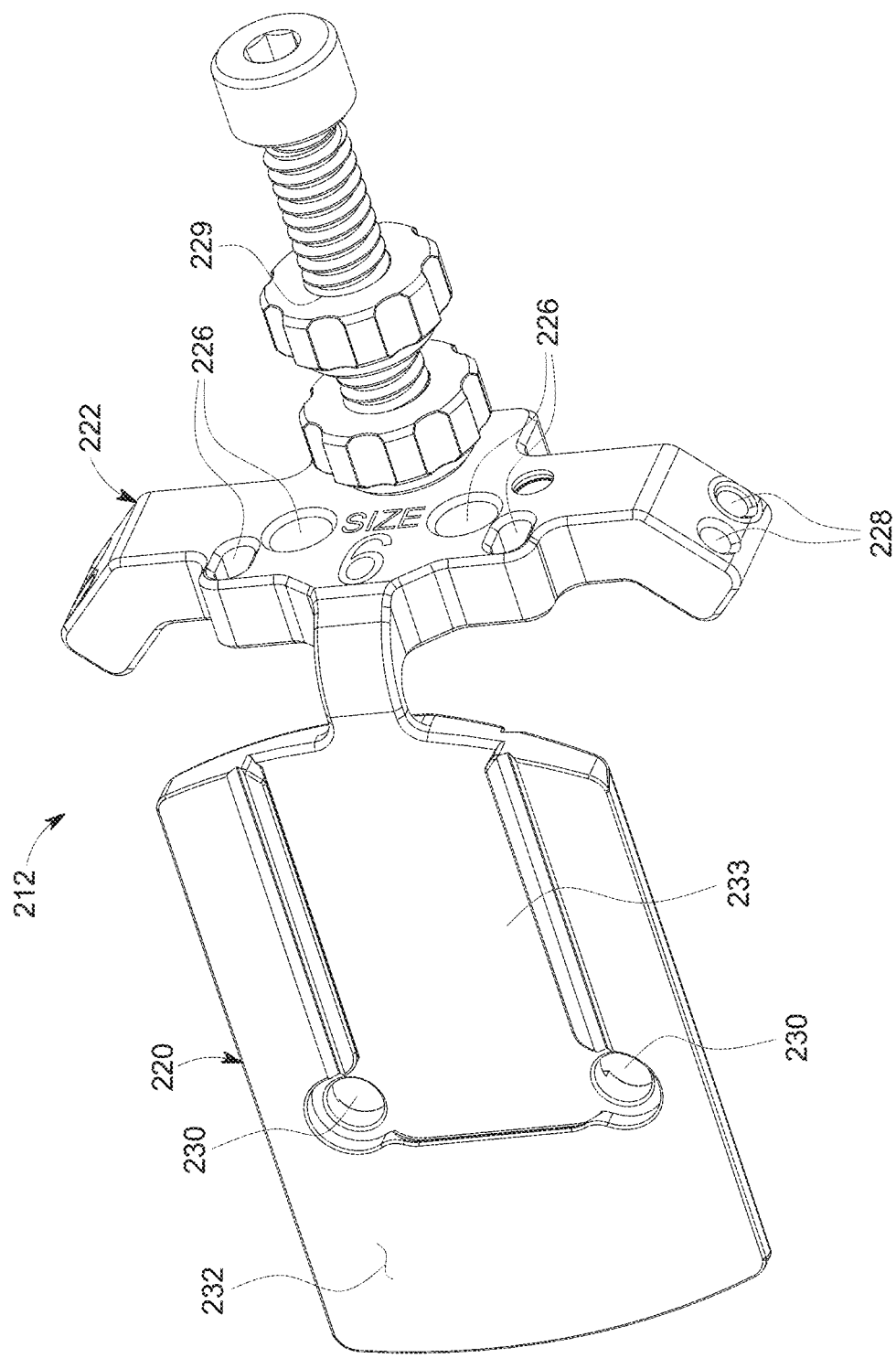
FIG. 79 illustrates a distal posterior perspective view of the tibial trial guide of FIG. 78, in accordance with an aspect of the present disclosure.
Figure 80:
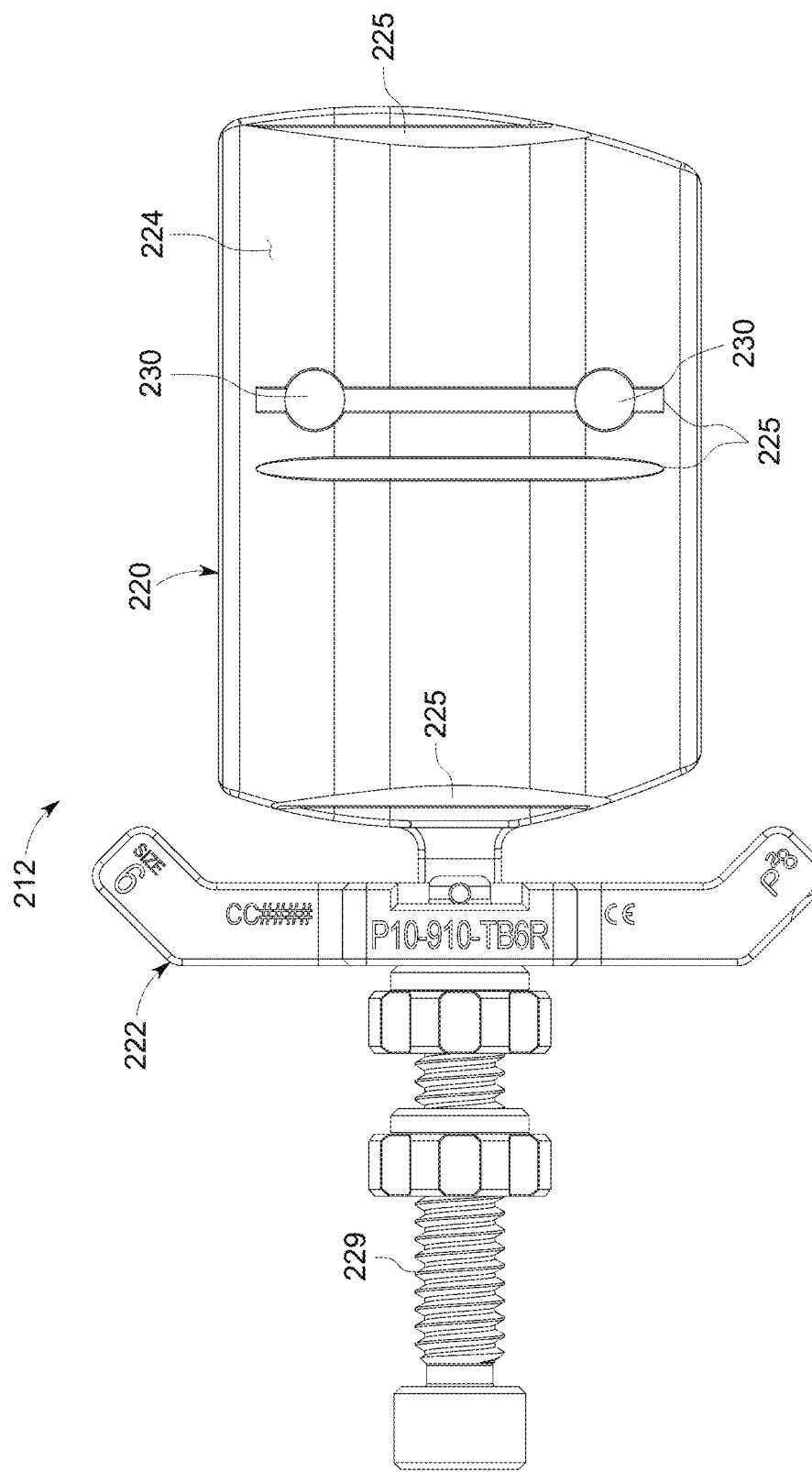
FIG. 80 illustrates a proximal view of the tibial trial guide of FIG. 78, in accordance with an aspect of the present disclosure.
Figure 81:
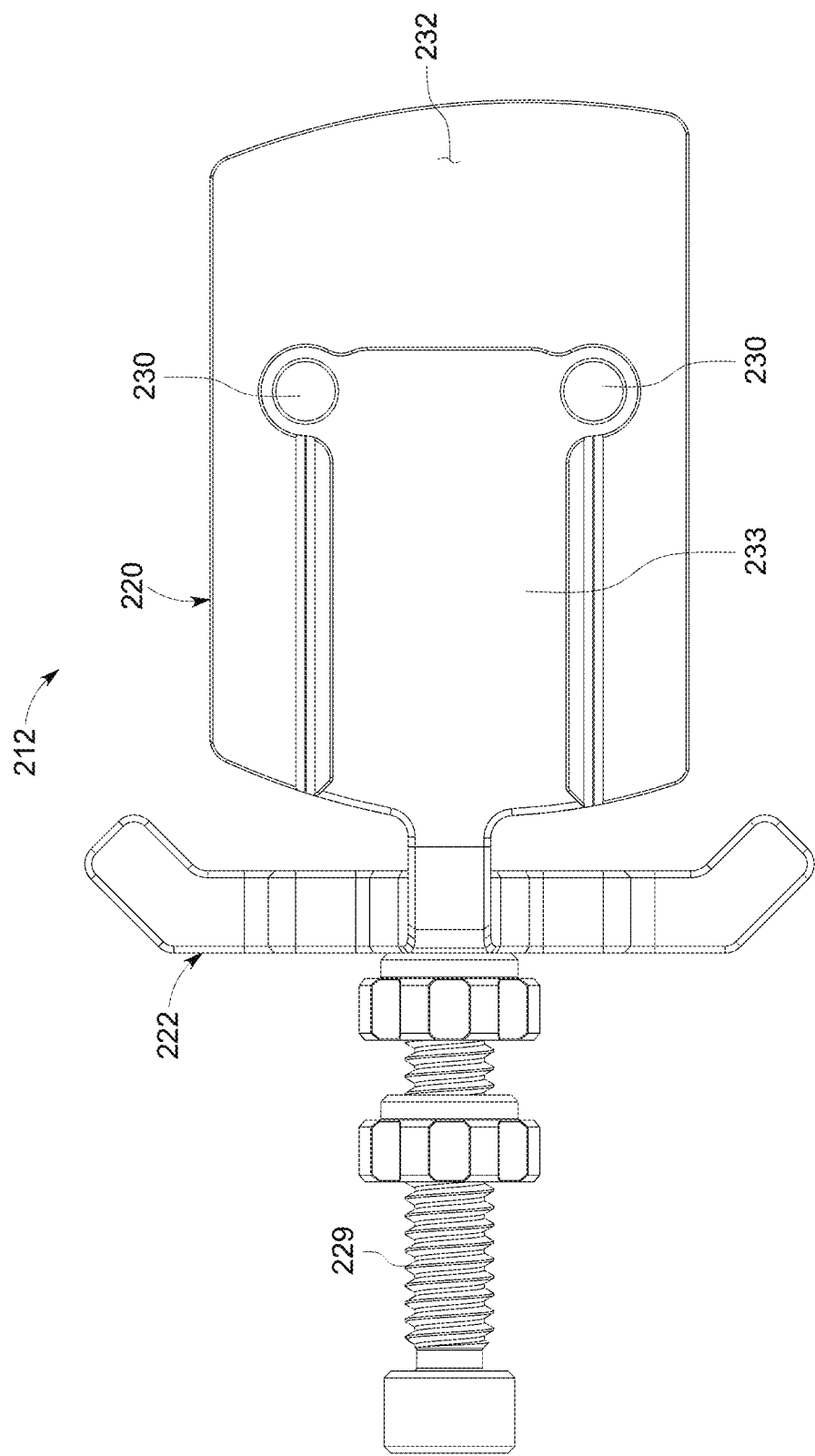
FIG. 81 illustrates a distal perspective view of the tibial trial guide of FIG. 78, in accordance with an aspect of the present disclosure.
Figure 82:
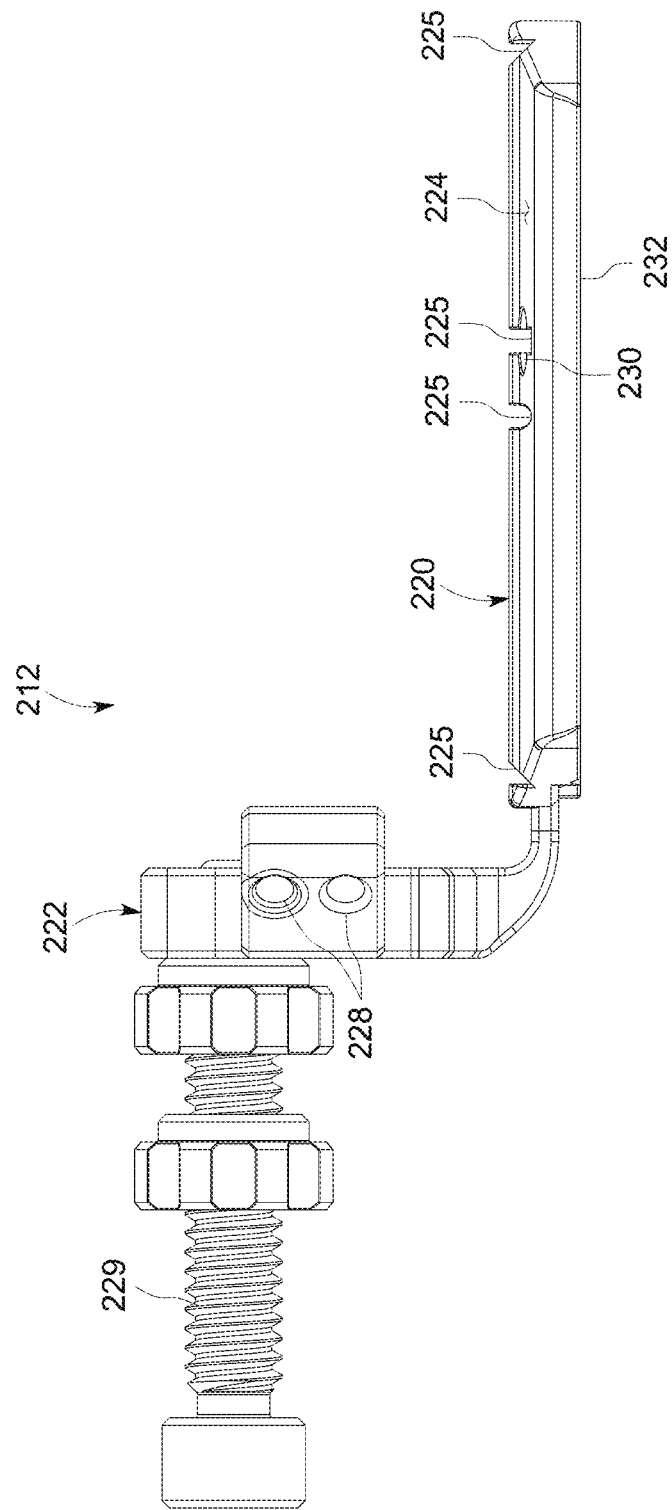
FIG. 82 illustrates a medial view of the tibial trial guide of FIG. 78, in accordance with an aspect of the present disclosure.
Figure 83:
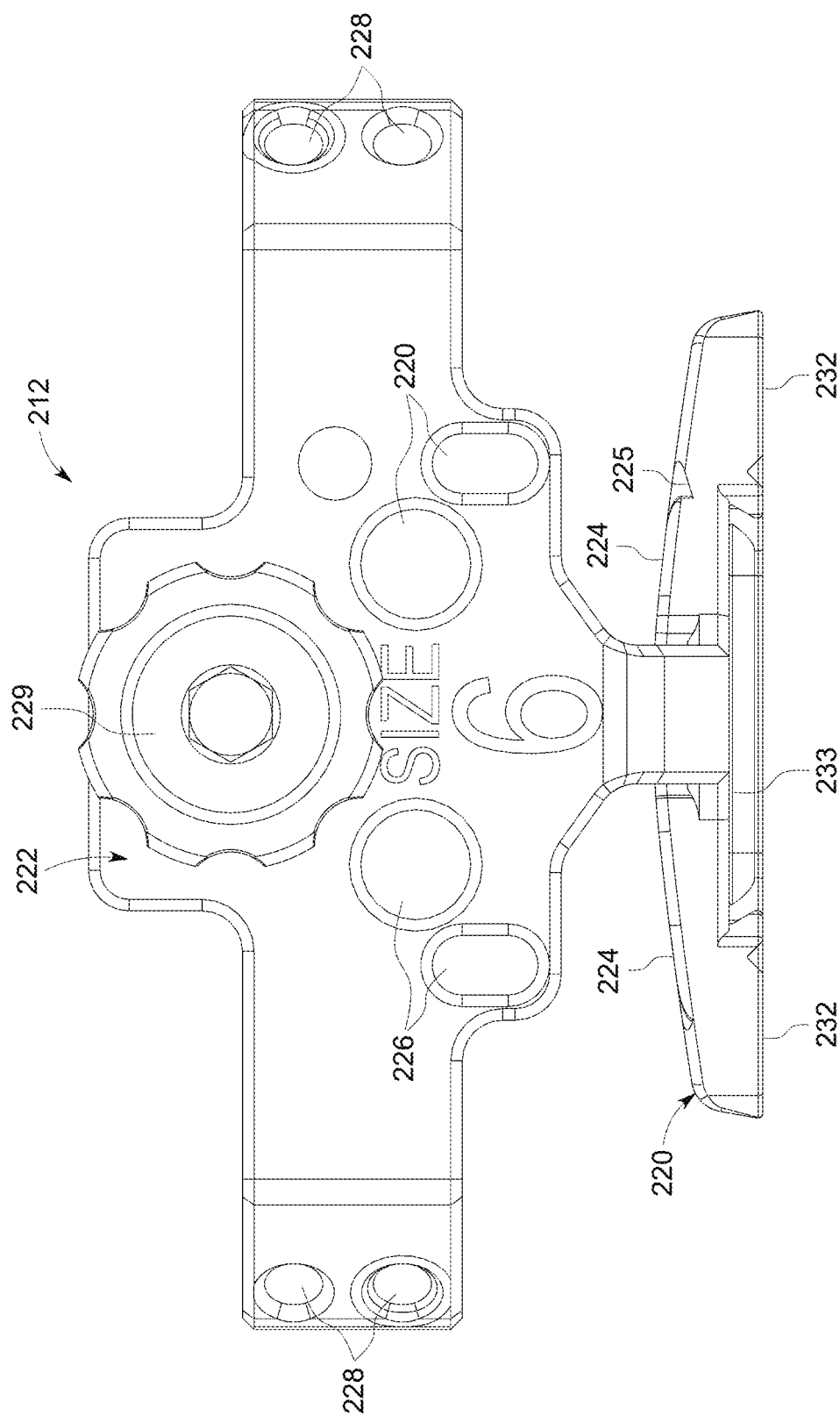
FIG. 83 illustrates an anterior view of the tibial trial guide of FIG. 78, in accordance with an aspect of the present disclosure.
Figure 84:
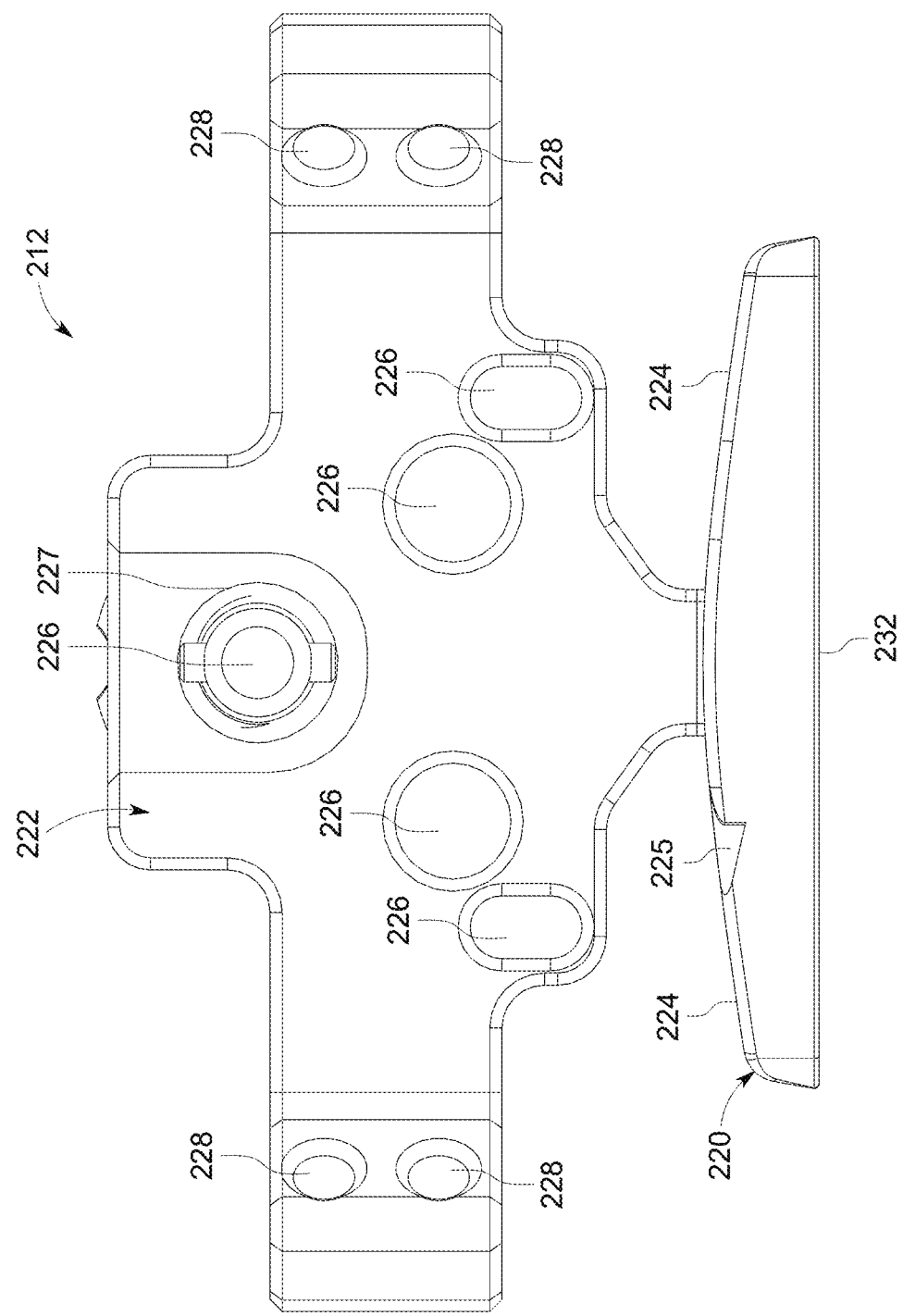
FIG. 84 illustrates a posterior view of the tibial trial guide of FIG. 78, in accordance with an aspect of the present disclosure.

As further shown in FIGS. 78-84, the tibial trial guide 212 may differ from the tibial trial guide 112 with respect to the configuration of the at least one through hole 230 of the base portion 220. As shown in FIGS. 78-84, the base portion 220 only includes a pair of medially-laterally spaced (anteriorly-posteriorly aligned) through holes 230 between the anterior-posterior center and posterior end of the base portion 220. Further, the recessed portion 233 of the distal insert side 232 of the base portion 220 may be void of a slot or indentation, as shown in FIGS. 79 and 81.

Figure 91:
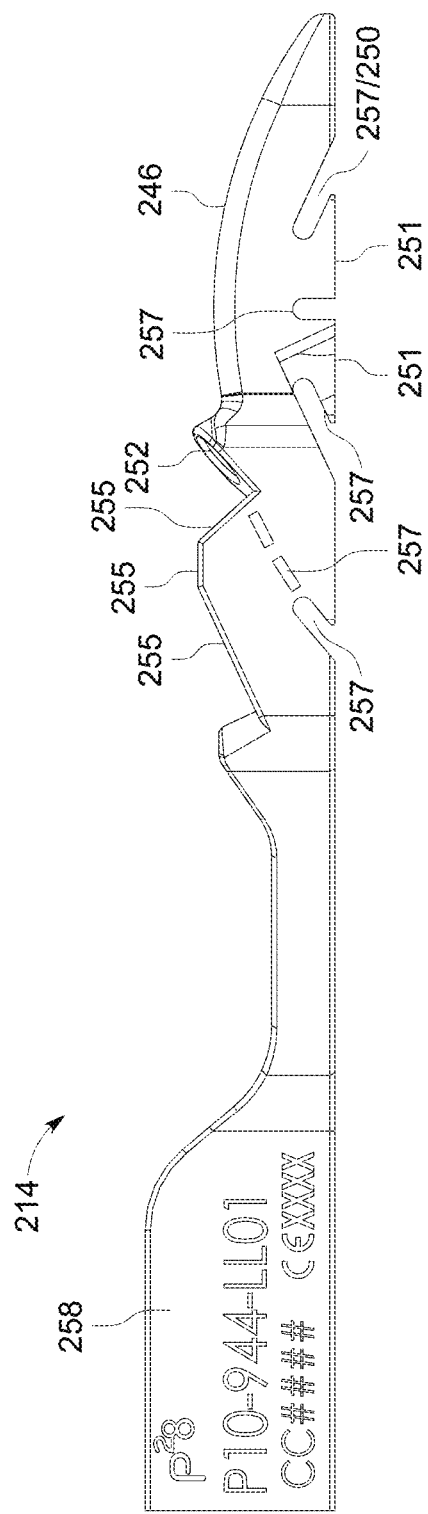
FIG. 91 illustrates a medial side view of the first talar trial guide of FIG. 87, in accordance with an aspect of the present disclosure.
Figure 92:
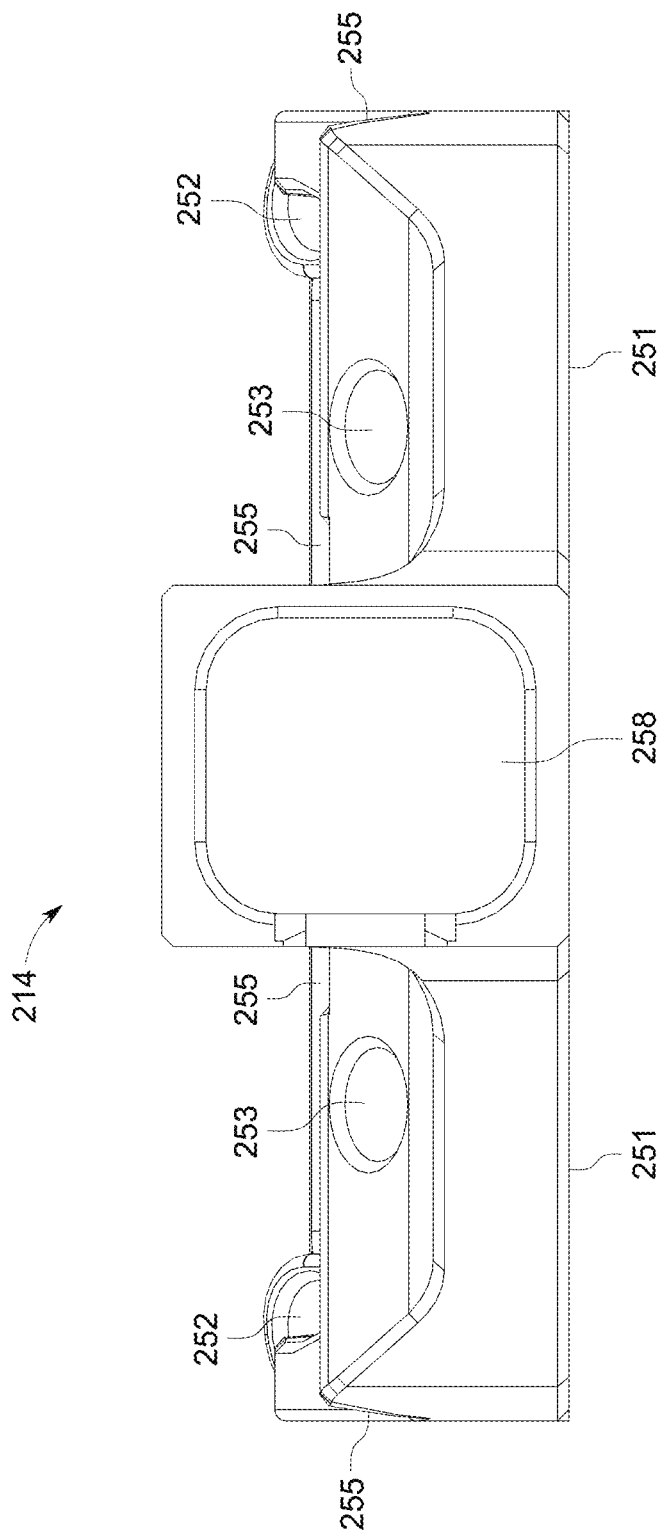
FIG. 92 illustrates an anterior view of the first talar trial guide of FIG. 87, in accordance with an aspect of the present disclosure.
Figure 93:
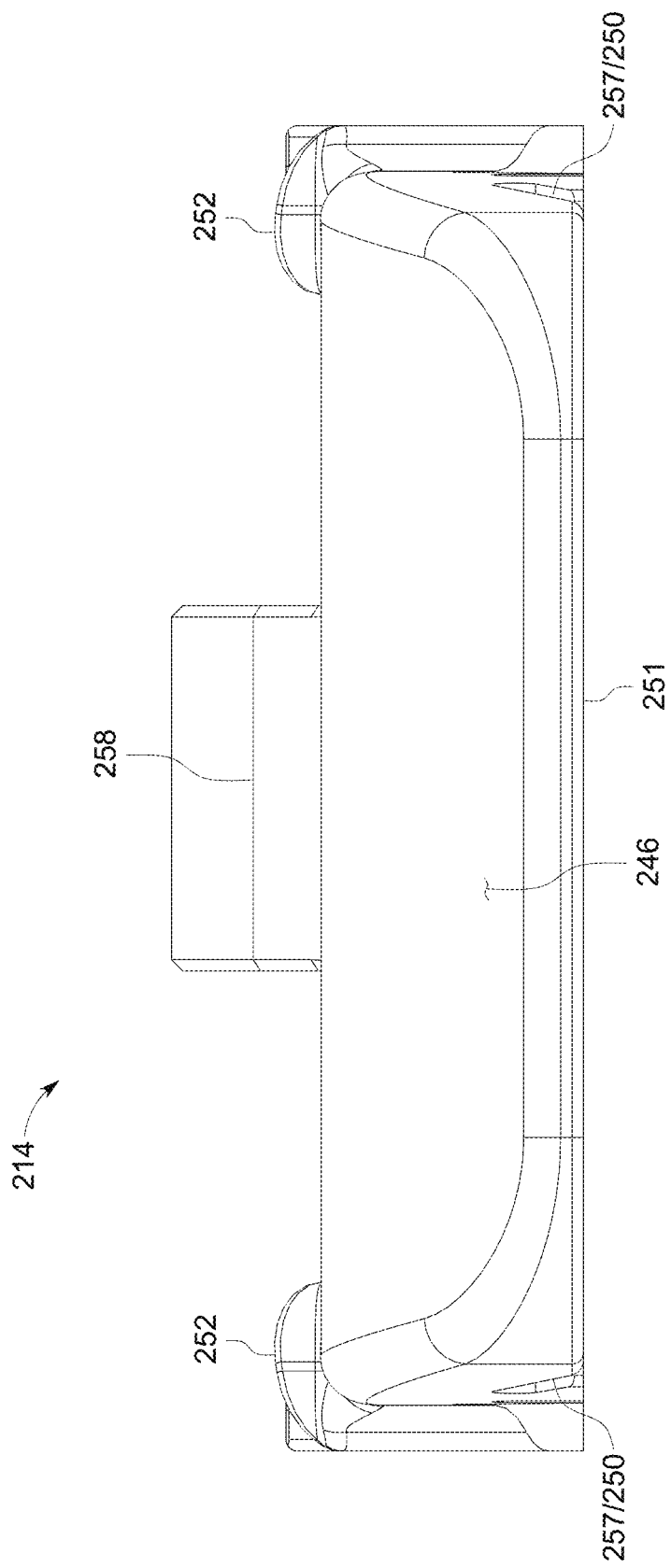
FIG. 93 illustrates posterior view of the first talar trial guide of FIG. 87, in accordance with an aspect of the present disclosure.
Figure 94:
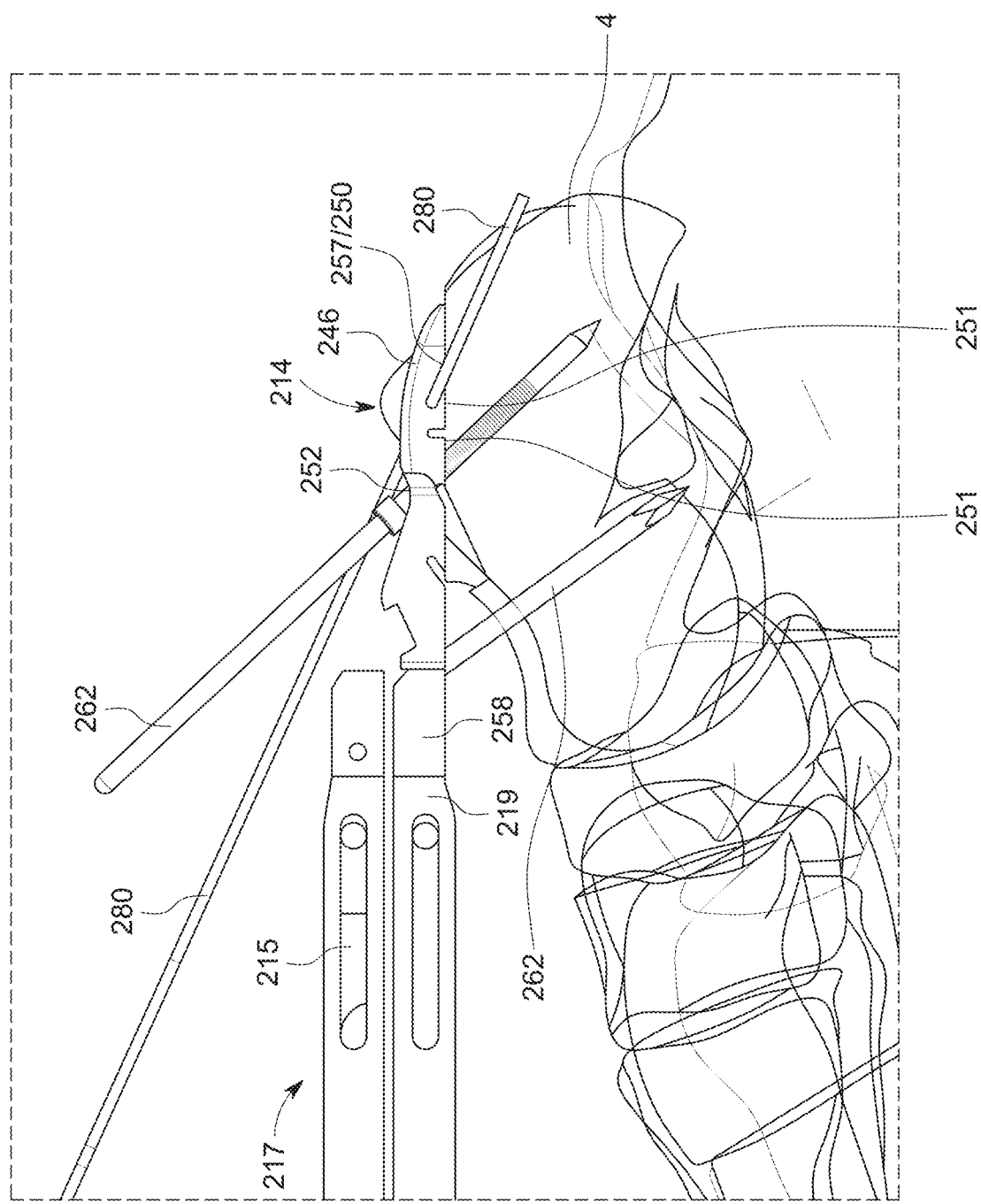
FIG. 94 illustrates a medial side view of the first talar trial guide and the distractor of FIG. 76 on a resected talus, and a bone cutting blade cutting a posterior chamfer on the resected talus via the first talar trial guide, in accordance with an aspect of the present disclosure.
Figure 95:
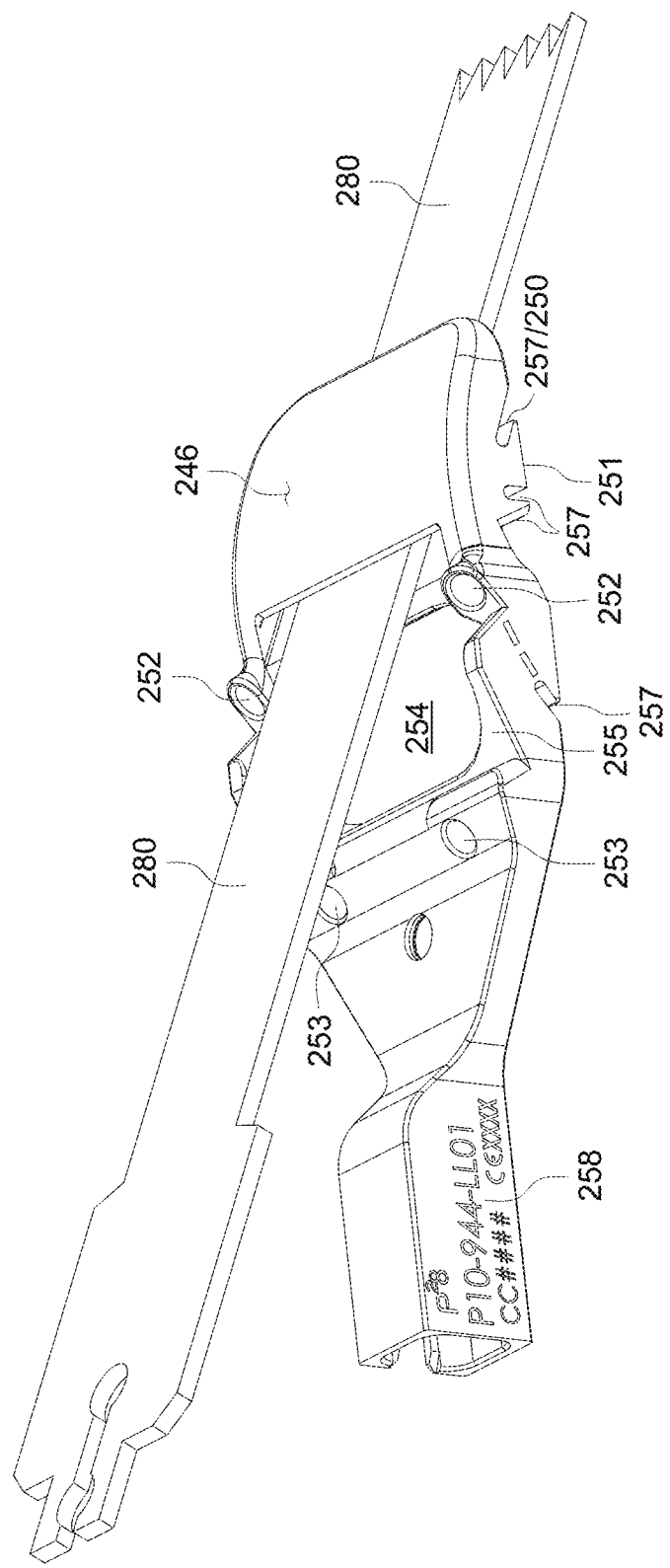
FIG. 95 illustrates an elevational anterior perspective view of the first talar trial guide of the TAR trial and guide system of FIG. 74 and a bone cutting blade cutting positioned within a cut slot thereof.
Figure 96:
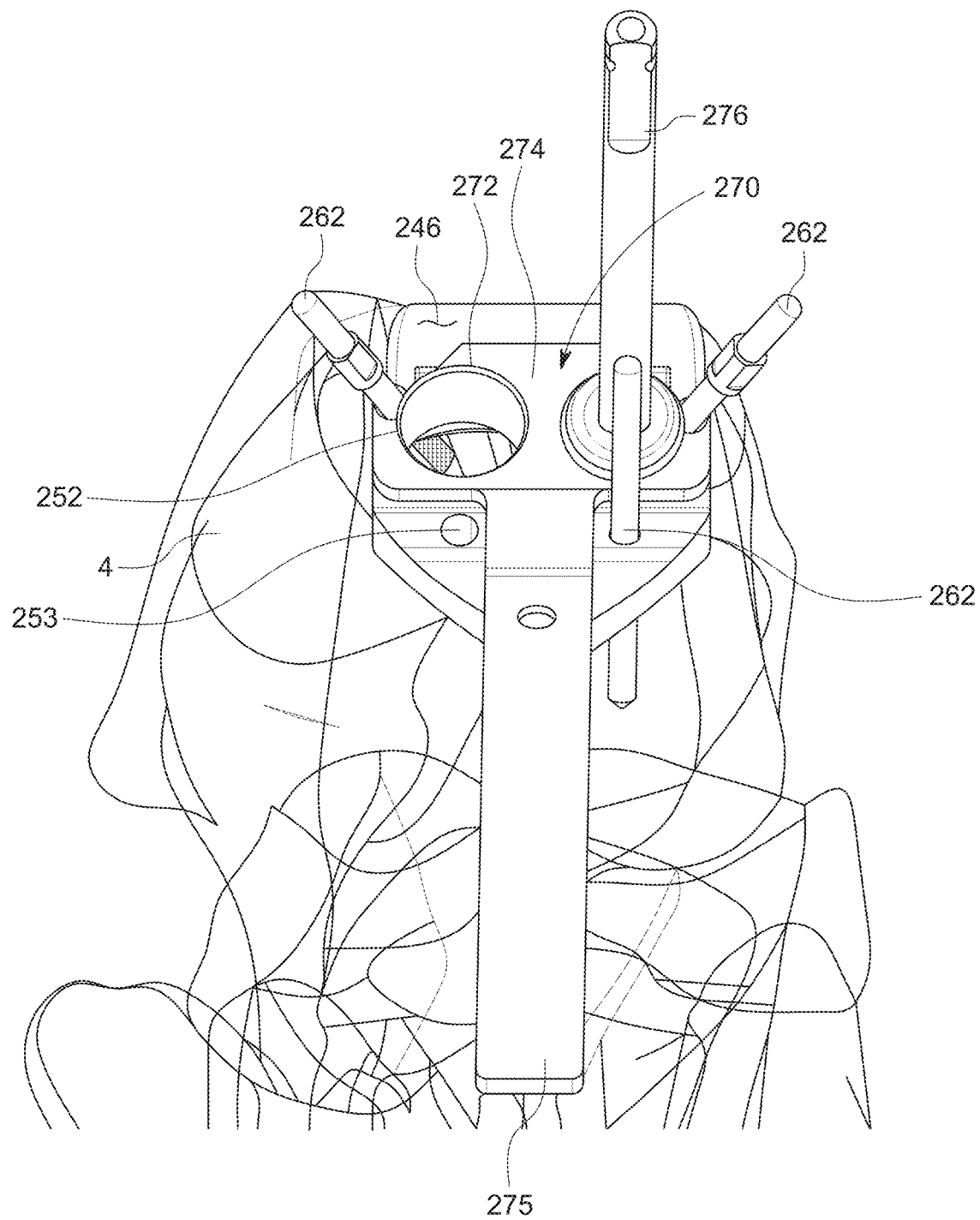
FIG. 96 illustrates an elevational anterior view of the first talar trial guide of the TAR trial and guide system of FIG. 74 on a resected talus, and a bone removal guide and bone cutting instrument cutting an anterior chamfer on the resected talus via the first talar trial guide, in accordance with an aspect of the present disclosure.
Figure 97:
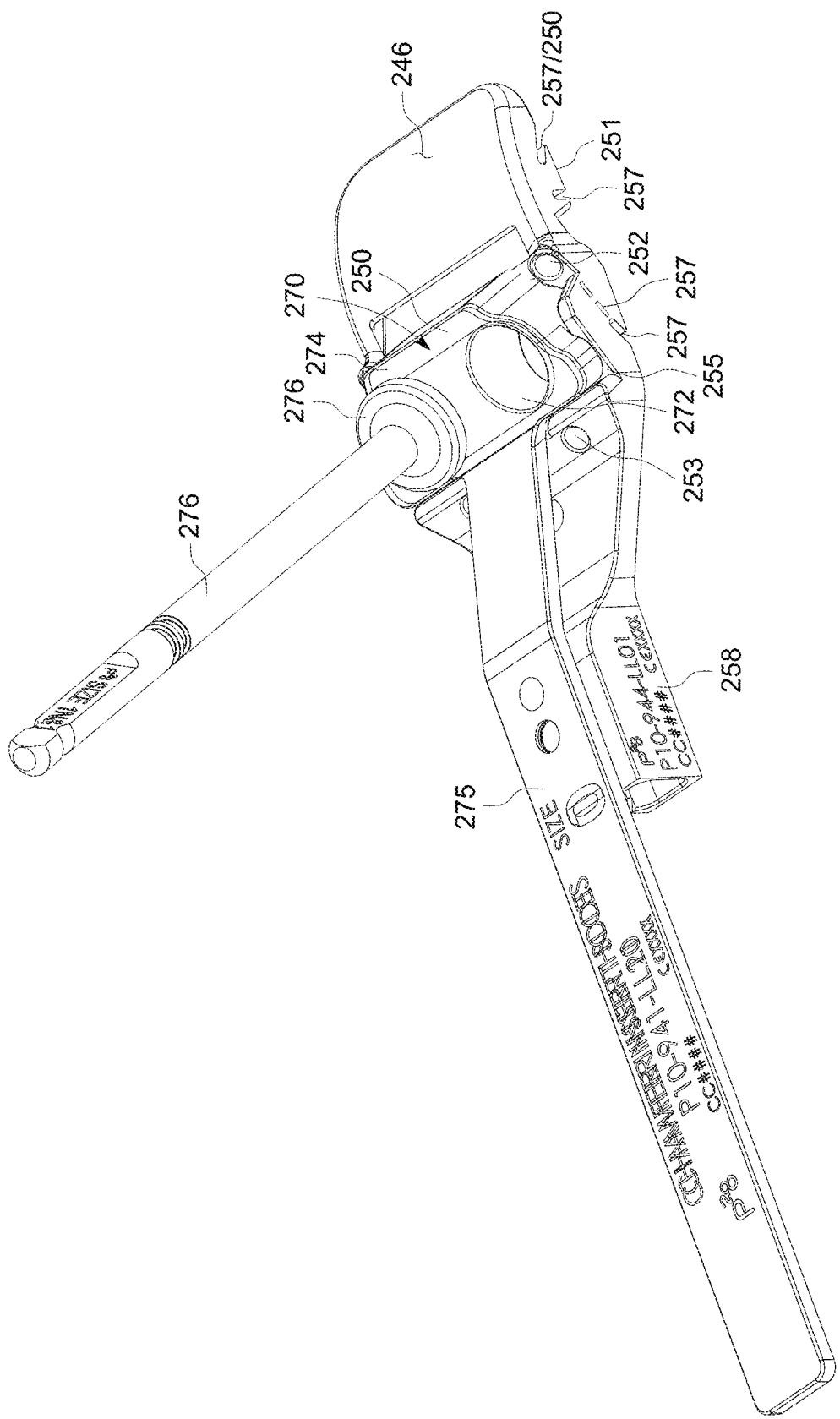
FIG. 97 illustrates an elevational anterior perspective view of the first talar trial guide of the TAR trial and guide system of FIG. 74 and a bone removal guide and bone cutting instrument engaged therewith, in accordance with an aspect of the present disclosure.
Figure 98:
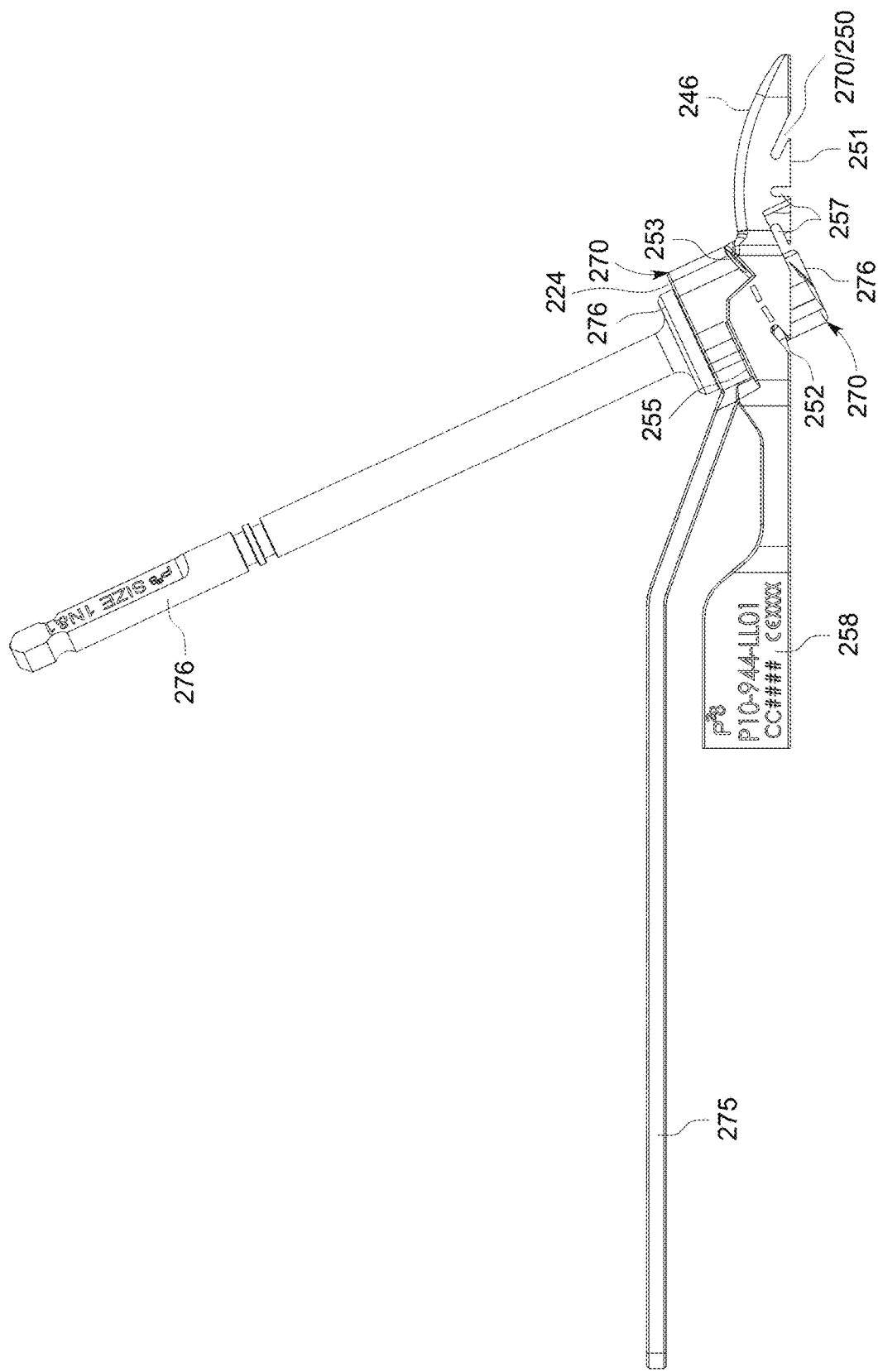
FIG. 98 illustrates a medial side view of the first talar trial guide, the bone removal guide and the bone cutting instrument of FIG. 97, in accordance with an aspect of the present disclosure.

As shown in FIGS. 87-95, the first talar trial guide 214 of the system 200 may differ from the talar trial guide 114 with respect to the configuration of the articulation surface 246. As shown in FIGS. 87-95, the articulation surface 246 comprises a smooth anteriorly-posteriorly arcuately convex surface that extends medially-laterally at least across the medial-lateral centerline of the first talar trial guide 214. In this way, the articulation surface 246 is thereby void of a anteriorly-posteriorly extending slot (or projection). In some embodiments, the articulation surface 246 may be defined by a single radius, as shown in FIG. 91. In some other embodiments, the articulation surface 246 may be defined by a plurality of differing radii. In some embodiments, the articulation surface 246 may be flat or linear medially-laterally.

It is noted that although the articulation surface 246 may correspond or approximate to the articulation surface of the 46 of the tibial insert 14, a tibial trail insert 216 (see FIGS. 116-119) may not be inserted between the tibial trial guide 112 and the first talar trial guide 214 and trialed, as discussed above with respect to system 100. Rather, the articulation surface 246 (and the reference lies/slots 257) may only be visually utilized to trial/examine the size, position an and orientation of the tibial insert 14. However, in some other embodiments the tibial trail insert 216 (see FIGS. 116-119) may be inserted between the tibial trial guide 112 and the first talar trial guide 214 and trialed, as discussed above with respect to system 100.

Figure 88:
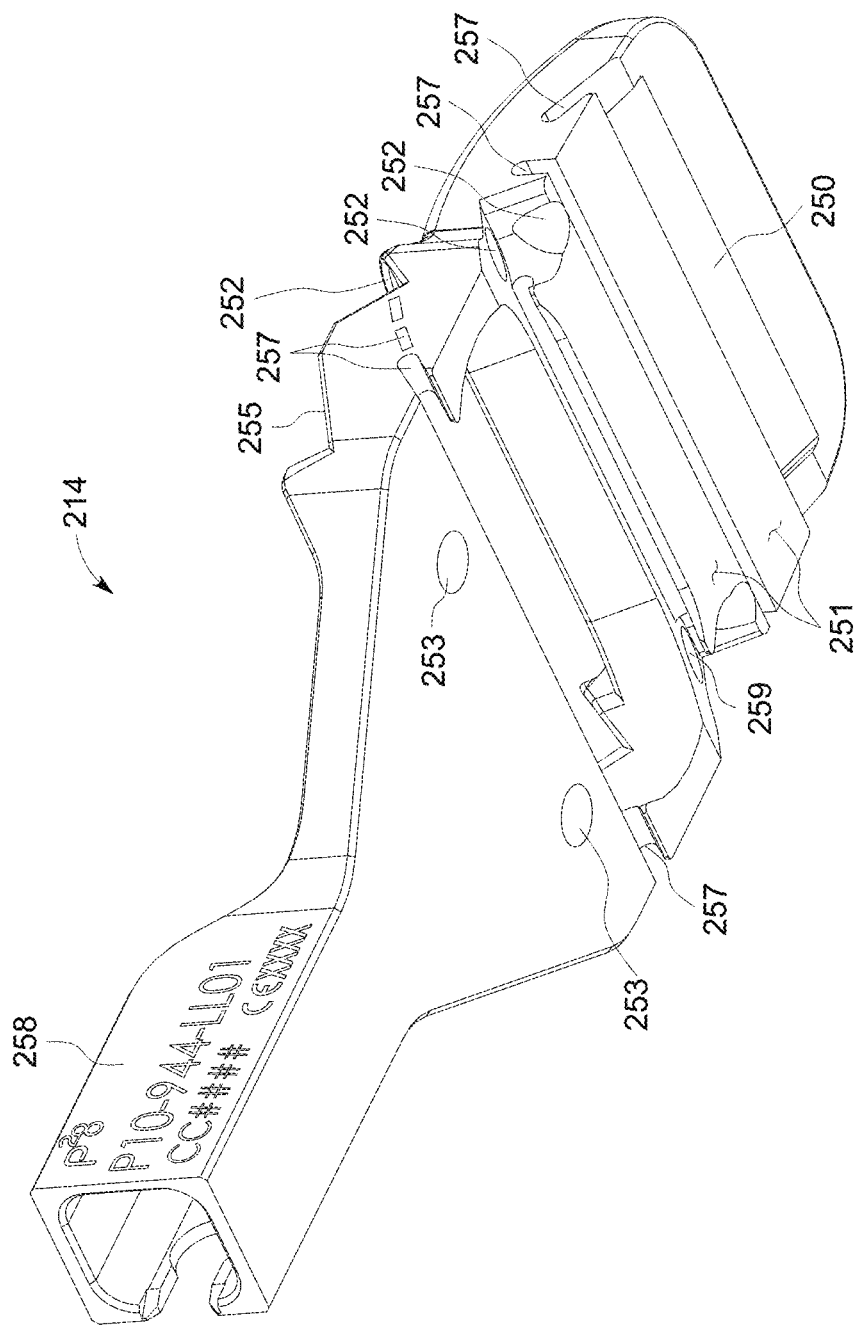
FIG. 88 illustrates a distal posterior perspective view of the first talar trial guide of FIG. 87, in accordance with an aspect of the present disclosure.
Figure 89:
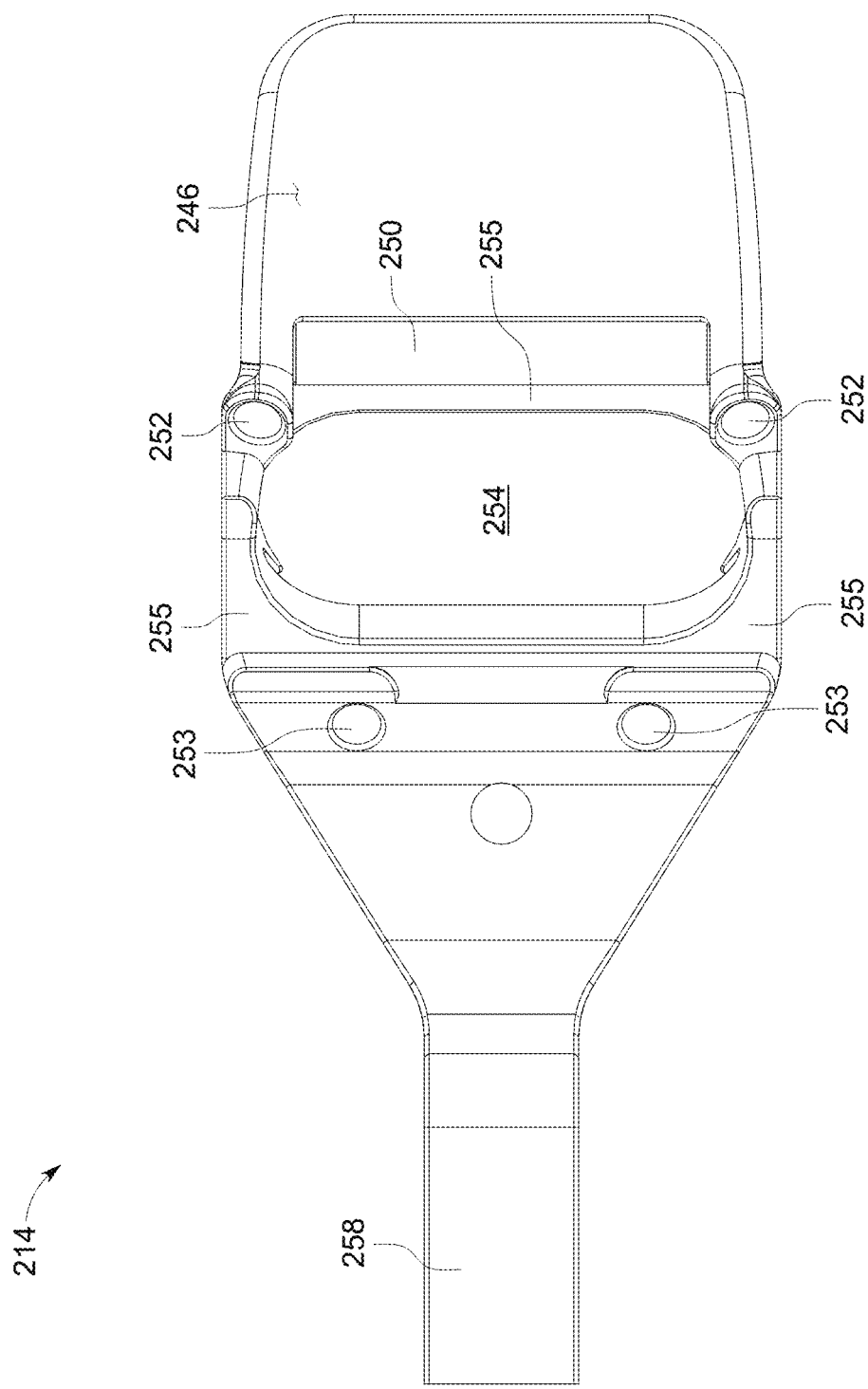
FIG. 89 illustrates a proximal view of the first talar trial guide of FIG. 87, in accordance with an aspect of the present disclosure.
Figure 90:
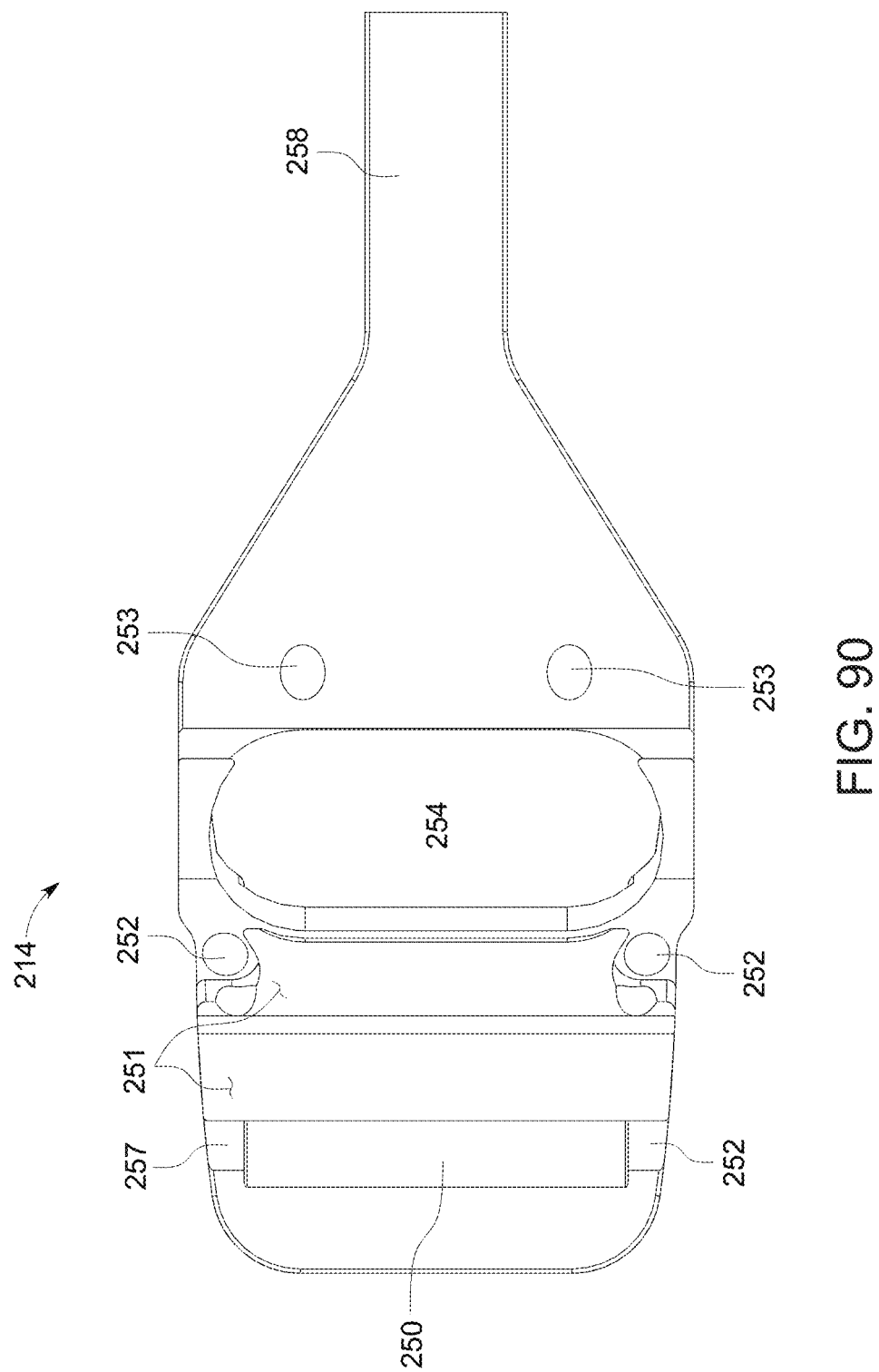
FIG. 90 illustrates a distal view of the first talar trial guide of FIG. 87, in accordance with an aspect of the present disclosure.

As discussed above and also shown in FIGS. 87-95, the first talar trial guide 214 of the system 200 may differ from the talar trial guide 114 with respect to the configuration of the anterior end portion 258. As shown in FIGS. 87-95, the anterior end portion 258 is configured as a socket (or projection) that mates with (i.e., accepts therein) a tool or an arm of the distractor 217. As shown in FIGS. 86 and 88, the anterior end portion 258 may include a socket with a key-hole shaped slot or opening configured to removably couple the anterior end portion 258 to a tool or an arm of the distractor 217.

Figure 99:
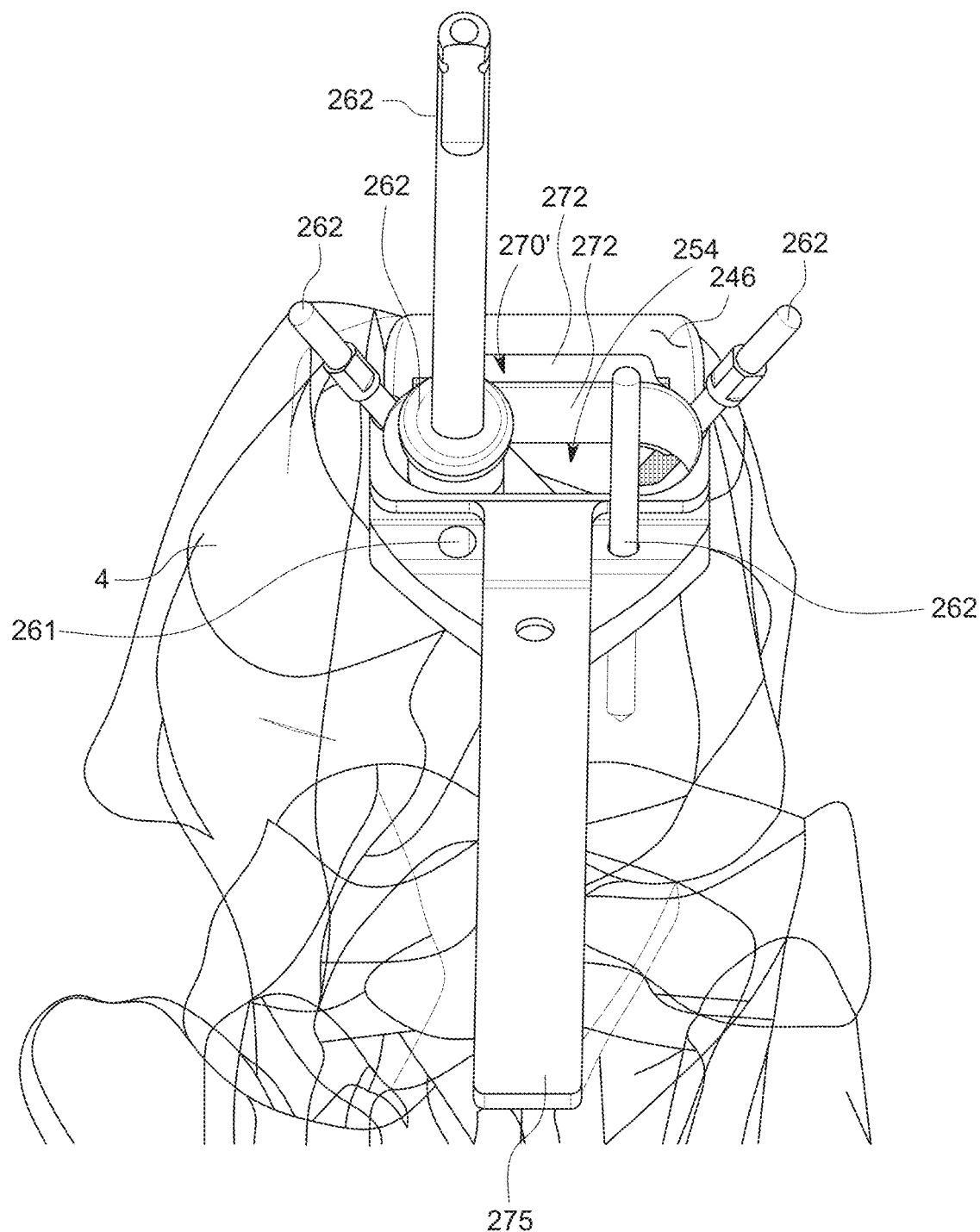
FIG. 99 illustrates an elevational anterior view of the first talar trial guide of the TAR trial and guide system of FIG. 74 on a resected talus, and another bone removal guide and bone cutting instrument further cutting an anterior chamfer on the resected talus via the first talar trial guide, in accordance with an aspect of the present disclosure.
Figure 100:
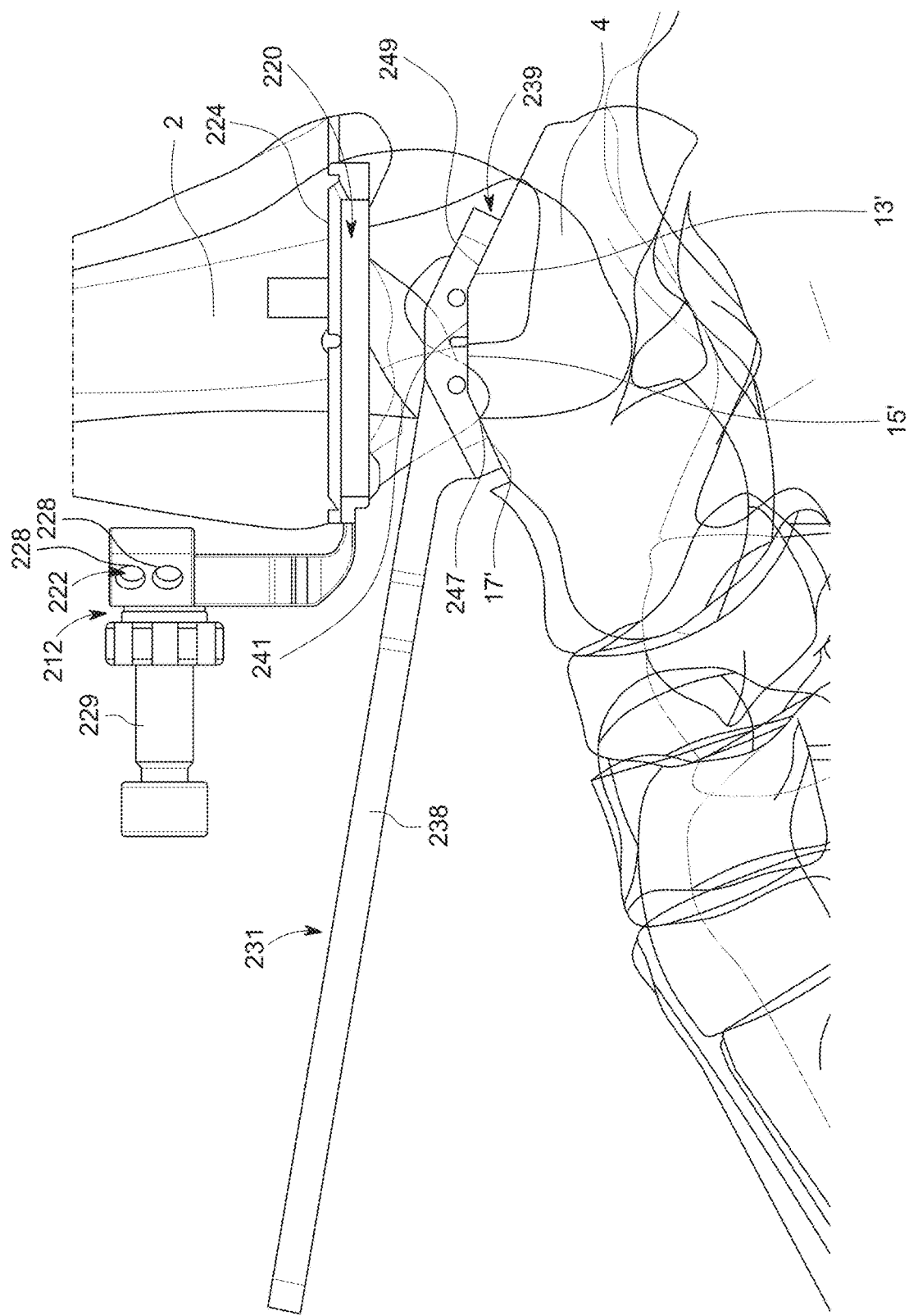
FIG. 100 illustrates the tibial trial guide of the TAR trial and guide system of FIG. 74 engaged with a resected distal tibia and a chamfer checker instrument of the TAR trial and guide system engaged with a resected and chamfered talus, in accordance with an aspect of the present disclosure.
Figure 101:
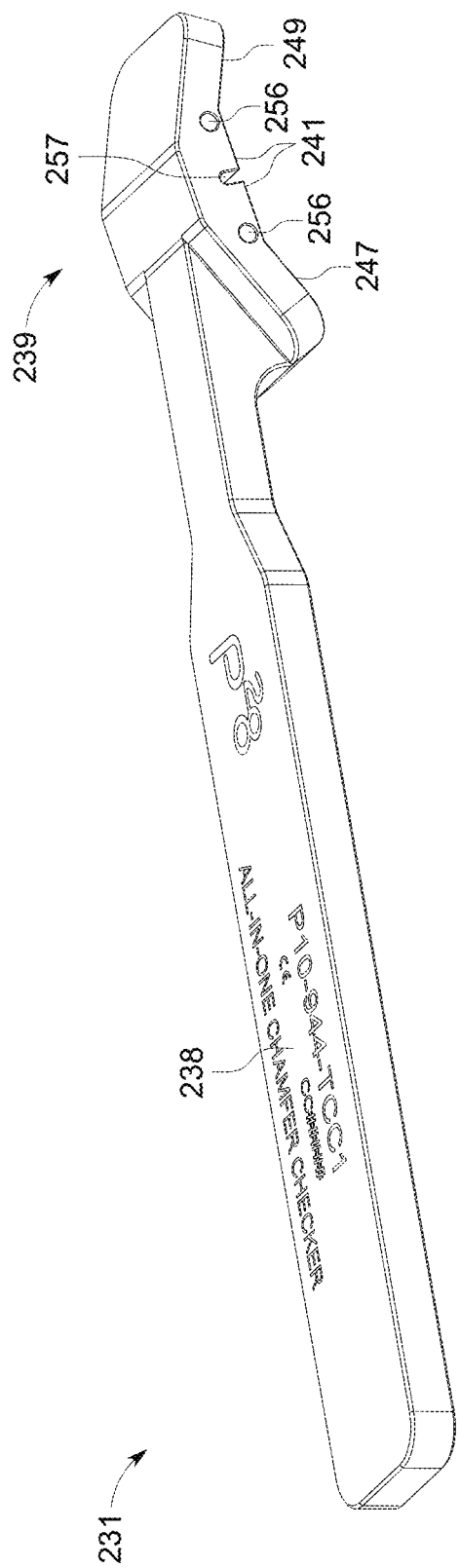
FIG. 101 illustrates an elevational anterior perspective view of the chamfer checker instrument of FIG. 100, in accordance with an aspect of the present disclosure.
Figure 102:
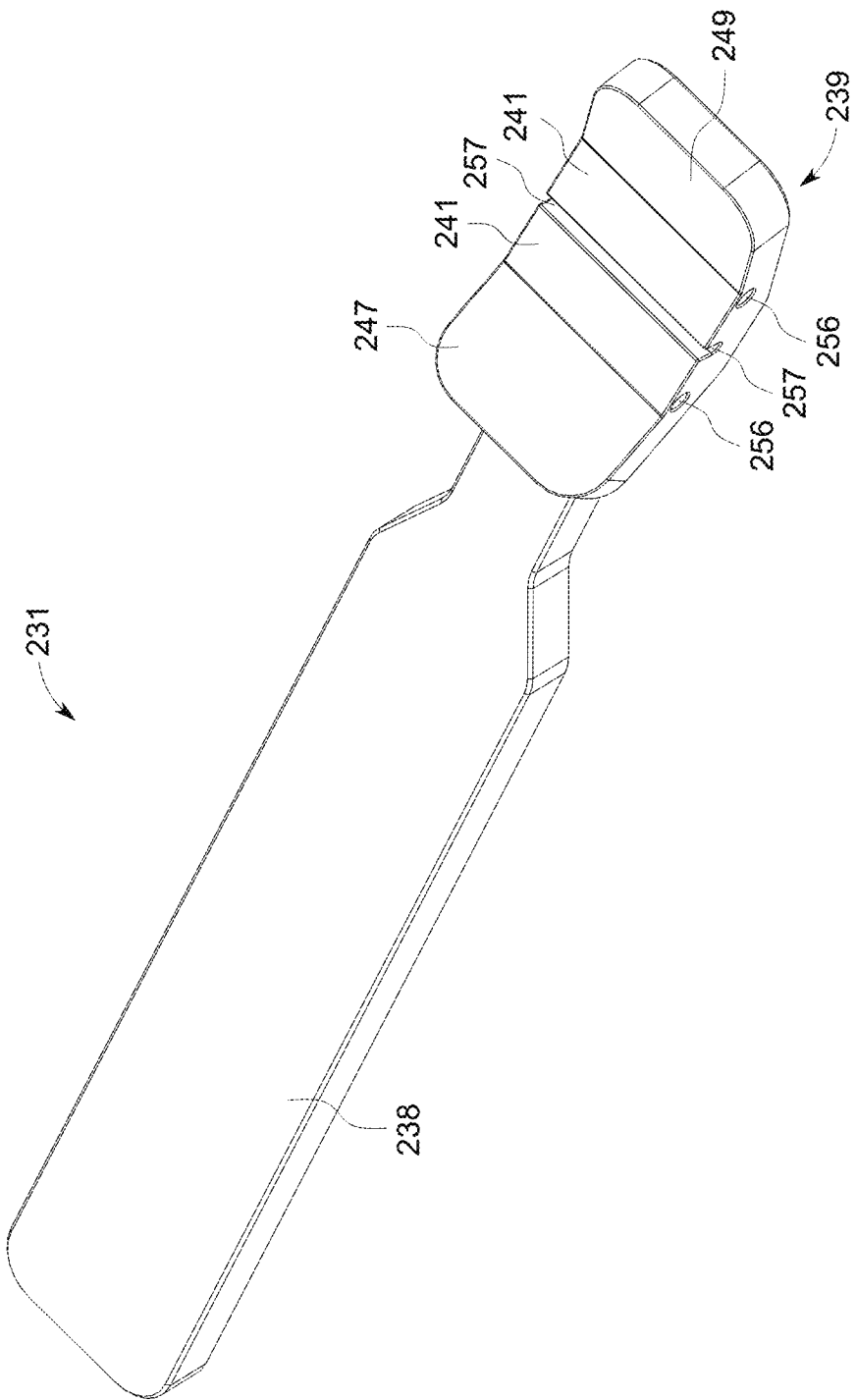
FIG. 102 illustrates an distal posterior perspective view of the chamfer checker instrument of FIG. 100, in accordance with an aspect of the present disclosure.

As shown in FIGS. 87-95, in some embodiments the multi-aperture bone removal guide 270 that is configured to couple to the support surface(s) 255 of the first talar trial guide 214 may include an elongated handle portion 275 that may be manually stabilized during use to keep the bone removal guide 270 firmly seated on the support surface(s) 255 of the first talar trial guide 214. Similarly, as shown in FIG. 99, the single-aperture bone removal guide 270' may include an elongated handle portion 275 that may be manually stabilized during use to keep the bone removal guide 270' firmly seated on the support surface(s) 255 of the first talar trial guide 214.

With reference to FIGS. 100-103, in some embodiments the system 200 may include a chamfer checker tool or instrument 231 that is configured to aide in ensuring the resected planar central surface 15', the chamfered planar posterior surface 13' (formed via the cut clot 250 of the first talar trial guide) and the chamfered planar anterior surface 17' (formed via the anterior window 254 of the first talar trial guide 214) of the resected talus 4 properly correspond (or match-up) with the planar central surface 15, the planar posterior surface 13 and the planar anterior surface 17, respectively, of the talar component 14 (see, FIGS. 38, 39 and 41). As shown in FIGS. 100-103, the chamfer checker tool 231 includes a handle portion 138 and an end portion 239. As shown in FIGS. 100-103, the end portion 239 of the chamfer checker tool 231 includes a planar central surface 241, a chamfered planar posterior surface 249 extending from the posterior end of the central surface 241, and a chamfered planar anterior surface 247 extending from the anterior end of the central surface 241 that correspond (or match) the planar central surface 15, the planar posterior surface 13 and the planar anterior surface 17, respectively, of the talar component 14 (see, FIGS. 38, 39 and 41).

As shown in FIGS. 100-103, the end portion 239 of the chamfer checker tool 231 further includes a center reference slot 257 that extends medially-laterally through the anterior-posterior center of the central surface 241, and thereby correspond to the anterior-posterior center of the central surface 241, the talar component 14 (and potentially the axis and/or anterior-posterior center of the talus 4 and/or tibia 2). The center reference slot 257 can thereby be utilized to visually inspect the anterior-posterior position of the talar component 14 when implanted on the talus 4.

Figure 103:
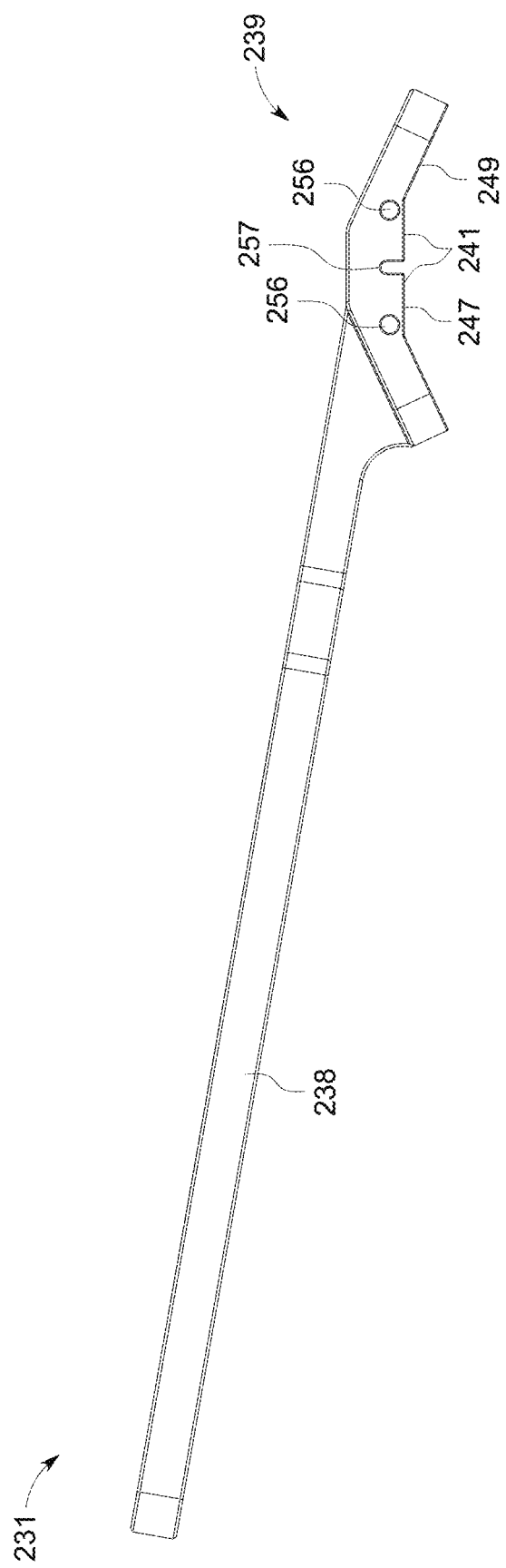
FIG. 103 illustrates a medial side view of the chamfer checker instrument of FIG. 100, in accordance with an aspect of the present disclosure.

The end portion 239 of the chamfer checker tool 231 may further include a pair of reference apertures 256, as shown in FIGS. 100-103. The reference apertures 256 may extend medially-laterally through the end portion 239 proximally of the central surface 241. The reference apertures 256 may be arranged such that a first reference aperture 256 is positioned tangent to a reference line extending along the chamfered planar posterior surface 249, and a second reference aperture 256 is positioned tangent to a reference line extending along the chamfered planar anterior surface 247, as shown in FIG. 103. The reference apertures 256 can thereby be utilized to visually inspect the position and orientation of the talar component 14 when implanted on the talus 4.

Figure 104:
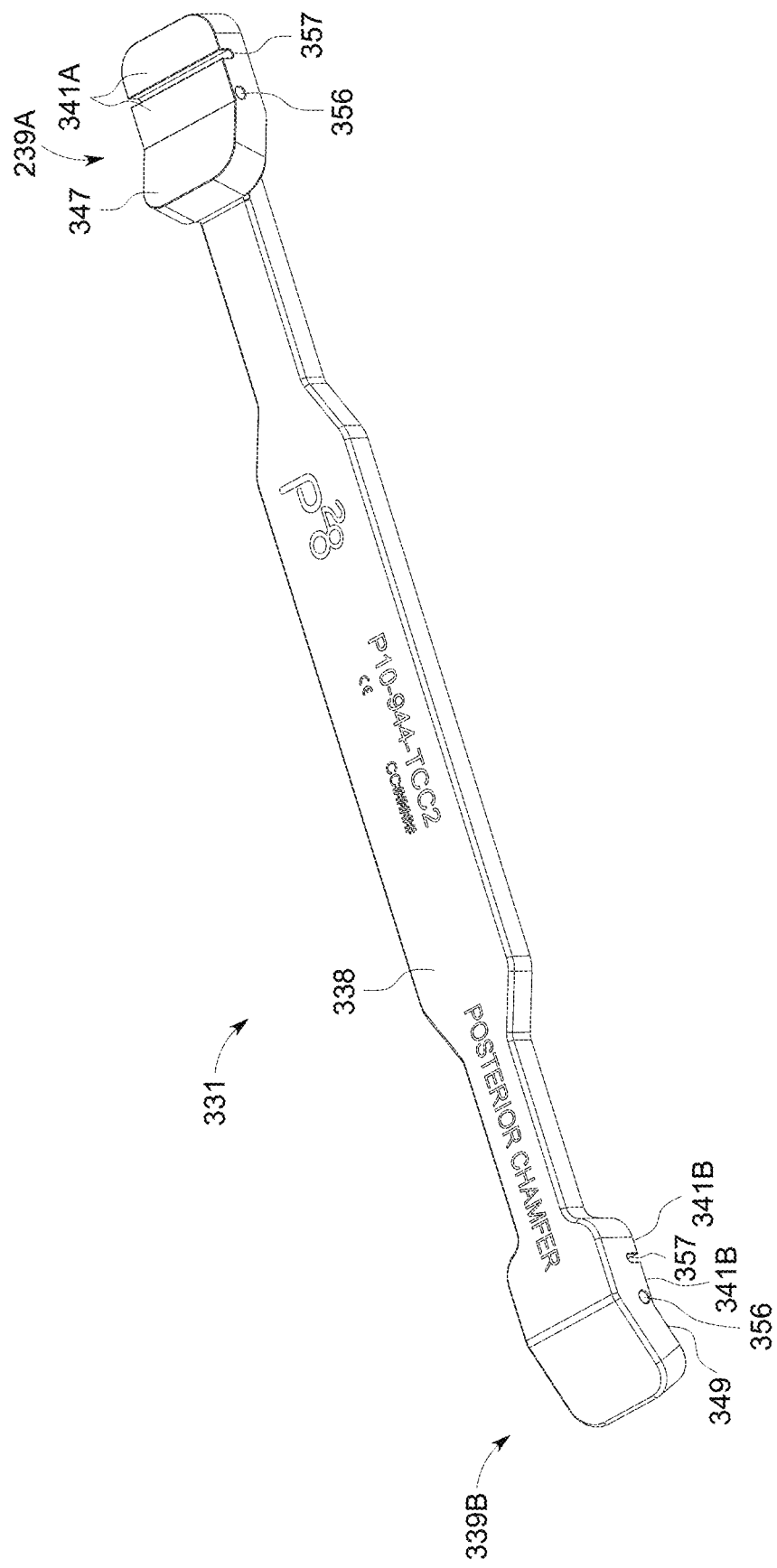
FIG. 104 illustrates an elevational anterior perspective view of another chamfer checker instrument for a TAR trial and guide system, in accordance with an aspect of the present disclosure.
Figure 105:
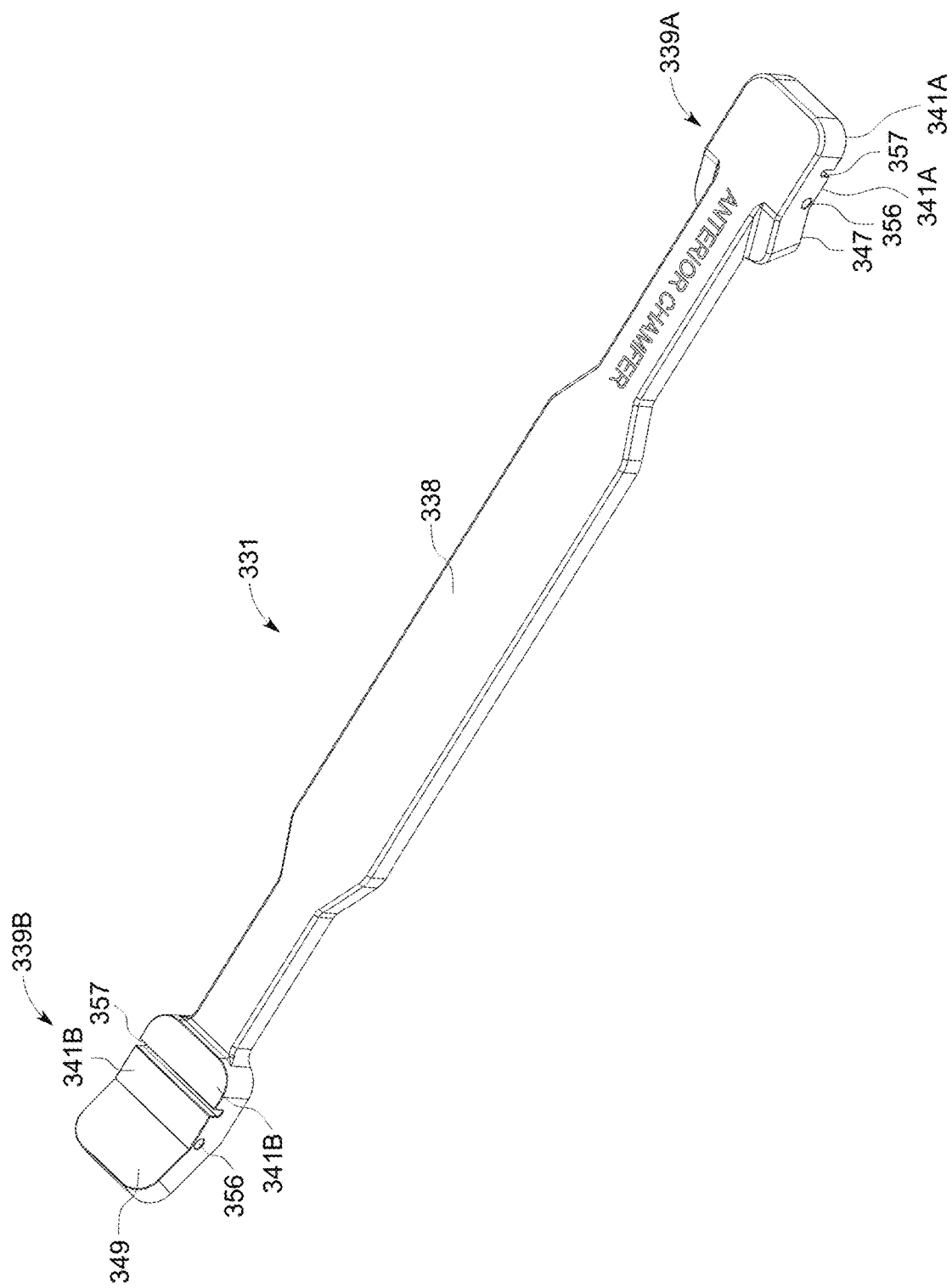
FIG. 105 illustrates a distal posterior perspective view of the chamfer checker instrument of FIG. 104, in accordance with an aspect of the present disclosure.
Figure 106:
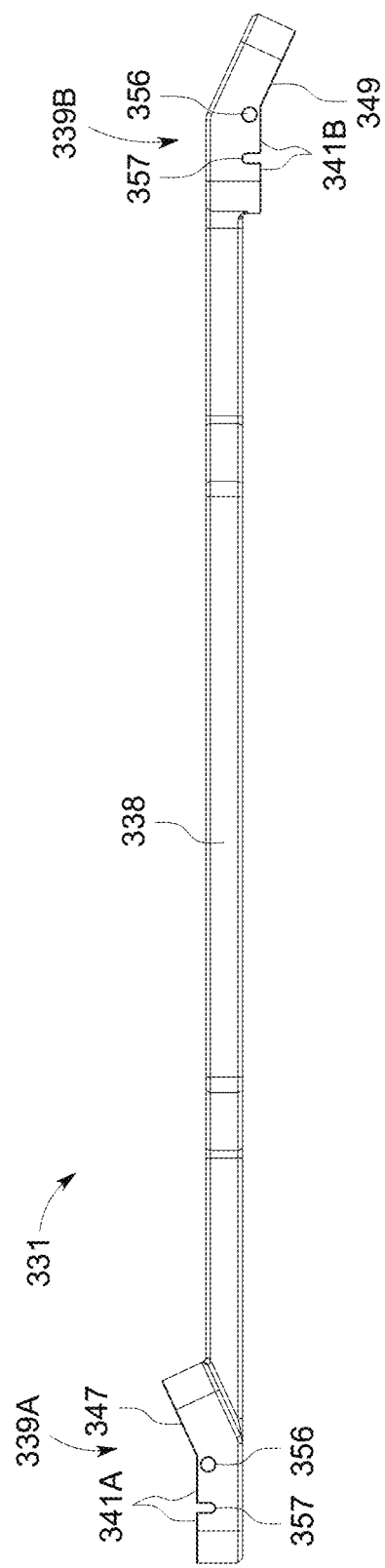
FIG. 106 illustrates a medial side view of the chamfer checker instrument of FIG. 104, in accordance with an aspect of the present disclosure.

FIGS. 104-106 illustrate another chamfer checker tool or instrument 331 that may be included in or utilized with the system 200. The chamfer checker tool 331 is similar to the chamfer checker tool 231 of FIGS. 100-103, and therefore like reference numerals preceded with "3" as opposed to "2" are used to indicate like components, portions, aspects, features and functions, and the description above directed thereto (including any alternative embodiments thereof) equally applies to the chamfer checker tool 331 and is not repeated hereinbelow only for brevity sake.

As shown in FIGS. 104-106, chamfer checker tool or instrument 331 differs from chamfer checker tool or instrument 331 in that it includes an anterior end portion 339A with a first central surface 241A and the chamfered planar anterior surface 247, and a posterior end portion 339B that with a second central surface 241B and the chamfered planar posterior surface 249. The handle portion 338 extends between the anterior end portion 339A and the posterior end portion 339B. The anterior end portion 339A can thereby be utilized to inspect/test the arrangement and configuration of the resected planar central surface 15' and the chamfered planar anterior surface 17', and the posterior end portion 339B can thereby be utilized to inspect/test the arrangement and configuration of the resected planar central surface 15' and the chamfered planar posterior surface 13'.

Figure 107:
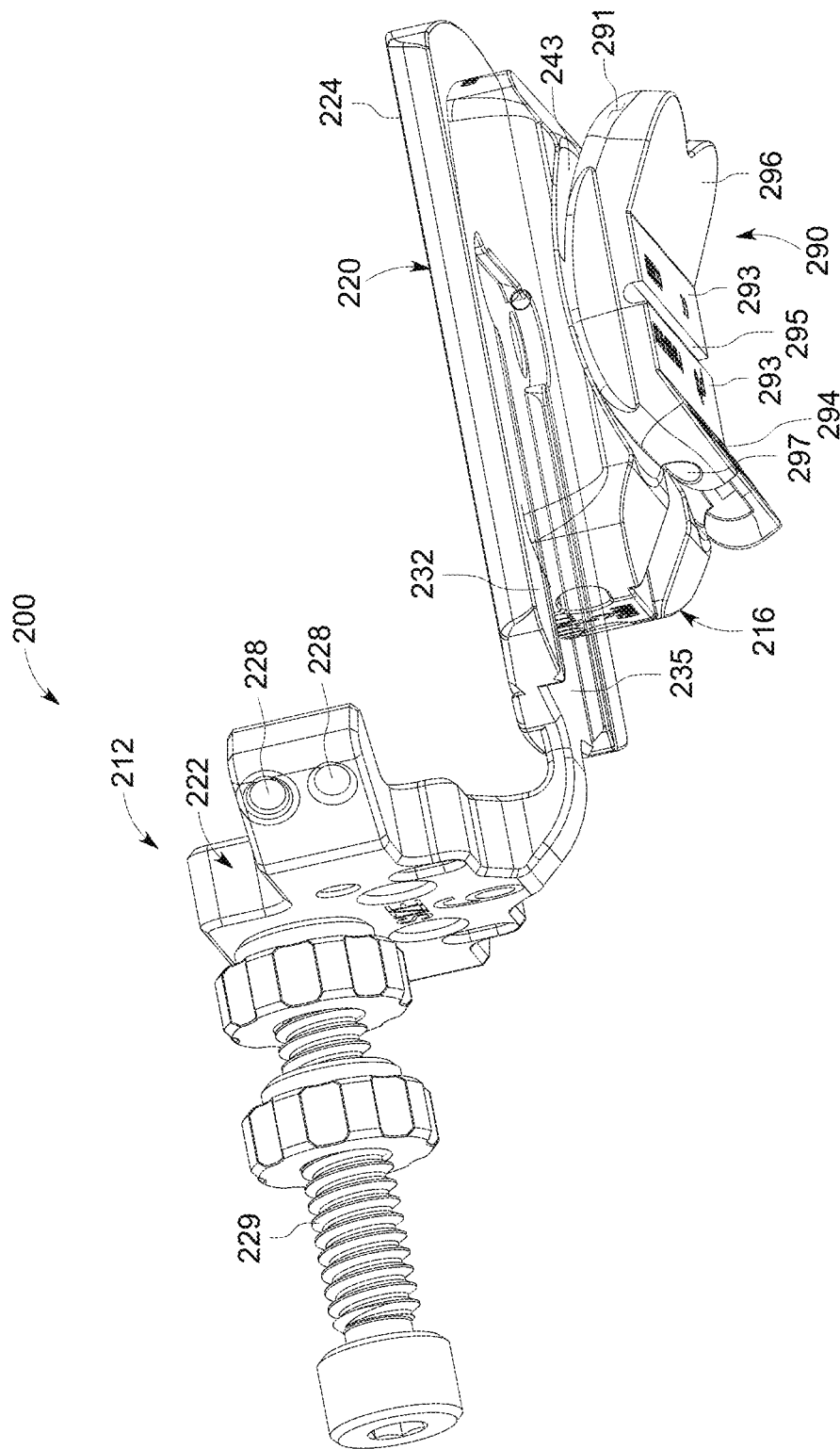
FIG. 107 illustrates a distal medial side perspective view of the tibial trial guide of FIG. 78 engaged with a tibial trial insert and a second talar trial guide of the TAR trial and guide system, in accordance with an aspect of the present disclosure.
Figure 108:
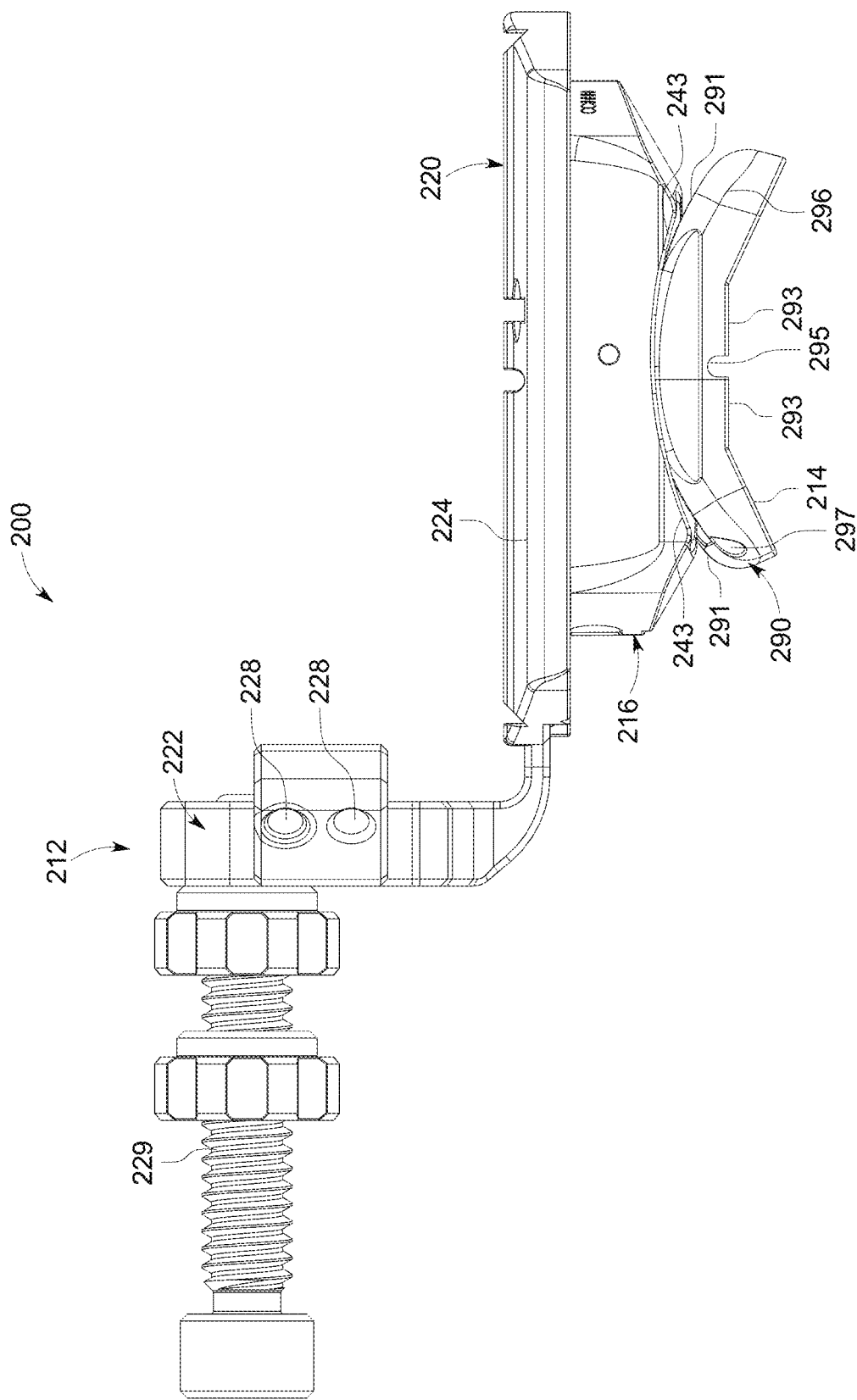
FIG. 108 illustrates a medial side view of the tibial trial guide, the tibial trial insert and the second talar trial guide of FIG. 107, in accordance with an aspect of the present disclosure.
Figure 109:
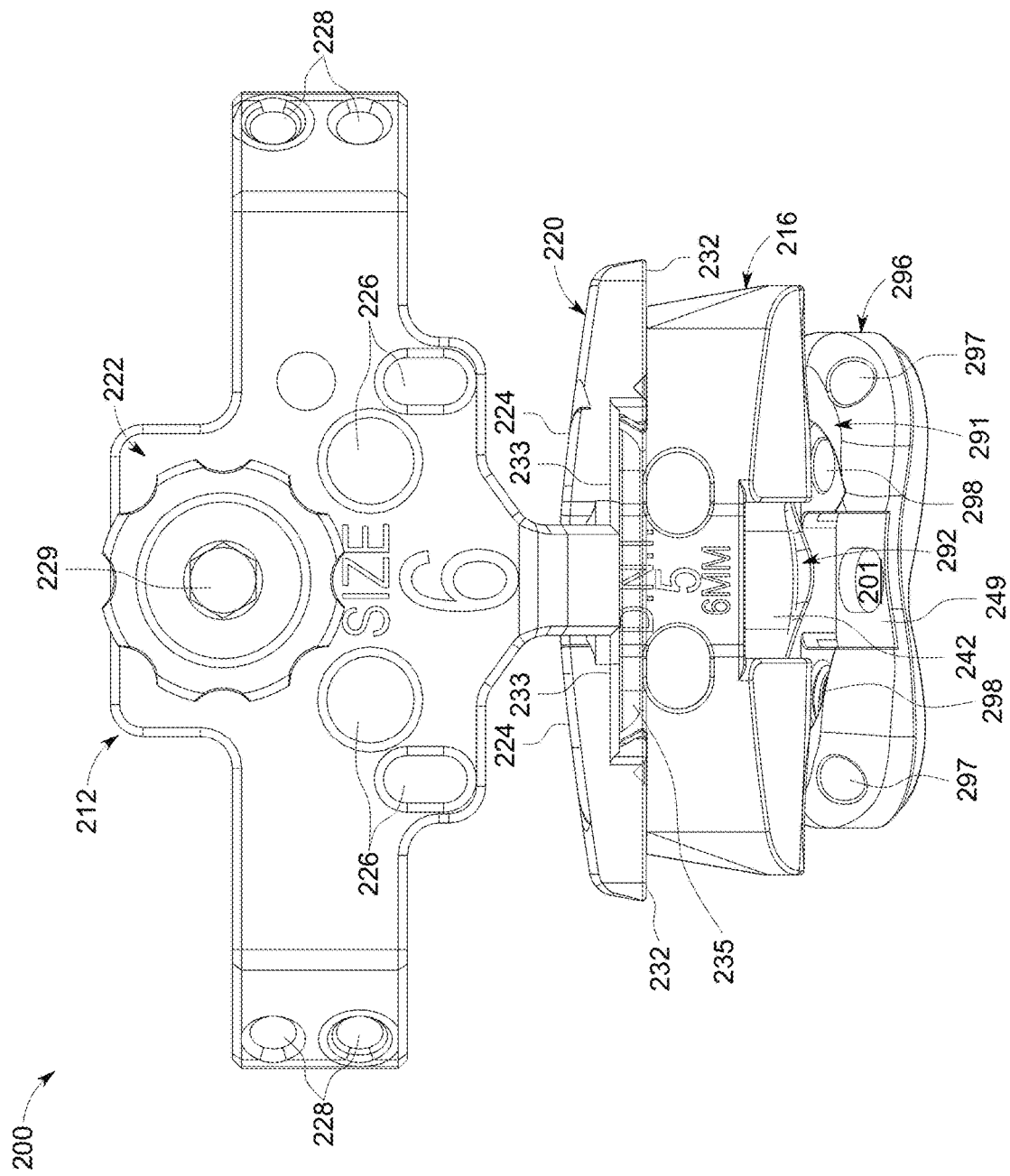
FIG. 109 illustrates an anterior view of the tibial trial guide, the tibial trial insert and the second talar trial guide of FIG. 107, in accordance with an aspect of the present disclosure.
Figure 110:
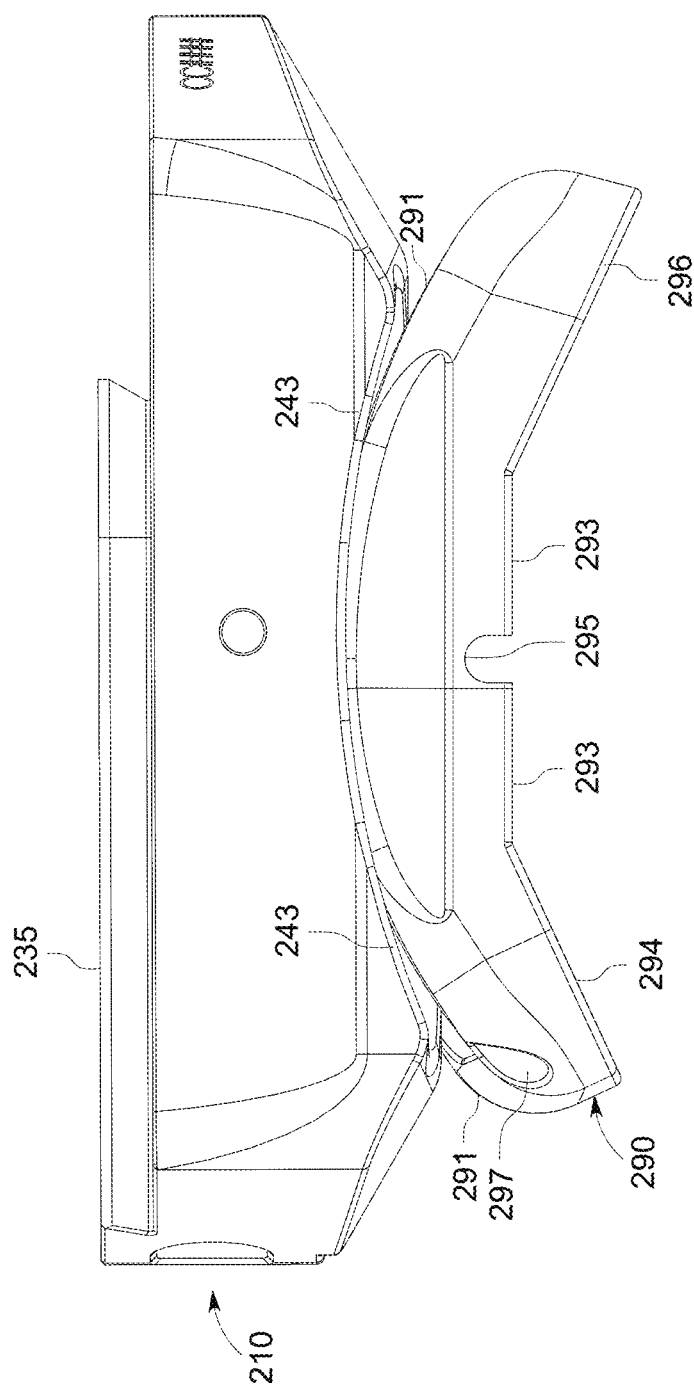
FIG. 110 illustrates a medial side view of the tibial trial insert and the second talar trial guide of FIG. 107, in accordance with an aspect of the present disclosure.
Figure 111:
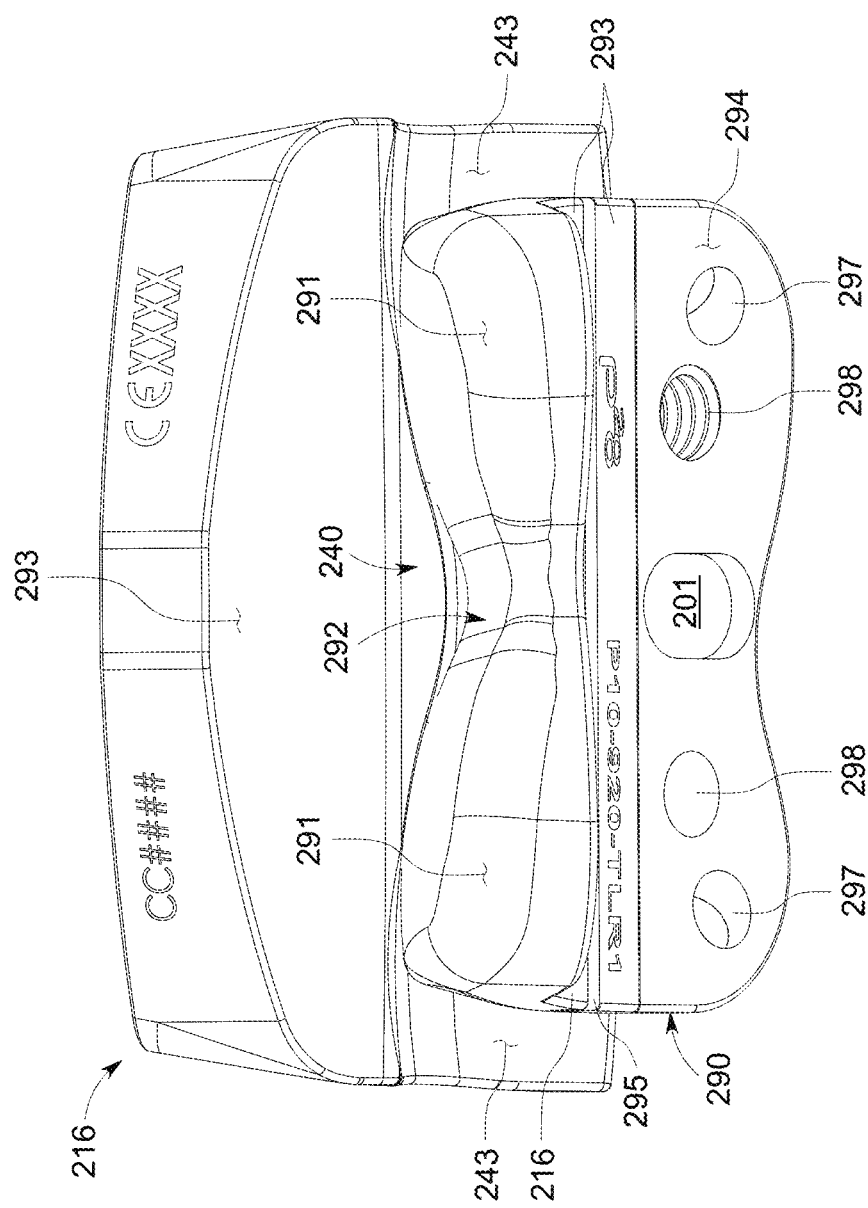
FIG. 111 illustrates an anterior view of the tibial trial insert and the second talar trial guide of FIG. 107, in accordance with an aspect of the present disclosure.

With reference to FIGS. 107-109, in some embodiments the system 200 may include a second talar trial guide 290 that is utilized with the tibial trial guide 212 and a tibial trial insert 216 after the resected talus 4 is chamfered via the first tibial trial guide 214 (i.e., after formation and inspection/trialing of the resected planar central surface 15', the chamfered planar posterior surface and the chamfered planar anterior surface 17' of the resected talus 4, as described above). As described above, the proximal projection 235 on the proximal side of the tibial trial insert 216 may be mated with the distal recessed portion or slot 233 of the distal insert side 232 of the base portion 220 of the tibial trial guide 212 to couple the tibial trial insert 216 to the tibial trial guide 212 within the ankle joint between the resected distal tibia 2 and the resected and chamfered talus 4 (the tibial trial guide 212 maybe previously coupled to the resected distal tibia 2 as described above).

The second talar trial guide 290 may also be positioned within the ankle joint between the resected distal tibia 2 and the resected and chamfered talus 4 such that the second talar trial guide 290 engages the resected and chamfered talus 4 and the tibial trial insert 216. As shown in FIGS. 110-119, the articulation surface 291 of the second talar trial guide 290 may engage and articulate with the articulation surface 243 of the tibial trial insert 216 to trial the tibial trial insert 216 (i.e., the tibial insert 16 corresponding thereto).

As described above, the configuration of the tibial trial insert 216 may correspond/match or closely approximate that of the tibial insert 16 in a mirrored relationship. For example, as shown in FIGS. 116-120, the articulation surface 243 of the tibial trial insert 216 may include medial and lateral surface portions that are medially-laterally and anteriorly-posteriorly arcuately concave, and an anteriorly-posteriorly arcuately concave and medially-laterally convex medial surface portion that extends medially-laterally between the medial and lateral surface portions. The articulation surface 46 of the tibial insert 16 may thereby be correspondingly or approximately likewise configured (in a proximally-distally mirrored relationship).

To allow the tibial trial insert 216 (and thereby the tibial insert 16) to be trialed in the ankle joint prior to the aperture formation in the resected and chamfered talus 4 that accept the bone engagement projection(s) 19 of the tibial insert 16), the articulation surface 291 of the second talar trial guide 290 may also correspond/match or closely approximate that of the tibial insert 16 and/or that of the talar implant 14. For example, as shown in FIGS. 111-113 and 115 the articulation surface 291 of the second talar trial guide 290 may include medial and lateral surface portions that are medially-laterally and anteriorly-posteriorly arcuately convex, and an anteriorly-posteriorly arcuately convex and medially-laterally concave medial surface portion 292 that extends medially-laterally between the medial and lateral surface portions. The articulation surface 46 of the tibial insert 16 may thereby be correspondingly or approximately likewise configured (in a proximally-distally mirrored relationship). The articulation surface 291 of the second talar trial guide 290 and the articulation surface 243 of the tibial trial insert 216 may thereby mate and articulate with each other in the same or substantially similar fashion as the talar implant 14 and the tibial insert 16 of the TAR prosthesis that they correspond to.

Figure 113:
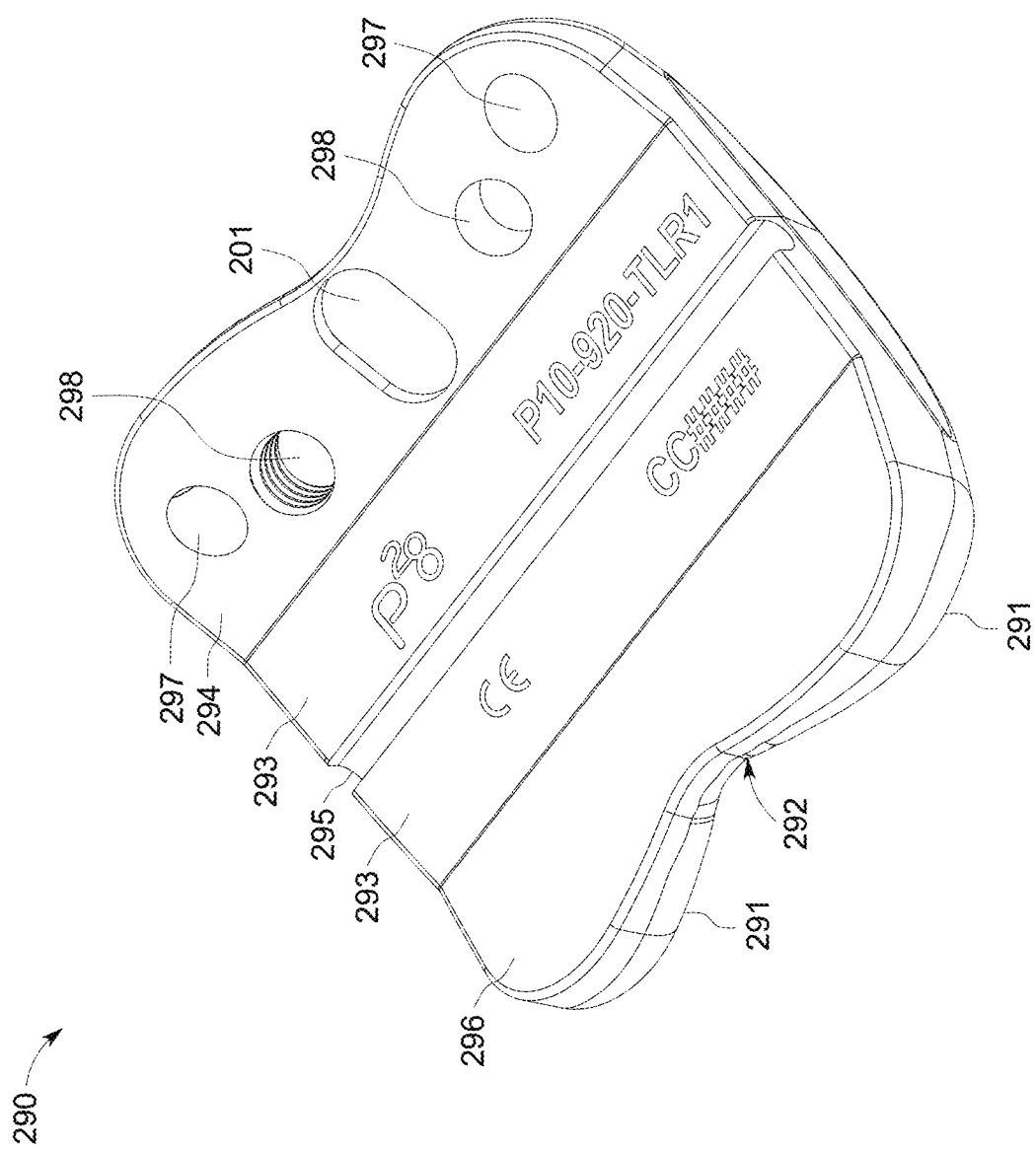
FIG. 113 illustrates a distal posterior perspective view of the second talar trial guide of FIG. 112, in accordance with an aspect of the present disclosure.
Figure 114:
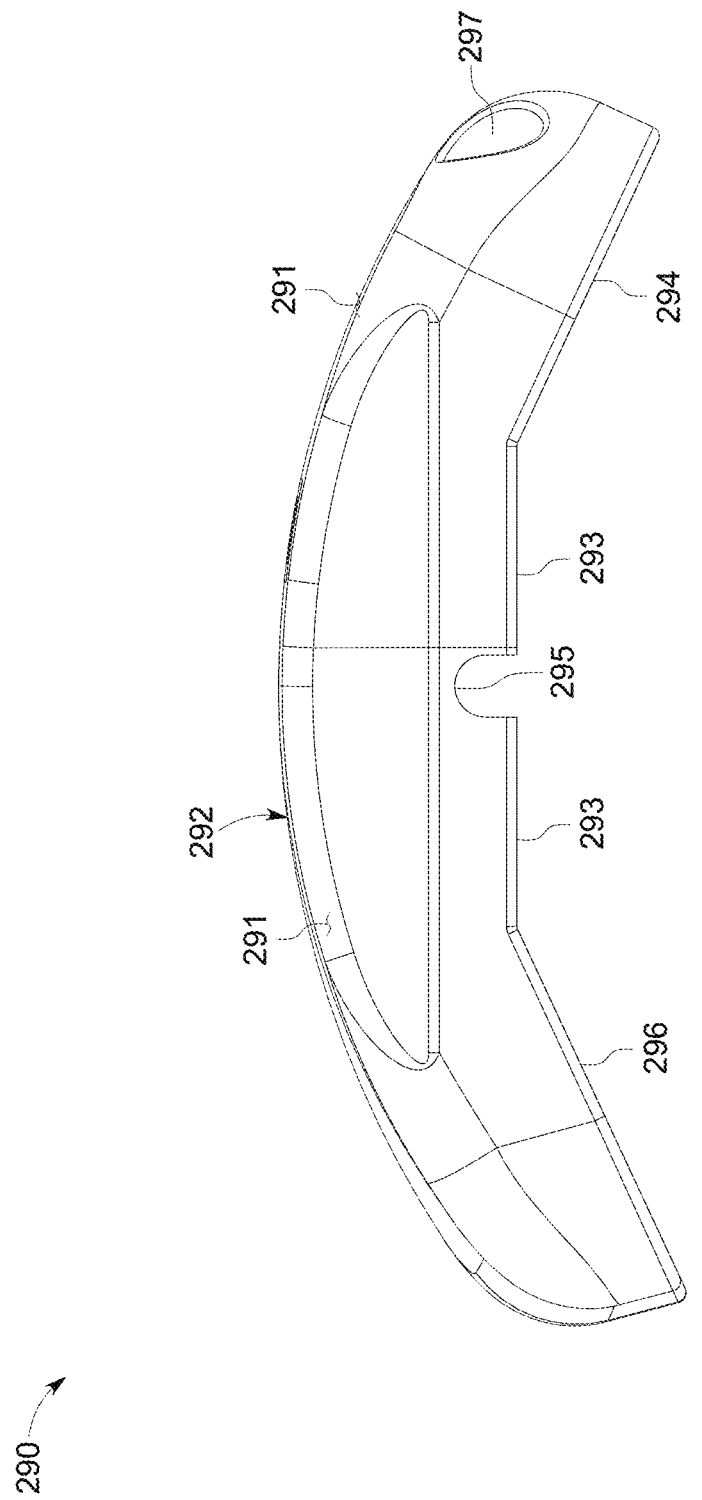
FIG. 114 illustrates a lateral side view of the second talar trial guide of FIG. 112, in accordance with an aspect of the present disclosure.
Figure 120:
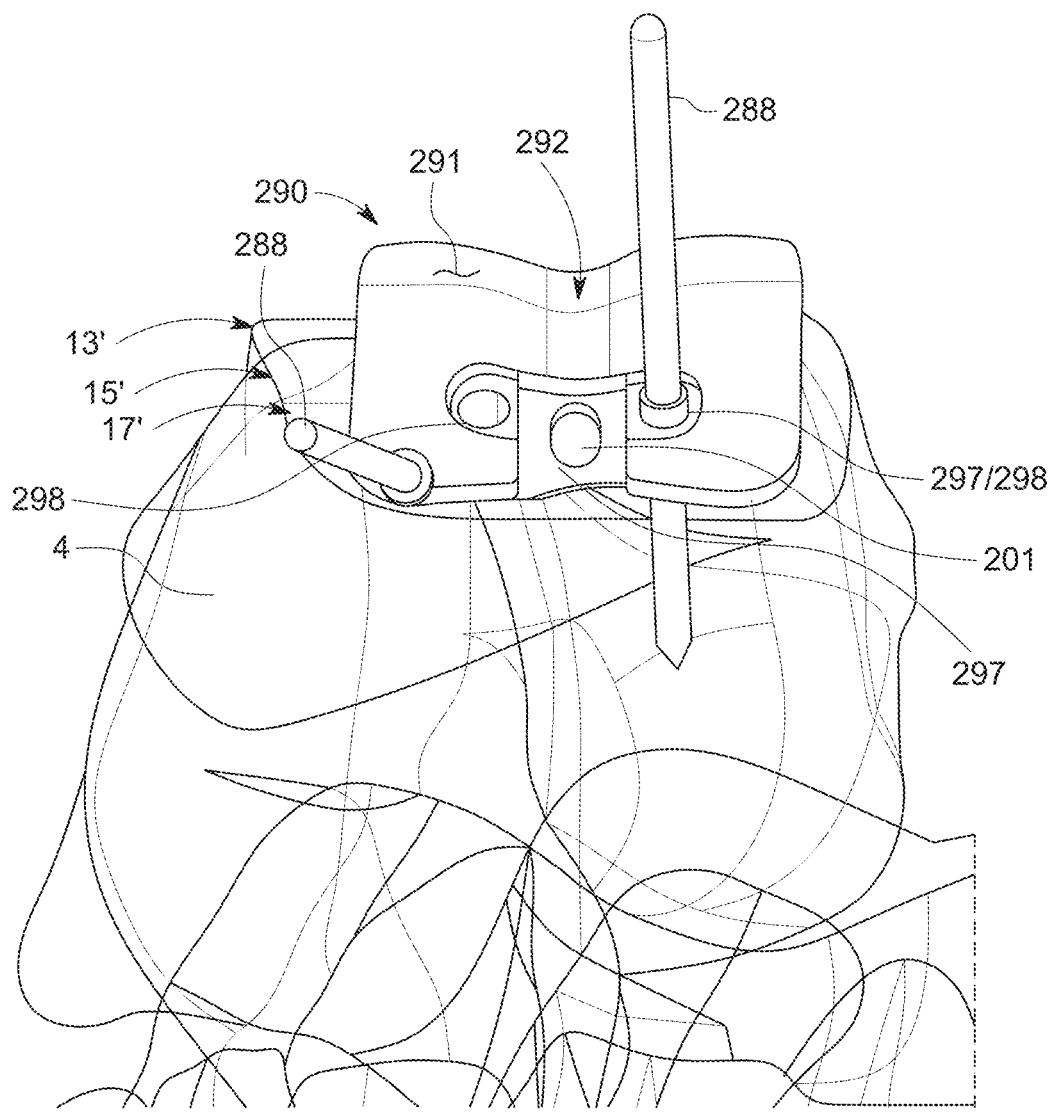
Figure 124:
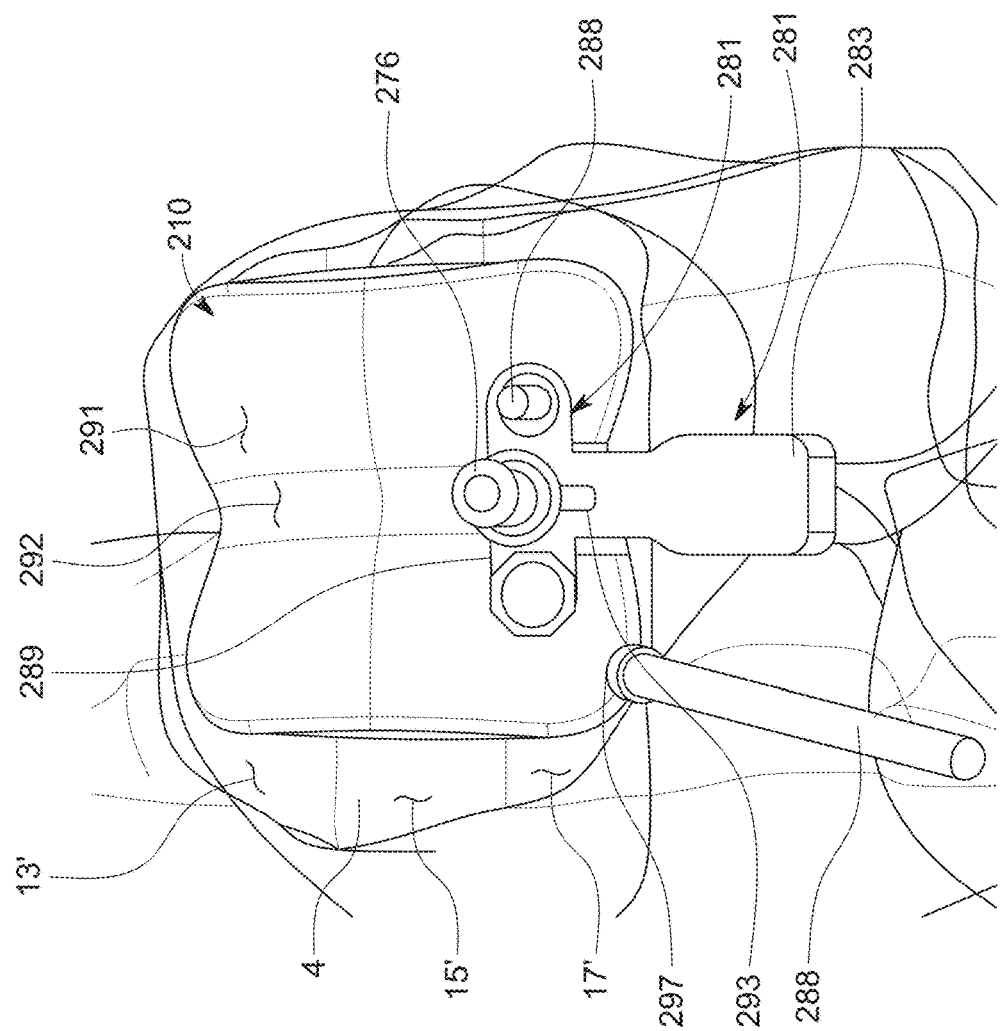

As shown in FIGS. 113 and 114, the distal engagement side 296 of the second talar trial guide 290 may include a plurality of planar surface portions that correspond to surfaces of the talar engagement side of the talar component 14. For example, the distal engagement side 296 of the second talar trial guide 290 may include a planar central surface portion 293, a planar posterior surface 296 and a planar anterior surface 294 that correspond to the planar central surface 15, the planar posterior surface 13 and the planar anterior surface 17, respectively, of the talar component 14, as shown in FIGS. 113 and 114. As also shown in FIGS. 113 and 114, the distal engagement side 296 of the second talar trial guide 290 may include a center reference slot 295 that extends medially-laterally through the planar central surface portion 293, and thereby corresponds to the anterior-posterior center of the planar central surface portion 293, the second talar trial guide 290 and/or the corresponding talar component 14 (and potentially the axis and/or anterior-posterior center of the talus 4 and/or tibia 2). The center reference slot 295 can thereby be utilized to visually inspect the anterior-posterior position of the second talar trial guide 290 when positioned on the talus 4, as shown in FIGS. 120, 124 and 125.

Figure 122:
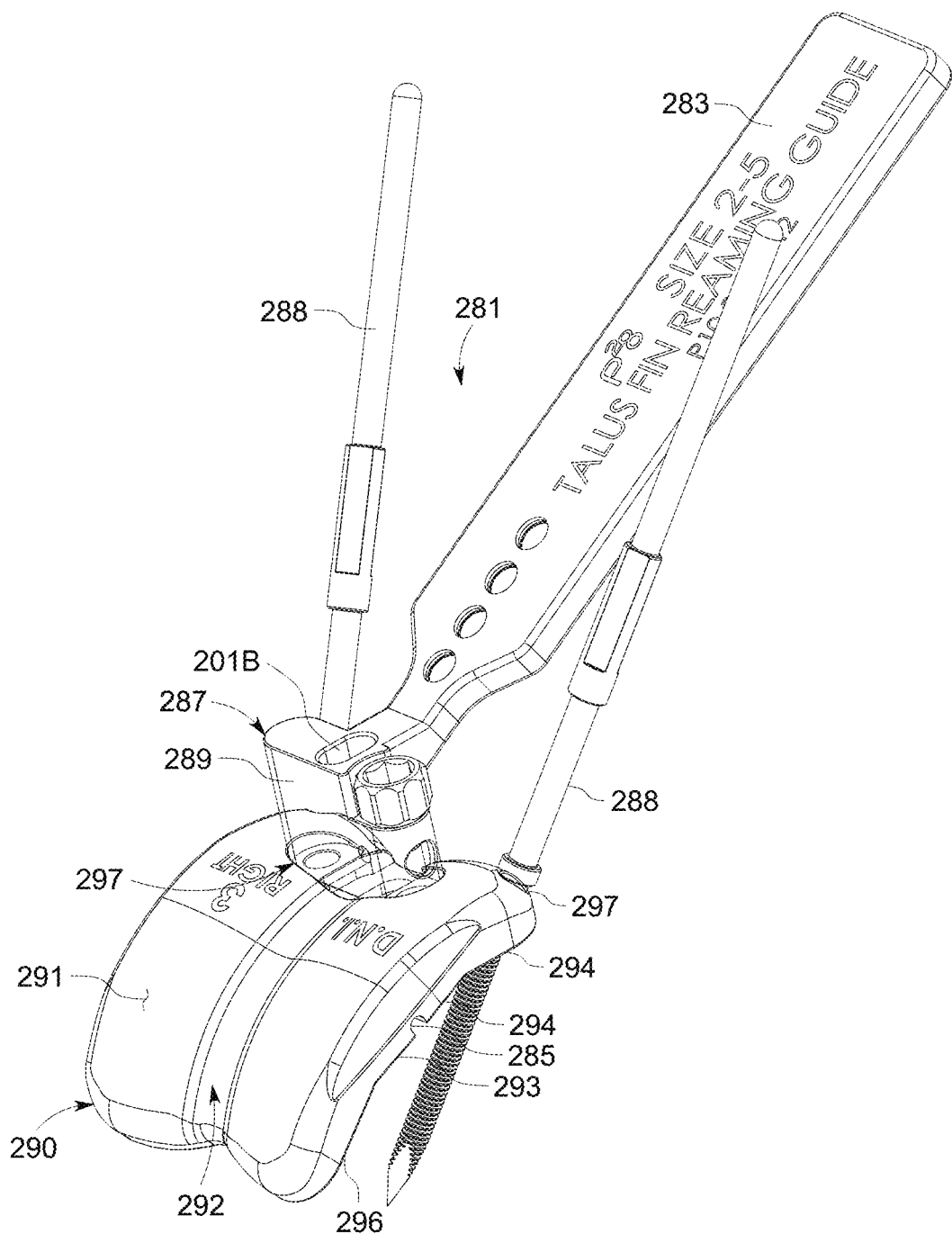
Figure 123:
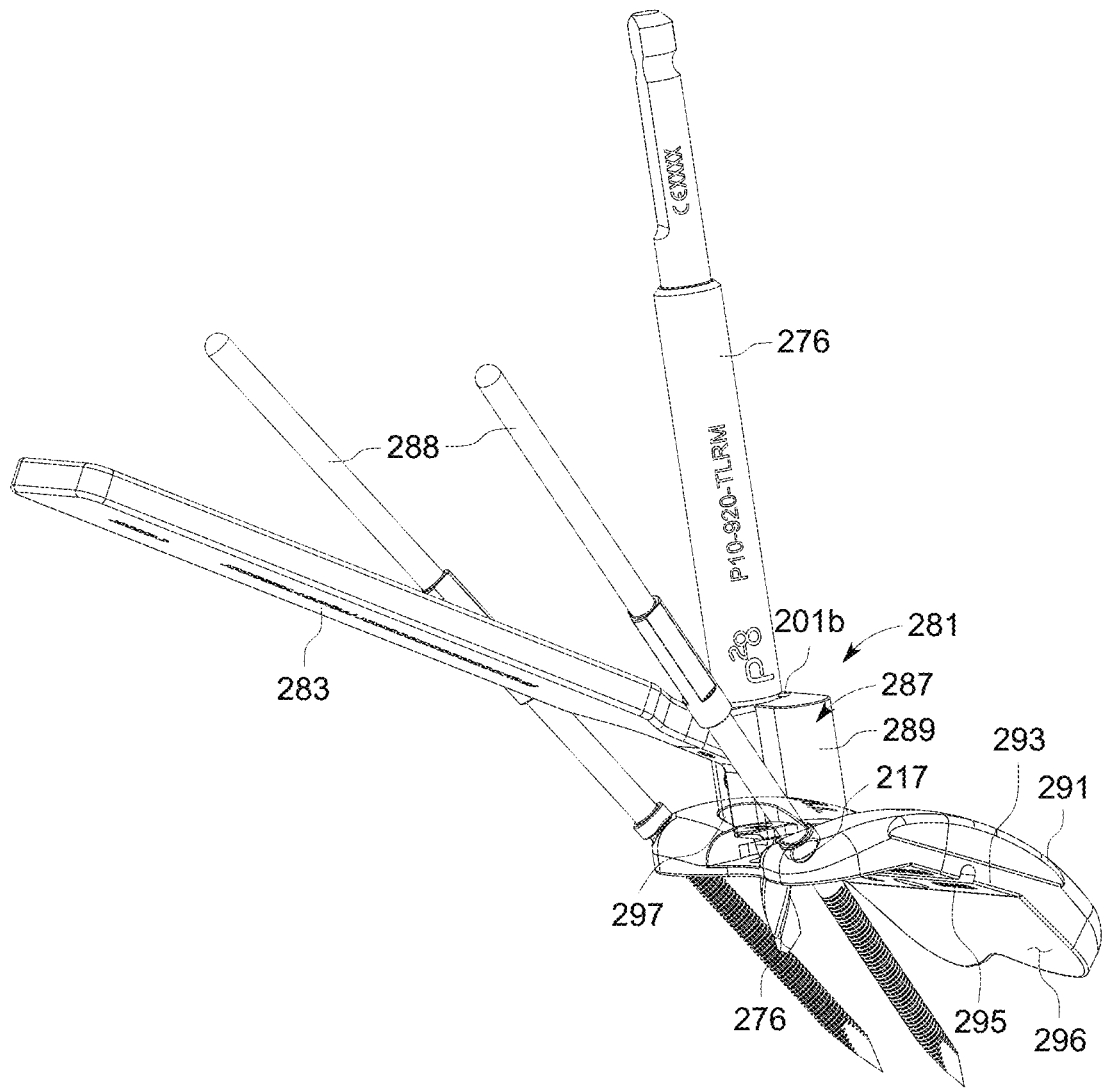

The second talar trial guide 290 may also include a plurality of pin apertures 297 extending proximally-distally through the second talar trial guide 290. For example, as shown in FIGS. 112, 113, 115 and 120-125, the second talar trial guide 290 may include at least a pair of anterior pin apertures 297 that extend through an anterior end portion thereof from the articulation surface 291 to the planar anterior surface 294. As shown in FIGS. 122 and 123, in some embodiments the pair of anterior pin apertures 297 may be configured to accept pin members 288 (e.g., smooth and/or shoulder pins) therethrough and into the anterior chamfer portion 17' of the resected talus 4 to couple the second talar trial guide 290 to the resected distal tibia 2, as shown in FIGS. 120, 124 and 125. As shown in FIGS. 122 and 123, in some embodiments the pair of anterior pin apertures 297 (and thus the pin members 288 extending therethrough) may converge medially-laterally as they extend distally from the second talar trial guide 290.

Figure 112:
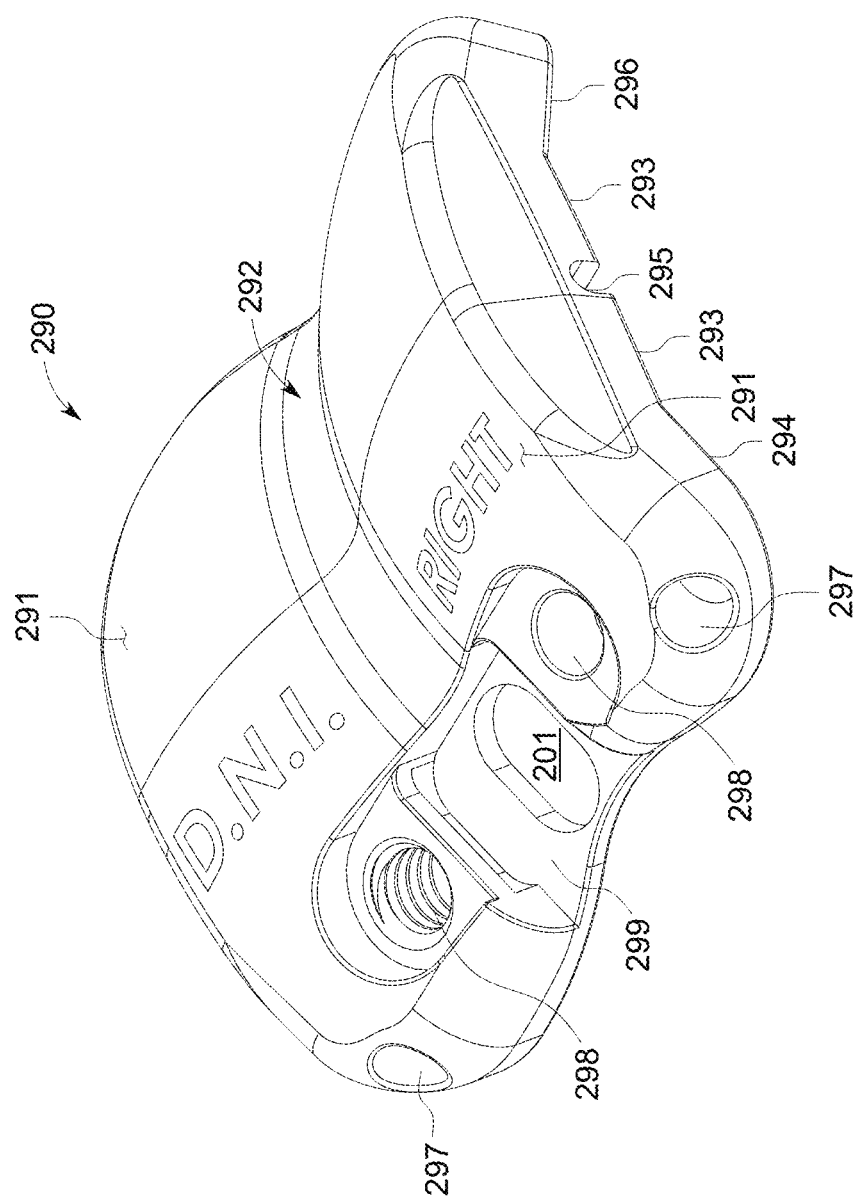
FIG. 112 illustrates an elevational anterior perspective view of the second talar trial guide of FIG. 107, in accordance with an aspect of the present disclosure.
Figure 115:
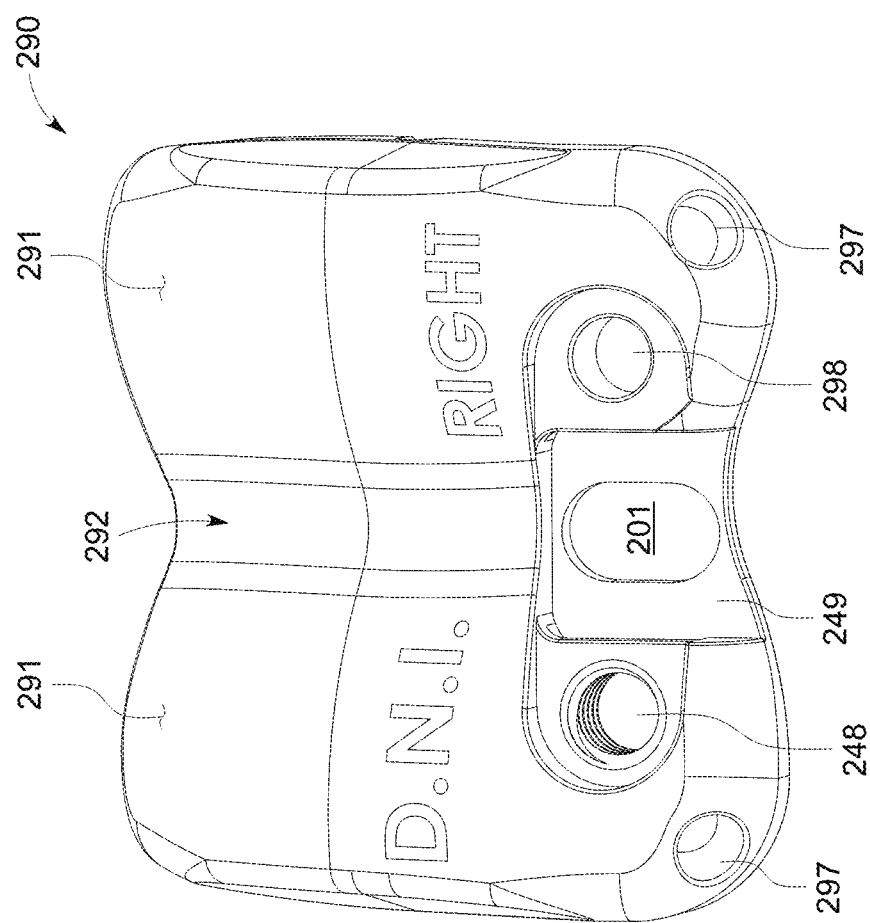
FIG. 115 illustrates an elevational anterior view of the second talar trial guide of FIG. 112, in accordance with an aspect of the present disclosure.
Figure 116:
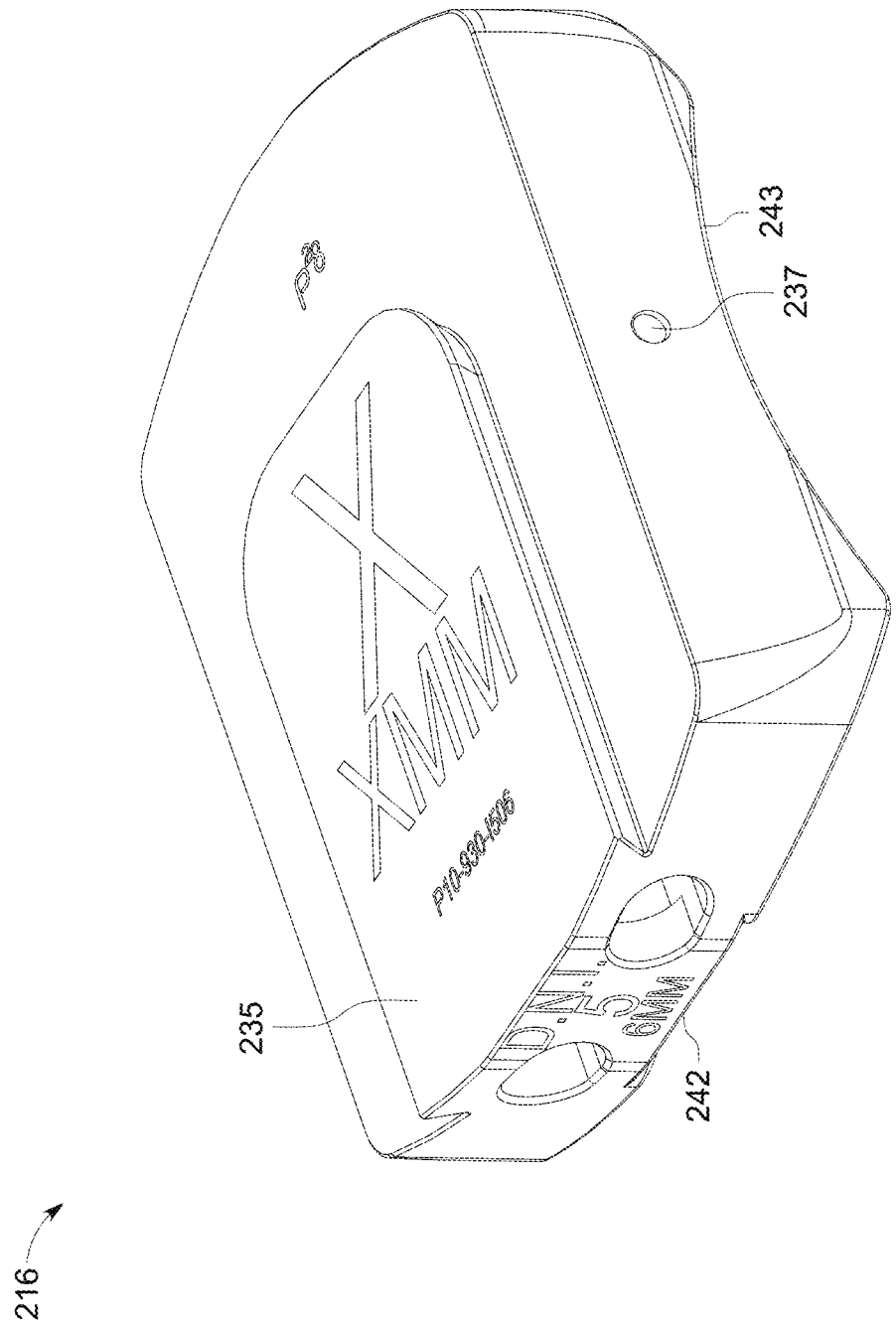
FIG. 116 illustrates an elevational anterior perspective view of the tibial trial insert of FIG. 107, in accordance with an aspect of the present disclosure.
Figure 117:
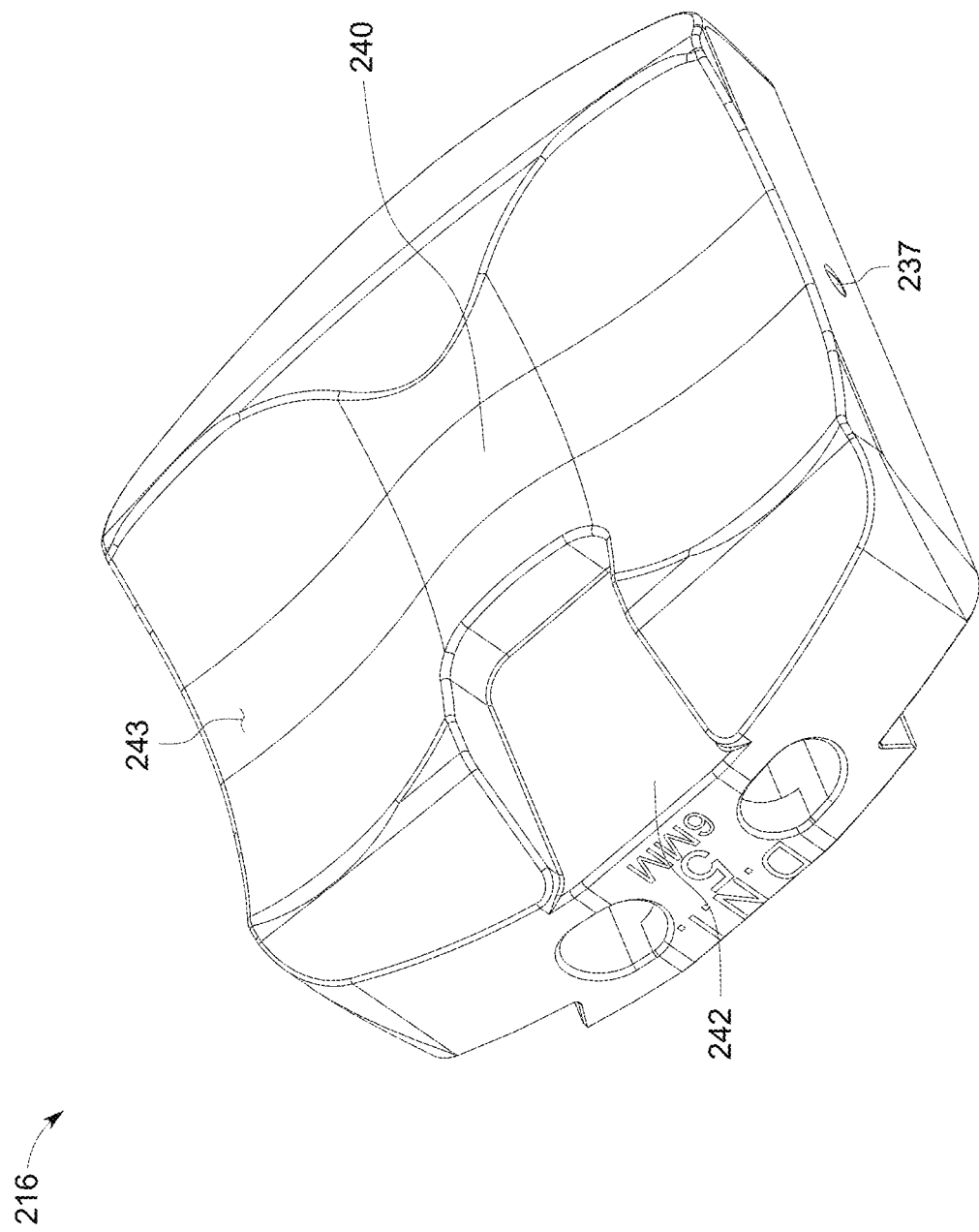
FIG. 117 illustrates a distal anterior perspective view of the tibial trial insert of FIG. 116, in accordance with an aspect of the present disclosure.
Figure 118:
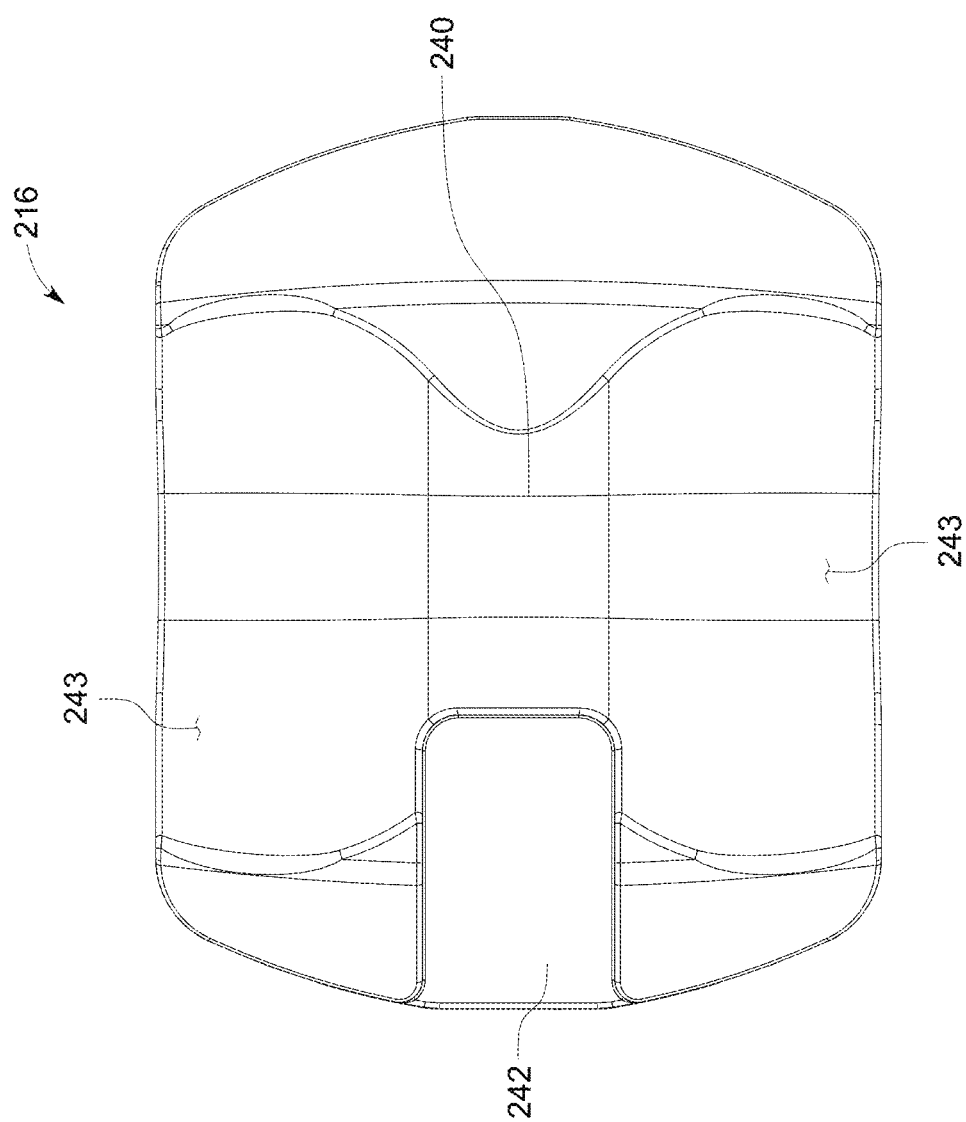
Figure 119:
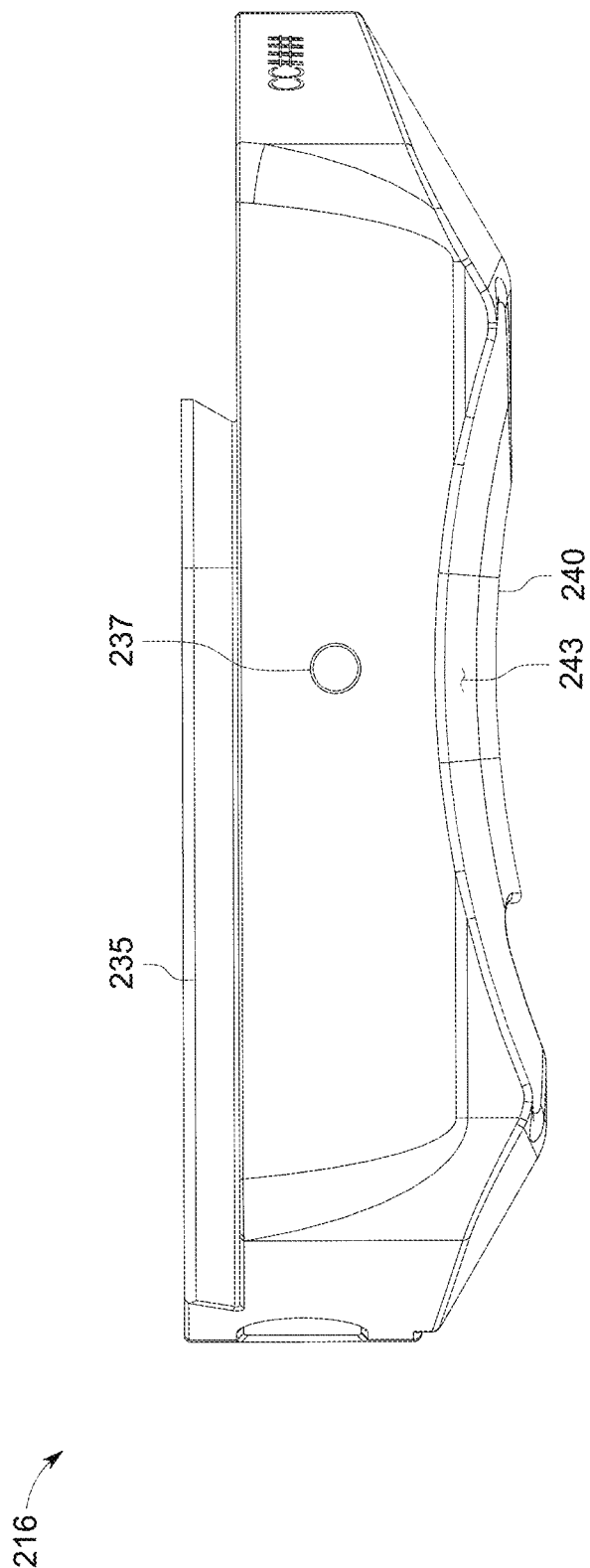

As also shown in FIGS. 112, 113, 115 and 120-125, the anterior portion of the second talar trial guide 290 may also include a guide recess 299, at least one guide aperture 298 and at least one bone aperture formation guide through hole 201. The recess 299, at least one guide aperture 298 and/or the bone aperture formation guide through hole 201 may be positioned medially-laterally between the pair of anterior pin apertures 297. As shown in FIGS. 112 and 115, in some embodiments the anterior portion of the second talar trial guide 290 may also include a pair of medially-laterally spaced guide apertures 298 that are positioned, at least partially, within the guide recess 299. In some such embodiments, the at least one bone aperture formation guide through hole 201 may be positioned medially-laterally between the pair of guide apertures 298.

As also shown in FIGS. 112 and 115, in some embodiments the at least one bone aperture formation guide through hole 201 may comprise one or more through holes that are anteriorly-posteriorly elongated or oblong. The position, size and orientation of the at least bone aperture formation guide through hole 201 may correspond to that of the at least one bone engagement projection 19 of the corresponding talar component 14. For example, the corresponding talar component 14 may include a single fin projection 15 that is anteriorly-posteriorly elongated or oblong, and the at least one bone aperture formation guide through hole 201 may comprise a corresponding single anteriorly-posteriorly elongated or oblong aperture. In some other embodiments, the corresponding talar component 14 may include a plurality of cylindrical/circular or irregular shaped projections 15, and the at least one bone aperture formation guide through hole 201 may comprise a plurality of corresponding cylindrical/circular or irregular shaped projections 15.

With reference to FIGS. 121-125, the system 200 may include a second talar trial guide bone aperture formation guide 287 configured to mate with the recess 299 and the at least one guide aperture 298 of the second talar trial guide 290 and a bone aperture formation instrument (e.g., a reamer) to form at least one aperture in the resected talus 4 (such as in the anterior chamfer portion 17' thereof) that corresponds to the bone engagement projection(s) 15 of the talar engagement side (e.g., such as the planar anterior surface 17 thereof) of the talar component 14.

As shown in FIGS. 121-125, the second talar trial guide bone aperture formation guide 287 may include a handle portion 283 and a head portion 289 that includes at least one second bone aperture formation guide through hole 201B. The head portion 289 is configured to mate/next within the guide recess 299, and includes at least one guide projection that is configured to extend into the at least one guide aperture 298, such that the at least one second bone aperture formation guide through hole 201B is aligned with or at least overlaps the at least one bone aperture formation guide through hole 201 of the second talar trial guide 290. In some embodiments, the head portion 289 may include at least one threaded guide projection that is configured to threadably couple with a threaded aperture of the at least one guide aperture 298. In some embodiments, the head portion 289 may include at least one non-threaded guide projection that is configured to couple with a non-threaded aperture of the at least one guide aperture 298.

As shown in FIGS. 123-125, the at least one second bone aperture formation guide through hole 201B is configured to accept a bone aperture formation instrument 276 therein such that the bone aperture formation instrument 276 (e.g., a reamer) forms at least one aperture in the resected talus 4 (such as in the anterior chamfer portion 17' thereof) that corresponds to the bone engagement projection(s) 15 of the talar engagement side (e.g., such as the planar anterior surface 17 thereof) of the talar component 14. In some embodiments, the at least one second bone aperture formation guide through hole 201B may be configured to allow the bone aperture formation instrument 276 to translate anteriorly-posteriorly therein (and in the at least one bone aperture formation guide through hole 201 of the second talar trial guide 290) to form an anteriorly-posteriorly elongated or oblong aperture in the resected talus 4 (such as in the anterior chamfer portion 17' thereof) that corresponds to at least one bone engagement fin 15 of the talar engagement side (e.g., such as the planar anterior surface 17) of the talar component 14.

In some embodiments, the system 200 may include a third talar trial guide 400 that is configured to trial a tibial trial insert 16 and form at least one aperture in a resected talus 4 that does not include the chamfered anterior and posterior surfaces (e.g., include a planar or flat proximal resected surface) for the implantation/engagement of a corresponding talar implant that includes a planar or flat talar engagement surface (not shown), as shown in FIGS. 126-133. As shown in FIGS. 128, 130, 132 and 133, the third talar trial guide 400 may include a planar distal talar bone engagement surface portion 418 that is configured to engage/abut the planar resected talus. As shown in FIGS. 128, 130, 132 and 133, the third talar trial guide 400 may also include a medially-laterally extending center reference slot 420 that represents the anterior-posterior center of a tibial trial insert articulation surface 404 of the third talar trial guide 400 and/or the corresponding talar implant.

As shown in FIGS. 126-133, the third talar trial guide 400 may include an anterior end portion 416 configured as a socket (or projection) that is configured to couple with an arm of the distractor 217. In some other embodiments, the anterior end portion 416 of the third talar trial guide 400 may be configured as a manually engageable handle.

As shown in FIGS. 126-133, the third talar trial guide 400 may include a pair of medially-laterally spaced anterior first pin apertures 414 that extend through the third talar trial guide 400 proximally-distally. The pair of first pin apertures 414 may be configured to accept pin members 424 (e.g., smooth pins) therethrough and into the flat resected talus 4. In some embodiments, the pair of first pin apertures 414 (and thereby the pin members 424 extending therethrough) may be aligned and/or oriented vertically, as shown in FIGS. 127 and 128.

As also shown in FIGS. 126-133, the third talar trial guide 400 may include a pair of medially-laterally spaced anterior second pin apertures 412 that extend through the third talar trial guide 400 proximally-distally. The pair of second pin apertures 412 may be configured to accept pin members 422 (e.g., threaded shoulder pins) therethrough and into the flat resected talus 4. In some embodiments, the pair of second pin apertures 412 (and thereby the pin members 422 extending therethrough) may be angled posteriorly and/or converge medially-laterally as they extend distally, as shown in FIGS. 127 and 128.

In some embodiments, the third talar trial guide 400 may include a window aperture 410 that extends through the third talar trial guide 400 proximally-distally, as shown in FIGS. 126-133. In some embodiments, the window 410 may be positioned, at least partially, medially-laterally between the pair of first pin apertures 414 and/or between the pair of second pin apertures 412. In some embodiments, the window 410 may be positioned, at least partially, anteriorly-posteriorly between the anterior end portion 416 and the tibial trial insert articulation surface 404 of the third talar trial guide 400.

To allow the tibial trial insert 216 (and thereby the tibial insert 16) to be trialed in the ankle joint prior to the aperture formation in the flat resected talus 4 that accept the bone engagement projection(s) 19 of the tibial insert 16), the articulation surface 404 of the third talar trial guide 400 may correspond/match or closely approximate that of the tibial insert 16 and/or that of the talar implant. For example, as shown in FIGS. 129 and 131, the articulation surface 404 of the third talar trial guide 400 may include medial and lateral surface portions that are medially-laterally and anteriorly-posteriorly arcuately convex, and an anteriorly-posteriorly arcuately convex and medially-laterally concave medial surface portion 406 that extends medially-laterally between the medial and lateral surface portions. The articulation surface 46 of the tibial insert 16 may thereby be correspondingly or approximately likewise configured (in a proximally-distally mirrored relationship). The articulation surface 404 of the third talar trial guide 400 and the articulation surface 243 of the tibial trial insert 216 may thereby mate and articulate with each other in the same or substantially similar fashion as the talar implant and the tibial insert 16 of the TAR prosthesis that they correspond to.

As shown in FIGS. 126-133, the third talar trial guide 400 may include at least one bone aperture formation guide through hole 408 that extends through the third talar trial guide 400 proximally-distally. In some embodiments, the at least one bone aperture formation guide through hole 408 comprises a pair of medially-laterally spaced bone aperture formation guide through holes 408, which may be angled posteriorly as then extend distally, as shown in FIGS. 126-133. In some embodiments, the at least one bone aperture formation guide through hole 408 may extend through an anterior portion of the articulation surface 243, as shown in FIGS. 126-133.

As shown in FIGS. 126-128, the at least one bone aperture formation guide through hole 408 is configured to accept a bone aperture formation instrument 430 (e.g., a reamer) therein such that the bone aperture formation instrument 430 forms at least one aperture in the resected talus (such as in an anterior portion thereof) that corresponds to the bone engagement projection(s) of the talar engagement side of the talar component that corresponds to the articulation surface 404 of the third talar trial guide 400.

The above disclosure describes a portion of a total ankle replacement (TAR) procedure and aspects, devices and systems used in that procedure. Additional understanding of the TAR procedure and the aspects, devices and systems may be found in U.S. Provisional Patent Application No. 62/779,436, filed Dec. 13, 2018, and entitled Joint Replacement Systems and Methods of Use and Assembly, International PCT Patent Application No. PCT/US2019/029009, filed Apr. 24, 2019, and entitled Implants and Methods of Use and Assembly, U.S. Provisional Patent Application No. 62/779,092, filed Dec. 13, 2018, and entitled Instruments, Guides and Related Methods for Total Ankle Replacement, the International PCT Patent Application filed on Dec. 13, 2019, and entitled Instruments, Guides and Related Methods for Total Ankle Replacement, U.S. Provisional Patent Application No. 62/890,611, filed Aug. 22, 2019, and entitled Patient Specific Instruments and Methods of Use, International PCT Patent Application No. PCT/US2019/066336, filed Dec. 13, 2019, and entitled Patient Specific Instruments and Methods of Use, U.S. Provisional Patent Application No. 62/899,703, filed Sep. 12, 2019, and entitled Joint Replacement Alignment Guides, Systems and Methods of Use and Assembly, the International PCT Patent Application filed on Dec. 13, 2019, and entitled Joint Replacement Alignment Guides, Systems and Methods of Use and Assembly, U.S. Provisional Patent Application No. 62/899,655, filed Sep. 12, 2019, and entitled Alignment Instruments and Methods for Use in Total Ankle Replacement, International PCT Patent Application No. PCT/US2019/066149, filed Dec. 13, 2019, and entitled Alignment Instruments and Methods for Use in Total Ankle Replacement, U.S. Provisional Patent Application No. 62/899,740, filed Sep. 12, 2019, and entitled Joint Replacement Alignment Guides, Systems and Methods of Use and Assembly, International PCT Patent Application No. PCT/US2019/066393, filed Dec. 13, 2019, and entitled Joint Replacement Alignment Guides, Systems and Methods of Use and Assembly, U.S. Provisional Patent Application No. 62/898,615, filed Sep. 11, 2019, and entitled Resection Guides, Sweeping Reamers, and Methods for Use in Total Ankle Replacement, International PCT Patent Application No. PCT/US2019/064948, filed Dec. 6, 2019, and entitled Resection Guides, Sweeping Reamers, and Methods for Use in Total Ankle Replacement, U.S. Provisional Patent Application No. 62/898,854, filed Sep. 11, 2019, and entitled Distractors Having Attachable Paddles, Impaction Devices, and Methods for Use in Total Ankle Replacement, International PCT Patent Application No. PCT/US2019/066398, filed Dec. 13, 2019, and entitled Distractors Having Attachable Paddles, Impaction Devices, and Methods for Use in Total Ankle Replacement, U.S. Provisional Patent Application No. 62/899,646, filed Sep. 12, 2019, and entitled Trial Insert Assembly, International PCT Patent Application No. PCT/US2019/065025, filed Dec. 6, 2019, and entitled Trial Insert Assembly, U.S. Provisional Patent Application No. 62/899,460, filed Sep. 12, 2019, and entitled Total Ankle Replacement Surgical Method, and the International PCT Patent Application filed on Dec. 13, 2019, and entitled Total Ankle Replacement Surgical Method, which are each hereby incorporated herein by reference in their entireties.

As may be recognized by those of ordinary skill in the art based on the teachings herein, numerous changes and modifications may be made to the above-described and other embodiments of the present disclosure without departing from the scope of the disclosure. The components of the instruments, guides, systems and related methods as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, systems and related methods (and components thereof) may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A total ankle replacement (TAR) trial and bone preparation guide system, configured to trial, and prepare a resected distal tibia and a resected talus for implantation therein and therebetween, a TAR prosthesis comprising a tibial component comprising a second tibial engagement surface and at least one bone engagement projection, a tibial insert configured to removably couple with the tibial component and comprising a second tibial articulation surface, and a talar component comprising a second talar engagement surface and a talar articulation surface that articulates with the second tibial articulation surface, wherein the system comprises tibial trial and bone preparation first component comprising:

a base portion comprising a first side defining a first tibial engagement surface configured to engage a resected distal tibia and at least one bone aperture formation guide through hole extending from the first tibial engagement surface to a second tibial insert engagement side; and an arm portion extending proximally from an anterior portion of the base portion configured to engage an anterior side of the resected distal tibia, and wherein the first side of the base portion of the first component includes at least one reference slot in the first tibial engagement surface that extends medially-laterally across at least a portion of the first tibial engagement surface and only partially through a thickness of the base portion between the first tibial engagement surface and the second tibial insert engagement side.

2. The system according to claim 1, wherein at least a portion of the first tibial engagement surface corresponds in size and shape to at least a portion of the second tibial engagement surface.

3. The system according to claim 2, wherein the first tibial engagement surface is convex medially-laterally.

4. The system according to claim 1, wherein the at least one reference slot comprises a plurality of reference slots in the first tibial engagement surface that each extend medially-laterally across at least a portion of the first tibial engagement surface, and wherein the plurality of reference slots are anteriorly-posteriorly spaced apart.

5. The system according to claim 4, wherein the plurality of reference slots comprise:

a center reference slot positioned in a medial-lateral center of the base portion corresponding to the medial-lateral center of the tibial component;

a bone aperture formation reference slot extending through at least a portion of the at least one bone aperture formation guide through hole;

an anterior reference slot positioned in an anterior end portion of the base portion corresponding to an anterior end of the tibial component; and a posterior reference slot positioned in a posterior end portion of the base portion corresponding to a posterior end of the tibial component.

6. The system according to claim 1, wherein the arm portion of the first component comprises a plurality of pin through holes extending therethrough anteriorly-posteriorly.

7. The system according to claim 6, wherein the arm portion of the first component comprises a medial wing and a lateral wing, the medial and lateral wings each comprising at least one pin through hole of the plurality of pin through holes, and wherein the at least one pin through hole of the medial and lateral wings converge medially-laterally as they extend posteriorly.

8. The system according to claim 7, wherein the plurality of pin through holes comprise at least one pair of aligned pin through holes that are medially-laterally spaced.

9. The system according to claim 1, wherein the arm portion of the first component comprises a positioning mechanism that is configured to engage the anterior side of the resected distal tibia and adjust the anterior-posterior position of the base portion of the first component relative to the resected distal tibia, the positioning mechanism comprising at least one adjustment screw threadably coupled with the arm portion.

10. The system according to claim 1, wherein the first talar engagement surface is planar and is configured to engage a planar portion of the resected talus.

11. The system according to claim 1, comprising:

a talar trial and bone preparation second component comprising:

a first talar engagement surface on a distal side of the second component configured to engage a portion of a resected talus;

a posterior trial articulation surface on a proximal side of the second component that is anteriorly-posteriorly arcuately convex;

an anterior window extending through the second component between the proximal side and the distal side thereof; and a posterior cut slot extending through the second component between the proximal side and the distal side thereof that is angled posteriorly as it extends from the proximal side to the distal side.

12. The system according to claim 11, further comprising a tibial trial insert comprising a distal side with a first talar trial engagement surface that is configured to engage the posterior trial articulation surface of the second component, and a proximal side configured to removably couple with the second tibial insert engagement side of the first component.

13. The system according to claim 12, wherein the second tibial insert engagement side of the first component comprises a coupling slot, and wherein the tibial trial insert comprises a coupling projection configured to removably mate within the coupling slot.

14. The system according to claim 13, wherein at least one through hole of the at least one bone aperture formation guide through hole is positioned within the coupling slot.

15. The system according to claim 12, wherein the configuration of the first talar trial engagement surface corresponds to at least a portion of the second tibial articulation surface.

16. The system according to claim 15, wherein the first talar trial engagement surface is arcuately concave anteriorly-posteriorly.

17. The system according to claim 12, wherein the first talar trial engagement surface comprises an anterior rail portion that extends medially-laterally and defines an engagement surface that is flat or convex anteriorly-posteriorly, and a posterior rail portion that extends medially-laterally and defines an engagement surface that is flat or convex anteriorly-posteriorly.

18. The system according to claim 12, wherein the first talar trial engagement surface further comprises a strut portion that extends anteriorly-posteriorly, and wherein the posterior trial articulation surface of the second component comprises a strut slot that extends anteriorly-posteriorly and is configured to accept the strut portion therein.

19. The system according to claim 11, wherein the distal side of the second component further comprises a medially-laterally extending center reference slot extending through the first talar engagement surface corresponding to the medial-lateral center of the talar component, the medially-laterally extending center reference slot being exposed at medial and lateral sides of the second component.

20. The system according to claim 11, wherein the posterior cut slot is exposed at medial and lateral sides of the second component at the distal side of the second component.

21. The system according to claim 11, wherein the distal side of the second component further comprises a medially-laterally extending anterior reference slot, the medially-laterally extending anterior reference slot being exposed at medial and lateral sides of the second component and corresponding to the position and orientation of an anterior-posterior pathway of the posterior trial articulation surface at the distal side of the second component.

22. The system according to claim 11, further comprising at least one anterior cut guide configured to engage the proximal side of the second component and extend at least partially over the anterior window, the at least one anterior cut guide comprising a bone cutting guide through hole configured to mate with at least one cutting implement to form an anterior chamfer on the resected talus.

23. The system according to claim 22, wherein the distal side of the second component further comprises a medially-laterally extending anterior cut reference slot, the medially-laterally extending anterior cut reference slot being exposed at medial and lateral sides of the second component and corresponding to the position and orientation of the anterior chamfer on the resected talus.

24. The system according to claim 11, wherein the posterior trial articulation surface corresponds in size and shape to at least a portion of the talar articulation surface of the talar component.

25. The system according to claim 11, wherein the posterior cut slot is positioned anteriorly-posteriorly between at least a portion of the posterior trial articulation surface and the anterior window, and wherein the posterior cut slot is configured to accept a cutting blade therethrough to form a posterior chamfer on the resected talus.

26. The system according to claim 11, wherein the second component further comprises a plurality of pin through holes extending therethrough between the proximal and distal sides thereof, and wherein the plurality of pin through holes of the second component comprise at least one pair of through holes that are medially-laterally spaced and converge medially-laterally as they extend from the proximal side to the and distal side of the second component.

27. The system according to claim 26, wherein the plurality of pin through holes of the second component comprise at least one pair of aligned pin through holes that are medially-laterally spaced.

28. The system according to claim 11, wherein the system further comprises a chamfer checker instrument, the chamfer checker instrument comprising at least one third talar engagement surface configured to engage the resected talus, a fourth talar engagement surface extending from the at least one third talar engagement surface configured to engage an anterior chamfer of the resected talus formed via the anterior window of the second component, and a fifth talar engagement surface extending from the at least one third talar engagement surface configured to engage a posterior chamfer of the resected talus formed via the posterior cut slot of the second component.

29. The system according to claim 11, wherein the system further comprises a talar chamfer trial comprising:
    a fifth talar engagement surface on a distal side of the talar chamfer trial configured to engage the resected talus;
    a second posterior trial articulation surface on a proximal side of the talar chamfer trial that comprises an anteriorly-posteriorly and medially-laterally arcuately convex portion;
    at least one bone aperture formation guide through hole; and
    a plurality of pin through holes extending between the proximal and distal sides thereof.

30. The system according to claim 29, wherein at least a portion of the second posterior trial articulation surface corresponds in size and shape to at least a portion of the second tibial engagement surface.

31. The system according to claim 29, wherein the fifth talar engagement surface comprises a first planar surface for engaging a planar surface of the resected talus, a second planar surface extending anteriorly from the first planar surface on a distal angle configured to engage an anterior chamfer surface of the resected talus formed via the anterior window of the second component, and a third planar surface extending posteriorly from the first planar surface on a distal angle configured to engage a posterior chamfer of the resected talus formed via the cut slot of the second component.

32. The system according to claim 1, wherein the at least one reference slot extends across the entirety of the medial-lateral width of the first tibial engagement surface.

33. The system according to claim 1, wherein the at least one reference slot extends to the medial-lateral sides of the base portion such that the reference slot is exposed at the medial-lateral sides of the base portion.

* * * * *

UNITED STATES PATENT AND TRADEMARK OFFICE
CERTIFICATE OF CORRECTION

PATENT NO. : 11,571,311 B2
APPLICATION NO. : 17/345137
DATED : February 7, 2023
INVENTOR(S) : Dogué et al.

It is certified that error appears in the above-identified patent and that said Letters Patent is hereby corrected as shown below:

In the Claims

Column 43, Line 4: Claim 12, Delete "surf ace" and insert -- surface --

Column 43, Line 32: Claim 18, Delete "surf ace" and insert -- surface --

Column 43, Line 52: Claim 21, Delete "surf ace" and insert -- surface --

Column 44, Line 28: Claim 28, Delete "surf ace" and insert -- surface --

Column 44, Line 31: Claim 28, Delete "surf ace" and insert -- surface --

Column 44, Line 37: Claim 29, Delete "surf ace" and insert -- surface --

Column 44, Line 40: Claim 29, Delete "surf ace" and insert -- surface --

Column 44, Line 49: Claim 30, Delete "surf ace" and insert -- surface --

Column 44, Line 53: Claim 31, Delete "surf ace" and insert -- surface --

Column 44, Line 57: Claim 31, Delete "surf ace" and insert -- surface --

Signed and Sealed this
Fourth Day of April, 2023

Katherine Kelly Vidal
*Director of the United States Patent and Trademark Office*